(12) United States Patent
Fan et al.

(10) Patent No.: US 8,207,318 B2
(45) Date of Patent: Jun. 26, 2012

(54) METHODS AND COMPOSITIONS FOR GENERATING RECOMBINANT NUCLEIC ACID MOLECULES

(75) Inventors: James Fan, Carlsbad, CA (US); John Carrino, San Diego, CA (US); Jonathan Chesnut, Carlsbad, CA (US); Knut Madden, Carlsbad, CA (US); Martin Gleeson, San Diego, CA (US); Robert Bennett, Encinitas, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/112,649

(22) Filed: Apr. 30, 2008

(65) Prior Publication Data

US 2009/0326208 A1  Dec. 31, 2009

Related U.S. Application Data

(63) Continuation of application No. 10/991,803, filed on Nov. 17, 2004, now abandoned, and a continuation-in-part of application No. 10/014,128, filed on Dec. 7, 2001, now Pat. No. 7,033,801.

(60) Provisional application No. 60/520,946, filed on Nov. 17, 2003, provisional application No. 60/326,092, filed on Sep. 28, 2001, provisional application No. 60/254,510, filed on Dec. 8, 2000.

(51) Int. Cl.
*C07H 21/02* (2006.01)
*C12Q 1/68* (2006.01)

(52) U.S. Cl. ........................... 536/23.1; 435/6.12

(58) Field of Classification Search .................. None
See application file for complete search history.

(56) References Cited

U.S. PATENT DOCUMENTS

| | | | |
|---|---|---|---|
| 4,661,450 A | 4/1987 | Kempe et al. | |
| 4,800,159 A | 1/1989 | Mullis et al. | |
| 5,162,209 A | 11/1992 | Scheele et al. | |
| 5,605,802 A | 2/1997 | Trono et al. | |
| 5,624,826 A | 4/1997 | Kato et al. | |
| 5,746,997 A | 5/1998 | Reed | |
| 5,766,891 A | 6/1998 | Shuman | |
| 5,851,808 A | 12/1998 | Elledge et al. | |
| 5,958,681 A | 9/1999 | Wetmur et al. | |
| 5,981,182 A | 11/1999 | Jacobs et al. | |
| 6,013,440 A | 1/2000 | Lipshutz et al. | |
| 6,140,086 A * | 10/2000 | Fox et al. | 435/91.41 |
| 6,174,669 B1 | 1/2001 | Hayashizaki et al. | |
| 6,238,884 B1 | 5/2001 | Short et al. | |
| 6,277,632 B1 | 8/2001 | Harney | |
| 6,280,977 B1 | 8/2001 | Liang et al. | |
| 6,291,213 B1 | 9/2001 | Rothstein | |
| 6,340,595 B1 | 1/2002 | Vogels et al. | |
| 6,537,776 B1 | 3/2003 | Short | |
| 6,548,277 B1 | 4/2003 | Shuman | |
| 6,653,106 B1 | 11/2003 | Shuman et al. | |
| 6,916,632 B2 * | 7/2005 | Chesnut et al. | 435/91.1 |
| 2001/0044137 A1 | 11/2001 | Heyman et al. | |
| 2002/0025561 A1 | 2/2002 | Hodgson | |
| 2002/0028444 A1 | 3/2002 | Harney et al. | |
| 2002/0068290 A1 | 6/2002 | Yarovinsky | |
| 2002/0182731 A1 | 12/2002 | Ji et al. | |

FOREIGN PATENT DOCUMENTS

| | | |
|---|---|---|
| EP | 0373914 | 6/1990 |
| EP | 0625572 | 11/1994 |
| EP | 1018549 | 6/1999 |
| WO | WO85/04898 | 11/1985 |
| WO | WO96/18744 | 6/1990 |
| WO | WO94/29443 | 12/1994 |
| WO | WO96/19497 | 6/1996 |
| WO | WO96/34981 | 11/1996 |
| WO | WO97/24455 | 7/1997 |
| WO | WO97/48716 | 12/1997 |
| WO | WO98/20122 | 5/1998 |
| WO | WO98/55502 | 12/1998 |
| WO | WO98/056943 | 12/1998 |
| WO | WO00/12687 | 3/2000 |
| WO | WO00/56878 | 9/2000 |
| WO | WO01/62892 | 8/2001 |
| WO | WO01/62943 | 8/2001 |
| WO | WO02/16594 | 2/2002 |

OTHER PUBLICATIONS

Heyman et al. Genome Research vol. 9:383-392. 1999.*
Arnott et al., "DNA-RNA Hybrid Secondary Structures", *Journal of Molecular Biology*, vol. 188, Apr. 20, 1986, 631-640.
Carninci et al., "High Efficiency Full-Length cDNA Cloning by Biotinylated CAP Trapper", *Genomics*, vol. 37, No. 3, Aug. 20, 1996, 327-336.
Carninci et al., "High Efficiency Selection of full-length cDNA by Improved Biotinylated Cap Trapper", *DNA Research*, vol. 4, No. 1, Feb. 28, 1997, 61-66.
Cheng et al., "Mutational analysis of 39 residues of vaccinia DNA topoisomerase identifies Lys-220, Arg-223, and Asn-228 as important for covalent catalysis", *The Journal of Biological Chemistry*, vol. 272, No. 13, Mar. 28, 1997, 8263-8269.

(Continued)

*Primary Examiner* — Samuel Woolwine
*Assistant Examiner* — Suchira Pande

(57) ABSTRACT

A method of generating a double stranded (ds) recombinant nucleic acid molecule covalently linked in both strands by contacting two or more ds nucleotide sequences with a topoisomerase under conditions such that both termini of at least one end of a first ds nucleotide sequence are covalently linked by the topoisomerase to both termini of at least one end of a second ds nucleotide sequence is provided. Also provided is a method for generating a ds recombinant nucleic acid molecule covalently linked in one strand, by contacting two or more ds nucleotide sequences with a type IA topoisomerase under conditions such that one strand, but not both strands, of one or both ends of a first ds nucleotide sequence are covalently linked by the topoisomerase. Compositions for performing such methods, and compositions generated from such methods also are provided, as are kits containing components useful for conveniently practicing the methods.

10 Claims, 34 Drawing Sheets

OTHER PUBLICATIONS

Cheng et al., "A catalytic domain of eukaryotic DNA topoisomerase I", *The Journal of Biological Chemistry*, vol. 273, No. 19, May 8, 1988, 11589-11595.

Cheng et al., "Conservation of structure and mechanism between eukaryotic topoisomerase I and site-specific recombinases", *Cell* vol. 92, No. 6, Mar. 20, 1998, 841-850.

Cheng et al., "DNA strand transfer catalyzed by vaccinia topoisomerase: litgation of DNAs containing a 3' mononucleotide overhang", *Nucleic Acids Research*, vol. 28, No. 9, 2000, 1893-1898.

Cheng et al., "Recombinogenic flap ligation pathway for intrinsic repair of topoisomerase 1 B-induced double-strand breaks", *Molecular and Cellular Biology*, vol. 20, No. 21, Nov. 2000, 8059-8068.

Cheng et al., "Site-specific DNA transesterification by vaccinia topoisomerase: Role of specific phosphates and nucleosides", *Biochemistry*, vol. 38, No. 50, Dec. 14, 1999, 16599-16612.

Chong et al., "Single-column purification of free recombinant proteins using a self-cleavable affinity tag derived from a protein splicing element", *Gene*, vol. 192, No. 2, Jun. 19, 1997, 271-281.

Digate et al., "Molecular Cloning and DNA Sequence Analysis of *Escherichia coli* top B, the Gene Encoding Topoisomerase III", *The Journal of Biological Chemistry*, vol. 264, No. 30, Oct. 25, 1989, 17924-17930.

Edery et al., "An Efficient Strategy to Isolate Full-Length cDNAs Based on an mRNA Cap Retention Procedure (CAPture)", *Molecular and Cellular Biology*, vol. 15, No. 6, Jun. 1995, 3363-3371.

Ericsson et al., "Characterization of ts 16, a Temperature-Sensitive Mutant of Vaccinia Virus", *Journal of Virology*, vol. 69, No. 11, Nov. 1995, 7072-7086.

Gross et al., "Vaccinia Virions Lacking the RNA Helicase Nucleoside Triphosphate Phosphohydrolase II Are Defective in Early Transcription", *Journal of Virology*, vol. 70, No. 12, Dec. 1996, 8549-8555.

Haghighat et al., "eIF4G Dramatically Enhances the Binding of el F4E to the mRNA 5'-Cap Structure", *The Journal of Biological Chemistry*, vol. 272, No. 35, Aug. 29, 1997, 21677-21680.

Haghighat et al., "The eIF4G-eIF4E Complex is the Target for Direct Cleavage by the Rhinovirus 2A Proteinase", *Journal of Virology*, vol. 70, No. 12, Dec. 1996, 8444-8450.

Henningfeld et al., "A Model for Topoisomerase I-Mediated Insertions and Deletions with Duplex DNA Substrates Containing Branches, Nicks, and Gaps", *Biochemistry*, vol. 34, No. 18, 1995, 6120-6129.

Heyman et al., "Genome-scale cloning and expression of individual open reading frames using topoisomerase I-mediated ligation", *Genome Research*, vol. 9, No. 4, Apr. 1999, 383-392.

Invitrogen Corporation, "Expression in S. Cerevisiae", *Invitrogen Catalogue*, Carlsbad, California, 1998, 18, 29, 43, 44, 49-52.

Janknecht et al., "Rapid and efficient purification of native histidine-tagged protein expressed by recombinant vaccinia virus", *Proceedings of the National Academy of Sciences*, vol. 88, No. Oct. 1, 1991, 8972-8976.

Kane et al., "Vaccinia Virus Morphogenesis Is Blocked by a Tmperature-Sensitive Mutation in the 17 Gene That Encodes a Virion Component", *Journal of Virology*, vol. 67, No. 5, May 1993, 2689-2698.

Kato et al., "Construction of a human full-length cDNA bank", *Gene*, vol. 150, No. 2, Dec. 15, 1994, 243-250.

Klemm et al., "Peptide Inhibitors of DNA Cleavage by Tyrosine Recombinases and Topoisomerases", *Journal of Molecular Biology*, vol. 299, No. 5, 2000, 1203-1216.

Klemperer et al., "Identification and Characterization of the orf Virus Type I Topoisomerase", *Virology*, vol. 206, No. 1, Jan. 10, 1995, 203-215.

Krogh et al., "Catalytic Mechanism of DNA Topoisomerase IB," *Molecular Cell*, vol. 5, No. 6, Jun. 2000, 1035-1041.

Krogh et al., "DNA strand transfer catalyzed by vaccinia topoisomerase: peroxidolysis and hydroxylaminolysis of the covalent protein-DNA intermediate", *Biochemistry*, vol. 39, No. 21, May 30, 2000, 6422-6432.

Krogh et al., "Effect of 2'-5' phosphodiesters on DNA transesterification by vaccinia topoisomerase", *The Journal of Biological Chemistry*, vol. 276, No. 24, Jun. 15, 2001, 20907-20912.

Krogh et al., "Vaccinia topoisomerase mutants illuminate conformational changes during closure of the protein clamp and assembly of a functional active site", *The Journal of Biological Chemistry*, Jul. 5, 2001, 1-38.

Krogh et al., "Melanoplus sanguinipes entomopoxvirus DNA topoisomerase: site-specific DNA transesterification and effects of 5'-bridging phosphorothiolates", *Virology*, vol. 264, No. 2, 1999, 441-451.

Liu et al., "Mapping the 5' and 3' Ends of *Tetrahymena thermophelia* mRNAs Using RNA Ligase Mediated Amplification of cDNA Ends (RLM-RACE)", *Nucleic Acids Research*, vol. 21, No. 21, 1993, 4954-4960.

Lockard et al., "Labeling of Eukaryotic Messenger RNA 5' Terminus with Phosphorus-32: Use of Tobacco Acid Pyrophosphatase for Removal of Cap Structures", *Gene Amplification and Analysis*, vol. 2, 1981, 229-251.

Maruyama et al., "Oligo-Capping: A Simple Method to Replace the Cap Structure of Eukaryotic mRNAs with Oligoribonucleotides", *Gene*, vol. 138, Nos. 1-2, Jan. 28, 1994, 171-174.

Matthews et al., "Analytical Strategies for the Use of DNA Probes", *Analytical Biochemistry*, vol. 169, No. 1, Feb. 15, 1988, 1-25

Morham et al., "Phenotypic selection and characterization of mutant alleles of a eukaryotic DNA topoisomerase I", *Genes & Development*, vol. 4, No. 4, 1990, 515-524.

Morham et al., "Covalent and Noncovalent DNA Binding by Mutants of Vaccinia DNA Topoisomerase I", *Journal of Biological Chemistry*, vol. 267, No. 22, Aug. 5, 1992, 15984-15992.

Nature Biotechnology, "New Products", *Nature Biotechnology*, http://biotech.nature.com, vol. 18, Mar. 2000, 356.

Palaniyar et al., "SFV topoisomerase: sequence specificity in a genetically mapped interval", *Virology*, vol. 221, 1996, 351-354.

Petersen et al., "Mutations within a conserved region of vaccinia topoisomerase affect the DNA cleavage-religation equilibrium", *J. Mol. Biol.*, vol. 263, No. 2, Academic Press Limited, 1996, 181-195.

Petersen et al., "Characterization of a DNA Topoisomerase Encoded by *Amsacta moorei* Entomopoxvirus", *Virology*, vol. 230, 1997, 197-206.

Petersen et al., "DNA strand transfer reactions catalyzed by vaccinia topoisomerase: hydrolysis and glycerololysis of the covalent protein-DNA intermediate", *Nucleic Acids Research*, vol. 25, No. 11, 1997, 2091-2097.

Petersen et al., "Histidine 265 is Important for Covalent Catalysis by Vaccinia Topoisormerase and is Conserved in all Eukaryotic Type I Enzymes", *Journal of Biological Chemistry*, vol. 272, No. 7, Feb. 14, 1997, 3891-3896.

Russell, "A recombination-based cloning system that decreases time to protein analysis", *American Biotechnology Laboratory*, vol. 18, No. 7, Jun. 30, 2000, 8 & 10.

Salazar et al., "The DNA strand in DNA.RNA hybrid duplexes is neither B-form nor A-form in solution", *Biochemistry*, vol. 32, No. 16, 1993, 4207-4215.

Sambrook et al., "Molecular Cloning—A Laboratory Manual," Second Edition, Cold Springs Harbor Laboratory Press Press, 1989, 2.53-2.54, 16.8-16.9, 16.20 and 16.22.

Schmitt et al., "Affinity purification of histidine-tagged proteins", Molecular Biology Reports vol. 18 (3), Jan. 1, 1993, 223-230.

Sekiguchi et al., "Domain structure of vaccinia DNA ligase", *Nucleic Acids Research*, vol. 25, No. 4, 1997, 727-734.

Sekiguchi et al., "Covalent Dna binding by vaccinia topoisomerase results in unpairing of the bond thymine base 5' of the scissile and Shuman", *Journal of Biological Chemistry*, vol. 271, No. 32, Aug. 9, 1996, 19436-19442.

Sekiguchi et al., "Identification of contacts between topoisomerase I and its target DNA by site-specific photocrosslinking", *The EMBO Journal*, vol. 15, No. 13, 1996, 3448-3457.

Sekiguchi et al., "Kinetic analysis of DNA and RNA strand transfer reactions catalyzed by vaccinia topoisomerase", *The Journal of Biological Chemistry*, vol. 272, No. 25, Jun. 20, 1997, 15721-15728.

Sekiguchi et al., "Mechanism of inhibition of vaccinia DNA topoisomerase by novobiocin and coumermycin", *The Journal of Biological Chemistry*, vol. 271, No. 4, Jan. 26, 1996, 2313-2322.

Sekiguchi et al., "Mutational analysis of vaccinia virus topoisomerase identifies residues involved in DNA binding", *Nucleic Acids Research*, vol. 25, No. 18, 1997, 3649-3656.

Sekiguchi et al., "Nick sensing by vaccinia virus DNA ligase requires a 5' phosphate at the nick and occupancy of the adenylate binding site on the enzyme", *The Journal of Virology*, vol. 71, No. 12, American Society for Microbiology, Dec. 1997, 9679-9684.

Sekiguchi et al., "Proteolytic footprinting of vaccinia topoisomerase bound to DNA", *The Journal of Biological Chemistry*, vol. 270, No. 19, May 12, 1995, 11636-11645.

Sekiguchi et al., "Requirements for noncovalent binding of vaccina topoisomerase I to duplex DNA", *Nucleic Acids Research*, vol. 22, No. 24, Dec. 11, 1994, 5360-5365.

Sekiguchi et al., "Resolution of a Holliday junction by vaccinia topoisomerase requires a spacer DNA segment 3' of the CCCTT/ cleavage sites", *Nucleic Acids Research*, vol. 28, No. 14, 2000, 2658-2663.

Sekiguchi et al., "Resolution of Holliday junctions by eukaryotic DNA topoisomerase I", *Proceedings of the National Academy of Sciences*, vol. 93, No. 2, Jan. 1996, 785-789.

Sekiguchi et al., "Site-specific ribonuclease activity of eukaryotic DNA topoisomerase I", *Molecular Cell*, vol. 1, No. 1, Dec. 1997, 89-97.

Sekiguchi et al., "Stimulation of vaccinia topoisomerase I by nucleoside triphosphates", *Journal of Biological Chemistry*, vol. 269, No. 47, Nov. 25, 1994, 29760-29764.

Sekiguchi et al., "Vaccinia topoisomerase binds circumferentially to DNA", *Journal of Biological Chemistry*, vol. 269, No. 50, Dec. 16, 1994, 31731-31734.

Shatkin et al., "Capping of Eucaryotic mRNAs", *Cell*, vol. 9, Dec. 1976, 645-653.

Shuman et al., "Characterization of Vaccinia Virus DNA Topoisomerase I Expressed in *Escherichia coli*", *Journal of Biological Chemistry*, vol. 263, Nov. 5, 1988, 16401-16407.

Shuman, "Novel approach to molecular cloning and polynucleotide synthesis using vaccinia DNA Topoisomerase", *The Journal of Biological Chemistry*, vol. 269, No. 51, Dec. 23, 1994, 32678-32684.

Shuman, "Analysis of topoisomerase—DNA interactions by electrophoretic mobility shift assay", Methods in Molecular Biology, vol. 95, 2001, 65-74.

Shuman, "DNA Strand Transfer Reactions Catalyzed by Vaccinia Topoisomerase I", *The Journal of Biological Chemistry*, vol. 267, No. 12, Apr. 25, 1992, 8620-8627.

Shuman et al., "Identification of a Vaccinia Virus Gene Encoding a Type I DNA Topoisomerase", *Proceedings of the National Academy of Sciences*, vol. 84, Nov. 1987, 7478-7482.

Shuman et al., "Insertional mutagenesis of the vaccinia virus gene encoding a type I DNA topoisomerase: evidence that the gene is essential for virus growth", *Virology*, vol. 170, No. 1, 1989, 302-306.

Shuman et al., "Intramolecular synapsis of duplex DNA by vaccinia topoisomeras", *The EMBO Journal*, vol. 16, No. 21, 1997, 6584-6589.

Shuman et al., "Mapping the active-site tyrosine of vaccinia virus DNA topoisomerase I", *Proceedings of the National Academy of Sciences*, vol. 86, No. 24, Dec. 1989, 9793-9797.

Shuman, "Polynucleotide ligase activity of eukaryotic topoisomerase I", *Molecular Cell*, vol 1, No. 5, Apr. 1998, 741-748.

Shuman, "Recombination mediated by vaccinia virus DNA topoisomerase I in *Escherichia coli* is sequence specific", *Proceedings of the National Academy of Sciences (PNAS)*, vol. 88, No. 22, Nov. 1991, 10104-10108.

Shuman, "Site-specific DNA cleavage by vaccinia virus DNA topoisomerase I. Role of nucleotide sequence and DNA secondary structure", *The Journal of Biological Chemistry*, vol. 266, No. 17, Jan. 15, 1991, 1796-1803.

Shuman et al., "Site-specific interaction of vaccinia virus topoisomerase I with base and sugar moieties in duplex DNA", *Journal of Biological Chemistry*, vol. 268, No. 25, The American Society for Biochemistry and Molecular Biology, Inc., Sep. 5, 1993, 18943-18950.

Shuman, "Site-specific Interaction of Vaccinia Virus Topoisomerase I with Duplex DNA. Minimal DNA Substrate for Strand Cleavage Iin Vitro", *The Journal of Biological Chemistry*, Erratum, vol. 266, No. 17, Jun. 15, 1991, 11372-11379.

Shuman, "Site-specific interaction of Vaccinia Virus Topoisomerase I with Duplex DNA. Minimal DNA Substrate for Strand Cleavage In Vitro", *Journal of Biological Chemistry*, vol. 266, No. 17, Jun. 15, 1991, 11372-11379.

Shuman et al., "Specific DNA Cleavage and Binding of Vaccinia Virus DNA Topoisomerase I", *The Journal of Biological Chemistry*, vol. 265, No. 29, Oct. 15, 1990, 17826-17836.

Shuman, "Two Classes of DNA End-Joining Reactions Catalyzed by Vaccinia Topoisomerase I", *The Journal of Biological Chemistry*, vol. 267, No. 24, Aug. 25, 1992, 16755-16758.

Shuman, "Vaccinia DNA topoisomerase I promotes illegitimate recombination in *Escherichia coli*", Proceedings of the National Academy of Sciences, vol. 86, No. 10, May 1989, 3489-3493.

Shuman, "Vaccinia virus DNA ligase: specificity, fidelity, and inhibition", *Biochemistry*, vol. 34, 1995, 16138-16147.

Shuman, "Vaccinia virus DNA topoisomerase: a model eukaryotic type IB enzyme", *Biochimica et Biophysica Acta*, vol. 1400, 1998, 321-337.

Stivers et al., "Stereochemical outcome and kinetic effects of Rp- and Sp-phosphorothioate substitution at the cleavage site of vaccinia type I DNA topoisomerase", *Biochemistry*, vol. 39, No. 18, 2000, 5561-5572.

Stivers et al., "Vaccinia DNA topoisomerase I: kinetic evidence for general acid-base catalysis and a conformational step", *Biochemistry*, vol. 33, No. 51, 1994, 15449-15458.

Stivers et al., "Vaccinia DNA topoisomerase I: single-turnover and steady-state kinetic analysis of the DNA strand cleavage and ligation reactions", *Biochemistry*, vol. 33, No. 1, 1994, 327-339.

Sykes et al., "Linear Expression Elements: a rapid, in vivo, method to screen for gene functions.", *Nature Biotechnology*, vol. 17, Apr. 1999, 355-359.

Theus et al., "A Simple Assay for Determining the Capping Efficiencies of RNA Polymerases Used for Inv Vitro Transcription", *BioTechniques*, vol. 9, No. 5, 1990, 610-615.

Wang et al., "Mutational analysis of 26 residues of vaccinia DNA topoisomerase identifies Ser-204 as important for DNA binding and cleavage", *Biochemistry*, vol. 36, No. 26, 1997, 7944-7950.

Wang et al., "Deletions at the carboxyl terminus of vaccinia DNA topoisomerase affect DNA binding and enhance distributivity in DNA relaxation", *Biochemistry*, vol. 36, No. 13, 1997, 3909-3916.

Wexler et al., "A Procedure to Amplify cDNA from dsRNA Templates Using the Polymerase Chain Reaction", *Methods in Molecular and Cellular Biology*, vol. 2, 1991, 273-279.

Wittschieben, et al., "Replacement of the active site tyrosine of vaccinia DNA topoisomerase by glutamate, cysteine or histidine converts the enzyme into a site-specific endonuclease", *Nucleic Acids Research*, vol. 26, No. 2, 1998, 490-496.

Wittschieben et al., "Mechanism of DNA transesterification by vaccinia topoisomerase: catalytic contributions of essential residues Arg-130, Gly-132, Tyr-136 and Lys-167", *Nucleic Acids Research*, vol. 25, No. 15, 1997, 3001-3008.

Wittschieben et al., "Mutational analysis of vaccinia DNA topoisomerase defines amino acid residues essential for covalent catalysis", *The Journal of Biological Chemistry*, vol. 269, No. 47, 1994, 29978-29983.

Woodfield et al., "Vaccinia topoisomerase and Cre recombinase catalyze direct ligation of activated DNA substrates containing a 3'-para-nitrophenyl phosphate ester", *Nucleic Acids Research*, vol. 28, No. 17, 2000, 3323-3331.

Yang et al., "A eukaryotic enzyme that can disjoin dead-end covalent complexes between DNA and type I topoisomerases", *Proceedings of the National Academy of Sciences*, vol. 93, No. 21, Oct. 1996, 11534-11539.

Yarovinsky, "Application of DNA Topoisomerase-Activated Adapters to Riboprobe Synthesis.", *BioTechniques*, vol. 28, No. 6, Jun. 2000, 1160-1165.

Zechiedrich et al., "Topoisomerase IV, not gyrase, decatenates products of site-specific recombination in *Escherichia coli*", *Genes & Development*, vol. 11, 1997, 2580-2592.

* cited by examiner

| SAMPLE # | GAL4+pA | VP16+pA | pGENE1LACZ | GAL4+p53+pA | VP16+T+pA | p53-VP16 |
|---|---|---|---|---|---|---|
| 1 | | | 0.25 µg | 0.37 µg | 0.37 µg | |
| 2 | | | 0.4 µg | 0.3 µg | 0.3 µg | |
| 3 | | | 0.4 µg | | | 0.6 µg |
| 4 | | | 0.4 µg | 10.3 µg | 10.3 µg | |
| 5 | | 10.3 µg | 0.4 µg | 10.3 µg | | |
| 6 | 10.3 µg | | 0.4 µg | | 10.3 µg | |
| 7 | | 4.5 ul PCR | 0.4 µg | 4.5 ul PCR | 4.5 ul PCR | |
| 8 | | | 0.4 µg | 4.5 ul PCR | | |
| 9 | 4.5 ul PCR | | 0.4 µg | | 4.5 ul PCR | |

| SAMPLE # | LacZ ACTIV |
|---|---|
| 1 | 240000 |
| 2 | 140000 |
| 3 | 1800000 |
| 4 | 1400000 |
| 5 | 54000 |
| 6 | 80000 |
| 7 | 320000 |
| 8 | 12000 |
| 9 | 42000 |

METHODS AND COMPOSITIONS FOR GENERATING RECOMBINANT NUCLEIC ACID MOLECULES

This application is a continuation of U.S. Ser. No. 10/991,803 filed Nov. 17, 2004 which claims the benefit of priority under 35 U.S.C. §119(e) of U.S. Ser. No. 60/520,946, filed Nov. 17, 2003; and is a Continuation-in-Part of U.S. Ser. No. 10/014,128, filed Dec. 7, 2001, now U.S. Pat. No. 7,033,801; which claims the benefit of priority under 35 U.S.C. §119(e) of U.S. Ser. No. 60/326,092, filed Sep. 28, 2001, and U.S. Ser. No. 60/254,510, filed Dec. 8, 2000 the disclosures of which are incorporated herein by reference in their entirety.

BACKGROUND OF THE INVENTION

1. Field of the Invention

The invention relates generally to compositions and methods for facilitating the construction of recombinant nucleic acid molecules, and more specifically to compositions for using one or more topoisomerases to generate covalently closed recombinant nucleic acid molecules and to methods of making such recombinant nucleic acid molecules.

2. Background Information

The advent of recombinant DNA technology has allowed the cloning and identification of genes from many different organisms, and the determination of the complete genomes of an ever-increasing number of organisms, including humans. The elucidation of a large number of new and uncharacterized genes creates a pressing need for technologies that enable rapid expression and analysis of these genes. The ability to construct recombinant nucleic acid molecules has provided a means to produce novel "gene products" and to express gene products, particularly heterologous gene products, in cells, tissues and organisms in which they are not normally produced. Thus, recombinant DNA technology has led, for example, to the fields of gene therapy, in which defective genes are replaced by copies of a normal gene; and "biopharming," in which, for example, a gene product such as an antibody, which normally is produced by an animal, is expressed in a plant, thereby allowing large scale production of the gene product.

Despite the great leaps in progress that have resulted from the discovery and development of recombinant DNA methods, a great number of steps often is required to prepare a novel DNA construct having desired properties. A significant bottleneck in recombinant DNA methodology is the requirement that each nucleic acid sequence that is to be used to prepare a construct must be cloned into a vector, the vector must be introduced into and amplified in a host cell (generally a bacterial cell), the amplified vector must be isolated from the host cell, and then must be transformed or transfected into the appropriate cell type for expression. Vectors with the appropriate functional elements such as a promoter, an origin of replication, a selectable marker, an epitope tag, or the like may need to be constructed. Such methods require multiple restriction enzyme digestion and ligation steps, in addition to numerous purification and characterization steps.

Methods and products are being developed to reduce the number of steps required to obtain a desired nucleic acid construct. For example, many commercial suppliers provide vectors that contain one or more functional elements of interest, and have cloning sites such that a desired nucleotide sequence can be cloned in frame with the sequences in the vector. However, such vectors are limited in that only the most commonly used elements such as particularly useful promoters or tags or the like can be included in the vectors in order for the vector to be commercially viable.

In some cases, there may be no need to covalently ligate together nucleic acid sequences that have been allowed to join. For example, non-covalently linked constructs formed by hybridization of complementary overhanging ends can be used to transfect cells with a reasonably high efficiency. However, such constructs effectively contain "nicks" at the sites of hybridization and, therefore, are more susceptible to endonuclease degradation than covalently linked sequences. Furthermore, constructs containing nicks are not suitable for certain further manipulations such as amplification by a polymerase chain reaction. Thus, a need exists to identify methods for facilitating the preparation of nucleic acid constructs. The present invention satisfies this need and provides additional advantages.

SUMMARY OF THE INVENTION

The present invention relates to methods of covalently linking, in one or both strands, two or more double stranded (ds) nucleotide sequences using one or more topoisomerases. As such, the invention also provides, in part, nucleotide sequences that can be covalently linked according to such methods, recombinant nucleic acid molecules generated therefrom, and compositions comprising the nucleotide sequence and/or recombinant nucleic acid molecules (e.g., reaction mixtures), wherein the nucleotide sequences contain at least one topoisomerase attached thereto (e.g., a covalently linked topoisomerase), at least one topoisomerase recognition site, or a combination thereof.

In particular embodiments, at least one topoisomerase recognition site can be internal, i.e., within one or more nucleotide sequences, or can be at or near one or both termini of a single stranded nucleotide sequence or one or both strands of double stranded nucleotide sequence; or at least one bound topoisomerase can be at or near one or both termini of a single stranded nucleotide sequence or one or both strands of a double stranded nucleotide sequence, and can be present on 5' overhang, a 3' overhang, or at a blunt end. For example, one or more of the at least one topoisomerase or the at least one topoisomerase recognition site can be located at or near a 5' terminus, at or near a 3' terminus, at or near both 5' termini, at or near both 3' termini, at or near a 5' terminus and a 3' terminus, at or near a 5' terminus and both 3' termini, or at or near a 3' terminus and both 5' termini. The invention provides methods for preparing and using nucleotide sequences and covalently linked recombinant nucleic acid molecules generated therefrom, compositions containing one or more of such nucleotide sequences or recombinant nucleic acid molecule, and nucleic acid molecules and compositions derived therefrom. In specific aspects, the invention provides nucleotide sequences 1) to which topoisomerases of various types (e.g., a type IA topoisomerase, a type IB topoisomerase, a type II topoisomerase, etc.) are attached (e.g., covalently bound); and/or 2) which contain two or more topoisomerase recognition sites that can be bound and/or cleaved by various types of topoisomerases; and/or 3) which contain a combination of such bound various topoisomerases and various topoisomerase recognition sites, as well as methods for preparing and using compositions comprising such nucleotide sequences.

The invention further provides methods for covalently linking two or more nucleotide sequences, wherein at least one of the nucleotide sequences contains at least one topoisomerase bound thereto or one topoisomerase recognition site. Further, when nucleotide sequences used in methods of the invention contain more than one topoisomerase, either on the same or different nucleotide sequences, the topoisomerase can be of the same type or of different types. Similarly, when nucleotide sequences used in methods of the invention contain more than one topoisomerase recognition site, either on the same or different nucleotide sequences, the topoisomerase recognition sites can be recognized by topoisomerases of the same type or of different types. Thus, the invention provides methods for covalently linking nucleotide sequences employing any one topoisomerase or topoisomerase recognition site. The invention also provides methods for covalently linking nucleotide sequences using any combination of topoisomerases and/or topoisomerase recognition sites. The invention also provides covalently linked recombinant nucleic acid molecules produced by such methods, and further provides compositions containing such recombinant nucleic acid molecules and uses of these molecules.

The present invention generally provides, in part, methods for covalently linking any number of nucleotide sequences (e.g., two, three, four, five, six, seven, eight, nine, ten, etc.), including nucleotide sequences containing different functional or structural elements. As such, the invention provides, in part, methods for covalently linking any number of nucleotide sequences (e.g., two, three, four, five, six, seven, eight, nine, ten, etc.) that confer different properties upon a covalently linked recombinant nucleic acid molecule generated therefrom. In many instances, the methods of the invention result in the formation of recombinant nucleic acid molecules having operative interactions of properties and/or elements of individual nucleotide sequences that are covalently linked to generate the recombinant nucleic acid molecules (e.g., an operative interaction/linkage between an expression control element and an open reading frame). Examples of 1) functional and structural elements and 2) properties that can be conferred upon a recombinant nucleic acid molecule generated according to a method of the invention include, but are not limited to, multiple cloning sites (e.g., nucleotide sequences that contain at least two restriction endonuclease cleavage sites), packaging signals (e.g., viral packaging signals such as adenoviral packaging signals, alphaviral packaging signals, etc.), restriction endonuclease cleavage sites, open reading frames (e.g., intein coding sequences, affinity purification tag coding sequences, etc.), expression control sequences (e.g., promoters, operators, etc.), and the like. Additional elements and properties that can be conferred by one or more nucleotide sequences upon a product recombinant nucleic acid molecule are exemplified herein or otherwise known in the art. The present invention also provides covalently linked recombinant nucleic acid molecules produced by the methods described above, as well as uses of these molecules and compositions containing these molecules.

The invention also includes in vivo and in vitro methods for generating RNA molecules. In specific embodiments, the invention includes methods for the in vitro generation of RNA molecules. In certain aspects, these methods may comprise, for example, (a) generating a reaction mixture in which a first double-stranded DNA molecule is contacted with a second double-stranded DNA molecule under conditions which allow for both strands of one end of the first double-stranded DNA molecule to become covalently linked to both strands of one end (i.e., the 5' and 3' termini) of the second double-stranded DNA molecule, (b) incubating the reaction mixture of (a) for a sufficient period of time to allow for the covalent linking of the first double-stranded DNA molecule to the second double-stranded DNA molecule, and (c) generating an RNA transcript from the product of (b) by in vitro transcription. Also, the first double-stranded DNA molecule may have promoter activity and may be operably connected to the second double-stranded DNA molecule in (b). Further, the first double-stranded DNA molecule and the second double-stranded DNA molecule may be covalently linked to each other by a topoisomerase. Additionally, the double-stranded DNA molecule produced in (b) may not contain a nick in either strand at the position where the first double-stranded DNA molecule and the second double-stranded DNA molecule are joined. In related methods, both strands of one end (i.e., the 5' and 3' termini) of the double-stranded DNA molecule product of (b) may be covalently linked by a topoisomerase to both strands of one end (i.e., the 5' and 3' termini) of a third double-stranded DNA molecule. In additional aspects, the double-stranded DNA molecules may be covalently linked in the order of the first double-stranded DNA molecule, the second double-stranded DNA molecule, and the third double-stranded DNA molecule. In specific instances, the third double-stranded DNA molecule may encode a polyadenylation signal and/or the second double-stranded DNA molecule may encode a polypeptide. Further, the second double-stranded DNA molecule may be generated by polymerase chain reaction. Additionally, one strand of each end of the first double-stranded DNA molecule and the second double-stranded DNA molecule which are joined may be topoisomerase-charged. Further, the topoisomerase may be a type IB topoisomerase or a catalytic domain of a type IB topoisomerase.

In related methods, transcription products generated by methods of the invention may be either translated in vitro to generate a polypeptide or introduced into cells, where they may be translated in vivo.

Further, promoters used in methods of the invention (e.g., method involving in vitro transcription) include T7 and T3 promoters.

When more than one RNA molecule is generated in methods of the invention, the individual RNA molecules may be generated in separate reaction vessels or may be generated in the same reaction vessel. Further, these individual RNA molecules may share sufficient sequence complementarity to allow for them to hybridize to each other. Typically, this will result in the formation of RNA which is at least partially double-stranded. Along these lines, the invention includes methods for the in vitro generation of double-stranded RNA molecules, these method may comprise, for example, (a) generating a reaction mixture in which a first double-stranded DNA molecule is contacted with a second double-stranded DNA molecule under conditions which allow for both strands of one end of the first double-stranded DNA molecule to become covalently linked to both strands of a first end of the second double-stranded DNA molecule, (b) incubating the reaction mixture of (a) for a sufficient period of time to allow for the covalent linking of the first double-stranded DNA molecule to the first end of the second double-stranded DNA molecule, and (c) generating a reaction mixture in which a first double-stranded DNA molecule is contacted with a second double-stranded DNA molecule under conditions which allow for both strands of one end of the first double-stranded DNA molecule to become covalently linked to both strands of a second end of the second double-stranded DNA molecule, (d) incubating the reaction mixture of (c) for a sufficient period of time to allow for the covalent linking of the first double-stranded DNA molecule to the second end of the second double-stranded DNA molecule, (e) mixing the products of (b) and (d), (f) generating RNA transcripts (e.g., sense and antisense RNA molecules) of the products of (e) by in vitro transcription, and (g) incubating the RNA transcripts produced in (f) under conditions which allow for the formation of double-stranded RNA molecules. Further, the first double-stranded DNA molecule may have promoter activity and may be operably connected to each of the second double-stranded DNA molecules in (b) and (d). Also, the first double-stranded DNA molecule and the second double-stranded DNA molecule may be covalently linked to each other by a topoisomerase. Additionally, the double-stranded DNA molecule produced in (b) may not contain a nick in either strand at the position where the first double-stranded DNA molecule and the second double-stranded DNA molecule are joined. Further, the second double-stranded DNA molecule may encode a polypeptide. Additionally, one or more of the double-stranded DNA molecules (e.g., the second double-stranded DNA molecule) may be generated by polymerase chain reaction. Also, in methods of the invention, one strand of each of the ends of the double stranded DNA molecules which are joined (e.g., the first double-stranded DNA molecule and the second double-stranded DNA molecule) may be topoisomerase-charged. In such instances, the topoisomerase may be, for example, a type IB topoisomerase or a catalytic domain of a type IB topoisomerase.

The invention further includes reaction mixtures for performing methods of the invention and/or containing molecules generated by methods of the invention. The invention thus includes, for example, reaction mixtures comprising (a) a first double-stranded DNA molecule which comprises a promoter, and (b) a second double-stranded DNA molecule. Also, one strand of one end of the first double-stranded DNA molecule may be topoisomerase-charged. Further, one strand of one end of the second double-stranded DNA molecule may be topoisomerase-charged. Additionally, topoisomerase-charged ends of the first double-stranded DNA molecule and the second double-stranded DNA molecule may be capable of hybridizing to each other.

The invention also provides compositions that contain nucleotide sequences and/or recombinant nucleic acid molecules as disclosed herein. For example, compositions of the invention include, but are not limited to, mixtures (e.g., reaction mixtures) containing a nucleotide sequence comprising at least one topoisomerase recognition site, and at least one topoisomerase that recognizes at least one of the at least one topoisomerase recognition sites of the nucleotide sequence. Compositions of the invention further include at least one nucleotide sequence comprising 1) at least one topoisomerase recognition site or at least one nucleotide sequence to which at least one topoisomerase is attached (e.g., covalently bound) and 2) one or more additional components. Examples of such additional components include, but are not limited to, topoisomerases; additional nucleotide sequence that can, but need not, comprise one or more topoisomerases or topoisomerase recognition sites; buffers; salts; polyamines (e.g., spermine, spermidine, etc.); water; or any other component as disclosed herein or as desired.

In one embodiment, the invention provides a method of using a topoisomerase (e.g., a type IA or type IB topoisomerase) to covalently link a first ds nucleotide sequence to at least a second ds nucleotide sequence, thereby generating a recombinant ds nucleic acid molecule that is covalently linked in at least one strand. Such a method can be used, for example, to covalently link three or more (e.g., 3, 4, 5, 6, 7, etc.) ds nucleotide sequences, so as to generate a recombinant ds nucleic acid molecule containing one strand that has no nicks. In particular embodiments of a method of generating a recombinant double stranded nucleic acid molecule that is covalently linked in only one strand, the topoisomerase is not a type IB topoisomerase.

In another embodiment, the invention provides a method of using a type IA topoisomerase and a type IB topoisomerase to covalently link at least two ds nucleotide sequences in at least one strand. For example, a first ds nucleotide sequence can contain a type IA topoisomerase at the 5' terminus of one end and a type IB topoisomerase at the 3' terminus of the second end of the same strand, thereby providing a means to covalently link a strand of the first ds nucleotide sequence to one or more other ds nucleotide sequences to generate a recombinant ds nucleic acid molecule that is covalently linked in one strand. In another embodiment, the present invention provides a method to covalently link two or more ds nucleotide sequences in both strands, for example, by contacting an end of a first ds nucleotide sequence having a type IA or a type IB topoisomerase bound thereto, to an end of a second ds nucleotide sequence having a type IA or type IB topoisomerase, respectively, bound thereto; or by contacting a first ds nucleotide sequence having a type IA topoisomerase and a type IB topoisomerase bound to the 5' terminus and 3' terminus, respectively, of an end, with a second ds nucleotide sequence. The invention also provides compositions comprising nucleic acid molecules with topoisomerase bound to a 5' terminus and/or a 3' terminus, as well as precursor nucleotide sequences having one or more topoisomerase recognition sites for preparing covalently linked recombinant nucleic acid molecules having a topoisomerase bound to a 5' and/or 3' terminus.

The present invention also relates to methods of generating a double stranded recombinant nucleic acid molecule, which is covalently linked in one or both strands, by contacting two or more (e.g., 2, 3, 4, 5, 6, 7, 8, 9, 10, etc) ds nucleotide sequences with at least one (e.g., 1, 2, 3, 4, 5, 6, 7, 8, 9, 10, etc.) topoisomerase. For example, the present invention provides methods for generating a ds recombinant nucleic acid molecule covalently linked in both strands, and methods for generating a ds recombinant nucleic acid molecule covalently linked in at least one strand.

A method for generating a ds recombinant nucleic acid molecule that is covalently linked in one strand generally is performed by contacting a site-specific topoisomerase (e.g., a type IA or type IB topoisomerase) and at least one (e.g., 1, 2, 3 4, 5, 6, 7, 8, 9, 10, etc.) ds nucleotide sequences to be joined under conditions such that at least one strand of an end of each ds nucleotide sequence is covalently linked to at least one strand of an end of any one or two other ds nucleotide sequences. Such a method can be used to generate, for example, a ds recombinant nucleic acid molecule, wherein one strand contains a nick at the site or sites at which the substrate ds nucleotide sequences are ligated. The present invention also provides recombinant nucleic acid molecules prepared by such a method, further provides nucleotide sequences used in such a method.

A method of generating a ds recombinant nucleic acid molecule covalently linked in at least one strand can be performed using various combinations of components. For example, the method can be performed by contacting at least one (e.g., 1, 2, 3 4, 5, 6, 7, 8, 9, 10, etc.) substrate ds nucleotide sequence to be linked and at least one (e.g., 1, 2, 3 4, 5, 6, 7, 8, 9, 10, etc.) site-specific topoisomerase (e.g., a type IA topoisomerase or type IB topoisomerase), wherein the topoisomerase cleaves one or both strands of the substrate ds nucleotide sequences and forms a stable complex with a nucleotide at a terminus of the cleavage site. The topoisomerase-charged end or topoisomerase-charged ds nucleotide sequence is then contacted with another end or ds nucleotide sequence, which is, or can be, charged with a topoisomerase, (e.g., a type IA or type IB topoisomerase) such that one strand, but not both strands, at one or both ends of the substrate ds nucleotide sequences is linked, thereby generating one or more ds recombinant nucleic molecules covalently linked in one strand. The site-specific type IA topoisomerase, and type IB topoisomerase when present, links one strand of each ds nucleotide sequence through the formation of a phosphodiester bond at each linkage site.

A method of generating a ds recombinant nucleic acid molecule that is covalently linked in at least one strand also can be performed by contacting at least one site-specific topoisomerase-charged ds nucleotide sequence (e.g., a ds nucleotide sequence charged with a type IA or a type IB topoisomerase), with at least a second topoisomerase-charged ds nucleotide sequence (e.g., a ds nucleotide sequence charged with a type IA or a type IB topoisomerase); or by contacting at least one topoisomerase-charged ds nucleotide sequence (e.g., a ds nucleotide sequence charged with a type IA or type IB topoisomerase) with at least one ds nucleotide sequence that contains a topoisomerase cleavage site, in the presence of excess topoisomerase; or by contacting at least one site-specific topoisomerase-charged ds nucleotide sequence (e.g., a ds nucleotide sequence charged with a type IA or a type IB topoisomerase) with at least one ds nucleotide sequence; or by contacting at least one ds nucleotide sequence that contains a site-specific topoisomerase cleavage site (e.g., a type IA or type IB topoisomerase cleavage site), and at least one ds nucleotide sequence, in the presence of an excess of site-specific topoisomerase (e.g., type IA or type IB topoisomerase, respectively). The present invention also provides recombinant nucleic acid molecules prepared by such a method, as well as compositions for performing such methods. Such compositions include, for example, a topoisomerase-charged ds nucleotide sequence, wherein topoisomerase is covalently linked to one or both 5' termini; a 5' terminus and one or both 3' termini; or both 5' termini and both 3' termini.

Such a method also can be performed by contacting 1) a first ds nucleotide sequence having a first end and a second end, wherein the first ds nucleotide sequence has a site-specific topoisomerase recognition site (e.g., a type IA or type II topoisomerase recognition site) at or near the 5' terminus of the first end or the second end; 2) at least a second ds nucleotide sequence having a first end and a second end; and 3) at least one (e.g., 1, 2, 3, 4, 5, 6, 7, 8, 9, 10, etc.) site specific topoisomerase, under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of the first ds nucleotide sequence, the topoisomerase preferably is stably bound to a 5' terminus. Preferably, upon cleavage by the topoisomerase, the cleaved ds nucleotide sequence comprises a 3' overhanging sequence.

The method also can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both ends; 2) at least a second ds nucleotide sequence that has, or can be made to have, a first end and a second end; and 3) at least one (e.g., 1, 2, 3, 4, 5, 6, 7, 8, 9, 10, etc.) site-specific type IA topoisomerase, under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence. As such, a method of the invention provides a means wherein any combination of ends can be linked, and wherein one strand of the product recombinant nucleic acid molecule is covalently linked and the second strand is not covalently linked (i.e., contains a nick).

A method of generating a ds recombinant nucleic acid molecule covalently linked in one strand, involving a first ds nucleotide sequence and at least a second ds nucleotide sequence, can further include a step of amplifying the ds recombinant nucleic acid molecule covalently linked in one strand. The amplification can be carried out by contacting the ds recombinant nucleic acid molecule with an amplification reaction primer pair, wherein a first primer of the primer pair can bind to the covalently linked strand, at or near one end of the first or second ds nucleotide sequence, and prime an amplification reaction in a direction toward the other (i.e., second or first, respectively) ds nucleotide sequence to generate a first extension product that is identical in nucleotide sequence to the nicked strand of the ds recombinant nucleic acid molecule. The second primer of the primer pair is selected such that it can bind to the first extension product, typically at or near the 3' terminus of the first extension product, and, in the presence of the first primer, can generate an amplification product using the covalently-linked strand and the first extension product (or extension products generated therefrom) as templates. For example, the method can be performed such that the topoisomerase recognition site (e.g., type IA topoisomerase recognition site) is at or near the first end of the first ds nucleotide sequence, and the method can further include contacting the generated ds recombinant nucleic acid molecule with an amplification reaction primer pair, wherein a forward primer is capable of binding at or near the second end of the first ds nucleotide sequence and wherein a reverse primer is capable of binding to a nucleotide sequence complementary to at least a portion of the second end of the second ds nucleotide sequence; and amplifying the ds recombinant nucleic acid molecule. By way of example, the first ds nucleotide sequence can include a coding region and the second ds nucleotide sequence can include a regulatory element, and the generated recombinant nucleic acid molecule can comprise an expressible nucleotide sequence.

A method for generating a ds recombinant nucleic acid molecule covalently linked in one strand also can be performed by contacting 1) a first ds nucleotide sequence having a first end and a second end, wherein the first ds nucleotide sequence has a site-specific topoisomerase recognition site (e.g., type IA or type II topoisomerase recognition site) at or near the 5' terminus of the first end or the second end or both; 2) at least a second ds nucleotide sequence that has, or can be made to have, a first end and a second end; 3) at least a third ds nucleotide sequence which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., at least one type IA topoisomerase), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand, involving a first ds nucleotide sequence that contains a site-specific topoisomerase recognition site (e.g., a type IA or type IB topoisomerase recognition site), or cleavage product thereof, at least a second ds nucleotide sequence, and at least a third ds nucleotide sequence can be performed such that any combination of ends are linked, and one strand at the ends being linked is covalently linked and one strand is nicked. Furthermore, in this embodiment, any of the ends can contain a type IA or type IB topoisomerase recognition site, or cleavage product thereof, provided that the first ds recombinant nucleotide molecule contains a type IA or type II topoisomerase recognition site at or near a 5' terminus, or cleavage product thereof, and only one topoisomerase or topoisomerase recognition site is present at the ends that are to be linked. For example, where the first ds nucleotide sequence comprises a type IA site-specific topoisomerase recognition site at or near each of said first end and said second end, the method further can include contacting the first ds nucleotide sequence and the second ds nucleotide sequence with at least a third ds nucleotide sequence which has, or can be made to have, a first end and a second end, each end further comprising a 5' terminus and a 3' terminus, under conditions such that the type IA topoisomerase can covalently link the 5' terminus of the first end of the first ds nucleotide sequence with the 3' terminus of the first end of the second nucleotide sequence, and the 5' terminus of the second end of the first ds nucleotide sequence with the 3' terminus of the first end of the third nucleotide sequence. It will be recognized that other combinations of ends and topoisomerase recognition sites, or cleavage products thereof, can be used in practicing a method of the invention.

In another embodiment, a method for generating a ds recombinant nucleic acid molecule covalently linked in one strand can be performed by contacting 1) a first ds nucleotide sequence having a first end and a second end, wherein the first ds nucleotide sequence has a site-specific topoisomerase recognition site (e.g., a type IA or type II topoisomerase recognition site) at or near the 5' terminus of an end and a type IB topoisomerase recognition site at or near the 3' terminus of the other end; 2) at least a second ds nucleotide sequence that has, or can be made to have, a first end and a second end; 3) at least one (e.g., 1, 2, 3, 4, 5, 6, 7, 8, 9, 10, etc.) site-specific type IA topoisomerase; and 4) at least one (e.g., 1, 2, 3, 4, 5, 6, 7, 8, 9, 10, etc.) type IB topoisomerase under conditions such that all components are in contact and the at least one topoisomerase can effect its activity. For example, the topoisomerase recognition site at or near a 5' terminus of the first ds nucleotide sequence can be a type IA topoisomerase such as *E. coli* topoisomerase I, *E. coli* topoisomerase III, or a eukaryotic topoisomerase III. Upon cleavage of a ds nucleotide sequence, the type IA topoisomerase preferably is stably bound to the 5' terminus, and the type IB topoisomerase preferably is stably bound at the 3' terminus. Preferably, upon cleavage by the topoisomerases, the cleaved ds nucleotide sequence comprises a 3' overhanging sequence and a 5' overhanging sequence.

Methods of the invention can further include contacting the ds recombinant nucleic acid molecule with one or more (e.g., 1, 2, 3, 4, 5, etc.) enzymes or agents having ligase activity (e.g., a DNA ligase such as T4 DNA ligase) I) to covalently link gaps, particularly nicks, in one or both strands of the product ds recombinant nucleic acid molecule to obtain a ds recombinant nucleic acid molecule covalently linked in both strands; 2) to link a product ds nucleic acid molecule to one or more other molecules; and/or 3) to circularize the product ds recombinant nucleic acid molecule.

A method for generating a ds recombinant nucleic acid molecule covalently linked in one strand, involving a first ds nucleotide sequence, a second ds nucleotide sequence, and at least a third ds nucleotide sequence, can further include a step for amplifying the ds recombinant nucleic acid molecule covalently linked in one strand using, for example, an amplification reaction such as a polymerase chain reaction. Such a method can be used to amplify any portion of the generated ds recombinant nucleic acid molecule, particularly all or a portion of the covalently linked strand, including a portion of the covalently linked strand that includes all or a part of each of the substrate first, second and third ds nucleotide sequences. For example, where the ds recombinant nucleic acid molecule comprises an end of the first ds nucleotide sequence linked to an end of the second ds nucleotide and an end of the third ds nucleotide sequence linked to the other end of the second ds nucleotide sequence, the amplification can be carried out by contacting the ds recombinant nucleic acid molecule with an amplification reaction primer pair, wherein a first primer of the primer pair is capable of binding to the covalently linked strand at or near one end of the first or third ds nucleotide sequence and priming an amplification reaction in a direction toward the second ds nucleotide sequence to generate a first extension product that is complementary to the covalently linked strand; and the second primer of the primer pair can bind to the first extension product, typically at or near the 3' terminus of the first extension product, which can include a sequence complementary to at least a portion of the second nucleotide sequence and can further include a sequence complementary to the third or first ds nucleotide sequence, respectively, and, in the presence of the first primer, can generate an amplification product using the covalently linked strand and the extension product (or extension products generated therefrom) as templates. The method can be performed such that the topoisomerase recognition site (e.g., type IA or type IB topoisomerase recognition site) is at or near the first end of the first ds nucleotide sequence, and the method further includes contacting the ds recombinant nucleic acid molecule with an amplification reaction primer pair, wherein a forward primer is capable of binding to a nucleotide sequence at or near the second end of the first ds nucleotide sequence and wherein a reverse primer is capable of binding to a nucleotide sequence complementary to at least a portion of the third ds nucleotide sequence; and amplifying the ds recombinant nucleic acid molecule. By way of example, the first ds nucleotide sequence can include a first regulatory element such as a transcriptional promoter and/or an operator (e.g., a tetracycline operator), the second ds nucleotide sequence can include a coding region, and the third ds nucleotide sequence can include a second regulatory element such as a transcriptional termination sequence. Furthermore, ends being linked according to a method of the invention can contain complementary overhanging sequences. The present invention also provides recombinant nucleic acid molecules or amplification products thereof produced using such a method.

Methods of the invention for generating a ds recombinant nucleic acid molecule covalently linked in one strand, are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); and 2) at least a second nucleotide sequence, under condition such that the topoisomerases can covalently link one strand, but not both strands, of one or both ends of the first ds nucleotide sequence with one or both ends of at least the second ds nucleotide sequence. The ds nucleotide sequences can contain a 3' hydroxyl group at the end of a strand being linked to a 5' terminus by topoisomerase, or a 3' hydroxyl group can be generated using a phosphatase. As disclosed herein, such a method can be performed using only a first ds nucleotide sequence and a second ds nucleotide sequence, or can include a third, fourth, fifth, or more ds nucleotide sequences as desired, wherein each nucleotide sequence is as defined, including optionally comprising one or two topoisomerase-charged termini. A second (or other) ds nucleotide sequence independently can have a topoisomerase covalently bound to a 5' terminus of one end or at both ends of the ds nucleotide sequence, and, unless indicated otherwise, the first and second (or other) ds nucleotide sequences can be the same or can be different.

Methods of the invention for generating a ds recombinant nucleic acid molecule covalently linked in one strand, are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); 2) at least a second nucleotide sequence which may or may not be charged with topoisomerase; and 3) at least a third nucleotide sequence which may or may not be charged with topoisomerase, under condition such that the topoisomerases can covalently link one strand, but not both strands, of one or both ends of the first ds nucleotide sequence with one or both ends of at least the second ds nucleotide sequence, or one or both ends of at least the third ds nucleotide sequence. The ds nucleotide sequences can contain a 3' hydroxyl group at the end of a strand being linked to a 5' terminus by topoisomerase, or a 3' hydroxyl group can be generated using a phosphatase. The second, third, (or other) ds nucleotide sequence independently can have a topoisomerase covalently bound to a 5' terminus of one end or at both ends of the ds nucleotide sequence, and, unless indicated otherwise, the first, second, third (or other) ds nucleotide sequences can be the same or can be different.

In another embodiment, a method for generating a ds recombinant nucleic acid molecule covalently linked in one strand can be performed by contacting 1) a first ds nucleotide sequence having a first end and a second end, wherein a site-specific topoisomerase (e.g., a type IA or type II topoisomerase) is bound at the 5' terminus of the first end, the second end, or both the first end and the second end; and 2) at least a second ds nucleotide sequence that has, or can be made to have, a first end and a second end, under conditions such that all components are in contact and the at least one topoisomerase can effect its activity. For example, a type IA topoisomerase such as *E. coli* topoisomerase 1, *E. coli* topoisomerase III, or a eukaryotic topoisomerase III, can be used. The ds nucleotide sequences can include a 3' overhanging sequence, a 5' overhanging sequence, or can be blunt ended.

In another embodiment, a method for generating a ds recombinant nucleic acid molecule covalently linked in one strand can be performed by contacting 1) a first ds nucleotide sequence having a first end and a second end, wherein a site-specific topoisomerase (e.g., a type IA or type II topoisomerase) is bound at the 5' terminus of the first end, the second end, or both the first end and the second end; 2) at least a second ds nucleotide sequence that has, or can be made to have, a first end and a second end; wherein a site-specific topoisomerase (e.g., a type IA or type II topoisomerase) can be bound at the 5' terminus of the first end, the second end, or both the first end and the second end; and 3) at least a third ds nucleotide sequence that has, or can be made to have, a first end and a second end, wherein a site-specific topoisomerase (e.g., a type IA or type II topoisomerase) can be bound at the 5' terminus of the first end, the second end, or both the first end and the second end; under conditions such that all components are in contact and the at least one topoisomerase can effect its activity. For example, the type IA topoisomerase can be *E. coli* topoisomerase I, *E. coli* topoisomerase III, or a eukaryotic topoisomerase III. The ds nucleotide sequences can include 3' overhanging sequences, 5' overhanging sequences, or can be blunt ended, or can have various combinations of such ends, which can facilitate directional linkage.

The present invention also relates to a method of generating a ds recombinant nucleic acid molecule covalently linked in one strand by 1) amplifying a portion of a first ds nucleotide sequence using a PCR primer pair, wherein at least one primer of the primer pair encodes a site-specific type IA topoisomerase recognition site, thereby producing an amplified first ds nucleotide sequence having a first end and a second end, wherein the first end, second end, or both ends have a topoisomerase recognition site at or near the 5 terminus; and 2) contacting a) the amplified first ds nucleotide sequence; b) at least a second ds nucleotide sequence having a first end and a second end; and c) at least one (e.g., 1, 2, 3, 4, 5, 6, 7, 8, 9, 10, etc.) site specific type IA topoisomerase, under conditions such that the at least one topoisomerase can cleave the first and/or second end of the amplified first ds nucleotide sequence having a type IA topoisomerase recognition site, and can effect its ligating activity. The PCR primer encoding the topoisomerase recognition site can further comprise a nucleotide sequence at its 5' terminus, i.e., 5' to the topoisomerase recognition site, such that, upon cleavage of the amplified first ds nucleotide sequence by a site specific topoisomerase, the ds nucleotide sequence contains a 3' overhanging sequence, which can be complementary to a 3' overhanging sequence of a second (or other) ds nucleotide sequence to which the first ds nucleotide sequence is to be linked according to a method of the invention for generating a ds recombinant nucleic acid molecule covalently linked in one strand. A second primer of the PCR primer pair can include the complement of a type IB topoisomerase recognition site, thereby producing an amplification product having a first end and a second end, wherein the amplification product comprises a type IA topoisomerase recognition site at or near the 5' terminus of one end and a type IB topoisomerase recognition site at or near the 3' terminus of the other end.

The present invention further relates to a ds recombinant nucleic acid molecule having, or which can be made to have, a first end and a second end, each end including a 5' terminus and a 3' terminus, wherein the ds recombinant nucleic acid molecule comprises a site-specific topoisomerase recognition site (e.g., type IA topoisomerase recognition site) at or near a 5' terminus of the first end, the second end, or both the first end and the second end. The ds recombinant nucleic acid molecule can further include a type IB topoisomerase recognition site at or near a 3' terminus of an end that does not include a type IA topoisomerase recognition site. The ds recombinant nucleic acid molecule can be a vector, or can be a component of a vector, for example, a component that allows for convenient insertion of a regulatory element or an origin of replication or the like.

The present invention also relates to a topoisomerase-charged ds recombinant nucleic acid molecule having a first end and a second end, each end having a 5' terminus and a 3' terminus, wherein a site-specific type IA topoisomerase is bound at the 5' terminus of the first end, the second end, or both the first end and the second end. For example, the topoisomerase-charged nucleic acid ds recombinant nucleic acid molecule can include a type IA topoisomerase bound at the 5' termini of each of the first and second ends. The topoisomerase-charged nucleic acid ds recombinant nucleic acid molecule can include, for example, a type IB topoisomerase bound at a 3' terminus of an end not bound by a type IA topoisomerase, or can contain a site-specific topoisomerase recognition site at an end not bound by a type IA topoisomerase. The topoisomerase-charged nucleic acid ds recombinant nucleic acid molecule can comprise a vector or a component thereof, or can comprise a regulatory element or coding sequence or any other nucleic acid molecule of interest.

In one aspect, the methods of the invention allow joining of two or more nucleic acid sequences in a desired orientation and/or order, which, if desired, can be further manipulated or used in a variety of assays or procedures, including a transcription or transfection procedure, which can be performed in vitro or in vivo, a translation reaction or other protein expression procedure, and the like. In another aspect, (1) three or more, four or more, five or more, etc., or (2) a population or library of the same or different ds nucleotide sequences can be linked according to a method of the invention. In still another aspect, the methods of the invention can be used to link each end of a single nucleic acid molecule to form a circular or supercoiled molecule. In addition, where two or more nucleic acid sequences have been joined, the ends of the resulting ds recombinant nucleic acid molecule can be covalently linked in one or both strands according to a method of the invention to circularize the molecule.

The nucleotide sequences to be linked can be derived from any source, and can be naturally occurring and chemically or recombinantly synthesized nucleic acid molecules such as cDNA, genomic DNA, plasmids, vectors, oligonucleotides, and the like. Furthermore, the nucleotide sequences can, but need not, contain one or more functional sequences such as gene regulatory elements; origins of replication; splice sites; polyadenylation sites; packaging signals; multiple cloning sites; open reading frames, which can encode, for example, tag sequences, detectable or selectable markers, cell localization domains, or other peptide or polypeptide, or can encode an antisense nucleic acid molecule, ribozyme, tRNA or other RNA molecule; and the like. As such, a method of the invention allows any number of nucleotide sequences, which can be the same or different, to be covalently linked in one or both strands, including, if desired, in a predetermined order or orientation or both.

The ds nucleotide sequences to be linked can be in any form, for example, linear, circular, or supercoiled, and are characterized, in part, in that each ds nucleotide sequence to be linked is a substrate for a selected topoisomerase or can be modified to be a substrate. The topoisomerase can be any topoisomerase that can covalently link one strand of a ds nucleotide sequence to one strand of another ds nucleotide sequence, preferably through a phosphodiester bond. The topoisomerase can be a site specific topoisomerase or can have relaxed specificity, and preferably forms a stable complex (e.g., a covalent complex) with one strand of the ds nucleotide sequence at or near the site at which cleavage is effected.

In certain aspects, the present invention provides methods for generating a ds recombinant nucleic acid molecule that is covalently linked in both strands. Such a method can be performed by contacting topoisomerase and the ds nucleotide sequences to be joined under conditions such that both strands of an end of one ds nucleotide sequence are ligated to both strands of an end of at least one (e.g., 1, 2, 3 4, 5, 6, 7, 8, 9, 10, etc.) other ds nucleotide sequence. As such, a method of the invention generates a ds recombinant nucleic acid molecule that is covalently linked in both strands and, therefore, does not contain a nick in either strand at the site or sites at which the substrate ds nucleotide sequences are ligated. The present invention also provides recombinant nucleic acid molecules prepared according to such a method.

A method of generating a ds recombinant nucleic acid molecule covalently linked in both strands can be performed using various combinations of components. For example, the method can be performed by contacting two or more substrate ds nucleotide sequences to be covalently linked and at least one topoisomerase, wherein the topoisomerase cleaves one or both strands of the ds nucleotide sequences and forms a stable complex with a nucleotide at a terminus of the cleavage site. The topoisomerase-charged ends or topoisomerase-charged ds nucleotide sequences are then contacted with each other such that each strand of the substrate ds nucleotide sequences is linked, thereby generating one or more covalently linked ds recombinant nucleic molecules. Preferably, the topoisomerase mediates the formation of a phosphodiester bond at each linkage site. The method also can be performed by contacting two or more topoisomerase-charged ds nucleotide sequences, either alone, or in the presence of excess topoisomerase, or by contacting one or more topoisomerase-charged ds nucleotide sequences with one or more ds nucleotide sequences that contain a topoisomerase cleavage site, and a topoisomerase. The present invention also provides recombinant nucleic acid molecules prepared by such a method.

In various embodiments, the topoisomerase can have a relatively relaxed specificity such that it can bind to and cleave a variety of different nucleotide sequences, or the topoisomerase can be a site-specific topoisomerase, which binds to and cleaves a specific nucleotide sequence. The topoisomerase also can be a type I topoisomerase, which cleaves one strand of a ds nucleotide sequence, or can be a type II topoisomerase, which cleaves both strands of a ds nucleotide sequence. Where the topoisomerase is a type I topoisomerase, cleavage is effected such that a linear ds nucleotide sequence is produced, and is topoisomerase-charged at one or both ends. Preferably, the strand of the ds nucleotide sequence that is complementary to the strand containing the bound topoisomerase forms an overhanging sequence.

An advantage of performing a method of the invention is that the ligation reaction performed by a topoisomerase occurs very quickly and over a wide range of temperatures. Another advantage of the methods of the invention is that generated ds recombinant nucleic acid molecules that are covalently linked in one or both strands can be used directly in a subsequent procedure, for example, as a substrate for an amplification reaction such as a polymerase chain reaction (PCR), or as a substrate for a transcription or translation or coupled transcription/translation reaction.

By way of example, a method of the invention for generating a ds recombinant nucleic acid molecule covalently linked in both strands, can be performed by contacting 1) a first ds nucleotide sequence having a first end and a second end, wherein, at the first end or second end or both, the first ds nucleotide sequence has a topoisomerase recognition site at or near the 3' terminus; 2) at least a second ds nucleotide sequence having a first end and a second end, wherein, at the first end or second end or both, the at least second double stranded nucleotide sequence has a topoisomerase recognition site at or near a 3' terminus; and 3) at least one site specific topoisomerase (e.g., a type IA and/or a type IB topoisomerase), under conditions such that all components are in contact and the topoisomerase can effect its activity. Preferably, the strand complementary to that containing the topoisomerase recognition sequence comprises a 5' hydroxyl group, and more preferably, upon cleavage by the topoisomerase, comprises a 5' overhanging sequence.

A method of generating a ds recombinant nucleic acid molecule covalently linked in both strands also can be performed by contacting 1) a ds nucleotide sequence having a first end and a second end, wherein each of the first end and second end contains a topoisomerase recognition site at or near the 3' terminus, and 2) a site specific topoisomerase, under conditions such that the components are in contact and the topoisomerase can effect its activity. For example, the topoisomerase can be a type IB topoisomerase such as a Vaccinia topoisomerase or an S. cerevisiae topoisomerase. Such a method provides a means to prepare a covalently closed circular or supercoiled ds recombinant nucleic acid molecule.

A method of generating a ds recombinant nucleic acid molecule covalently linked in both strands also can be performed by contacting 1) a first ds nucleotide sequence having a first end and a second end, wherein the first ds nucleotide sequence has a topoisomerase recognition site at or near the 5' terminus of the first end or the second end or both; 2) at least a second ds nucleotide sequence having a first end and a second end, wherein the at least second double stranded nucleotide sequence has a topoisomerase recognition site at or near the 5' terminus of the first end or the second end or both; and 3) at least one site specific topoisomerase, under conditions such that all components are in contact and the at least one topoisomerase can effect its activity. For example, the topoisomerase can be a type IA topoisomerase such as E. coli topoisomerase I, E. coli topoisomerase III, or a eukaryotic topoisomerase III. Upon cleavage of a ds nucleotide sequence, the topoisomerase preferably is stably bound to the 5' terminus. The 3' terminus of the end containing the topoisomerase recognition site, or bound topoisomerase, can comprise a 3' hydroxyl group, or can be modified to comprise a 3' hydroxyl group. Preferably, upon cleavage by the topoisomerase, the cleaved ds nucleotide sequence comprises a 3' overhanging sequence.

The methods of the invention as exemplified herein can be performed using two or more site specific topoisomerases, wherein the first, second or other ds nucleotide sequence substrates correspondingly have, at or near a 3' terminus or 5' terminus of an end, a topoisomerase recognition site for one of the two or more topoisomerases. The use of two or more topoisomerases, and corresponding topoisomerase recognition sites, can facilitate the joining of the ds nucleotide sequences in a predetermined order, orientation, or combination thereof. Thus, it will be recognized that, where a method of the invention is exemplified using a topoisomerase, the method similarly can be performed using two or more topoisomerases. In some cases, reference is made to the use of at least one topoisomerase, and, unless indicated otherwise, the methods can be performed using one, two, three or more topoisomerases, provided the substrate ds nucleotide sequences contain the appropriate topoisomerase recognition sites. Similar considerations are relevant to topoisomerase-charged ds nucleotide sequence substrates, including that the topoisomerases can be the same or different.

The present invention provides methods for generating a ds recombinant nucleic acid molecule that is covalently linked in both strands. Such a method can be performed by contacting 1) a first ds nucleotide sequence having a first end and a second end, wherein the first ds nucleotide sequence has a topoisomerase recognition site at or near the 3' terminus and a topoisomerase recognition site at or near the 5' terminus of the first end or of the second end or of both ends; 2) at least a second ds nucleotide sequence having a first end and a second end; and 3) at least two (e.g., 2, 3, 4, 5, 6, 7, 8, 9, 10, etc.) site specific topoisomerases, under conditions such that all components are in contact and each of the topoisomerases can effect its activity. Upon cleavage of the termini of the substrate first ds nucleotides sequence by the topoisomerases, the 5' terminus or the 3' terminus of one or both of the first or second ends can comprise an overhanging sequence, or can be blunt ended, or a first end can contain an overhang and the second end can be blunt ended. Where present, an overhanging sequence of a first end will generally have sufficient complementarity to an overhanging sequence of a second (or other) end to allow for specific hybridization of the two ends to each other. Further, when the first and second ends are on different molecules, methods of the invention result in the two molecules becoming linked and when the first and second ends are on the same molecule, the methods result in the molecule becoming circularized.

The number of different topoisomerases useful in such an embodiment will depend, in part, on whether the first ds nucleotide sequence contains topoisomerase recognition sites at only the first end or the second end, or contains topoisomerase recognition sites at both ends, and further, where the ds nucleotide sequence contains topoisomerase recognition sites on both ends, whether the 3' recognition sites or the 5' recognition sites are different. In addition, the method can be performed such that one or more of the at least second ds nucleotide sequences also can contain a topoisomerase recognition site at or near the 3' terminus and/or a topoisomerase recognition site at or near the 5' terminus of the first end or of the second end or of both ends, wherein the topoisomerase recognition sites at or near the 3' terminus or the 5' terminus or both of the other ds nucleotide sequence can the same as or different from the topoisomerase recognition sites in the first ds nucleotide sequence. As such, the number of different topoisomerases further can depend on the number of different substrate ds nucleotide sequences being linked according to a method of the invention.

An advantage of performing a method of the invention using a site specific topoisomerase is that the first ds nucleotide sequence, the second ds nucleotide sequence, and one or more additional ds nucleotide sequences can be covalently linked, in one or both strands, in a predetermined directional orientation. An additional advantage is that a product comprising nucleotide sequences spanning the linkage site can be selected in vitro by performing an amplification reaction using a first primer that selectively hybridize to a sequence downstream of the linkage site and a second primer complementary to a sequence upstream of the linkage site, for example, amplification primers specific for the termini or sequences near the termini of a ds recombinant nucleic acid molecule covalently linked in both strands. A ds recombinant nucleic acid molecule, covalently linked in one or both strands, generated according to a method of the invention can be used directly in further procedures such as, for example, for transfecting a cell; as a template for performing amplification (e.g., PCR); in an in vitro transcription reaction; in a coupled transcription/translation reaction; for linkage to other nucleotide sequences using a restriction endonuclease site, which can be contained in a multiple cloning site; or for chromosomal integration via homologous recombination. Accordingly, a ds recombinant nucleic acid molecule generated according to a method of the invention can be useful, without further manipulation, for various purposes.

In an aspect of the invention, the first ds nucleotide sequences are derived from at least a first population of nucleic acid molecules, for example, from a cDNA library or a combinatorial library such as a combinatorial library of synthetic oligonucleotides, and the second ds nucleotide sequences are derived from at least a second population of ds nucleotide sequences. According to a method of the invention, linking of first ds nucleotide sequences with second ds nucleotide sequences provides a means to generate combinatorial populations of ds recombinant nucleic acid molecules that are covalently linked in one or both strands. In accordance with such a method, one or more target nucleic acid molecules also can be linked with the recombinant nucleic acid molecules of the population to produce additional populations. Such populations of combinatorial molecules can be further manipulated or analyzed, for example, by protein expression and screening for fusion proteins having desirable characteristics.

In one embodiment, a method of the invention is performed such that the first ds nucleotide sequence comprises an open reading frame, for example, an isolated cDNA or coding sequence or exon of a gene, and a second ds nucleotide sequence comprises a regulatory element such as a promoter, which can be operatively covalently linked to the 5' end of the coding sequence such that the coding sequence can be transcribed therefrom. A second ds nucleotide sequence also can comprise two or more regulatory elements, for example, a promoter, an internal ribosome entry site and an ATG initiator methionine codon, in operative linkage with each other, which can be operatively covalently linked to the 5' end of a first ds nucleotide sequence comprising a coding sequence according to a method of the invention. Such a method can further include contacting a third ds nucleotide sequence comprising, for example, a polyadenylation signal and/or a suppressible STOP codon, which can be operatively covalently linked to the 3' end of the coding sequence. Such a method can be useful for generating an expressible nucleic acid molecule, which can be transcribed, translated, or both as a functional unit. In addition, or alternatively, a ds nucleotide sequence encoding a detectable marker, for example, an epitope tag, can be operatively linked to a first or second (or other) ds nucleotide sequence according to a method of the invention. The generation of a ds recombinant nucleic acid molecule having a desired directional orientation of the nucleotide sequences in such a construct can be facilitated by including complementary 5' or 3' overhanging sequences at the termini of the ds nucleotide sequences to be covalently linked together by the topoisomerase.

In an embodiment, a method of the invention is performed such that at least the first ds nucleotide sequence or the at least second ds nucleotide sequence is one of a plurality of nucleotide sequences, for example, a cDNA library, a combinatorial library of nucleotide sequences, or a variegated population of nucleotide sequences. In another embodiment, a method of the invention includes further contacting a ds recombinant nucleic acid molecule, covalently linked in one or both strands, with a PCR primer pair, and amplifying all or a portion of the covalently linked ds recombinant nucleic acid molecule. In addition to generating a large amount of product, the amplification reaction can be selective for constructs comprising a desired covalently linked ds recombinant nucleic acid molecule, particularly where the ds nucleotide sequences to be covalently linked comprise complementary overhanging sequences. As such, a method of the invention provides an in vitro selection means that is suitable for high throughput analysis.

A method for generating a ds recombinant nucleic acid molecule covalently linked in both strands is exemplified by contacting 1) a first ds nucleotide sequence having a first end and a second end, wherein, at the first end, second end, or both ends, the first ds nucleotide sequence has a topoisomerase covalently bound to the 3' terminus ("topoisomerase-charged"); and 2) at least a second ds nucleotide sequence, which can, but need not, be charged with topoisomerase. Preferably, the topoisomerase-charged ds nucleotide sequence or sequences contain a 5' hydroxyl group at the ends having the bound topoisomerase, although 5' hydroxy groups also can be generated using a phosphatase. The methods of the invention can be performed using only a first ds nucleotide sequence and a second ds nucleotide sequence, or can include a third, fourth or more ds nucleotide sequences as desired, wherein each nucleotide sequence is as defined above. A first or second (or other) ds nucleotide sequence independently can have a topoisomerase covalently bound to a 3' terminus of one end or at both ends of the nucleotide sequence, and, unless indicated otherwise, the first and second (or other) ds nucleotide sequences can be the same or can be different.

Methods of the invention for generating a ds recombinant nucleic acid molecule covalently linked in both strands are further exemplified by contacting 1) a first ds nucleotide sequence having a first end and a second end, wherein, at the first end, second end, or both ends, the first ds nucleotide sequence has a topoisomerase covalently bound to a 5' terminus (i.e., a topoisomerase-charged 5' terminus); and 2) at least a second nucleotide sequence, which can, but need not, be charged with topoisomerase. The topoisomerase-charged ds nucleotide sequence or sequences can contain a 3' hydroxyl group at the ends containing the bound topoisomerase, or a 3' hydroxyl group can be generated using a phosphatase. As disclosed herein, such a method can be performed using only a first ds nucleotide sequence and a second ds nucleotide sequence, or can include a third, fourth or more ds nucleotide sequences as desired, wherein each nucleotide sequence is as defined, including comprising at least one topoisomerase-charged 5' terminus. A first or second (or other) ds nucleotide sequence independently can have a topoisomerase covalently bound to a 5' terminus of one end or of both ends of the ds nucleotide sequence, and, unless indicated otherwise, the first and second (or other) ds nucleotide sequences can be the same or can be different.

A method of the invention is additionally exemplified by contacting 1) a first ds nucleotide sequence having a first end and a second end, wherein, at the first end, second end, or both ends, the first ds nucleotide sequence has a first topoisomerase covalently bound to the 5' terminus and a second topoisomerase covalently bound to the 3' terminus of the first end, the second end, or both ends (i.e., one or both ends contain a topoisomerase-charged 5' terminus and a topoisomerase-charged 3' terminus); and 2) at least a second ds nucleotide sequence, which, preferably, has, or can be made to have, hydroxyl groups at the 5' terminus and 3' terminus of an end to be covalently linked to an end of the first ds nucleotide sequence containing the topoisomerases. The method also can be performed wherein either the 5' terminus or 3' terminus of the end containing a topoisomerase-charged 3' terminus or topoisomerase-charged 5' terminus, respectively, contains a topoisomerase recognition site, wherein the method further includes contacting the components with a topoisomerase that can effect its activity with respect to the topoisomerase recognition site. Such a method of the invention can be performed using only a first ds nucleotide sequence and a second ds nucleotide sequence, or can include a third, fourth or more ds nucleotide sequence as desired, wherein the ds nucleotide sequences are as defined for the first ds nucleotide sequence, the second ds nucleotide sequence, or a combination thereof. A first or second (or other) ds nucleotide sequence independently can, but need not, have one or more topoisomerases covalently bound to a 5' terminus, 3' terminus, or both 5' and 3' termini of the second end (i.e., the undefined end). Unless indicated otherwise, the first and second (or other) ds nucleotide sequences can be the same or can be different.

The present invention further relates to a method of generating a ds recombinant nucleic acid molecule covalently linked in both strands by 1) amplifying a portion of a first ds nucleotide sequence using a PCR primer pair, wherein at least one primer of the primer pair encodes a complement of a topoisomerase recognition site, thereby producing an amplified first ds nucleotide sequence having a first end and a second end, wherein the first end or second end or both has a topoisomerase recognition site at or near the 3' terminus; and 2) contacting a) the amplified first ds nucleotide sequence; b) at least a second ds nucleotide sequence having a first end and a second end, wherein the first end or second end or both has a topoisomerase recognition site, or cleavage product thereof, at or near the 3' terminus and has, or can be made to have, a hydroxyl group at the 5' terminus of the same end; and c) a site specific topoisomerase, under conditions such that the topoisomerase can cleave the end of the amplified first ds nucleotide sequence having a topoisomerase recognition site and the end (or ends) of the at least second ds nucleotide sequence having a topoisomerase recognition site, and can effect its ligating activity. The PCR primer that encodes a complement of a topoisomerase recognition site can have a hydroxyl group at its 5' terminus, or the amplified first ds nucleotide sequence generated using the primer can be contacted with a phosphatase to generate a hydroxyl group at its 5' terminus. The PCR primer encoding the complement of a topoisomerase recognition site also can comprise a nucleotide sequence at its 5' terminus such that, upon cleavage by a site specific topoisomerase of a first ds nucleotide sequence amplified using the primer, the ds nucleotide sequence contains a 5' overhanging sequence, which is complementary to a 5' overhang of a second (or other) ds nucleotide sequence to which the first ds nucleotide sequence is to be covalently linked according to a method of the invention.

The present invention also relates to a method of generating a ds recombinant nucleic acid molecule covalently linked in both strands by 1) amplifying a portion of a first ds nucleotide sequence using a PCR primer pair, wherein at least one primer of the primer pair encodes a topoisomerase recognition site, thereby producing an amplified first ds nucleotide sequence having a first end and a second end, wherein the first end, second end, or both ends have a topoisomerase recognition site at or near the 5' terminus; and 2) contacting a) the amplified first ds nucleotide sequence; b) at least a second ds nucleotide sequence having a first end and a second end, wherein the first end, second end, or both ends have a topoisomerase recognition site at or near the 5' terminus and have, or can be made to have, a hydroxyl group at the 3' terminus of the same end; and c) at least one site specific topoisomerase, under conditions such that the at least one topoisomerase can cleave the first and/or second end of the amplified first ds nucleotide sequence having a topoisomerase recognition site and the end (or ends) of the at least second ds nucleotide sequence having a topoisomerase recognition site, and can effect its ligating activity. The amplified first ds nucleotide sequence generally has a hydroxyl group at the 3' terminus of the end containing the topoisomerase recognition site, or can be modified to contain such a 3' hydroxyl group. The PCR primer encoding the topoisomerase recognition site can further comprise a nucleotide sequence at its 5' terminus, i.e., 5' to the topoisomerase recognition site, such that, upon cleavage of the amplified first ds nucleotide sequence by a site specific topoisomerase, the ds nucleotide sequence contains a 3' overhanging sequence, which is complementary to a 3' overhanging sequence of a second (or other) ds nucleotide sequence to which the first ds nucleotide sequence is to be covalently linked according to a method of the invention.

The present invention further relates to a method of generating a ds recombinant nucleic acid molecule covalently linked in both strands by 1) amplifying a portion of a first ds nucleotide sequence using a PCR primer pair, wherein at least one primer of the primer pair includes a topoisomerase recognition site and a nucleotide sequence complementary to a topoisomerase recognition site, thereby producing an amplified first ds nucleotide sequence having a first end and a second end, wherein the amplified first ds nucleotide sequence has a topoisomerase recognition site at or near the 5' terminus and a topoisomerase recognition site at or near the 3' terminus of the first end, second end, or both ends; and 2) contacting a) the amplified first ds nucleotide sequence; b) at least a second ds nucleotide sequence having a first end and a second end, wherein the second ds nucleotide sequence has, or can be made to have, a 5' hydroxyl group and a 3' hydroxyl group at the first end, second end, or both ends; and c) at least two site specific topoisomerases, under conditions such that i) at least one topoisomerase can cleave the topoisomerase recognition site at or near the 5' terminus of the first and/or second end of the amplified first ds nucleotide sequence, and can effect its ligating activity, and ii) at least one topoisomerase can cleave the topoisomerase recognition site at or near the 3' terminus of the end of the amplified first ds nucleotide sequence, and can effect its ligating activity. Accordingly, the present invention provides a ds nucleotide sequence containing, at one or both ends, a topoisomerase recognition site at or near the 5' terminus and a topoisomerase recognition site at or near the 3' terminus. In addition, the invention provides such a ds nucleotide sequence, which is topoisomerase-charged at the 5' terminus, the 3' terminus, or both termini.

The present invention further relates to an isolated oligonucleotide containing a recognition site of a type IA site specific topoisomerase and/or a nucleotide sequence complementary to a recognition site of a type IB site specific topoisomerase, such an oligonucleotide being useful, for example, as a primer for a primer extension reaction or as one of a primer pair for performing an amplification reaction such as PCR, as well as products generated by incubation with a topoisomerase. Such an oligonucleotide, which is referred to an oligonucleotide primer, can be one of a primer pair, which can be useful, for example, for generating a ds nucleic acid amplification product that contains, at one end, a topoisomerase recognition site (e.g., a type IA or type II topoisomerase recognition site) at or near the 5' terminus and, at the same end, a topoisomerase recognition site (e.g., a type IB topoisomerase recognition site) at or near the 3' terminus. Generally, the oligonucleotide primer is about 12 to 100 nucleotides in length, and usually about 15 to 50 nucleotides in length, particularly about 18 to 30 nucleotides in length, wherein, when present, the nucleotide sequence of the type IA topoisomerase recognition site and the nucleotide sequence complementary to the type IB topoisomerase recognition site can, but need not, be separated by at least one or a few (e.g., 1, 2, 3, 4, 5, 6, 7, 8, etc.) nucleotides.

An oligonucleotide primer of the invention can further contain a nucleotide sequence encoding (or complementary to) any other nucleotide sequence or peptide of interest, for example, one or more (e.g., 1, 2, 3, 4, 5, 6, 7, 8, etc.) restriction endonuclease recognition sites, a peptide tag, and, if desired, one or more additional type IA, type II or type IB topoisomerase recognition sites, thereby allowing selection of one or more convenient or readily available topoisomerases for practicing a method of the invention. The oligonucleotide primer can further comprise a nucleotide sequence at its 5' terminus, i.e., 5' to the topoisomerase recognition site (e.g., type IA or type II topoisomerase recognition site) or to the nucleotide sequence complementary to a type IB topoisomerase recognition site, such that, upon cleavage of the amplified first ds nucleotide sequence by a site specific topoisomerase, the ds nucleotide sequence contains a 3' or 5' overhanging sequence, respectively, which is complementary to a 3' or 5' overhanging sequence, respectively, of a second (or other) ds nucleotide sequence to which the first ds nucleotide sequence is to be covalently linked according to a method of the invention, or the oligonucleotide primer can be designed such that, upon cleavage of an amplified ds nucleotide sequence generated therefrom, a blunt end topoisomerase-charged ds nucleotide sequence is generated.

The present invention also provides a primer pair, which includes at least one oligonucleotide primer as defined above, wherein one of the primers is useful as a forward primer and the primer is useful as a reverse primer in an amplification reaction. The first and/or second primer in such a primer pair can, but need not, include a type IA topoisomerase recognition site, a nucleotide sequence complementary to a type IB topoisomerase recognition site, or both, and can include any other nucleotide sequence of interest. In one embodiment, the primer pair includes at least two oligonucleotide primers of the invention, wherein one oligonucleotide primer is useful as a forward primer and the second oligonucleotide primer is useful as a reverse primer, such a primer pair being useful, for example, for generating a ds nucleotide sequence amplification product having topoisomerase recognition sites at both termini of both ends, wherein the type IA or type IB or both topoisomerase recognition sites at the termini are the same or different. Accordingly, primer pairs of the invention include, for example, a first primer encoding a type IA topoisomerase recognition site and a second primer encoding a nucleotide sequence complementary to a type IB topoisomerase recognition site; a first primer encoding a type IA topoisomerase recognition site and a second primer encoding a type IA topoisomerase recognition site, which can be the same or different as that encoded by the first primer; a first primer encoding a nucleotide sequence complementary to a type IB topoisomerase recognition site and a second primer encoding a nucleotide sequence complementary to a type IB topoisomerase recognition site, which can be the same or different from that encoded by the first primer; a first primer encoding a type IA topoisomerase recognition site and a second primer encoding a type II recognition site or a nucleotide sequence complementary thereto; a first primer encoding a nucleotide sequence complementary to a type IB topoisomerase recognition site and a second primer encoding a type II topoisomerase recognition site or a nucleotide sequence complementary thereto; a first primer encoding a type II topoisomerase recognition site or a nucleotide sequence complementary thereto and a second primer encoding a type II topoisomerase recognition site or a nucleotide sequence complementary thereto, which is the same or different from the type II topoisomerase recognition site of the first primer. The present invention also provides kits containing one or more primer pairs of the invention, for example, one or more of the primer pairs exemplified above, or can contain three primers, for example, a first primer encoding a type IA topoisomerase recognition site, a second primer encoding a nucleotide sequence complementary to a type IB topoisomerase recognition site, and a third primer encoding a type II topoisomerase recognition site or a nucleotide sequence complementary thereto, such a kit allowing a convenient means to generate a primer extension or amplification product that can be covalently linked according to a method of the invention.

Accordingly, the present invention further relates to a ds nucleotide sequence, which has a first end and a second end, and which contains a topoisomerase recognition site (e.g., a type IA or type II topoisomerase recognition site) at or near the 5' terminus and a type IB topoisomerase recognition site at or near the 3' terminus of the first end, the second end, or of both ends. In addition, the present invention provides a ds nucleotide sequence as defined above, except wherein the ds nucleotide sequence is a topoisomerase-charged molecule, comprising a stably bound type IA topoisomerase or a type IB topoisomerase or both, at one or both ends, as desired.

In one embodiment, the first ds nucleotide sequence comprises or encodes an expressible nucleotide sequence such as a nucleotide sequence encoding a polypeptide, an antisense nucleotide sequence, a ribozyme, a tRNA (e.g., a suppressor tRNA), a triplexing nucleotide sequence or the like, and the second (or other) ds nucleotide sequence comprises a transcription regulatory element such as a promoter (e.g., a GAL4 promoter), an enhancer, a silencer, a translation start site, or a polyadenylation signal, or encodes a translation regulatory element such as an initiator methionine, a STOP codon, a cell compartmentalization domain, a homology domain, or the like, or a combination thereof in operative linkage. A second (or other) ds nucleotide sequence, which can be an amplified second (or other) ds nucleotide sequence prepared as for the amplified first ds nucleotide sequence, also can comprise a detectable label, for example, an enzyme, a substrate for an enzyme, a fluorescent compound, a luminescent compound, a chemiluminescent compound, a radionuclide, a paramagnetic compound, and biotin; or can include a tag, which can be an oligonucleotide tag or can be a peptide tag, for example, a polyhistidine tag, a V5 epitope, or a myc epitope.

In another embodiment, a method of the invention is performed using a first ds nucleotide sequence that encodes a polypeptide, or a domain thereof, and a second (or other) ds nucleotide sequence that encodes a transcription activation domain or a DNA binding domain. Such a method can be used to generate covalently linked ds recombinant nucleic acid molecules, covalently linked in one or both strands, that encode chimeric polypeptides useful for performing a two hybrid assay system, particularly a high throughput two hybrid assay. In still another embodiment, the first ds nucleotide sequences comprises a plurality of nucleotide sequences, which can be a cDNA library, a combinatorial library of nucleotide sequences, a variegated population of nucleotide sequences, or the like.

A method of the invention provides a means to generate a ds recombinant nucleic acid molecule, covalently linked in one or both strands, useful for site specific insertion into a target genomic DNA sequence. The target genomic DNA sequence can be any genomic sequence, particularly a gene, and preferably a gene for which some or all of the nucleotide sequence is known. The method can be performed utilizing two sets of amplification primer pairs such as PCR primer pairs and a ds nucleotide sequence. The ds nucleotide sequence has a first end and a second end and generally encodes a polypeptide, for example, a selectable marker, wherein the ds nucleotide sequence comprises a topoisomerase recognition site or cleavage product thereof at the 3' terminus of each end and, optionally, a hydroxyl group at the 5' terminus of each end, and wherein, preferably, the 5' termini comprise overhanging sequences, which are different from each other. Similarly, the ds nucleotide sequence can comprise a topoisomerase recognition site (or cleavage product thereof) at or near the 5' terminus of one or both ends and, optionally, a hydroxyl group at the 3' terminus of one or both end, and wherein one or both of the 3' termini can comprise overhanging sequences, which can be the same as or different from each other; or the 5' terminus and 3' terminus of one or both ends of the ds nucleotide sequence each can comprise a topoisomerase recognition site or cleavage product thereof (see FIGS. 4 and 5).

The two sets of PCR primer pairs generally are selected such that, in the presence of an appropriate DNA polymerase such as Taq polymerase and a template comprising the sequences to be amplified, the primers amplify portions of a genomic DNA sequence that are upstream (and adjacent to) and downstream (and adjacent to) of the target site for insertion of the polypeptide (e.g., selectable marker). The sets of PCR primer pairs also are designed such that the amplification products contain a topoisomerase recognition site at least at the end to be covalently linked in one or both strands to the selectable marker, including at or near the 5' terminus, the 3' terminus, or both termini, as appropriate for the particular method of the invention being practiced. As such, the first PCR primer pair can include, for example, 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, and a nucleotide sequence complementary to a 3' sequence of a target genomic DNA sequence; and 2) a second primer, which comprises a nucleotide sequence of the target genomic DNA upstream of the 3' sequence to which the first primer is complementary. The second PCR primer pair includes I) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, and a nucleotide sequence of a 5' sequence of a target genomic DNA sequence, wherein the 5' sequence of the target genomic DNA is downstream of the 3' sequence of the target genomic DNA to which the first primer of the first PCR primer pair is complementary; and 2) a second primer, which comprises a nucleotide sequence complementary to a 3' sequence of the target genomic DNA that is downstream of the 5' sequence of the target genomic DNA contained in the first primer.

Upon contact of the ds nucleotide sequence comprising the selectable marker, the PCR amplification products, and at least one topoisomerase, a ds recombinant nucleic acid molecule, covalently linked in one or both strands, is generated according to a method of the invention. The generated ds recombinant nucleic acid molecule is useful for performing homologous recombination in a genome, for example, to knock-out the function of a gene in a cell, or to confer a novel phenotype on the cell containing the generated ds recombinant nucleic acid molecule. The method can further be used to produce a transgenic non-human organism having the generated recombinant nucleic acid molecule stably maintained in its genome.

The present invention also relates to compositions prepared according to the methods of the invention, and to compositions useful for practicing the methods. Such compositions can include one or more reactants used in the methods of the invention and/or one or more ds recombinant nucleic acid molecules produced according to a method of the invention. Such compositions can include, for example, one or more topoisomerase-charge ds nucleotide sequences; one or more primers useful for preparing a ds nucleotide sequence containing a topoisomerase recognition site at one or both termini of one or both ends of an amplification product prepared using these primers; one or more topoisomerases; one or more substrate ds nucleotide sequences, including, for example, nucleotide sequences encoding tags, markers, regulatory elements, or the like; one or more ds recombinant nucleic acid molecules covalently linked in one or both strands, produced according to a method of the invention; one or more cells containing or useful for containing a ds nucleotide sequence, primer, or recombinant nucleic acid molecule as disclosed herein; one or more polymerases for performing a primer extension or amplification reaction; one or more reaction buffers; and the like. In one embodiment, a composition of the invention comprises two or more different topoisomerase-charged ds nucleotide sequences. The composition can further comprise at least one topoisomerase. A composition of the invention also can comprise a site specific topoisomerase and a ds recombinant nucleic acid molecule covalently linked in one or both strands, wherein the recombinant nucleic acid molecule contains at least one topoisomerase recognition site for the site specific topoisomerase in each strand. The topoisomerase recognition site in one strand can be any distance from a topoisomerase recognition site in the complementary strand, for example, wherein a topoisomerase recognition site in one strand is within about 100 nucleotides of a topoisomerase recognition site in the complementary strand, or wherein the recognition sites are within about 50 nucleotides of each other, or within about 20 nucleotides of each other, or less.

Methods of the invention also can be used to link at least one end of a double stranded nucleic acid molecule (e.g., DNA or RNA) to at least one end of a single stranded nucleic acid molecule (e.g., DNA or RNA). Furthermore, the methods of the invention can be used to link at least one end of a single stranded nucleic acid molecule (e.g., DNA or RNA) to at least one end of a second (or other) single stranded nucleic acid molecule (e.g., DNA or RNA). In appropriate circumstances, the methods of the invention can be used to circularize nucleic acid molecules, including to concatenate and circularize nucleic acid molecules. Thus, one or more ds nucleotide sequences disclosed herein as useful in an aspect or embodiment of the invention can be replaced with one or more single stranded nucleotide sequences. The invention further includes compositions used in such methods and nucleic acid molecules produced by such methods. Thus, for example, the invention includes single-stranded nucleic acid molecules to which a site-specific topoisomerase (e.g., a type IA topoisomerase, a type IB topoisomerase, a type II topoisomerase, etc.) is attached to the 5' or 3' terminus. Methods for joining single stranded nucleic acid molecules to other single stranded nucleic acid molecules are described, for example, in Internatl. Publ. No. WO 00/56878, which is incorporated herein by reference.

The present invention provides methods for joining DNA molecules to RNA molecules, as well as compositions used in such methods and nucleic acid molecules produced by such methods. Thus, nucleotide sequences of the invention can comprise, for example, DNA (e.g., cDNA, genomic DNA, plasmid DNA, synthetic DNA, etc.) or RNA (e.g., mRNA, rRNA, tRNA, synthetic RNA, ribozymes, etc.). Examples of such methods are set out, for example, in FIG. 8 and in Internatl. Publ. No. WO 98/56943, which is incorporated herein by reference.

The present invention also relates to a kit, which contains components that can be useful for practicing a method of the invention. A kit of the invention can contain, for example, one or more topoisomerase-charged ds nucleotide sequence substrates, which can include one or more control nucleotide sequences that can be useful, for example, to test the accuracy or fidelity of the components of the kit; one or more topoisomerases; one or more primers, which can comprise a topoisomerase recognition site, a nucleotide sequence complementary to a topoisomerase recognition site, or both; one or more cells, which can contain or be useful for containing a nucleotide sequence of the kit or a nucleic acid molecule generated using the kit; one or more reagents, polymers, buffers, or the like, for performing a method using the kit; instructions for performing a method using the kit, for example, instructions for covalently linking one strand of first nucleotide sequence to one strand of at least a second nucleotide sequence, either or both of which can be single stranded or double stranded nucleotide sequences, or instructions for covalently linking both strands of a first ds nucleotide sequence to both strands of at least a second ds nucleotide sequence; and the like.

In one aspect, a kit of the invention contains a ds nucleotide sequence having a first end and a second end and encoding a polypeptide, which can be expressed, for example, a selectable marker, wherein the ds nucleotide sequence comprises a topoisomerase recognition site or cleavage product thereof at the 3' terminus of one or both ends. Optionally, the ds nucleotide sequence contains a hydroxyl group at the 5' terminus of one or both of the other ends, preferably at the end containing the topoisomerase recognition site or that is topoisomerase-charged. In particular embodiments, one or both 5' termini comprise overhanging sequences, which can be the same or can be different from each other.

A kit of the invention also can contain a ds nucleotide sequence having a first end and a second end, and encoding a polypeptide to be expressed, for example, a selectable marker, wherein the ds nucleotide sequence comprises a topoisomerase recognition site or cleavage product thereof at the 5' terminus of one or both ends. Optionally, the ds nucleotide sequence contains a hydroxyl group at the 3' terminus of one or both ends, and preferably, one or both 3' termini comprise overhanging sequences, which can be the same or can be different from each other. In addition, a kit of the invention can contain a ds nucleotide sequence having a first end and a second end, and encoding a polypeptide to be expressed, for example, a selectable marker, wherein the ds nucleotide sequence comprises a topoisomerase recognition site or cleavage product thereof at the 5' terminus and the 3' terminus of one or both ends. As such, it should be recognized that a kit of the invention can include any of various combinations of such ds nucleotide sequences comprising one or more topoisomerase recognition sites or topoisomerase-charged ds nucleotide sequences, including ds nucleotide sequences having a topoisomerase recognition site at a terminus or both termini of one or both ends and that is topoisomerase-charged at one or more termini.

A kit of the invention also can contain a ds nucleotide sequence comprising a regulatory element or other nucleotide sequence, for example, a coding sequence, and a topoisomerase recognition site or cleavage product thereof at a 3' terminus of at least a first end and, optionally, a hydroxyl group at the 5' terminus of an end containing the recognition site; or comprising a topoisomerase recognition site or cleavage product thereof at a 5' terminus of at least a first end, and, optionally, a hydroxyl group at the 3' terminus of the end containing the recognition site; or comprising a topoisomerase recognition site at the 5' terminus and 3' terminus of at least a first end. Preferably, the kit contains a variety of upstream regulatory elements, a variety of downstream regulatory elements, a variety of elements useful detecting or identifying a molecule containing the element, and combinations thereof. For example, the kit can contain a variety of gene promoter elements, which are constitutively active or inducible in one or a few or many different types of cells, elements that permit or facilitate ribosome binding such as an internal ribosome entry site, an element encoding a Kozak sequence or an initiator methionine, or the like. In addition, or alternatively, the kit can contain a variety of downstream regulatory elements such a polyadenylation signal sequences, sequences that terminate transcription or translation, or the like; and also can contain enhancers, silencers, and the like. Similarly, the kit can contain elements encoding detectable markers such as epitope tags, or the like. Preferably, the kit contains a variety of such elements, each of which contains at least one topoisomerase recognition site. More preferably, the elements further contain an overhanging sequence such that they can be operatively covalently linked to each other or to a ds nucleotide sequence encoding a polypeptide such as a selectable marker according to a method of the invention.

Optionally, a kit of the invention can contain element specific primers, which can be used to amplify a construct containing one of the variety of elements included in the kit. Where the kit contains such primers, the ds nucleotide sequences comprising the regulatory or other element has a nucleotide sequence that can be specifically bound by the primer such that extension of the primer through and including the regulatory element can be effected. In particular, the kit can contain element specific forward and reverse primers, which can be combined to produce a primer pair useful for amplifying, for example, a recombinant nucleic acid molecule containing a particular 5' regulatory element and a particular 3' regulatory element of the kit. Such a primer pair can selectively amplify a desired functional ds recombinant nucleic acid molecule covalently linked in both strands generated according to a method of the invention, but does not amplify partial reaction products.

In another embodiment, a kit of the invention contains a first ds nucleotide sequence, which has a first end and a second end, contains a topoisomerase recognition site, or cleavage product thereof, at one or both 3' termini, and encodes a transcription activation domain; and a second ds nucleotide sequence, which has a first end and a second end, contains a topoisomerase recognition site, or cleavage product thereof, at one or both 3' termini, and encodes a DNA binding domain; or contains a first ds nucleotide sequence, which has a first end and a second end, contains a topoisomerase recognition site, or cleavage product thereof, at one or both 5' termini, and encodes a transcription activation domain; and a second ds nucleotide sequence, which has a first end and a second end, and optionally contains a topoisomerase recognition site, or cleavage product thereof, at one or both 5' termini, and encodes a DNA binding domain. A kit of the invention also can contain a first ds nucleotide sequence, which has a first end and a second end, and encodes a transcription activation domain, and a second ds nucleotide sequence, which has a first end and a second end, and encodes a DNA binding domain, wherein at least the first ds nucleotide sequence or the second ds nucleotide sequence contains a topoisomerase recognition site; or cleavage product thereof, at a 5' terminus and a 3' terminus of at least one end, and wherein the other ds nucleotide contains a 3' hydroxyl and 5' hydroxyl at the end to be covalently linked to the end of the ds nucleotide sequence comprising the recognition sites.

Such a kit is useful, for example, for generating a ds recombinant nucleic acid molecule covalently linked in both strands, or a ds recombinant nucleic acid molecule covalently linked in one strand, encoding chimeric polypeptides for performing a two hybrid assay. The kit can further contain a primer pair, which can amplify a nucleotide sequence to be operatively linked to the first or second ds nucleotide sequence, wherein at least one primer of the primer pair comprises a topoisomerase recognition site, a complement of a topoisomerase recognition site, or both. Preferably, an amplification product generated using such a primer pair contains, following cleavage by a site-specific topoisomerase, a 3' or 5' overhanging sequence that is complementary to the first or second ds nucleotide sequence to which it is to be covalently linked. Such a kit can facilitate the generation of recombinant polynucleotides that comprise a first or second nucleotide sequence of the kit and encode a chimeric polypeptide useful for performing a two hybrid assay.

In another embodiment, a kit of the invention contains a first ds nucleotide sequence having a first end and a second end, each end having a 5' terminus and a 3' terminus; and instructions for using a topoisomerase to covalently linking the 5' terminus and 3' terminus of at least one of the first end and the second end to a 5' terminus and a 3' terminus of a second ds nucleotide sequence. Such a kit also can contain a second (or more) ds nucleotide sequence, to which the first ds nucleotide sequence can be covalently linked in both strands according to the instructions. In addition, the kit can contain a topoisomerase, for example, a type IB topoisomerase such as a Vaccinia type IB topoisomerase. The first ds nucleotide sequence is such a kit can contain at least one topoisomerase recognition site at or near the 5' terminus or 3' terminus of the first end or second end or both ends, for example, a type IB topoisomerase recognition site at or near a 3' terminus of one or both ends; or can have a topoisomerase bound to at least one terminus of the first end or second or both ends, for example, a type IB topoisomerase bound to a 3' terminus of the first end or second end or both.

The present invention further relates to a method of generating ds recombinant RNA molecules. Such a method can be performed, for example, by I) contacting a) a first topoisomerase-charged ds nucleotide sequence having a first end and a second end, each end having a 5' terminus and a 3' terminus, wherein each of said first end and said second end includes a topoisomerase bound at the 3' terminus and a hydroxyl group at the 5' terminus; and b) at least second topoisomerase-charged ds nucleotide sequence having a first end and a second end, each end having a 5' terminus and a 3' terminus, wherein said at least second topoisomerase-charged ds nucleotide sequence comprises a promoter for an RNA polymerase, and wherein said first end or said second end or both has a topoisomerase bound at the 3' terminus and a hydroxyl group at the 5' terminus, under conditions such that an end of a first ds nucleotide sequence having a topoisomerase covalently bound thereto contacts an end of the at least second ds nucleotide sequence having a topoisomerase covalently bound thereto, thereby generating a ds recombinant nucleic acid molecule covalently linked in both strands; and 2) contacting the ds recombinant nucleic acid molecule covalently linked in both strands with an RNA polymerase specific for the promoter, under conditions suitable for transcription of RNA by the RNA polymerase and hybridization of transcribed complementary RNA molecules, thereby generating ds RNA molecules (see Appendix A, which is incorporated herein by reference; see, e.g., pages A45-A98). According to the present method, the RNA polymerase promoter any such promoter, including, for example, a viral RNA polymerase promoter such as a T3, promoter, a T7 promoter, an SP6 promoter, and the like. In many instances, the promoter is a promoter that is suitable for use in an in vitro transcription system Accordingly, ds nucleic acid molecules having an RNA polymerase promoter linked in one or both strands also are provided, as are ds RNA molecules generated therefrom.

The invention thus provides methods for generating nucleic acid molecules that allow for the expression and/or generation of ds RNA molecules. For example, using methods of the invention, two nucleic acid segments can be connected to each other, wherein one of the nucleic acid segments comprises nucleic acid which functions as a promoter and the other nucleic acid segment comprises nucleic acids which can be transcribed to form at least one strand of a ds RNA molecule. Thus, ds RNA molecules can be prepared by transcription (e.g., in vitro transcription) of a nucleic molecule (e.g., a DNA molecule) which encodes one strand or both strands of the ds RNA molecule. When the nucleic acid molecule encodes both strands of the ds RNA molecule, these strands can be produced as a single transcript or as separate transcripts. When both strands are produced as a single transcript, the two complementary portions of the transcript can be connected by a linker which forms a single stranded region when the complementary regions anneal to each other. This linker region can be of any suitable length (e.g., three, four, five, six, seven, eight, nine, ten, etc. nucleotides).

Further nucleic acid molecules that can be used to express double stranded RNA molecules can comprise nucleic acid segments comprising a promoter connected to nucleic acid that is to be transcribed, wherein these two segments are linked in one strand or in both strands. In many instances, when nucleic acid segments are joined in only one strand, either the nucleic acid segment which comprises a promoter activity or the other nucleic acid segment will contain a bound topoisomerase molecule. As described elsewhere herein, in many instances, this topoisomerase molecule will be bound to a 3' terminus of the topoisomerase adapted nucleic acid segment. In instances where only one end of termini that are joined contains a bound topoisomerase, the other end that is involved in the joining reaction can, but need not, contain a topoisomerase recognition sequence.

The invention further includes methods for generating ds RNA molecule employing nucleic acid molecules of the invention. In one aspect, the invention include performing in vitro transcription on nucleic acid molecules described herein. In vitro transcription reactions are known in the art and are described, for example, in U.S. Pat. No. 5,256,555 (which is incorporated herein by reference), and elsewhere herein.

A method of producing ds RNA molecules as disclosed herein can further include a step of contacting the ds RNA molecules with an enzyme that cleaves the ds RNA molecules, and particularly with an enzyme that cleaves the ds RNA molecule into oligoribonucleotides of a desired length (see Appendix A, e.g., pages A1 A44). Thus in one embodiment, the method includes contacting the ds RNA molecules with an enzyme that cleaves the ds RNA molecules into ds oligoribonucleotide molecules consisting of about 21 (e.g., 19, 20, 21, 22, or 23) nucleotides in each strand, thereby generating diced ds oligoribonucleotide molecules. The enzyme used according to the present method can be any enzyme that cleaves ds RNA molecules, including, for example, a dicer enzyme such as the BLOCK-iT™ dicer enzyme (Invitrogen Corp.; Carlsbad Calif.).

In one aspect, the generated diced ds oligoribonucleotide molecules consist of two strands of 19 to 21 nucleotides each. In another aspect, the generated diced ds oligoribonucleotide molecules consist of two strands of 19 to 21 nucleotides each, wherein the ds oligoribonucleotide molecules further contains an at least one (e.g., 1, 2, 3, 4, etc.) nucleotide overhang at one or both ends (e.g., 2 nucleotide overhangs on both ends). In still another aspect, the diced ds oligoribonucleotide molecules have short interfering RNA (siRNA); i.e., the method generates diced siRNA (d-siRNA) molecules.

In many instances, ds oligoribonucleotides will be molecules that are about 21 to 23 nucleotides in length with two nucleotide overhangs on each end (e.g., two nucleotide 3' overhangs). Thus, when a ds oligoribonucleotide is 23 nucleotides in length with two nucleotide overhangs on each end, it will typically be composed of two RNA strands, each of which is each 21 nucleotides in length.

A method of generating diced ds oligoribonucleotide molecules as disclosed herein can further include a step of isolating the diced ds oligoribonucleotide molecules, thereby obtaining isolated diced ds oligoribonucleotide molecules. Such a method can be performed using any convenient methods for isolating such oligoribonucleotides, including, for example, chromatographic (e.g., gel filtration chromatography such as HPLC, affinity chromatography, or electrophoresis) using readily available reagents or commercially available kits. As such, a method of the invention provides a means to obtain, for example, isolated d-siRNA molecules, which can be used to reduce or inhibit gene expression in a cell. Accordingly, the present invention also relates to a method of reducing or inhibiting expression of a target gene in a cell by contacting cells including the target cell with d-siRNA molecules obtained according to a method of the invention, whereby the d-siRNA reduces or inhibits expression of the target gene in the cell.

The present invention further relates to compositions produced according to the methods of the invention, including ds RNA molecules, compositions containing diced ds oligoribonucleotide molecules and/or d-siRNA molecules, and isolated diced ds oligoribonucleotide molecules and/or d-siRNA molecules. The present invention also provides kits for practicing the invention methods, including, for example, kits containing reagents for generating a ds RNA molecule having an RNA polymerase promoter at one or both ends, reagents for dicing such a ds RNA molecule and/or for isolating diced ds oligoribonucleotide molecules, and the like.

BRIEF DESCRIPTION OF THE FIGURES

FIG. 1A discloses SEQ ID NOS: 34, 39, 34, 39, 34 and 39, respectively, in order of appearance. FIG. 1B discloses SEQ ID NOS: 34, 39, 33, 43, 46, 44, 47 and 45, respectively, in order of appearance.

In FIGS. 2A and 2B, one (FIG. 2B) or both (FIG. 2A) of the overhang sequences are palindromic in nature. Sequences are shown in conventional orientation, with the top strand in a 5' to 3' orientation from left to right, and the bottom strand in a 3' to 5' orientation from left to right. Number in parentheses above or below sequence indicates SEQ ID NO.

FIG. 3A shows the amount of each construct used for transfection. A "p" preceding an amount or volume of reactant indicates plasmid form, "l" indicates linear form, and "PCR" indicates PCR amplification reaction mixture.

FIG. 3B shows the level of β-galactosidase activity ("LacZ activity") associated with each transfected sample. Increased LacZ activity is indicative of a positive interaction.

FIG. 5A shows a first ds nucleotide sequence having a topoisomerase linked to each of the 5' terminus and 3' terminus of one end, and further shows linkage of the first ds nucleotide sequence to a second ds nucleotide sequence.

FIG. 5B shows a first ds nucleotide sequence having a topoisomerase bound to the 3' terminus of one end, and a second ds nucleotide sequence having a topoisomerase bound to the 3' terminus of one end, and further shows a covalently linked ds recombinant nucleic acid molecule generated due to contacting the ends containing the topoisomerase-charged substrate ds nucleotide sequences.

FIG. 5C shows a first ds nucleotide sequence having a topoisomerase bound to the 5 terminus of one end, and a second ds nucleotide sequence having a topoisomerase bound to the 5' terminus of one end, and further shows a covalently linked ds recombinant nucleic acid molecule generated due to contacting the ends containing the topoisomerase-charged substrate ds nucleotide sequences.

FIG. 5D shows a ds nucleotide sequence having a topoisomerase linked to each of the 5' terminus and 3' terminus of both ends, and further shows linkage of the topoisomerase-charged ds nucleotide sequence to two ds nucleotide sequences, one at each end. The topoisomerases at each of the 5' termini and/or at each of the 3' termini can be the same or different.

FIG. 19 shows the T7 promoter (SEQ ID NO: 61) and its complement (SEQ ID NO: 62).

DETAILED DESCRIPTION OF THE INVENTION

The present invention relates to methods of using one or more topoisomerases to generate a recombinant nucleic acid molecule from two or more nucleotide sequences. In a first aspect, the invention provides a method for generating a ds recombinant nucleic acid molecule that is covalently linked in one strand. Such a method is directed to linking a first and at least a second nucleotide sequence with at least one (e.g., 1, 2, 3, 4, 5, 6, 7, 8, 9, 10, etc.) topoisomerase (e.g., a type IA, type IB, and/or type II topoisomerase) such that one strand, but not both strands, is covalently linked (see, for example, FIG. 4). In a second aspect, the invention provides a method for generating a ds recombinant nucleic acid molecule covalently linked in both strands. Such a method is directed to linking a first and at least a second nucleotide sequence with at least one topoisomerase, such that ligated ends are covalently linked in both strands (i.e., the ds recombinant nucleic acid molecule contain no nicks at the positions where ends were ligated; see, for example, FIG. 5). In a third aspect, the invention provides a method for generating a recombinant nucleic acid molecule covalently linked in one strand, wherein the substrate nucleotide sequences linked according to the method include at least one single stranded nucleotide sequence, which can be covalently linked to a second (or more) single stranded nucleotide sequence or to a ds nucleotide sequence (see, for example, FIG. 8).

Figure 9:
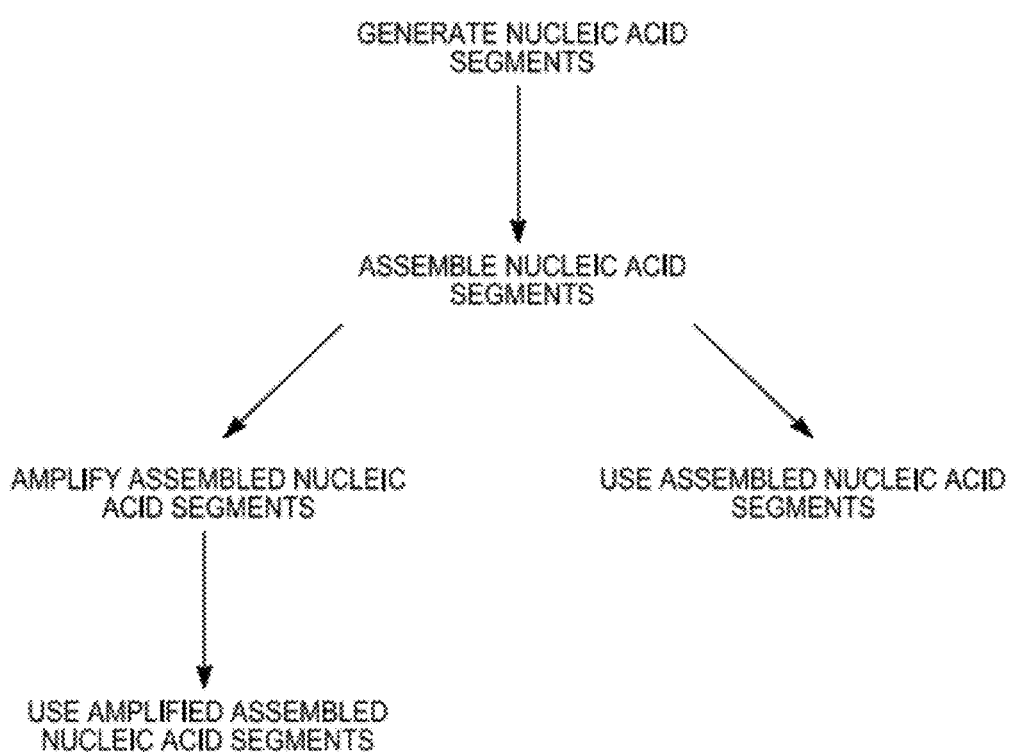
FIG. 9 provides a schematic outline exemplifying methods of the invention. In the first step, nucleotide sequences to be assembled are generated using an amplification method such as PCR. In the second step, the nucleotide sequences generated in the first step are assembled using a method of the invention (e.g., a method utilizing a topoisomerase to covalently link at least one strand of one nucleotide sequence to at least one strand of a second (or other) nucleotide sequence). In the third step as exemplified, assembled nucleic acid molecules (i.e., recombinant nucleic molecules) generated in the second step can be used directly or can be amplified, then used for any purpose as disclosed herein or otherwise desired.

Covalently linked recombinant nucleic acid molecules assembled using the methods of the invention can be used directly, or can be amplified, first, then used for any number of procedures as exemplified herein or otherwise known in the art. As disclosed herein, covalently linked recombinant nucleic acid molecules can be generated from nucleotide sequence in any of a number of ways (see, for example, FIG. 9). The nucleotide sequences useful in practicing the methods can be obtained using any of various well known methods, including, for example, by chemical synthesis, by isolation of restriction fragments or other cleavage products of genomic DNA, or by isolation of RNA, which can be used directly or converted to a cDNA using a reverse transcription method. Where the nucleotide sequences to be used according to a method of the invention lack one or more termini or regions suitable for generation of a recombinant nucleic acid molecule, the termini and/or regions can be added to the nucleotide sequence, for example, by an amplification reaction such as PCR, wherein one or both primers encode the desired sequence or a complement thereof (e.g., a topoisomerase recognition site, an overhanging sequence, etc) or by ligating one or more (e.g., one, two, three, four, etc.) adapter linkers, which can contain, for example, one or more topoisomerase recognition sites, or the nucleotide sequence can be modified using, for example, a method such as site directed mutagenesis to convert, for example, a sequence resembling a topoisomerase site to an actual topoisomerase recognition site. The nucleotide sequences having suitable termini and/or regions then can be assembled using methods of the invention as disclosed herein. The covalently linked recombinant nucleic acid molecule generated therefrom then can be amplified in vivo or in vitro, then used in any number of methods or processes, including those exemplified herein or otherwise known in the art. The covalently linked recombinant nucleic acid molecules also can be used directly for applications such as in vitro transcription/translation, recombinational cloning, or for transforming or transfecting cells. Accordingly, the present invention provides versatile methods for manipulating nucleotide sequences and for generating covalently linked recombinant nucleic acid molecules having desirable characteristic, and further provides compositions containing such nucleotide sequences and/or recombinant nucleic acid molecules, as well as methods of using the covalently linked recombinant nucleic acid molecules.

A method for generating a ds recombinant nucleic acid molecule covalently linked in one strand can be performed by contacting a first ds nucleotide sequence which has a site-specific topoisomerase recognition site (e.g., a type IA or a type II topoisomerase recognition site), or a cleavage product thereof, at a 5' or 3' terminus, with a second (or other) ds nucleotide sequence, and optionally, a topoisomerase (e.g., a type IA, type IB, and/or type II topoisomerase), such that the second nucleotide sequence can be covalently attached to the first nucleotide sequence. As disclosed herein, the methods of the invention can be performed using any number of nucleotide sequences, typically ds nucleotide sequences wherein at least one of the nucleotide sequences has a site-specific topoisomerase recognition site (e.g., a type IA, or type II topoisomerase), or cleavage product thereof, at one or both 5' termini (see, for example, FIGS. 4A-4F).

A method for generating a ds recombinant nucleic acid molecule covalently linked in both strands can be performed, for example, by contacting a first ds nucleotide sequence having a first end and a second end, wherein, at the first end or second end or both, the first ds nucleotide sequence has a topoisomerase recognition site (or cleavage product thereof) at or near the 3' terminus; at least a second ds nucleotide sequence having a first end and a second end, wherein, at the first end or second end or both, the at least second double stranded nucleotide sequence has a topoisomerase recognition site (or cleavage product thereof) at or near a 3' terminus; and at least one site specific topoisomerase (e.g., a type IA and/or a type IB topoisomerase), under conditions such that all components are in contact and the topoisomerase can effect its activity. A covalently linked ds recombinant nucleic acid generated according to a method of this aspect of the invention is characterized, in part, in that it does not contain a nick in either strand at the position where the ds nucleotide sequences are joined. In one embodiment, the method is performed by contacting a first ds nucleotide sequence and a second (or other) ds nucleotide sequence, each of which has a topoisomerase recognition site, or a cleavage product thereof, at the 3' termini or at the 5' termini of two ends to be covalently linked. In another embodiment, the method is performed by contacting a first ds nucleotide sequence having a topoisomerase recognition site, or cleavage product thereof, at the 5' terminus and the 3' terminus of at least one end, and a second (or other) ds nucleotide sequence having a 3' hydroxyl group and a 5' hydroxyl group at the end to be linked to the end of the first ds nucleotide sequence containing the recognition sites. As disclosed herein, the methods can be performed using any number of ds nucleotide sequences having various combinations of termini and ends (see, for example, FIG. 5A-5D).

Topoisomerases are categorized as type I, including type IA and type IB topoisomerases, which cleave a single strand of a double stranded nucleic acid molecule, and type II topoisomerases (gyrases), which cleave both strands of a nucleic acid molecule. Type IA and IB topoisomerases cleave one strand of a ds nucleotide sequence. Cleavage of a ds nucleotide sequence by type IA topoisomerases generates a 5' phosphate and a 3' hydroxyl at the cleavage site, with the type IA topoisomerase covalently binding to the 5' terminus of a cleaved strand. In comparison, cleavage of a ds nucleotide sequence by type IB topoisomerases generates a 3' phosphate and a 5' hydroxyl at the cleavage site, with the type IB topoisomerase covalently binding to the 3' terminus of a cleaved strand. As disclosed herein, type I and type II topoisomerases, as well as catalytic domains and mutant forms thereof, are useful for generating ds recombinant nucleic acid molecules covalently linked in both strands according to a method of the invention.

Type IA topoisomerases include *E. coli* topoisomerase I, *E. coli* topoisomerase III, eukaryotic topoisomerase II, archeal reverse gyrase, yeast topoisomerase III, *Drosophila* topoisomerase 111, human topoisomerase III, *Streptococcus pneumoniae* topoisomerase III, and the like, including other type IA topoisomerases (see Berger, Biochim. Biophys. Acta 1400: 3-18, 1998; DiGate and Marians, *J. Biol. Chem.* 264:17924-17930, 1989; Kim and Wang, *J. Biol. Chem.* 267:17178-17185, 1992; Wilson et al., *J. Biol. Chem.* 275:1533-1540, 2000; Hanai et al., Proc. Natl. Acad. Sci., USA 93:3653-3657, 1996, U.S. Pat. No. 6,277,620, each of which is incorporated herein by reference). *E. coli* topoisomerase III, which is a type IA topoisomerase that recognizes, binds to and cleaves the sequence 5'-GCAACTT-3', can be particularly useful in a method of the invention (Zhang et al., *J. Biol. Chem.* 270: 23700-23705, 1995, which is incorporated herein by reference). A homolog, the traE protein of plasmid RP4, has been described by Li et al. (*J. Biol. Chem.* 272:19582-19587, 1997) and can also be used in the practice of the invention. A DNA-protein adduct is formed with the enzyme covalently binding to the 5'-thymidine residue, with cleavage occurring between the two thymidine residues.

Type IB topoisomerases include the nuclear type I topoisomerases present in all eukaryotic cells and those encoded by vaccinia and other cellular poxviruses (see Cheng et al., *Cell* 92:841-850, 1998, which is incorporated herein by reference). The eukaryotic type IB topoisomerases are exemplified by those expressed in yeast, *Drosophila* and mammalian cells, including human cells (see Caron and Wang, *Adv. Pharmacol.* 29B:271-297, 1994; Gupta et al., *Biochim. Biophys. Acta* 1262:1-14, 1995, each of which is incorporated herein by reference; see, also, Berger, supra, 1998). Viral type IB topoisomerases are exemplified by those produced by the vertebrate poxviruses (vaccinia, Shope fibroma virus, ORF virus, fowlpox virus, and molluscum contagiosum virus), and the insect poxvirus (*Amsacta moorei* entomopoxvirus) (see Shuman, *Biochim. Biophys. Acta* 1400:321-337, 1998; Petersen et al., *Virology* 230:197-206, 1997; Shuman and Prescott, *Proc. Natl. Acad. Sci., USA* 84:7478-7482, 1987; Shuman, *J. Biol. Chem.* 269:32678-32684, 1994; U.S. Pat. No. 5,766,891; PCT/US95/16099; PCT/US98/12372, each of which is incorporated herein by reference; see, also, Cheng et al., supra, 1998).

Type II topoisomerases include, for example, bacterial gyrase, bacterial DNA topoisomerase IV, eukaryotic DNA topoisomerase II, and T-even phage encoded DNA topoisomerases (Roca and Wang, *Cell* 71:833-840, 1992; Wang, *J. Biol. Chem.* 266:6659-6662, 1991, each of which is incorporated herein by reference; Berger, supra, 1998). Like the type IB topoisomerases, the type II topoisomerases have both cleaving and ligating activities. In addition, like type IB topoisomerase, substrate ds nucleotide sequences can be prepared such that the type II topoisomerase can form a covalent linkage to one strand at a cleavage site. For example, calf thymus type II topoisomerase can cleave a substrate ds nucleotide sequence containing a 5' recessed topoisomerase recognition site positioned three nucleotides from the 5' end, resulting in dissociation of the three nucleotide sequence 5' to the cleavage site and covalent binding the of the topoisomerase to the 5' terminus of the ds nucleotide sequence (Andersen et al., supra, 1991). Furthermore, upon contacting such a type II topoisomerase-charged ds nucleotide sequence with a second nucleotide sequence containing a 3' hydroxyl group, the type II topoisomerase can ligate the sequences together, and then is released from the recombinant nucleic acid molecule. As such, type II topoisomerases also are useful for performing methods of the invention.

Structural analysis of topoisomerases indicates that the members of each particular topoisomerase families, including type IA, type IB and type II topoisomerases, share common structural features with other members of the family (Berger, supra, 1998). In addition, sequence analysis of various type IB topoisomerases indicates that the structures are highly conserved, particularly in the catalytic domain (Shuman, supra, 1998; Cheng et al., supra, 1998; Petersen et al., supra, 1997). For example, a domain comprising amino acids 81 to 314 of the 314 amino acid vaccinia topoisomerase shares substantial homology with other type IB topoisomerases, and the isolated domain has essentially the same activity as the full length topoisomerase, although the isolated domain has a slower turnover rate and lower binding affinity to the recognition site (see Shuman, supra, 1998; Cheng et al., supra, 1998). In addition, a mutant vaccinia topoisomerase, which is mutated in the amino terminal domain (at amino acid residues 70 and 72) displays identical properties as the full length topoisomerase (Cheng et al., supra, 1998). In fact, mutation analysis of vaccinia type IB topoisomerase reveals a large number of amino acid residues that can be mutated without affecting the activity of the topoisomerase, and has identified several amino acids that are required for activity (Shuman, supra, 1998). In view of the high homology shared among the vaccinia topoisomerase catalytic domain and the other type IB topoisomerases, and the detailed mutation analysis of vaccinia topoisomerase, it will be recognized that isolated catalytic domains of the type IB topoisomerases and type IB topoisomerases having various amino acid mutations can be used in the methods of the invention.

The various topoisomerases exhibit a range of sequence specificity. For example, type II topoisomerases can bind to a variety of sequences, but cleave at a highly specific recognition site (see Andersen et al., *J. Biol. Chem.* 266:9203-9210, 1991, which is incorporated herein by reference). In comparison, the type IB topoisomerases include site specific topoisomerases, which bind to and cleave a specific nucleotide sequence ("topoisomerase recognition site"). Upon cleavage of a ds nucleotide sequence by a topoisomerase, for example, a type IB topoisomerase, the energy of the phosphodiester bond is conserved via the formation of a phosphotyrosyl linkage between a specific tyrosine residue in the topoisomerase and the 3' nucleotide of the topoisomerase recognition site. Where the topoisomerase cleavage site is near the 3' terminus of the nucleic acid molecule, the downstream sequence (3' to the cleavage site) can dissociate, leaving a nucleic acid molecule having the topoisomerase covalently bound to the newly generated 3' end (see FIG. 1).

A method of the invention for generating a ds recombinant nucleic acid molecule covalently linked in one strand, can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both; 2) at least a second ds nucleotide sequence that has, or can be made to have, a first end and a second end; and 3) at least one (e.g., 1, 2, 3, 4, 5, 6, 7, 8, 9, 10, etc.) site-specific topoisomerase (e.g., a type IA or a type IB topoisomerase recognition site), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand can be performed such that any combination of ends are linked, and wherein one strand at the ends being linked is covalently linked and the other strand is not covalently linked, but contains a nick. For example, the first ds nucleotide sequence can comprise a coding sequence, wherein the ATG start codon is at or near the first end and a poly A signal is encoded at or near the second end; and a second ds nucleotide sequence can comprise a promoter element, which functions when positioned upstream of a coding sequence, and the first end is upstream of the second end, the method can be performed wherein a site-specific topoisomerase recognition site (e.g., a type IA or a type II topoisomerase recognition site) is at or near the 5' terminus of the first end of the first ds nucleotide sequence, and wherein the contacting is performed under conditions such that the topoisomerase (e.g., a type IA or a type II topoisomerase) can covalently link the 5' terminus of the first end of the first ds nucleotide sequence to the 3' terminus of the first end of the second ds nucleotide sequence, thereby generating a ds recombinant nucleic acid molecule, in which a polypeptide can be expressed from the coding sequence. Alternatively, the method can be performed wherein the topoisomerase recognition site (e.g., a type IA or a type II topoisomerase recognition site) is at or near the 5 terminus of the second end of the first ds nucleotide sequence, and wherein the contacting is performed under conditions such that the topoisomerase (e.g., a type IA or a type II topoisomerase recognition site) can covalently link the 5' terminus of the second end of the first ds nucleotide sequence to the 3' terminus of the first end of the second ds nucleotide sequence, thereby generating a ds recombinant nucleic acid molecule from which an antisense molecule can be expressed.

As another example using the first ds nucleotide sequence and second ds nucleotide sequence described above, the method can be performed, wherein the topoisomerase recognition site (e.g., a type IA or a type II topoisomerase recognition site) is at or near the 5' terminus of each of the first end and the second end of the first ds nucleotide sequence, and wherein the contacting is performed under conditions such that the type IA topoisomerase can covalently link the 5' terminus of the first end of the first ds nucleotide sequence to the 3' terminus of the first end of the second ds nucleotide sequence, and the 5' terminus of the second end of the first ds nucleotide sequence to the 3' terminus of the second end of the second ds nucleotide sequence. As such, the ds recombinant nucleic acid molecule generated by the method is circularized, and includes a nick in each strand opposite the location where a strand was covalently linked by a topoisomerase (e.g., a type IA or a type II topoisomerase). Furthermore, the promoter of the second ds nucleotide sequence can initiate expression of the first ds nucleotide sequence. In one embodiment, the circularized ds recombinant nucleic acid molecule comprises a vector.

As another example using the first ds nucleotide sequence and second ds nucleotide sequence described above, the method can be performed, wherein the topoisomerase recognition site (e.g., a type IA or a type II topoisomerase recognition site) is at or near the 5' terminus of each of the first end and the second end of the first ds nucleotide sequence, and wherein the contacting is performed under conditions such that the topoisomerase (e.g., a type IA or a type II topoisomerase) can covalently link the 5' terminus of the first end of the first ds nucleotide sequence to the 3' terminus of the second end of the second ds nucleotide sequence, and the 5' terminus of the second end of the first ds nucleotide sequence to the 3' terminus of the first end of the second ds nucleotide sequence. As such, the ds recombinant nucleic acid molecule generated by the method is circularized, and includes a nick in each strand opposite the location where a strand was covalently linked by topoisomerase (e.g., a type IA or a type II topoisomerase recognition site). Furthermore, the promoter of the second ds nucleotide sequence can initiate expression of an antisense sequence. In one embodiment, the circularized ds recombinant nucleic acid molecule comprises a vector.

As disclosed herein, a method of generating a ds recombinant nucleic acid molecule covalently linked in one strand, involving a first ds nucleotide sequence and at least a second ds nucleotide sequence, can further include a step for amplifying the ds recombinant nucleic acid molecule covalently linked in one strand. The amplification reaction can be carried out by contacting the ds recombinant nucleic acid molecule with an amplification reaction primer pair, wherein a first primer of the pair is capable of binding to the covalently linked strand, at or near one end of the first or second ds nucleotide sequence, and priming an amplification reaction toward the other ds nucleotide sequence to generate a first extension product that is identical in nucleotide sequence to the nicked strand of the ds recombinant nucleic acid molecule; and the second primer of the pair is capable of binding to the first extension product, typically at or near the 3' terminus, and, in the presence of the first primer, can generate an amplification product using the covalently linked strand and the extension product (or extension products generated therefrom) as templates. For example, the method can be performed such that the type IA topoisomerase recognition site is at or near a first end of the first ds nucleotide sequence, and the method further includes contacting the ds recombinant nucleic acid molecule with an amplification reaction primer pair, wherein a forward primer is capable of binding at or near the second end of the first ds nucleotide sequence, and wherein a reverse primer is capable of binding to a nucleotide sequence complementary to at least a portion of the second end of the second ds nucleotide sequence; and amplifying the ds recombinant nucleic acid molecule. The first ds nucleotide sequence can include a coding region and the second ds nucleotide sequence can include a regulatory element.

A method of generating a ds recombinant nucleic acid molecule covalently linked in one strand also can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of the first end or the second end or both; 2) at least a second ds nucleotide sequence that has, or can be made to have, a first end and a second end; 3) at least a third ds nucleotide sequence which has, or can be made to have, a first end and a second end, each end further comprising a 5' terminus and a 3' terminus; and 4) at least one (e.g., 1, 2, 3, 4, 5, 6, 7, 8, 9, 10, etc.) site-specific topoisomerase (e.g., a type IA or a type II topoisomerase recognition site), under conditions such that all components are in contact and the at least one topoisomerase can effect its activity. For example, the topoisomerase can be a type IA topoisomerase such as *E. coli* topoisomerase I, *E. coli* topoisomerase III, or a eukaryotic topoisomerase III. Upon cleavage of a ds nucleotide sequence, the topoisomerase preferably is stably bound to the 5' terminus. Preferably, upon cleavage by the topoisomerase, the cleaved ds nucleotide sequence comprises a 3' overhanging sequence.

A method of the invention for generating a ds recombinant nucleic acid molecule covalently linked in one strand, involving a first ds nucleotide sequence that contains a site-specific topoisomerase recognition site (e.g., a type IA or a type IB topoisomerase recognition site), or cleavage product thereof, at least a second ds nucleotide sequence, and at least a third ds nucleotide sequence can be performed such that any combination of ends are linked, and one strand at the ends being linked is covalently linked and one strand is nicked. According to this embodiment, any of the ends can contain a type IA, type II, or type IB topoisomerase recognition site, or can comprise a cleavage product thereof, provided that the first ds recombinant nucleotide molecule contains a topoisomerase recognition site (e.g., a type IA or a type II topoisomerase recognition site) at or near a 5' terminus, or a cleavage product thereof, and only one topoisomerase or topoisomerase recognition site is present at the ends that are to be linked. For example, where the first ds nucleotide sequence comprises a site-specific type IA topoisomerase recognition site at or near each of the first end and the second end, the method further can include contacting the first ds nucleotide sequence and the second ds nucleotide sequence with at least a third ds nucleotide sequence which has, or can be made to have, a first end and a second end, each end further comprising a 5' terminus and a 3' terminus, under conditions such that the topoisomerase (e.g., a type IA or a type II topoisomerase) can covalently link the 5' terminus of the first end of the first ds nucleotide sequence with the 3' terminus of the first end of the second nucleotide sequence, and the 5' terminus of the second end of the first ds nucleotide sequence with the 3' terminus of the first end of the third nucleotide sequence. It will be recognized that other combinations of ends and topoisomerase recognition sites, or cleavage products thereof, can be used to perform such a method of the invention.

A method of the invention also can be performed by contacting a first ds nucleotide sequence and a second ds nucleotide sequence with at least a third ds nucleotide sequence, which comprises a first end and a second end, each end further comprising a 5' terminus and a 3' terminus, wherein the third ds nucleotide sequence comprises a type IB topoisomerase recognition site at or near the 3' terminus of said first end, or said second end, or both said first end and said second end; and at least one (e.g., 1, 2, 3, 4, 5, 6, 7, 8, 9, 10, etc.) type IB topoisomerase under conditions such that the type IB topoisomerase can covalently link the 3' terminus of the first end or second end of the third ds nucleotide sequence to the 5' terminus of the first end or second end of the second ds nucleotide sequence. In such a method, where the third ds nucleotide sequence comprises a type IB topoisomerase recognition site at or near the 3' terminus of the first end, the contacting can be performed under conditions such that the type IB topoisomerase can covalently link the 3' terminus of the first end of the third ds nucleotide sequence to the 5' terminus of the first end of the second ds nucleotide sequence. It will be recognized that other combinations of ends and topoisomerase recognition sites, or cleavage products thereof, can be used to perform such a method of the invention.

In another embodiment, a method for generating a ds recombinant nucleic acid molecule covalently linked in one strand can be performed by contacting 1) a first ds nucleotide sequence having a first end and a second end, wherein the first ds nucleotide sequence has a site-specific topoisomerase recognition site (e.g., a type IA or a type II topoisomerase recognition site) at or near the 5' terminus of an end and a type IB topoisomerase recognition site at or near the 3' terminus of the other end; 2) at least a second ds nucleotide sequence that has, or can be made to have, a first end and a second end; 3) at least one (e.g., 1, 2, 3, 4, 5, 6, 7, 8, 9, 10, etc.) site-specific topoisomerase (e.g., a type IA or a type II topoisomerase); and 4) at least one (e.g., 1, 2, 3, 4, 5, 6, 7, 8, 9, 10, etc.) type IB topoisomerase under conditions such that all components are in contact and the at least one topoisomerase can effect its activity. For example, the topoisomerase, for which a recognition site is at or near the 5' terminus, can be a type IA topoisomerase such as E. coli topoisomerase I, E. coli topoisomerase III, or a eukaryotic topoisomerase III. Upon cleavage of a ds nucleotide sequence, the type IA topoisomerase preferably is stably bound to the 5' terminus, and the type IB topoisomerase preferably is stably bound at the 3' terminus. Preferably, upon cleavage by the topoisomerases, the cleaved ds nucleotide sequence comprises a 3' overhanging sequence and a 5' overhanging sequence. The method can further include contacting the ds recombinant nucleic acid molecule with a DNA ligase, thereby generating a ds recombinant nucleic acid molecule covalently linked in both strands.

A method of generating a ds recombinant nucleic acid molecule covalently linked in one strand by contacting a first ds nucleotide sequence, a second ds nucleotide sequence, and at least a third ds nucleotide sequence, can further include a step for amplifying the ds recombinant nucleic acid molecule, particularly the covalently linked strand. The amplification can be carried out by contacting the ds recombinant nucleic acid molecule with an amplification reaction primer pair, wherein a first primer of the pair can bind selectively to the covalently linked strand at or near one end of the first or second ds nucleotide sequence and prime an amplification reaction toward the other ds nucleotide sequence to generate a first extension product that is complementary to the covalently-linked strand; and the second primer of the pair can bind selectively to the first extension product, typically at or near the 3' terminus, and, in the presence of the first primer, can generate an amplification product using the covalently linked strand and the extension product (or extension products derived therefrom) as templates. The method can be performed such that the topoisomerase recognition site (e.g., a type IA or a type IB topoisomerase recognition site) is at or near the first end of the first ds nucleotide sequence, and can further include contacting the ds recombinant nucleic acid molecule with an amplification reaction primer pair, wherein a forward primer is capable of binding to a nucleotide sequence at or near the second end of the first ds nucleotide sequence and wherein a reverse primer is capable of binding to a nucleotide sequence complementary to at least a portion of the third ds nucleotide sequence; and amplifying the ds recombinant nucleic acid molecule. The first ds nucleotide sequence can include a coding region and the third ds nucleotide sequence can include a regulatory element. Furthermore, the ends being linked can contain complementary overhanging sequences.

Figure 4A:
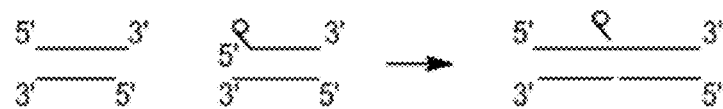
FIGS. 4A to 4F represent various embodiments of the composition and methods for generating a ds recombinant nucleic acid molecule covalently linked in one strand. Topoisomerase is shown as a solid circle, and is either attached to a terminus of a substrate ds nucleotide sequence or is released following a linking reaction.
Figure 4B:
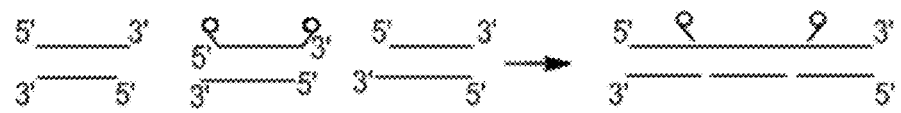
Figure 4C:
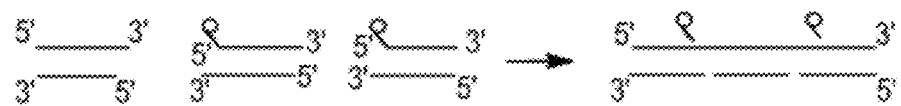
Figure 4D:
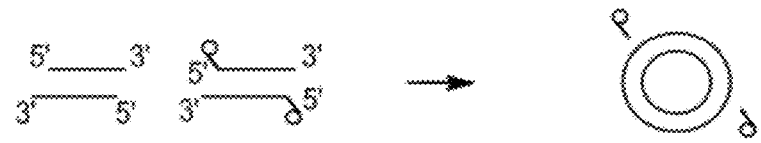
Figure 4E:
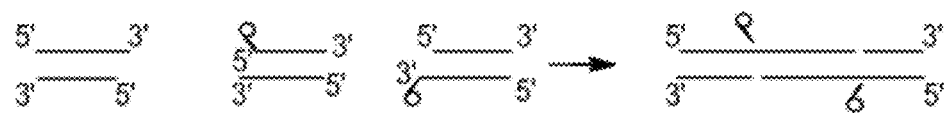
Figure 4F:
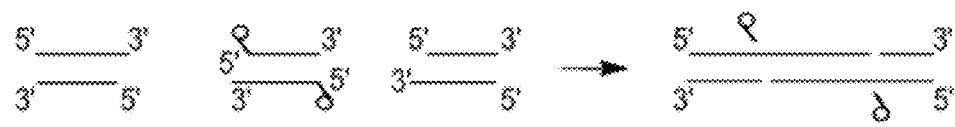

Representative embodiments of the disclosed methods for generating a ds recombinant nucleic acid molecule covalently linked in one strand are illustrated in FIGS. 4A-4F. In FIG. 4A, one of the ds nucleotide sequences has a topoisomerase attached to the 5' terminus of one end such that, when this molecule, which has a 3' overhang, is contacted with a second ds nucleotide sequence having a substantially complementary 3' overhang, under suitable conditions, the nucleotides comprising the 3' overhangs can hybridize and the topoisomerases can catalyze ligation. FIG. 4B shows a first ds nucleotide sequence having topoisomerase molecules linked to the 5' terminus and 3' terminus of two different ends of one nucleotide sequence, and further shows linkage of the first ds nucleotide sequence to two other nucleotide sequences to generate a nucleic acid molecule which has one strand without any nicks and another strand with two nicks. FIG. 4C shows a first ds nucleotide sequence having a topoisomerase molecule linked to the 5' terminus of one end and a second ds nucleotide sequence having a topoisomerase molecule linked to the 5' terminus of one end, and further shows linkage of the first and second ds nucleotide sequence to one other nucleotide sequence to generate a nucleic acid molecule which has one strand without any nicks and another strand with two nicks. In FIG. 4D, one of the ds nucleotide sequences to be linked has site-specific type IA topoisomerases attached to the 5' terminus of both ends such that, when the nucleotide sequences are contacted the complementary 3' overhangs can hybridize and the topoisomerases catalyze ligation. FIG. 4E shows another example of linking three ds nucleotide sequences together, using one ds nucleotide sequence that is topoisomerase-charged with a type IA topoisomerase at a 5' terminus and another ds nucleotide sequence that is topoisomerase-charged with a type IB topoisomerase at a 3' terminus of the opposite strand to be linked, such that when the nucleotide sequences are contacted the complementary 3' overhangs can hybridize and the topoisomerases catalyze ligation. FIG. 4F illustrates another example of linking three ds nucleotide sequences together, in this case using one ds nucleotide sequence that is topoisomerase-charged with a topoisomerase (e.g., a type IA or a type II topoisomerase) at a 5' terminus and with a type IB topoisomerase at a 3' terminus of the opposite strand, such that when the nucleotide sequences are contacted under suitable conditions, the complementary 3' overhangs can hybridize and the topoisomerases catalyze ligation.

The examples set forth in FIGS. 4A-4F show the ends of the ds nucleotide sequences opposite those being linked as having blunt ends, and shows the being linked as having 3' overhanging sequences. However, the substrate ds nucleotide sequences can have any ends and overhangs as desired, including both ends being blunt and/or complementary, or combinations thereof, such that the ends can be ligated to each other, for example, to form circular molecules or to other nucleic acid molecules having an appropriate end. Thus, one or more of the blunt ends as shown in FIGS. 4A-4F can be substituted with a nucleotide sequence comprising a 5' overhang or a 3' overhang, either of which can constitute a single nucleotide such as a thymidine residue or multiple nucleotides (e.g., two, three, four, five, six, seven, eight, nine, ten, eleven, twelve, thirteen, fourteen, fifteen, etc. nucleotides), which can be the same or different. In certain embodiments of the disclosed methods, a first ds nucleotide sequence contains a blunt end to be linked, and a second ds nucleotide sequence contains an overhang at the end which is to be linked by a site-specific topoisomerase (e.g., a type IA or a type IB topoisomerase), wherein the overhang includes a sequence complementary to that comprising the blunt end, thereby facilitating strand invasion as a means to properly position the ends for the linking reaction.

As exemplified in FIGS. 4A-4C, the ds recombinant nucleic acid molecule generated using the methods of this aspect of the invention include those in which one strand (not both strands) is covalently linked at the ends to be linked (i.e. ds recombinant nucleic acid molecules generated using these methods contain a nick at each position where two ends were joined). These embodiments are particularly advantageous in that a polymerase can be used to replicate the ds recombinant nucleic acid molecule by initially replicating the covalently linked strand. For example, a thermostable polymerase such as a polymerase useful for performing an amplification reaction such as PCR can be used to replicate the covalently linked strand, whereas the strand containing the nick does not provide a suitable template for replication.

Figure 5A:
FIGS. 5A to 5D illustrate various embodiments of compositions and methods of the invention for generating a covalently linked ds recombinant nucleic acid molecule. Topoisomerase is shown as a solid circle, and is either attached to a terminus of a substrate ds nucleotide sequence or is released following a linking reaction. As illustrated, the substrate ds nucleotide sequences have 5' overhangs, although they similarly can have 3' overhangs or can be blunt ended. In addition, while the illustrated ds nucleotide sequences are shown having the topoisomerases bound thereto (topoisomerase-charged), one or more of the termini shown as having a topoisomerase bound thereto also can have a topoisomerase recognition site (i.e., one or more termini containing a topoisomerase recognition site), in which case the joining reaction would further require addition of one or more site specific topoisomerases, as appropriate.
Figure 5B:
Figure 5C:
Figure 5D:
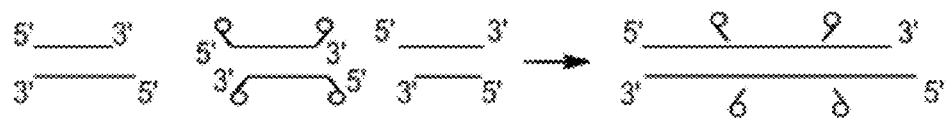

The present invention also provides methods of covalently ligating the ends of two different ds nucleotide sequences or two ends of the same ds nucleotide sequence, such that the product generated is ligated in both strands and, therefore, does not contain a nick. Representative embodiments of this aspect of the invention are illustrated in FIG. 5. For example, in FIG. 5A, one of the ds nucleotide sequences has topoisomerase molecules attached to the 3' terminus and the 5' terminus of one end such that, when this molecule, which has a 5' overhang, is contacted with a second ds nucleotide sequence having a substantially complementary 5' overhang, under suitable conditions, the nucleotides comprising the 5' overhangs can hybridize and the topoisomerases can catalyze ligation of both strands of the ds nucleotide sequences. In FIG. 5B, each end of the ds nucleotide sequences to be linked has a topoisomerase molecule attached to the 3' terminus such that, when the nucleotide sequences are contacted under suitable conditions, nucleotides comprising the 5' overhangs can hybridize and the topoisomerases catalyze ligation (compare FIG. 5C, in which each of the ds nucleotide sequences to be linked has a topoisomerase attached to the 5' termini of the ends to be linked). FIG. 5D illustrates linking three ds nucleotide sequences together via a ds nucleotide sequence that is topoisomerase-charged at both termini of both ends. Similarly to FIG. 4, the examples set forth in FIGS. 5A-5D show the ends of the ds nucleotide sequences that are not being linked as having blunt ends. As discussed with respect to FIG. 4, however, the substrate ds nucleotide sequences utilized in methods as exemplified in FIG. 5 can have any ends as desired, including topoisomerase-charged ends, such that the ends can be ligated to each other, for example, to form circular molecules or to other nucleic acid molecules having an appropriate end, blunt ends, 5' overhangs, 3' overhangs, and the like, as desired.

A covalently bound topoisomerase, in addition to catalyzing a ligation reaction, also can catalyze the reverse reaction, for example, religation of the 3' nucleotide of the recognition sequence, to which the type IB topoisomerase is linked through the phosphotyrosyl bond, and the nucleotide sequence that, prior to cleavage, comprised the 5' terminus of the ds nucleotide sequence, and which, following cleavage, contains a free 5' hydroxy group. As such, methods have been developed for using a type IB topoisomerase to produce recombinant nucleic acid molecules. For example, cloning vectors containing a bound type IB topoisomerase have been developed and are commercially available (Invitrogen Corp., La Jolla Calif.). Such cloning vectors, when linearized, contain a covalently bound type IB topoisomerase at each 3' end ("topoisomerase-charged"). Nucleotide sequences such as those comprising a cDNA library, or restriction fragments, or sheared genomic DNA sequences that are to be cloned into such a vector are treated, for example, with a phosphatase to produce 5' hydroxyl termini, then are added to the linearized topoisomerase-charged vector under conditions that allow the topoisomerase to ligate the nucleotide sequences at the 5' terminus containing the hydroxyl group and the 3' terminus of the vector that contains the covalently bound topoisomerase. A nucleotide sequence such as a PCR amplification product, which is generated containing 5' hydroxyl ends, can be cloned into a topoisomerase-charged vector in a rapid joining reaction (approximately 5 minutes at room temperature). The rapid joining and broad temperature range inherent to the topoisomerase joining reaction makes the use of topoisomerase-charged vectors ideal for high throughput applications, which generally are performed using automated systems.

Type II topoisomerases have not generally been used for generating recombinant nucleic acid molecules or cloning procedures, whereas type IB topoisomerases, as indicated above, are used in a variety of procedures. As disclosed herein, type IA topoisomerases can be used in a variety of procedures similar to those described for the type IB topoisomerases. However, previously described methods of using type IB topoisomerases to ligate two or more nucleotide sequences have suffered from the disadvantage that the bound topoisomerase only effects the joining of the 3' end of the strand to which it is attached and a second strand containing a 5' hydroxyl group. Since the topoisomerase cannot ligate the complementary strands, the nucleic acid molecules that are generated contain nicks. While the presence of such nicks does not prevent the use of the recombinant molecules for transfection of a host cells, as the nicks generally are resolved intracellularly, the presence of such nicks in double stranded nucleic acid molecules significantly limits direct use of the recombinant molecules. For example, a strand of a nucleic acid molecule containing a nick cannot be amplified by PCR because the primer extension reaction terminates at the nick. Thus, nucleic acid constructs prepared using a topoisomerase according to previously described methods generally must be further treated, for example, with a DNA ligase, to obtain a ds recombinant nucleic acid molecule that is covalently linked in both strands and, therefore, useful for subsequent manipulations such as PCR.

Previously described methods for preparing nucleic acid constructs also generally required numerous steps, particularly where more than two nucleotide sequences are to be ligated, and even more so where the sequences must be ligated in a predetermined orientation. For example, the nucleotide sequences to be linked generally are ligated sequentially to produce intermediate constructs, each of which must be cloned, amplified in a host cell, isolated, and characterized. The constructs containing the correct sequences then must be isolated in a sufficient quantity and form such that the next nucleotide sequence can be ligated, and the process of cloning, amplifying, isolating and characterizing performed again to identify the proper construct. Clearly, as the number of different nucleotide sequences to be joined increases, so do the number of essentially repetitive procedures that must be performed, thus resulting in an expensive, laborious and lengthy process.

Figure 1A:
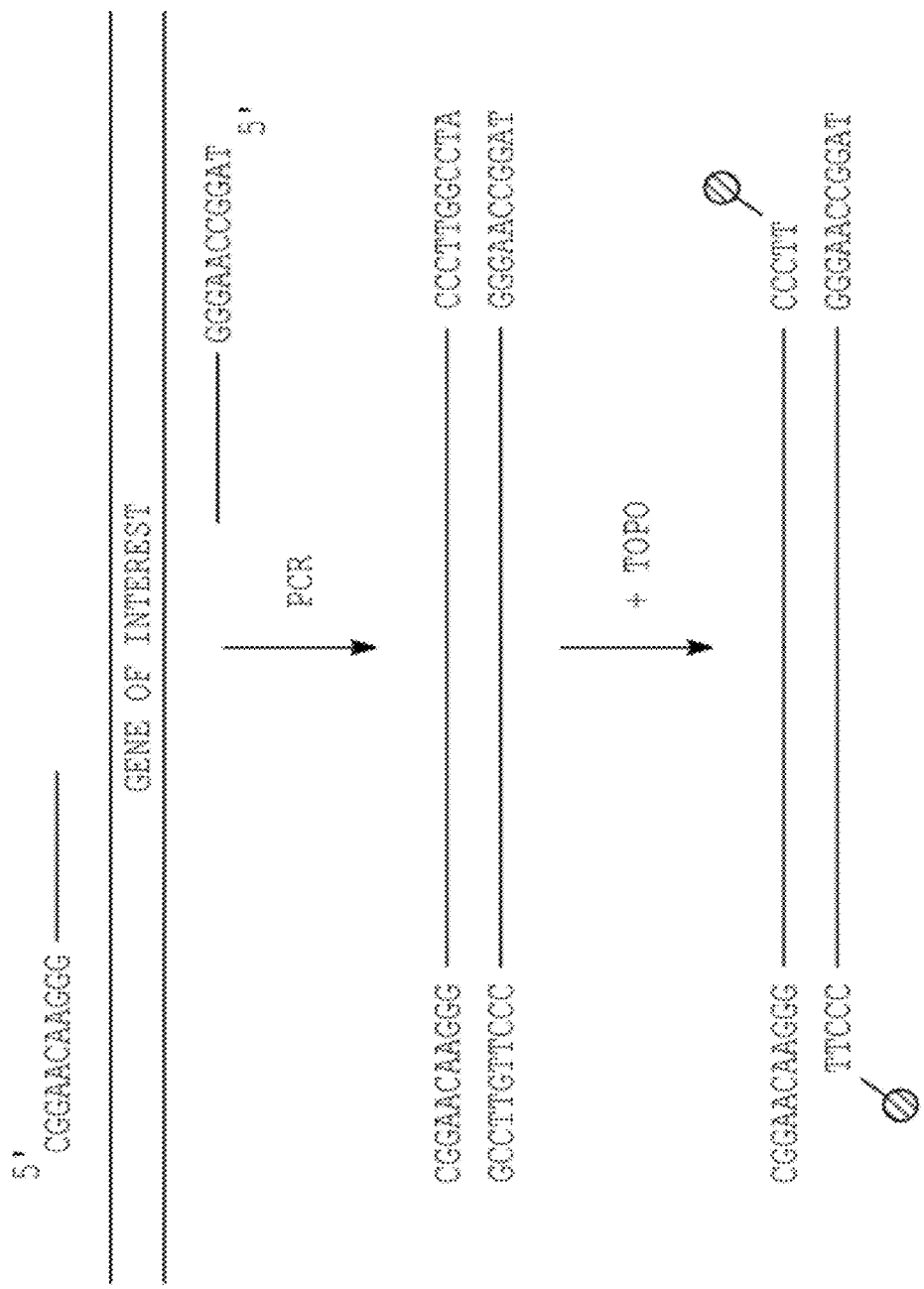
FIGS. 1A and 1B depict generating a covalently linked double stranded nucleotide sequence containing an element on each end according to a method of the invention. "PCR" indicates polymerase chain reaction; "TOPO" indicates topoisomerase; topoisomerase shown as circle attached to sequence; "P1" and "P2" indicate PCR primers. Topoisomerase recognition site is indicated in bold print.
Figure 1B:
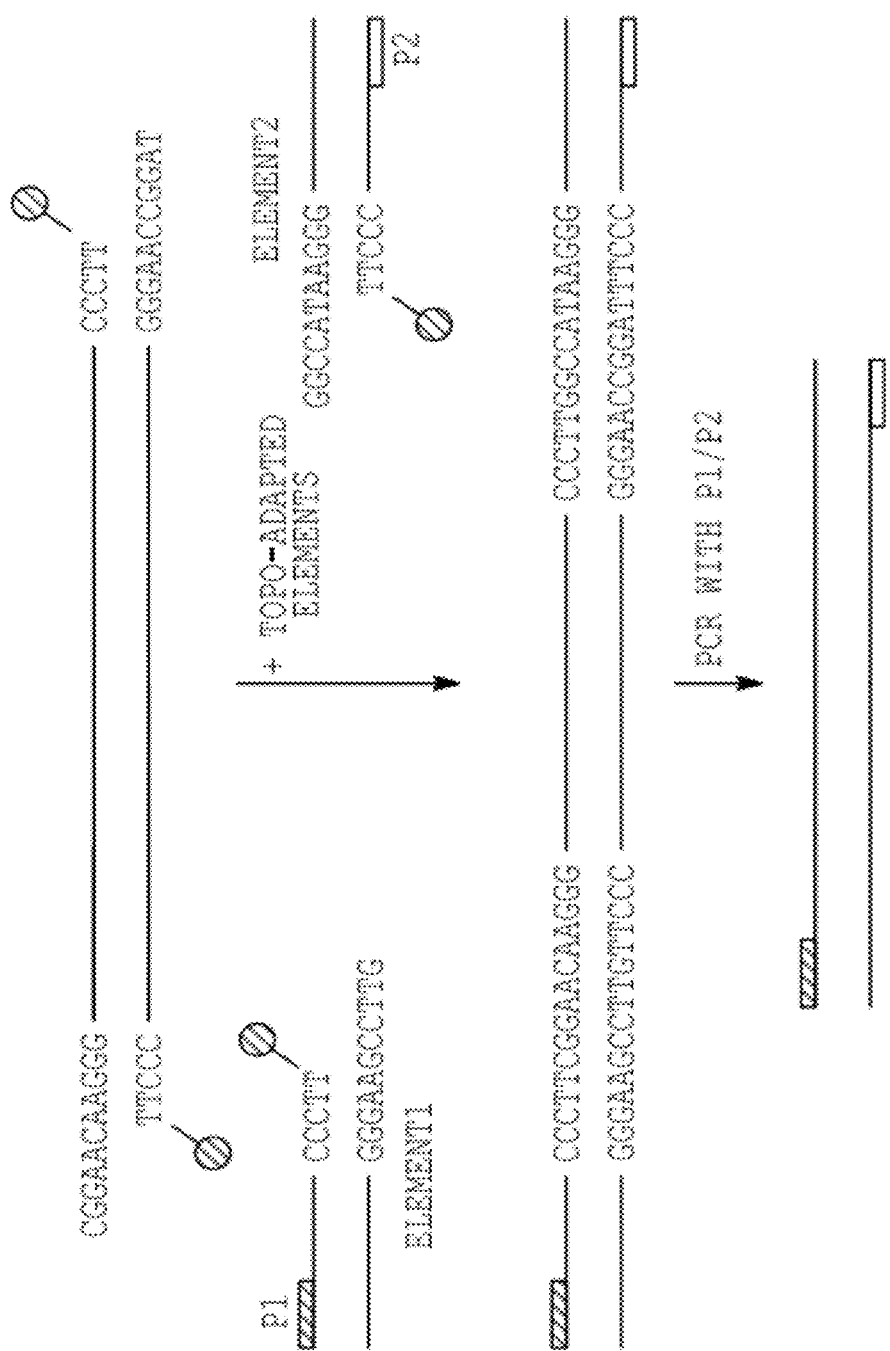

As disclosed herein, an advantage of a method of the invention for generating a ds recombinant nucleic acid molecule covalently linked in both strands is that there is no need to perform a separate ligation reaction in order to obtain a functional ds recombinant nucleic acid molecule covalently linked in both strands (see FIGS. 1 and 5). In addition, a method of this aspect of the invention can be performed such that, where a number of different ds nucleotide sequences are to be covalently linked in a predetermined orientation, there is no requirement that intermediate constructs be cloned, characterized and isolated before proceeding to a subsequent step (see Example 1.B). As such, the methods of this aspect of the invention provide a means to generate a ds recombinant nucleic acid molecule covalently linked in both strands much more quickly and at a substantially lower cost than was possible using previously known methods.

As an additional advantage, the generated ds recombinant nucleic acid molecules covalently linked in both strands are in a form that can be used directly in further procedures, for example, particular procedures involving extension or a primer such as a PCR amplification procedure, or other transcription or translation procedure, because the generated construct does not contain nicks at the sites where the ds nucleotides sequences have been joined. As disclosed herein, a method of the invention for generating a ds recombinant nucleic acid molecule covalently linked in one strand, in certain embodiments, also is advantageous in that the generated ds recombinant nucleic acid molecules are in a form that can be used directly in further procedures, for example, particular procedures involving extension of a primer such as a PCR amplification procedure, or other transcription or translation procedure, because in certain embodiments, the generated ds recombinant nucleic acid molecule contains one strand that does not contain a nick at the sites where the ds nucleotides sequences were joined.

The term "nucleotide sequence" or "ds nucleotide sequence" is used herein to refer to a discrete nucleic acid molecule. When used as such, the term "nucleotide sequence" is used merely for convenience such that the components in a composition or used in a method of the invention can be clearly distinguished. Thus, reference is made, for example, to "ds nucleotide sequences", which, in a method of the invention, correspond to the reactants (substrates) used to produce a recombinant "nucleic acid molecule" product.

Certain methods of the invention are exemplified generally herein with reference to the use of type IB topoisomerase such as the Vaccinia topoisomerase, or a type IA topoisomerase. However, it will be recognized that the methods also can be performed using a topoisomerase other than that exemplified, merely by adjusting the components accordingly. For example, as described in greater detail below, methods are disclosed for incorporating a type IB topoisomerase recognition site at one or both 3' termini of a linear ds nucleotide sequence using a PCR primer comprising, at least in part, a nucleotide sequence complementary to the topoisomerase recognition site. In comparison, a topoisomerase recognition site for a type IA or, if desired, type II topoisomerase, can be incorporated into a ds nucleotide sequence by using a PCR primer that contains the recognition site.

Cleavage of a ds nucleotide sequence by a site specific type IB topoisomerase results in the generation of a 5' overhanging sequence in the strand complementary to and at the same end as that containing the covalently bound topoisomerase. Furthermore, as disclosed herein, PCR primers can be designed that can incorporate a type IB topoisomerase recognition site into a ds nucleotide sequence, and that further can produce, upon cleavage of the ds nucleotide sequence by the topoisomerase, a 5' overhanging sequence in the complementary strand that has a defined and predetermined sequence. As such, the methods are readily adaptable to generating a ds recombinant nucleic acid molecule having the component ds nucleotide sequence operatively linked in a predetermined orientation. In view of the present disclosure, it will be recognized that PCR primers also can be designed such that a type IA topoisomerase recognition site can be introduced into a ds nucleotide sequence, including a library of diverse sequences, and, if desired, such that upon cleavage by a site-specific topoisomerase, generates a 3' overhanging sequence.

A method of generating a ds recombinant nucleic acid molecule covalently linked in both strands, as disclosed herein, extends the previously known methods by providing a topoisomerase at or near the terminus of each ds nucleotide sequence to be covalently linked. For example, with respect to a type IB topoisomerase, the method provides a topoisomerase recognition site, or a cleavage product thereof (i.e., a covalently bound type IB topoisomerase), at or near the 3' terminus of each linear ds nucleotide sequence to be linked. As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including vaccinia virus DNA topoisomerase I, which then can cleave the strand after the 3'-most thymidine of the recognition site to produce a nucleotide sequence comprising 5'-(C/T)CCTT-PO$_4$-TOPO, i.e., a complex of the topoisomerase covalently bound to the 3' phosphate through a tyrosine residue in the topoisomerase (see Shuman, *J. Biol. Chem.* 266:11372-11379, 1991; Sekiguchi and Shuman, *Nucl. Acids Res.* 22:5360-5365, 1994; each of which is incorporated herein by reference; see, also, U.S. Pat. No. 5,766,891; PCT/US95/16099; PCT/US98/12372). In comparison, the nucleotide sequence 5'-GCAACTT-3' is the topoisomerase recognition site for type IA *E. coli* topoisomerase III.

Topoisomerase-charged ds nucleotide sequences, including those containing a topoisomerase covalently attached to a 5' terminus or 3' terminus or both, of one or both ends of the ds nucleotide sequence, can be generated by any of a number of methods. In some cases and under the appropriate conditions, type I topoisomerases can cleave a single stranded nucleotide sequence. For example, a domain comprising the amino-terminal 67 kDa domain of *E. coli* topoisomerase I, which is a type IA topoisomerase, can cleave a single stranded nucleotide sequence containing the topoisomerase recognition site. Where conditions are such that the topoisomerases can cleave a single stranded nucleotide sequence, cleavage of a ds nucleotide sequence containing topoisomerase recognition sites at the 5' and 3' termini of one end of ds nucleotide sequence can be performed in parallel. Alternatively, where one or both of the topoisomerases requires a ds nucleotide sequence for recognition and cleavage, the reactions are performed serially, wherein the more terminal (distal) of the topoisomerase recognition sites is cleaved first, then the more internal (proximal) site, which remains in a double stranded context, is cleaved. For example, a ds nucleotide sequence containing an *E. coli* topoisomerase III recognition site at or near a 5' terminus of an end and a Vaccinia type IB topoisomerase recognition site at or near the 3' terminus of the same end, and wherein the type IB recognition site is closer to the end than the type IA recognition site, the ds nucleotide sequence can be incubated with the Vaccinia topoisomerase, to produce a type IB topoisomerase-charged ds nucleotide sequence, then with the *E. coli* topoisomerase, to produce a ds nucleotide sequence having the type IA topoisomerase bound to the 5' terminus and the type IB topoisomerase bound to the 3' terminus. Accordingly, the invention includes methods for producing ds nucleotide sequence comprising a topoisomerase attached to one or both termini of at least one end, and further provides such topoisomerase-charged ds nucleotide sequences.

As used herein, the term "cleavage product," when used in reference to a topoisomerase recognition site, refers to a nucleotide sequence that has been cleaved by a topoisomerase, generally at its recognition site, and comprises a complex of the topoisomerase covalently bound, in the case of type IA or type II topoisomerase, to the 5' phosphate group of the 5' terminal nucleotide in the topoisomerase recognition site, or in the case of a type IB topoisomerase to the 3' phosphate group of the 3' terminal nucleotide in the topoisomerase recognition site. Such a complex, which comprises a topoisomerase cleaved ds nucleotide sequence having the topoisomerase covalently bound thereto, is referred to herein as a "topoisomerase-activated" or a "topoisomerase-charged" nucleotide sequence. Topoisomerase-activated ds nucleotide sequences can be used in a method of the invention, as can ds nucleotide sequences that contain an uncleaved topoisomerase recognition site and a topoisomerase, wherein the topoisomerase can cleave the ds nucleotide sequence at the recognition site and become covalently bound thereto.

In one embodiment of a method of generating a ds recombinant nucleic acid molecule covalently linked in both strands, a topoisomerase recognition site is present at or near the 3' terminus of the end of each nucleotide sequence to be linked such that, in the presence of a type IB topoisomerase, each nucleotide sequence is cleaved to produce a 3' terminus, which contains the topoisomerase covalently bound thereto (see FIG. 1). The nucleotide sequences to be covalently linked also can contain a 5' hydroxy group at the same end as that containing the topoisomerase recognition site, or a 5' hydroxyl group can be generated using a phosphatase. Upon contact of such nucleotide sequences, the site specific topoisomerase can ligate each strand containing a 3' phosphate to a respective 5' hydroxyl group, thereby generating a ds recombinant nucleic acid molecule covalently linked in both strands, which can be produced as a linear, circular, or positively or negatively supercoiled nucleic acid molecule.

Preferably, the 5' termini of the ends of the nucleotide sequences to be linked by a type IB topoisomerase according to a method of certain aspects of the invention contain complementary 5' overhanging sequences, which can facilitate the initial association of the nucleotide sequences, including, if desired, in a predetermined directional orientation. Alternatively, the 5' termini of the ends of the nucleotide sequences to be linked by a type IB topoisomerase according to a method of certain aspects of the invention contain complementary 5' sequences wherein one of the sequences contains a 5' overhanging sequence and the other nucleotide sequence contains a complementary sequence at a blunt end of a 5' terminus, to facilitate the initial association of the nucleotide sequences through strand invasion, including, if desired, in a predetermined directional orientation. The term "5'overhang" or "5' overhanging sequence" is used herein to refer to a strand of a ds nucleotide sequence that extends in a 5' direction beyond the terminus of the complementary strand of the ds nucleotide sequence. Conveniently, a 5' overhang can be produced as a result of site specific cleavage of a ds nucleotide sequence by a type IB topoisomerase (see Example 1).

Preferably, the 3' termini of the ends of the nucleotide sequences to be linked by a type IA topoisomerase according to a method of certain aspects of the invention contain complementary 3' overhanging sequences, which can facilitate the initial association of the nucleotide sequences, including, if desired, in a predetermined directional orientation. Alternatively, the 3' termini of the ends of the nucleotide sequences to be linked by a topoisomerase (e.g., a type IA or a type II topoisomerase) according to a method of certain aspects of the invention contain complementary 3' sequences wherein one of the sequences contains a 3' overhanging sequence and the other nucleotide sequence contains a complementary sequence at a blunt end of a 3' terminus, to facilitate the initial association of the nucleotide sequences through strand invasion, including, if desired, in a predetermined directional orientation. The term "3'overhang" or "3' overhanging sequence" is used herein to refer to a strand of a ds nucleotide sequence that extends in a 5' direction beyond the terminus of the complementary strand of the ds nucleotide sequence. Conveniently, a 3' overhang can be produced upon cleavage by a type IA or type II topoisomerase.

Figure 2A:
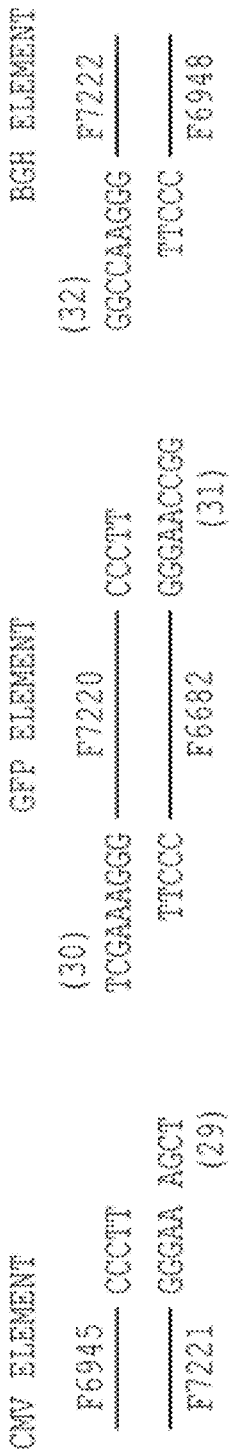
FIGS. 2A to 2C show the ends of PCR products representing a cytomegalovirus promoter element ("CMV"), a green fluorescent protein element ("GFP"), and a bovine growth hormone polyadenylation signal ("BGH") element. Primers used to construct the PCR products of FIGS. 2A, 2B and 2C are indicated by an "F" number (see Table 1). The portion of one or both ends including the topoisomerase recognition site (CCCTT) is shown. Bold print indicates overhanging sequences.
Figure 2B:
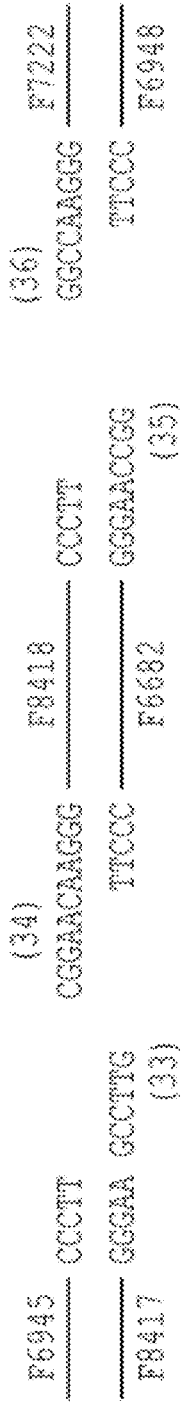
Figure 2C:
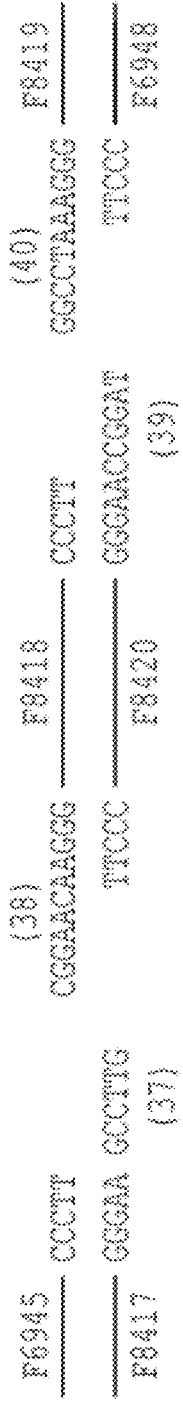

The 3' or 5' overhanging sequences can have any sequence, though generally the sequences are selected such that they allow ligation of a predetermined end of one ds nucleotide sequence to a predetermined end of a second nucleotide sequence according to a method of the invention (FIG. 2C, see, also Example 1.B). As such, while the 3' or 5' overhangs can be palindromic, they generally are not because ds nucleotide sequences having palindromic overhangs can associate with each other, thus reducing the yield of a ds recombinant nucleic acid molecule covalently linked in both strands comprising two or more ds nucleotide sequences in a predetermined orientation. For example, the 5' overhanging sequences of ds nucleotide sequences shown in FIG. 2A are palindrome and, therefore, the association, for example, of a first CMV element with a second CMV element through the AGCT overhang is just as likely as the association of a CMV element with a GFP element through the AGCT overhang. As such, the efficiency of generating a construct comprising an operatively covalently linked construct containing, in order from 5' to 3', a CMV element, a GFP element and a BGH element would be reduced as compared to the efficiency of generating such a construct using the elements as shown in FIG. 2C. The elements shown in FIG. 2B contain palindromic overhangs at one end of the GFP element and at the end of the BGH element shown and, therefore, would be less efficient than the elements of FIG. 2C, but more efficient than those in FIG. 2A, for generating the desired construct.

A nucleotide sequence used in the methods and kits of the current invention can be designed to contain a bridging phosphorothioate to prevent religation after topoisomerase-cleavage. For example, where the topoisomerase is E. coli topoisomerase III, the bridging phosphorothioate can be incorporated between the two thymidines of the GCAACTT cleavage/recognition sequence. When cleaved, the clipped sequence contains a 3'-SH instead of a 3'-OH, thus preventing religation (see Burgin et al, Nucl. Acids Res. 23:2973-2979, 1995).

A ds nucleotide sequence useful in a method or kit of an aspect of the invention can be amplified by an amplification method such as PCR to contain a topoisomerase recognition site at a 3' or 5' terminus of an end. Furthermore, one or both primers used for PCR can be designed such that, upon cleavage of an amplified ds nucleotide sequence, the cleaved ds nucleotide sequence contains a 5' or 3' overhang at one or both ends. In one embodiment, PCR primers are designed such that the 5' overhanging sequence on a first ds nucleotide sequence is complementary to a 5' overhanging sequence on a second (or other) ds nucleotide sequence, thereby facilitating the association of the nucleotide sequences, preferably in a predetermined orientation, whereupon they can be covalently linked according to a method of the invention. In accordance with the invention, by designing unique overhanging sequences for the different ds nucleotide sequence to be linked, any number of ds nucleotide sequences can be linked in a desired order and/or orientation.

It should be recognized that PCR is used in two ways with respect to the methods of the invention. In one aspect, PCR primers are designed to impart particular characteristics to a desired ds nucleotide sequence, for example, a ds nucleotide sequence that encodes a transcriptional or translational regulatory element or a coding sequence of interest such as an epitope tag or cell compartmentalization domain. In this aspect, the PCR primers can be designed such that, upon amplification, the ds nucleotide sequence contains a topoisomerase recognition site at one or both ends, as desired. As disclosed herein, the PCR primer also can include an additional sequence such that, upon cleavage of the amplification product by a site specific topoisomerase, the cleaved ds nucleotide sequence contains a 5' or 3' overhanging sequence at the topoisomerase cleaved end. In an embodiment of the invention involving a topoisomerase that binds and cleaves a 5' terminus (e.g., an embodiment involving a type IA topoisomerase), the PCR primers can be designed to contain a bridging phosphorothioate linkage (see above), which can block religation after topoisomerase cleavage and can assist in the generation of a topoisomerase-charged amplification product.

Overhanging sequences generated using PCR can include a single nucleotide overhang that is generated as an artifact of the PCR reaction. For example, a polymerase such at Taq, which does not have a proof-reading function and has an inherent terminal transferase activity, is commonly used, and produces PCR products containing a single, non-template derived 3' A overhang at each end. These amplification products can be linked to topoisomerase-charged ds nucleotide sequences containing a single 3' T overhang or a single 3' dU overhang, which, for a T/A cloning reaction, can be a vector (see U.S. Pat. Nos. 5,487,993 and 5,856,144, each of which is incorporated herein by reference), at one or both ends, using the methods of the invention.

Figure 6:
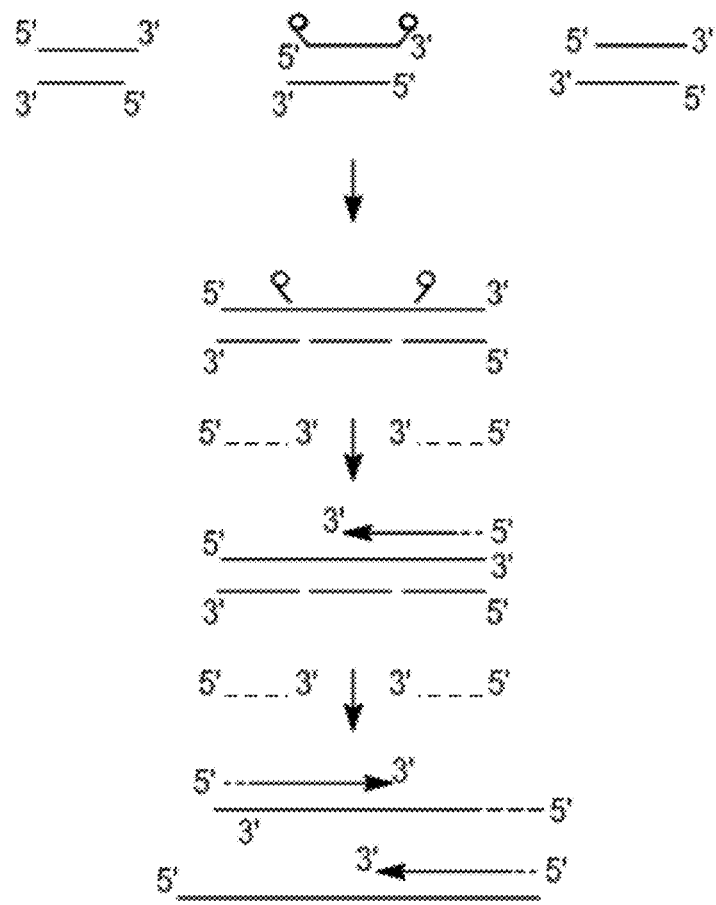
FIG. 6 illustrates the generation of an expressible ds recombinant nucleic acid molecule and amplification of the expressible ds recombinant nucleic acid molecule. Topoisomerase is shown as a solid circle, and is either attached to a terminus of a substrate ds nucleotide sequence or is released following a linking reaction. The expressible ds recombinant nucleic acid molecule is generated from three ds nucleotide sequences, including a nucleotide sequence comprising a promoter, a nucleotide sequence comprising a coding sequence, and a nucleotide sequence comprising a polyadenylation signal. Generation of the nucleic acid molecule can be facilitated by the incorporation of complementary 5' and/or 3' overhanging sequences at the ends of the ds nucleotides sequences to be joined. The expressible ds recombinant nucleic acid molecule is generated by contacting a first ds nucleotide sequence having a type IA topoisomerase at a 5' terminus of a first end and a type IB topoisomerase at a 3' terminus of a second end, with a second ds nucleotide sequence and a third double stranded nucleotide sequence. The expressible ds recombinant nucleic acid molecule is amplified using a first primer that hybridizes to the second ds recombinant nucleic acid molecule upstream of the promoter, and a second primer that hybridizes to the third ds recombinant nucleic acid molecule downstream of the polyadenylation signal.

PCR also is used to amplify a covalently linked ds recombinant nucleic acid molecule covalently linked in one or both strands, generated by a method of the invention. For example, as illustrated in FIG. 6, a method of the invention can generate an expressible ds recombinant nucleic acid molecule from three substrate ds nucleotide sequences, including a nucleotide sequence comprising a promoter, a nucleotide sequence comprising a coding sequence, and a nucleotide sequence comprising a polyadenylation signal. The generation of the ds recombinant nucleic acid molecule can be facilitated by the incorporation of complementary 3' (or 5') overhanging sequences at the ends of the ds nucleotides sequences to be joined. For example, the expressible ds recombinant nucleic acid molecule can be generated by contacting a first ds nucleotide sequence having a type IA topoisomerase at a 5' terminus of a first end and a type IB topoisomerase at a 3' terminus of a second end with a second ds nucleotide sequence and a third double stranded nucleotide sequence. By designing a PCR primer pair containing a first primer that is specific for a portion of the nucleotide sequence comprising the promoter that is upstream from the promoter, and a second primer that is specific for a portion of the nucleotide sequence comprising the polyadenylation signal that is down stream of the signal, only a full length functional ds recombinant nucleic molecule containing the promoter, coding sequence and polyadenylation signal in the correct (predetermined) orientation will be amplified. In particular, partial reaction products, for example, containing only a promoter linked to the coding sequence, and reaction products containing nicks are not amplified. Thus, PCR can be used to specifically design a ds nucleotide sequence such that it is useful in a method of the invention, and to selectively amplify only those reaction products having the desired components and characteristics.

As used herein, the term "covalently linked," when used in reference to a ds recombinant nucleic acid molecule, means that the nucleic acid molecule is generated from at least two ds nucleotide sequences that are ligated together, in both strands, by a topoisomerase mediated ligation. It should be recognized, for example, that a topoisomerase covalently bound to one of the ds nucleotide sequences to be covalently linked can be the same as or different from the topoisomerase covalently bound to the other ds nucleotide sequence. Thus, a Vaccinia topoisomerase can be covalently bound to one ds nucleotide sequence and another poxvirus or eukaryotic nuclear type IB topoisomerase can be bound to the other strand. Generally, however, the topoisomerases, where different, are members of the same family, for example, type IA or type IB or type II, although, where the topoisomerases are covalently bound, for example, to a 5' phosphate and generate complementary 3' overhangs, the topoisomerase can be from different families, for example, type IA and type 11.

The term "covalently linked" also is used herein in reference to a single stranded or double stranded nucleic acid molecule that is generated from at least two nucleotide sequences that are ligated together in one strand. For example, a ds recombinant nucleic acid molecule that is generated when a first topoisomerase-charged ds nucleotide sequence that includes one topoisomerase bound at or near a 5' terminus contacts a second ds nucleotide sequence under conditions such that the topoisomerases can covalently link the 5' terminus of the first ds nucleotide sequence to which it is bound, to the 3' terminus of the second ds nucleotide sequence, can generate a ds recombinant nucleic acid molecule covalently linked in one strand.

In one embodiment, a ds recombinant nucleic acid molecule covalently linked in both strands generated according to a method of the invention does not contain a nick in either strand at the site where two nucleotide sequences are ligated, although it can contain nicks elsewhere in the molecule. In a method for generating a ds recombinant nucleic acid molecule covalently linked in one strand, a ds recombinant nucleic acid molecule is generated that contains a nick at least at the position where ends were linked in the complementary strands. This nicked ds recombinant nucleic acid molecule can be converted to a ds recombinant nucleic acid molecule covalently linked in both strands by introducing the nicked ds recombinant nucleic acid molecule into a cell, or by subjecting the ds recombinant nucleic acid molecule to a ligation reaction, such as using a ligase, as is well known in the art.

The term "recombinant" is used herein to refer to a nucleic acid molecule that is produced by linking at least two nucleotide sequences according to a method of the invention. As such, a ds recombinant nucleic acid molecule encompassed within the present invention is distinguishable from a nucleic acid molecule that may be produced in nature, for example, during meiosis. For example, a ds recombinant nucleic acid molecule covalently linked in both strands generated according to a method of certain aspects of the invention can be identified by the presence of the two topoisomerase recognition sites, one present in each of the complementary strands, at or near the site at which the ds nucleotide sequences were joined.

A method of the invention can be performed by contacting a first ds nucleotide sequence having a first end and a second end, wherein at the first end or second end or both, the first ds nucleotide sequence has a topoisomerase recognition site, or cleavage product thereof, at or near the 3' terminus and has (or can be made to have, for example, by contact with a phosphatase) a hydroxyl group at the 5' terminus of the same end; at least a second ds nucleotide sequence having a first end and a second end, wherein at the first end or second end or both, the at least second ds nucleotide sequence has a topoisomerase recognition site, or cleavage product thereof, at or near the 3' terminus and has (or can be made to have) a hydroxyl group at the 5' terminus of the same end; and a topoisomerase, under conditions such that the components are in contact and the topoisomerase can effect its activity. Upon contact of the topoisomerase with the first and second (or other) ds nucleotide sequences, and cleavage, where necessary, each nucleotide sequence comprises at the cleavage site a covalently bound topoisomerase at the 3' terminus and has, or can have, a hydroxyl group at the 5' terminus such that, upon contact, the first and at least second nucleotide sequences are covalently linked in both strands. Accordingly, the invention provides a ds recombinant nucleic acid molecule covalently linked in both strands produced by such a method.

As used herein, the term "at or near," when used in reference to the proximity of a topoisomerase recognition site to the 3' (type IB) or 5' (type IA or type II) terminus of a nucleotide sequence, means that the site is within about 1 to 100 nucleotides from the 3' terminus or 5' terminus, respectively, generally within about 1 to 20 nucleotides from the terminus, and particularly within about 2 to 12 nucleotides from the respective terminus. An advantage of positioning the topoisomerase recognition site within about 10 to 15 nucleotides of a terminus is that, upon cleavage by the topoisomerase, the portion of the sequence downstream of the cleavage site can spontaneously dissociate from the remaining nucleotide sequence, which contains the covalently bound topoisomerase (referred to generally as "suicide cleavage"; see, for example, Shuman, supra, 1991; Andersen et al., supra, 1991). Where a topoisomerase recognition site is greater than about 12 to 15 nucleotides from the terminus, the nucleotide sequence upstream or downstream of the cleavage site can be induced to dissociate from the remainder of the sequence by modifying the reaction conditions, for example, by providing an incubation step at a temperature above the melting temperature of the portion of the duplex including the topoisomerase cleavage site.

An additional advantage of constructing a first or second (or other) ds nucleotide sequence to comprise, for example, a type IB topoisomerase recognition site about 2 to 15 nucleotides from one or both ends is that a 5' overhang is generated following cleavage of the ds nucleotide sequence by a site specific topoisomerase. Such a 5' overhanging sequence, which would contain 2 to 15 nucleotides, respectively, can be designed using a PCR method as disclosed herein to have any sequence as desired. Thus, where a cleaved first ds nucleotide sequence is to be covalently linked to a selected second (or other) ds nucleotide sequence according to a method of the invention, and where the selected sequence has a 5' overhanging sequence, the 5' overhang on the first ds nucleotide sequence can be designed to be complementary to the 5' overhang on the selected second (or other) ds sequence such that the two (or more) sequences are covalently linked in a predetermined orientation due to the complementarity of the 5' overhangs. As discussed above, similar methods can be utilized with respect to 3' overhanging sequences generated upon cleavage by, for example, a type IA or type II topoisomerase.

As used herein, reference to a nucleotide sequence having "a first end" and "a second end" means that the nucleotide sequence is linear. A substrate ds nucleotide sequence can be linear or circular, including supercoiled, although, as a result of cleavage by one or more topoisomerase, a linear topoisomerase-charged ds nucleotide sequence generally is produced. For example, a circular ds nucleotide sequence containing two type IB topoisomerase recognition sites within about 100 nucleotides of each other and in the complementary strands, preferably within about twenty nucleotides of each other and in the complementary strands, can be contacted with a site specific type IB topoisomerase such that each strand is cleaved and the intervening sequence dissociates, thereby generating a linear ds nucleotide sequence having a topoisomerase covalently bound to each end.

It should be recognized that reference to a first end or a second end of a ds nucleotide sequence is not intended to imply any particular orientation of the nucleotide sequence, and is not intended to imply a relative importance of the ends with respect to each other. Where a nucleotide sequence having a first end and second end is a double stranded nucleotide sequence, each end contains a 5' terminus and a 3' terminus. Thus, reference is made herein, for example, to a nucleotide sequence containing a topoisomerase recognition site at a 3' terminus and a hydroxyl group at the 5' terminus of the same end, which can be the first end or the second end.

A method of the invention can be performed using only a first ds nucleotide sequence and a second ds nucleotide sequence, or can additionally include a third, fourth or more ds nucleotide sequences as desired. Generally, each such nucleotide sequence contains a topoisomerase recognition site, or a cleavage product thereof, at or near at least one 3' or 5' terminus, and can contain a hydroxyl group at the 5' terminus of the same end, or a hydroxyl group can be generated using a phosphatase. Where a nucleotide sequence does not contain a topoisomerase recognition site at or near an end to be linked to a second nucleotide sequence, a topoisomerase recognition site can be introduced into the nucleotide sequence using a method as disclosed herein, for example, by PCR amplification of the sequence using a primer comprising a complement of the topoisomerase recognition site.

The terms "first nucleotide sequence," "second nucleotide sequence," "third nucleotide sequence," and the like, are used herein only to provide a means to indicate which of several nucleotide sequences is being referred to. Thus, absent any specifically defined characteristic with respect to a particular nucleotide sequence, the terms "first," "second," "third" and the like, when used in reference to a nucleotide sequence, or a population or plurality of nucleotide sequences, are not intended to indicate any particular order, importance or other information about the nucleotide sequence. Thus, where an exemplified method refers, for example, to using PCR to amplify a first ds nucleotide sequence such that the amplification product contains a topoisomerase recognition site at one or both ends, it will be recognized that, similarly, a second (or other) ds nucleotide sequence also can be so amplified.

The term "at least a second nucleotide sequence" is used herein to mean one or more nucleotide sequences in addition to a first nucleotide sequence. Thus, the term can refer to only a second nucleotide sequence, or to a second nucleotide sequence and a third nucleotide sequence (or more). As such, the term "second (or other) nucleotide sequence" or second (and other) nucleotide sequences" is used herein in recognition of the fact that the term "at least a second nucleotide sequence" can refer to a second, third or more nucleotide sequences. It should be recognized that, unless indicated otherwise, a nucleotide sequence encompassed within the meaning of the term "at least a second nucleotide sequence" can be the same or substantially the same as a first nucleotide sequence. For example, a first and second ds nucleotide sequence can be the same except for having complementary 5' overhanging sequences produced upon cleavage by a topoisomerase such that the first and second ds nucleotide sequences can be covalently linked using a method of the invention. As such, a method of the invention can be used to produce a concatenate of first and second ds nucleotide sequences, which, optionally, can be interspersed, for example, by a third ds nucleotide sequence such as a regulatory element, and can contain the covalently linked sequences in a predetermined directional orientation, for example, each in a 5' to 3' orientation with respect to each other.

As disclosed herein, a method of the invention provides a means to covalently link, two or more ds nucleotides in a predetermined directional orientation. The term "directional orientation" or "predetermined directional orientation" or "predetermined orientation" is used herein to refer to the covalent linkage, of two or more nucleotide sequences in a particular order. Thus, a method of the invention provides a means, for example, to covalently link, a promoter regulatory element upstream of a coding sequence, and to covalently link a polyadenylation signal downstream of the coding region to generate a functional expressible ds recombinant nucleic acid molecule; or to covalently link two coding sequences such that they can be transcribed and translated in frame to produce a fusion polypeptide.

A method of the invention also can be performed by contacting a first ds nucleotide sequence having a first end and a second end, wherein at the first end or second end or both, the first ds nucleotide sequence has a type IB topoisomerase covalently bound at the 3' terminus (topoisomerase-charged) and has (or can be made to have) a hydroxyl group at the 5' terminus of the same end; and at least a second type IB topoisomerase-charged ds nucleotide sequence, which has (or can be made to have) a hydroxyl group at the 5' terminus at the same end. Upon contact of the topoisomerase-activated first and at least second nucleotide sequences at the ends containing the topoisomerase and a 5' hydroxyl group, phosphodiester bonds are formed in each strand, thereby generating a ds recombinant nucleic acid molecule covalently linked in both strands.

The invention further provides methods for linking two or more (e.g., two, three, four, five, six, seven, etc.) nucleotide sequences, wherein the linked ds recombinant nucleic acid molecule is covalently linked in one strand, but not both strands, (i.e. the ds recombinant nucleic acid molecule contains a nick in one strand at each position where two ends were joined to generate the ds recombinant nucleic acid molecule. Using the schematic shown in FIG. 4A for purposes of illustration, the invention includes methods for linking at least two nucleotide sequences comprising contacting a first ds nucleotide sequence having a first end and a second end, wherein at the first end at the second end or at both ends, the first ds nucleotide sequence has a site-specific type IA topoisomerase covalently bound to the 5' termini; and a second ds nucleotide sequence which does not have topoisomerase covalently bound to either termini of at least one end. Further, the second nucleotide sequence will typically have hydroxyl groups at the 3' termini of the end being joined to the first ds nucleotide sequence. In many instances, the two nucleotide sequences to be joined will have either 3' or 5' overhangs with sufficient sequence complementarity to allow for hybridization. In related embodiments, the first and second ds nucleotide sequences described above may be first and second ends of the same ds nucleotide sequence. Thus, connection of the two ends results in the formation of a circularized molecule.

Using the schematic shown in FIG. 4B for purposes of illustration, the invention includes methods for joining three or more nucleotide sequences. While any number of variations of the invention are possible, three nucleotide sequences may be joined by the use of a linker molecule which contains topoisomerases at both the 5' and 3' termini of one end. Thus, upon joining of the three nucleotide sequences, a single nucleotide sequence is formed which contains a first strand with no nicks at the junction points, and a second strand with nicks at the junction points. This process has the advantage of employing a single topoisomerase modified molecule to join three nucleotide sequences together.

The invention further provides methods for covalently linking both strands of two or more (e.g., two, three, four, five, six, seven, etc.) ds nucleotide sequences. Using the schematic shown in FIG. 5A for purposes of illustration, the invention includes methods for linking at least two nucleotide sequences comprising contacting a first ds nucleotide sequence having a first end and a second end, wherein at the first end at the second end or at both ends, the first ds nucleotide sequence has two topoisomerases (e.g., a type IA and a type IB topoisomerase) one each covalently bound to the 3' and 5' termini; and a second ds nucleotide sequence which does not have topoisomerase covalently bound to either termini of at least one end. Further, the second nucleotide sequence will often have hydroxyl groups at the 5' and 3' termini of the end being joined to the first ds nucleotide sequence. In many instances, the two nucleotide sequences to be joined will have either 3' or 5' overhangs with sufficient sequence complementarity to allow for hybridization. In related embodiments, the first and second ds nucleotide sequences as described above can be first and second ends of the same ds nucleotide sequence. Thus, connection of the two ends results in the formation of a circularized molecule.

Using the schematic shown in FIG. 5D for purposes of illustration, the invention includes methods for joining three or more nucleotide sequences. While any number of variations of the invention are possible, three nucleotide sequences may be joined by the use of a linker molecule which contains topoisomerases at both the 5' and 3' termini of each end. Thus, upon joining of the three nucleotide sequences, a single nucleotide sequence is formed which contains no nicks at the junction points. This process has the advantage of employing a single topoisomerase modified molecule to join three nucleotide sequences together.

The present invention also provides compositions, and kits containing such compositions, including kits containing component useful for performing methods of the invention. In one aspect, a composition of the invention comprises isolated components characteristic of a step of a method of the invention. For example, a composition of the invention can comprise two or more of the same or different topoisomerase-charged ds nucleotide sequences. As used herein, the term "different," when used in reference to the ds nucleotide sequences of a composition of the invention, means that the ds nucleotide sequences share less than 95% sequence identity with each when optimally aligned, generally less than 90% sequence identity, and usually less than 70% sequence identity. Thus, ds nucleotide sequences that, for example, differ only in being polymorphic variants of each other or that merely contain different 5' or 3' overhanging sequences are not considered to be "different" for purposes of a composition of the invention. In comparison, different ds nucleotide sequences are exemplified by a first sequence encoding a polypeptide and second sequence comprising a regulatory element, or a first sequence encoding a first polypeptide a second sequence encoding a non-homologous polypeptide.

Where a composition of the invention comprises more than two different isolated ds nucleotide sequences or more than two different topoisomerase-charged ds nucleotide sequences, each of the ds nucleotide sequences is different from each other, i.e., they are all different from each other. However, it will be recognized that each of the ds nucleotide sequences, for example, a sequence referred to as a first ds nucleotide sequence, generally comprises a population of such nucleotide sequences, which are identical or substantially identical to each other. Thus, it should be clear that the term "different" is used in comparing, for example, a first (or population of first) ds nucleotide sequences with a second (and other) ds nucleotide sequence. A composition comprising two or more different topoisomerase-charged ds nucleotide sequences can further comprise a topoisomerase. Examples of such ds nucleotide sequences comprising the components of a composition of the invention are disclosed herein and include, for example, coding sequences, transcriptional regulatory element, translational regulatory elements, elements encoding a detectable or selectable markers such as an epitope tag or an antibiotic resistance gene, elements encoding polypeptide domains such as cell compartmentalization domains or signal peptides, and the like.

As used herein, the term "isolated" means that a molecule being referred to is in a form other than that in which it exists in nature. In general, an isolated nucleotide sequence, for example, can be any nucleotide sequence that is not part of a genome in a cell, or is separated physically from a cell that normally contains the nucleotide sequence. It should be recognized that various compositions of the invention comprise a mixture of isolated ds nucleotide sequences. As such, it will be understood that the term "isolated" only is used in respect to the isolation of the molecule from its natural state, but does not indicate that the molecule is an only constituent.

A composition of the invention can comprise two different ds nucleotide sequences, each of which contains a topoisomerase recognition site at or near one or both ends, and a site specific topoisomerase, which can bind to and cleave the ds nucleotide sequences at the topoisomerase recognition site. Optionally, at least one of the different ds nucleotide sequences can be a topoisomerase-charged ds nucleotide sequence. Preferably, the topoisomerase covalently bound to the topoisomerase-charge ds nucleotide sequence is of the same family as the topoisomerase in the composition.

Various combinations of components can be used in a method of the invention. For example, the method can be performed by contacting a topoisomerase-activated first ds nucleotide sequence; a second ds nucleotide sequence having a first end and a second end, wherein at the first end or second end or both, the second nucleotide sequence has a topoisomerase recognition site at or near the 3' terminus, and a hydroxyl group at the 5' terminus of the same end; and a topoisomerase. Where the 5' terminus of one or both ends to be linked has a 5' phosphate group, a phosphatase also can be contacted with the components of the reaction mixture. Upon such contacting, the topoisomerase can cleave the second nucleotide sequence to produce a topoisomerase-activated second ds nucleotide sequence, the phosphatase, if necessary, can generate a 5' hydroxyl group at the same end, and the second ds nucleotide sequence then can be covalently linked to the topoisomerase-activated first ds nucleotide sequence. As such, it will be recognized that a composition of the invention can comprise any of various combinations of components useful for performing a method of the invention.

In general, a method of the invention for generating a ds recombinant nucleic acid molecule covalently linked in both strands is based on the determination that a ds recombinant nucleic acid molecule covalently linked in both strands can be produced by contacting a first ds nucleotide sequence with a second ds nucleotide sequence, wherein the first and second sequences each have, at the ends to be linked, a topoisomerase recognition site, for example, 5'-(CIT)CCTT-3' (Shuman, supra, 1991; U.S. Pat. No. 5,766,891). Upon cleavage, the site specific topoisomerase is covalently bound at the 3' terminus. Where the cleaved nucleotide sequences also contain a 5' hydroxy group at the same end as the bound topoisomerase, and the ends of the two nucleotide sequences associate, the topoisomerase on each 3' terminus can covalently link that terminus to a 5' hydroxyl group on the associated nucleotide sequence (see FIG. 1).

As used herein, reference to contacting a first nucleotide sequence and at least a second nucleotide sequence "under conditions such that all components are in contact" means that the reaction conditions are appropriate for the topoisomerase-cleaved ends of the nucleotide sequences to come into sufficient proximity such that a topoisomerase can effect its enzymatic activity and covalently link the 3' or 5' terminus of a first nucleotide sequence to a 5' or 3' terminus, respectively, of a second nucleotide sequence. Examples of such conditions, which include the reaction temperature, ionic strength, pH, and the like, are disclosed herein, and other appropriate conditions as required, for example, for particular 5' overhanging sequences of the termini generated upon topoisomerase cleavage, can be determined empirically or using formulas that predict conditions for specific hybridization of nucleotide sequences, as is well known in the art (see, for example, (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference).

In one embodiment, a method of the invention provides a means to render an open reading from a cDNA or an isolated genomic DNA sequence expressible by operatively linking one or more regulatory elements to the putative coding sequence. Accordingly, a first ds nucleotide sequence comprising an open reading frame can be amplified by PCR using a primer pair that generates an amplified first ds nucleotide sequence having a topoisomerase recognition site at one or both ends, as desired, preferably such that, upon cleavage by the site specific topoisomerase, one or both ends contains a defined 5' or 3' overhang. Where both ends of the amplified first ds nucleotide sequence are so constructed, the 5' or 3' overhanging sequences generally, but not necessarily, are different from each other. The amplified first ds nucleotide sequence then can be contacted with a second ds nucleotide sequence comprising a desired regulatory element such as a promoter and, in certain embodiments, a topoisomerase recognition site, and with a topoisomerase, such that the second nucleotide sequence is operatively covalently linked to the 5' end of the coding sequence according to a method of the invention.

In such a method, a second (or other) ds nucleotide sequence also can comprise two or more regulatory elements, for example, a promoter, an internal ribosome entry site and an ATG initiator methionine codon, or the like, or other sequence of interest, for example, an sequence encoding an epitope tag, in operative linkage with each other, and which can be operatively covalently linked to the 5' end of a first ds nucleotide sequence comprising a coding sequence. Such a method can further include contacting a third ds nucleotide sequence comprising, for example, a polyadenylation signal, which can be operatively covalently linked according to a method of the invention to the 3' end of the coding sequence, thereby generating an expressible ds recombinant nucleic acid molecule. As such, a method of the invention provides a means for generating a functional ds recombinant nucleic acid molecule that can be transcribed, translated, or both as a functional unit. As disclosed herein, the inclusion of complementary 5' or 3' overhanging sequences generated by topoisomerase cleavage at the termini of the ds nucleotide sequences to be linked together by the site specific topoisomerase facilitates the generation of a ds recombinant nucleic acid molecule having a desired directional orientation of the nucleotide sequences in the construct.

In another embodiment, a method of the invention is performed such that the first ds nucleotide sequence or a second (or other) ds nucleotide sequence, or combination thereof, is one of a plurality of nucleotide sequences. As used herein, the term "plurality," when used in reference to a first or at least a second nucleotide sequence, means that the nucleotide sequences are related but different. For purposes of the present invention, the nucleotide sequences of a plurality are "related" in that each nucleotide sequence in the plurality contains at least a topoisomerase recognition site, or a cleaved form thereof, at one or more termini. Furthermore, the nucleotide sequences of a plurality are "different" in that they can comprise, for example, a cDNA library, a combinatorial library of nucleotide sequences, a variegated population of nucleotide sequences, or the like. Methods of making cDNA libraries, combinatorial libraries, libraries comprising variegated populations of nucleotide sequences, and the like are well known in the art (see, for example, U.S. Pat. Nos. 5,837, 500; 5,622,699; 5,206,347; Scott and Smith, *Science* 249: 386-390, 1992; Markland et al., *Gene* 109:13-19, 1991; O'Connell et al., *Proc Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference).

The present invention further provides a method of generating a ds recombinant nucleic acid molecule covalently linked in both strands by amplifying a portion of a first nucleotide sequence using a PCR primer pair, wherein at least one primer of the primer pair encodes a topoisomerase recognition site or a complement thereof, thereby producing a first ds nucleotide sequence having a first end and a second end, wherein the first end or second end or both has a topoisomerase recognition site at the 3' terminus and/or the 5' terminus; and contacting the first ds nucleotide sequence; at least a second ds nucleotide sequence having a first end and a second end, wherein the first end or second end or both has a topoisomerase recognition site at the 3' terminus and/or the 5' terminus, or a cleavage product thereof; and a topoisomerase (see FIG. 1). When contacted under conditions such that an end of the first ds nucleotide sequence having a topoisomerase recognition site and an end of the at least second ds nucleotide sequence having a topoisomerase recognition site can associate, a ds recombinant nucleic acid molecule covalently linked in both strands is generated.

As disclosed herein, a PCR method using primers designed to incorporate a topoisomerase recognition site at one or both ends of an amplified ds nucleotide sequence provides a convenient means for producing ds nucleotide sequences useful in a method of the invention. In certain embodiments, at least one of the primers of a primer pair is designed such that it comprises, in a 5' to 3' orientation, a nucleotide sequence complementary to a topoisomerase recognition site, and a nucleotide sequence complementary to the 3' end of a target nucleic acid molecule to be amplified (i.e., a target specific region). In addition, the primer can contain, in a position 5' to the complement of the topoisomerase recognition site, a desired nucleotide sequence of any length (generally about 1 to 100 nucleotide, usually about 2 to 20 nucleotides, and particularly about 4 to 12 nucleotides), which, upon cleavage of the amplification product by a site specific topoisomerase, forms a desired 5' overhang. The second primer of the PCR primer pair can be complementary to a desired sequence of the nucleotide sequence to be amplified, and can comprise a complement to a topoisomerase recognition site, a sequence that would generate a 5' overhang upon cleavage by a site specific topoisomerase, or any other sequence, as desired.

Such a primer can comprise or encode any other sequence of interest, including, for example, a site specific integration recognition site such as an att site, a lox site, or the like, or, as discussed above, can simply be used to introduce a topoisomerase recognition site into a ds nucleotide sequence comprising such a sequence of interest. A ds recombinant nucleic acid molecule generated according to a method of the invention and containing a site specific integration recognition site such as an att site or lox site can be integrated specifically into a desired locus such as into a vector, a gene locus, or the like, that contains the required integration site, for example, an att site or lox site, respectively, and upon contact with the appropriate enzymes required for the site specific event, for example, lambda Int and IHF proteins or Cre recombinase, respectively. The incorporation, for example, of attB or attP sequences into a ds recombinant nucleic acid molecule covalently linked in both strands according to a method of the invention allows for the convenient manipulation of the nucleic acid molecule using the GATEWAY™ Cloning System (Invitrogen Corp., La Jolla Calif.).

In one embodiment, a construct generated according to a method of the invention is further amplified by a PCR reaction or other amplification reaction. Direct PCR of a ds recombinant nucleic acid molecule generated according to a method of the invention is possible because the construct is covalently linked in at least one strand. As such, PCR can be used to generate a large amount of the construct. More importantly, as indicated above, PCR provides an in vitro selection method for obtaining only a desired product generated according to a method of the invention, without obtaining partial reaction products. For example, a method of the invention can be used to generate a ds recombinant nucleic acid molecule covalently linked in both strands comprising, operatively linked in a 5' to 3' orientation, a first ds nucleotide sequence comprising a promoter, a second ds nucleotide sequence comprising a coding region, and a third ds nucleotide sequence comprising a polyadenylation signal.

As disclosed herein, a construct having a predetermined orientation can be generated by including complementary 5' overhanging sequences on the ends of the ds nucleotide sequences to be joined. By selecting a PCR primer pair including a first primer complementary to the first ds nucleotide sequence and upstream of the promoter sequence, and a second primer complementary to the third ds nucleotide sequence and downstream of the polyadenylation signal, a functional amplification product comprising the promoter, coding region and polyadenylation signal can be generated. In contrast, partial reaction products that lack either the first ds nucleotide sequence or third ds nucleotide is not amplified because either the first or second primer, respectively, would not hybridize to the partial product. In addition, a construct lacking the second ds nucleotide sequence would not be generated due to the lack of complementarity of the 5' overhanging sequences of the first and third ds nucleotide sequences. As such, a method of the invention provides a means to obtain a desired functional ds recombinant nucleic acid molecule covalently linked in both strands.

The use of PCR in such a manner further provides a means to screen a large number of nucleic acid molecules generated according to a method of the invention in order to identify constructs of interest. Since methods for utilizing PCR in automated high throughput analyses are routine and well known, it will be recognized that the methods of the invention can be readily adapted to use in a high throughput system. Using such a system, a large number of constructs can be screened in parallel, and partial or incomplete reaction products can be identified and disposed of, thereby preventing a waste of time and expense that would otherwise be required to characterize the constructs or examine the functionality of the constructs in further experiments.

The methods of the invention have broad application to the field of molecular biology. As discussed in greater detail below, the methods of the invention can be used, for example, to label DNA or RNA probes, to perform directional cloning (see Example 1.B), to generate sense or antisense RNA molecules (see Example 2.A), to prepare bait or prey constructs for performing a two hybrid assay (see Example 2.C), to prepare linear expression elements (see Examples 2.A and 2.B), and to prepare constructs useful for coupled in vitro transcription/translation assays (see Example 2.B). For example, a method of generating ds recombinant nucleic acid molecules covalently linked in both strands provides a means to generate linear expression elements (LEEs), which consist of a linear nucleic acid molecule comprising two or more nucleotide sequences such as a promoter or other regulatory element linked to an open reading frame (see Example 1). LEEs have been reported to efficiently transfect cells, thus bypassing a requirement for cloning the expression element in a vector (Sykes and Johnston, *Nat. Biotechnol.* 17:355-359, 1999). The components of a LEE can be noncovalently linked, or can be covalently linked via a ligation reaction. The preparation of noncovalently linked LEEs requires using PCR primers containing deoxyuridine residues to amplify each nucleotide sequence component, then treating the PCR products with uracil-DNA glycosylase to generate overhanging ends that can hybridize. However, the efficiency of transfection using such noncovalently linked LEEs is variable, and, in some cases, much lower than the efficiency of covalently linked LEEs (Sykes and Johnston, supra, 1999). Furthermore, such LEEs are not suitable for use as templates for PCR amplification because the primer extension reaction cannot proceed past nicks in the template and, therefore, is terminated producing incomplete reaction products.

A method of the invention provides a straightforward and simple means to generate covalently linked LEEs, thereby avoiding the inconvenient and additional steps previously described for preparing a LEE, as well as reducing variability in transfection efficiency as observed using noncovalently linked LEEs. For example, a first ds nucleotide sequence, which encodes an open reading frame of interest, can be amplified by PCR as disclosed herein to contain a topoisomerase recognition site, or cleavage product thereof, on one or both ends. Furthermore, the PCR primers can be designed such that, upon cleavage of the amplified first ds nucleotide sequence by a site specific topoisomerase, the cleavage product contains a predetermined and desired 5' overhanging sequence. A second nucleotide sequence (and a third or more, as desired), in addition to containing a topoisomerase recognition site, or cleavage product thereof, can include or encode a regulatory element, for example, a promoter, an enhancer, a silencer, a splice acceptor site, a translation start site, a ribosome recognition site or internal ribosome entry site, a polyadenylation signal, an initiator methionine codon, or a STOP codon, or can encode any other desired sequence such as an epitope tag or cell compartmentalization domain. Preferably, the second (or other) ds nucleotide sequence to be covalently linked to the first ds nucleotide sequence has a 5' overhanging sequence that is complementary to the 5' overhang at the end of the first ds nucleotide sequence to which it is to be linked. Upon contact of such nucleotide sequences in presence of a topoisomerase a promoter, for example, can be operatively covalently linked to the 5' terminus of the open reading frame, and a polyadenylation signal can be operatively covalently linked to the 3' terminus of the open reading frame, thereby generating a covalently linked functional LEE (see Example 1).

Examples of regulatory elements useful in the present invention are disclosed herein and include transcriptional regulatory elements, translational regulatory elements, elements that facilitate the transport or localization of a nucleotide sequence or polypeptide in (or out of) a cell, elements that confer a detectable phenotype, and the like. Transcriptional regulatory elements include, for example, promoters such as those from cytomegalovirus, Moloney leukemia virus, and herpes virus, as well as those from the genes encoding metallothionein, skeletal actin, phosphoenolpyruvate carboxylase, phosphoglycerate, dihydrofolate reductase, and thymidine kinase, as well as a GAL4 promoter and promoters from viral long terminal repeats (LTRs) such as Rous sarcoma virus LTR; enhancers, which can be constitutively active such as an immunoglobulin enhancer, or inducible such as SV40 enhancer; and the like. For example, a metallothionein promoter is a constitutively active promoter that also can be induced to a higher level of expression upon exposure to a metal ion such as copper, nickel or cadmium ion. In comparison, a tetracycline (tet) inducible promoter is an example of a promoter that is induced upon exposure to tetracycline, or a tetracycline analog, but otherwise is inactive. A transcriptional regulatory element also can be a tissue specific regulatory element, for example, a muscle cell specific regulatory element, such that expression of an encoded product is restricted to the muscle cells in an individual, or to muscle cells in a mixed population of cells in culture, for example, an organ culture. Muscle cell specific regulatory elements including, for example, the muscle creatine kinase promoter (Sternberg et al., *Mol. Cell. Biol.* 8:2896-2909, 1988, which is incorporated herein by reference) and the myosin light chain enhancer/promoter (Donoghue et al., *Proc. Natl. Acad. Sci., USA* 88:5847-5851, 1991, which is incorporated herein by reference) are well known in the art. Other tissue specific promoters, as well as regulatory elements only expressed during particular developmental stages of a cell or organism are well known in the art.

Regulatory or other elements useful in generating a construct according to a method of the invention can be obtained in various ways. In particular, many of the elements are included in commercially available vectors and can be isolated therefrom and can be modified to contain a topoisomerase recognition site at one or both ends, for example, using a PCR method as disclosed herein. In addition, the sequences of or encoding the elements useful herein generally are well known and disclosed in publications. In many cases, the elements, for example, many transcriptional and translational regulatory elements, as well as cell compartmentalization domains, are relatively short sequences and, therefore, are amenable to chemical synthesis of the element or a nucleotide sequence encoding the element. Thus, in one embodiment, an element comprising a composition of the invention, useful in generating a ds recombinant nucleic acid molecule according to a method of the invention, or included within a kit of the invention, can be chemically synthesized and, if desired, can be synthesized to contain a topoisomerase recognition site at one or both ends of the element and, further, to contain an overhanging sequence following cleavage by a site specific topoisomerase.

A topoisomerase-charged vector can be generated in the following manner (*Genome Res.* 9: 383-392, 1999): A vector is linearized with a restriction enzyme that leaves "sticky ends". Using a ligase such as T4 DNA ligase, adapter oligonucleotides are ligated to both ends, and both strands, of the linearized DNA. The adapter oligonucleotides contain and position a 5'-CCCTT-3' Vaccinia topoisomerase type I recognition sequence such that it can be cleaved by topoisomerase and trap the covalent topoisomerase-DNA complex at each 3' end of the vector. The adapted vector is then incubated with purified Vaccinia topoisomerase and an annealing oligonucleotide that complete the "topoisomerase sites" at each end of the vector. The annealing oligonucleotide acts to leave a break, or nick, in the "bottom" strand opposite the last T in the 5'-CCCTT-3' containing oligonucleotide. The oligonucleotide adapter fragments that are "downstream" of the topoisomerase cleavage site (the "leaving groups") are released upon topoisomerase cleavage and are removed in the topoisomerase-vector purification process. In the absence of the 5' hydroxyl from the "leaving group", topoisomerase is trapped in a covalent complex with the DNA ends to produce a topoisomerase-charged vector.

Where ds nucleotide sequences are to be covalently linked according to a method of the invention, the nucleotide sequences generally are operatively linked such that the recombinant nucleic acid molecule that is generated has a desired structure and performs a desired function or encodes a desired expression product. As used herein, the terms "operatively linked," and "operably connected," or the like, mean that two or more nucleotide sequences are positioned with respect to each other such that they act as a unit to effect a function attributable to one or both sequences or a combination thereof. The term "operatively covalently linked" is used herein to refer to operatively linked nucleotide sequences generated according to a method of the invention for generating a ds recombinant nucleic acid molecule covalently linked in one or both strands. For example, a nucleotide sequence containing an open reading frame can be operatively linked to a promoter such that the promoter confers its regulatory effect on the open reading frame similarly to the way in which it would effect expression of an open reading frame that it normally is associated with in a genome in a cell. Similarly, two or more nucleotide sequences comprising open reading frames can be operatively linked in frame such that, upon transcription and translation, a chimeric fusion polypeptide is produced.

Although a ds recombinant nucleic acid molecule covalently linked in one or both strands, generated according to a method of the invention generally is linear, the construct generated also can be a circularized ds recombinant nucleic acid molecule. Furthermore, a circular ds recombinant nucleic acid molecule can be generated such that it has the characteristics of a vector, and contains, for example, regulatory elements (expression control sequences) required for replication in a prokaryotic host cell, a eukaryotic host cell, or both; can contain a nucleotide sequence encoding a polypeptide that confers antibiotic resistance; a multiple cloning site; or the like. An advantage of such a method is that the generated ds recombinant nucleic acid molecule, which is circularized according to a method of the invention, can be transformed or transfected into an appropriate host cell, wherein the construct is amplified. Thus, in addition to an in vitro method such as PCR, which can be used to generate large amounts of a linear ds recombinant nucleic acid molecule generated according to a method of the invention, an in vivo method using a host cell can be used for obtaining a large amount of a circularized product generated according to a method of the invention. Such elements including bacterial origins of replication, antibiotic resistance genes, and the like, which comprise a topoisomerase recognition site according to the present invention, can be useful components to include in a kit of the invention as disclosed herein.

It should be recognized that a linear ds recombinant nucleic acid molecule covalently linked in one or both strands, also can be cloned into a vector, which can be a plasmid vector or a viral vector such as a bacteriophage, baculovirus, retrovirus, lentivirus, adenovirus, vaccinia virus, semliki forest virus and adeno-associated virus vector, all of which are well known and can be purchased from commercial sources (Promega, Madison Wis.; Stratagene, La Jolla Calif.; GIBCO/BRL, Gaithersburg Md.). If desired, the vector can be linearized and modified according to a method of the invention, for example, using a PCR method, to contain a topoisomerase recognition site, or cleavage product thereof, at one or both 3' termini, or can be constructed by one skilled in the art (see, generally, *Meth. Enzymol.*, Vol. 185, Goeddel, ed. (Academic Press, Inc., 1990); Jolly, *Canc. Gene Ther.* 1:51-64, 1994; Flotte, *J. Bioenerg. Biomemb.* 25:37-42, 1993; Kirshenbaum et al., *J. Clin. Invest.* 92:381-387, 1993; each of which is incorporated herein by reference).

Viral expression vectors can be particularly useful where a method of the invention is practiced for the purpose of generating a ds recombinant nucleic acid molecule covalently linked in one or both strands, that is to be introduced into a cell, particularly a cell in a subject. Viral vectors provide the advantage that they can infect host cells with relatively high efficiency and can infect specific cell types or can be modified to infect particular cells in a host.

Viral vectors have been developed for use in particular host systems and include, for example, baculovirus vectors, which infect insect cells; retroviral vectors, other lentivirus vectors such as those based on the human immunodeficiency virus (HIV), adenovirus vectors, adeno-associated virus (AAV) vectors, herpesvirus vectors, vaccinia virus vectors, and the like, which infect mammalian cells (see Miller and Rosman, *BioTechniques* 7:980-990, 1992; Anderson et al., *Nature* 392: 25-30 Suppl., 1998; Verma and Somia, *Nature* 389:239-242, 1997; Wilson, *New Engl. J. Med.* 334:1185-1187 (1996), each of which is incorporated herein by reference). For example, a viral vector based on an HIV can be used to infect T cells, a viral vector based on an adenovirus can be used, for example, to infect respiratory epithelial cells, and a viral vector based on a herpesvirus can be used to infect neuronal cells. Other vectors, such as AAV vectors can have greater host cell range and, therefore, can be used to infect various cell types, although viral or non-viral vectors also can be modified with specific receptors or ligands to alter target specificity through receptor mediated events.

The present invention also provides methods for preparing recombinant nucleic acid molecules containing viral nucleic acid sequences, as well as covalently linked recombinant nucleic acid molecules prepared by such methods and compositions containing the recombinant nucleic acid molecules. Viral vectors derived from adenoviruses, for example, have been used for introducing expressible polynucleotides into cells, including in methods of gene therapy. Adenoviral vectors are particularly attractive vehicles for delivering genes into respiratory epithelial cells. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells (see Kozarsky and Wilson, *Curr. Opin. Genet. Develop.* 3:499-503, 1993, presenting a review of adenovirus-based gene therapy; Bout et al., *Human Gene Ther.* 5:3-10, 1994, demonstrating the use of adenovirus vectors to transfer genes to the respiratory epithelia of rhesus monkeys; see, also, Rosenfeld et al., *Science* 252:431-434, 1991; Rosenfeld et al., *Cell* 68:143-155, 1992; Mastrangeli et al., *J. Clin. Invest.* 91:225-234, 1993; Internatl. Publ. Nos. WO94/12649 and WO 96/17053; U.S. Pat. No. 5,998,205; and Wang et al., *Gene Ther.* 2:775-783, 1995, each of which is incorporated herein by reference. Accordingly, the present invention provides methods of generating vectors containing adenoviral sequences, and further provides methods of using such adenoviral vectors for introducing a polynucleotide into cells such as respiratory epithelial cells.

Viral vectors derived from adeno-associated viruses (AAV) and herpesviruses also can be used for introducing a polynucleotide into cells, particularly mammalian cells, in vitro and in vivo, for example, for a gene therapy procedure (Walsh et al., *Proc. Soc. Exp. Biol. Med.* 204:289-300, 1993; U.S. Pat. No. 5,436,146; Wagstaff et al., *Gene Ther.* 5:1566-70, 1998, each of which is incorporated herein by reference). For example, viral vectors derived from herpesvirus are particularly useful for applications where it is desired to introduce and express a polynucleotide in nerve cells. Accordingly, the present invention also provides methods of generating vectors containing herpesvirus or AAV nucleotide sequences, and further provides methods of using such viral vectors for introducing a polynucleotide into cells.

As such, the present invention provides methods for preparing recombinant nucleic acid molecules having one or more functional properties of viral vectors (e.g., adenoviral vectors, alphaviral vectors, herpes viral vectors, AAV vectors, etc.). In particular embodiments, methods of the invention include the covalently linking nucleotide sequences, wherein one or more of the nucleotide sequences contains regions of a viral genome that confer a function characteristic of the virus from which the nucleotide sequence was derived, for example, the ability to replicate in one or few specific host cells, the ability to be packaged into viral particles, and the like.

In particular embodiments, the invention includes methods for preparing adenoviral vectors by covalently linking at least one (e.g., one, two, three, four, etc.) nucleotide sequence comprising adenoviral sequences to one or more other nucleotide sequences. Specific examples of adenoviral vectors and nucleotide sequences that can be used to prepare adenoviral vectors are disclosed in U.S. Pat. Nos. 5,932,210, 6,136,594, and 6,303,362, each of which is incorporated herein by reference. Adenoviral vectors prepared by methods of the invention can be replication competent or replication deficient. For example, when a replication deficient adenoviral vector is desired, the adenoviral nucleotide sequence can contain deletions of all or part of one or more of the E1a region, the E1b region, and the E3 region. Adenoviral vectors containing deletions of these regions are described, for example, in U.S. Pat. No. 6,136,594. Accordingly, adenoviral vectors prepared by methods of the invention are provided, as are compositions containing the vectors, and uses of such vectors, for example, use of the adenoviral vectors to deliver a heterologous polynucleotide to cells of a mammal (e.g., a human). Thus, the invention provides methods for preparing vectors suitable for use in gene therapy protocols. Typically, such vectors are replication deficient.

In specific embodiments, adenoviral vectors of the invention comprise substantially the entire adenoviral genome, except that one or more of the E1a region, the E1b region, and the E3 region are deleted. In further specific embodiments, non-adenoviral nucleotide sequences can be present in one or more of the E1a region, the E1b region, and the E3 region. In particular embodiments, adenoviral vectors prepared by methods of the invention contain at least one origin of replication and/or a selection marker, for example, a prokaryotic origin of replication, which allows for amplification of the vector in prokaryotic cells such as *E. coli* cells.

As described above, AAV and herpesvirus vectors also can be prepared according to the methods of the invention. In addition, the alphaviral vectors (e.g., Sindbis virus vectors, Semliki Forest virus vectors, Ross River virus vectors, Venezuelan equine encephalitis virus vectors, Western equine encephalitis virus vectors, Eastern equine encephalitis virus vectors, etc.) can be prepared according to a method of the invention. As such, the present invention provides herpesvirus vectors, AAV vectors, alphaviral vectors, and the like, prepared by such methods, compositions containing such viral vectors, and methods of using the viral vectors.

In particular embodiments, the invention includes methods for preparing alphaviral vectors by covalently linking at least one nucleotide sequence comprising alphaviral sequences to one or more other nucleotide sequences. Specific examples of alphaviral vectors and nucleotide sequences thereof useful for preparing alphaviral vectors are described in U.S. Pat. Nos. 5,739,026 and 6,224,879; Gibco/BRL Instruction Manual No. 10179-018, "SFV Gene Expression System" (Gaithersburg Md.); and Invitrogen Sindbis Expression System manual, catalog no. K750-01 (version E; Carlsbad Calif.), each of which is incorporated herein by reference. In specific embodiments, alphavirus nucleotide sequences used in methods of the invention to prepare alphaviral vectors contain one or more packaging signals, which can, but need not, be of alphaviral origin; one or more subgenomic promoters; one or more nucleotide sequences encoding a non-structural protein such as nsp1, nsp2, nsp3, nsp4, etc.; and combinations thereof.

Alphaviral vectors of the invention can be introduced into cells as DNA or RNA molecules. When DNA forms of the vectors are introduced into cells, expression control sequences (e.g., inducible, repressible or constitutive expression control sequences) can be used to generate RNA molecules, from which one or more non-structural proteins can be translated. In specific embodiments, the non-structural proteins form an RNA dependent RNA polymerase that can amplify RNA molecules corresponding to all or a portion of the transcript generated from the DNA form of the alphaviral vector. As such, these non-structural proteins can catalyze the production of additional copies of RNA molecules from RNA templates, resulting in RNA amplification. Further, one or more nucleotide sequences, for which high levels of expression are desired, can be operatively linked to a subgenomic promoter, thus resulting in the production of high levels of RNA corresponding to the one or more nucleotide sequences.

In an exemplary embodiment, alphaviral vectors prepared by methods of the invention comprise DNA, wherein an inducible promoter directs transcription of an RNA molecule encoding nsp1, nsp2, nsp3, and nsp4 of a Sindbis virus, and wherein a Sindbis subgenomic promoter is operatively linked to a nucleotide sequence that is not of Sindbis viral origin. The invention also provides alphaviral vectors prepared by methods of the invention, methods of using such alphaviral vectors, and compositions containing such alphaviral vectors.

The invention further provides methods for covalently linking nucleotide sequences, wherein one or more of the nucleotide sequences contains one or more (e.g., one, two, three, four, etc.) viral packaging signals (e.g., one or more packaging signal derived from a virus referred to above). The presence of such packaging signals directs the packaging of the recombinant nucleic acid molecule viral vector prepared by methods of the invention. One method for preparing packaged viral vectors is by introducing or expressing the viral vectors, which are prepared according to a method of the invention, into packaging cell lines, which express proteins suitable for the production of virus-like particles. Accordingly, the invention provides packaged recombinant nucleic acid molecules of the invention, methods for preparing such packaged nucleic acid molecules, and compositions containing the packaged nucleic acid molecules.

It will be recognized that a nucleotide sequence to be covalently linked to one or more other nucleotide sequences according to a method of the invention can be any nucleotide sequence, and generally is a nucleotide sequence providing some desirable structural or functional feature to the covalently linked recombinant nucleic acid molecule generated thereby. For example, the nucleotide sequence can contain a restriction endonuclease site or recombinase recognition site, or can comprise a multiple cloning site, which contains two or more restriction endonuclease site or recombinase recognition site or combinations thereof. As such, the present invention also provides methods for preparing a covalently linked recombinant nucleic acid molecule containing one or more (e.g., one, two, three, four, five, six, etc.) multiple cloning sites, which can be the same or different, and can be adjacent to each other or separated by one or more other nucleotide sequences in the covalently linked recombinant nucleic acid molecule. Thus, one or more nucleotide sequences used in a method of the invention can comprise one or more multiple cloning sites. One or more multiple cloning sites also can be added to nucleotide sequences used to prepare the recombinant nucleic acid molecules, for example, by attaching linkers that contain the one or more multiple cloning sites. In related aspects, the invention includes recombinant nucleic acid molecules that are prepared by methods of the invention and contain one or more multiple cloning sites, as well as the use of one or more these multiple cloning sites to modify recombinant nucleic acid molecules prepared by methods of the invention. The invention also provides recombinant nucleic acid molecules produced by such a method, as well as uses of these molecules and compositions containing these molecules. In one embodiment, the generated recombinant nucleic acid molecule further comprises nucleotides sequences that allow the recombinant nucleic acid molecule to function as a vector, for example, viral nucleotide sequences such as adenovirus, herpesvirus, retrovirus, AAV, or alphavirus nucleotide sequences.

Nucleotide sequences useful in a method of the invention also can also comprise or encode one or more operators. Operators are well known in the art and include, for example, the tryptophan operator of the tryptophan operon of *E. coli*. The tryptophan repressor, when bound to two molecules of tryptophan, binds to the *E. coli* tryptophan operator and, when suitably positioned (i.e., operatively linked) with respect to the promoter, blocks transcription. Another example of an operator suitable for use with the invention is operator of the *E. coli* tetracycline operon. Components of the tetracycline resistance system of *E. coli* can function in eukaryotic cells and are useful for regulating gene expression in eukaryotic cells, for example, mammalian cells such as human cells. The tetracycline repressor, which binds to tetracycline operator in the absence of tetracycline and represses gene transcription, also has been expressed in plant cells at sufficiently high concentrations to repress transcription from a promoter containing tetracycline operator sequences (Gatz et al., *Plants* 2:397-404, 1992). Tetracycline regulated expression systems are described, for example in U.S. Pat. No. 5,789,156, which is incorporated herein by reference. Additional examples of operators that can be used in a method or to generate a composition of the invention include the Lac operator and the operator of the molybdate transport operator/promoter system of *E. coli* (see, for example, Cronin et al., *Genes Devel.* 15:1461-1467, 2001; Grunden et al., *J. Biol. Chem.* 274:24308-24315, 1999, each of which is incorporated herein by reference).

Thus, in particular embodiments, the invention provides methods for preparing covalently linked recombinant nucleic acid molecules that contain one or more operators, which can be used to regulate expression of an operatively linked expressible polynucleotide in prokaryotic cells or eukaryotic cells. As will be recognized, when such a recombinant nucleic acid molecule, which contains an operator, is placed under conditions in which transcriptional machinery is present, either in vivo or in vitro, regulation of expression of an operatively linked polynucleotide can be modulated by contacting the nucleic acid molecule with a repressor and one or more metabolites that facilitate binding of an appropriate repressor to the operator. Accordingly, the present invention further provides methods for preparing covalently linked recombinant nucleic acid molecules that encode one or more repressors, which modulate the function of operators, as well as the recombinant nucleic acid molecules produced by such methods, compositions containing the recombinant nucleic acid molecules, and uses of the recombinant nucleic acid molecules and the compositions.

A method of the invention can be used to operatively covalently link a first ds nucleotide sequence containing an open reading frame to a second (and other) ds nucleotide sequence containing an open reading frame such that a nucleic acid molecule encoding a chimeric polypeptide is generated. The chimeric polypeptide comprises a fusion polypeptide, in which the two (or more) encoded peptides (or polypeptides) are translated into a single product, i.e., the peptides are covalently linked through a peptide bond. For example, a first ds nucleotide sequence can encode a cell compartmentalization domain, such as a plasma membrane localization domain, a nuclear localization signal, a mitochondrial membrane localization signal, an endoplasmic reticulum localization signal, or the like, or a protein transduction domain such as the human immunodeficiency virus TAT protein transduction domain, which can facilitate translocation of a peptide linked thereto into a cell (see Schwarze et al., *Science* 285:1569-1572, 1999; Derossi et al., *J. Biol. Chem.* 271:18188, 1996; Hancock et al., *EMBO J.* 10:4033-4039, 1991; Buss et al., *Mol. Cell. Biol.* 8:3960-3963, 1988; U.S. Pat. No. 5,776,689 each of which is incorporated herein by reference). Such a domain can be useful to target a fusion polypeptide comprising the domain and a polypeptide encoded by a second ds nucleotide sequence, to which it is covalently linked according to a method of the invention, to a particular compartment in the cell, or for secretion from or entry into a cell. As such, the invention provides a means to generate ds recombinant nucleic acid molecules covalently linked in both strands that encode a chimeric polypeptide.

A fusion polypeptide expressed from a nucleic acid molecule generated according to a method of the invention also can comprise a peptide having the characteristic of a detectable label or a tag such that the express fusion polypeptide can be detected, isolated, or the like. For example, a ds nucleotide sequence containing a topoisomerase recognition site, or cleavage product thereof, as disclosed herein, can encode an enzyme such as alkaline phosphatase, β-galactosidase, chloramphenicol acetyltransferase, luciferase, or other enzyme; or can encode a peptide tag such as a polyhistidine sequence (e.g., hexahistidine), a V5 epitope, a c-myc epitope; a hemagglutinin A epitope, a FLAG epitope, or the like. Expression of a fusion polypeptide comprising a detectable label can be detected using the appropriate reagent, for example, by detecting light emission upon addition of luciferin to a fusion polypeptide comprising luciferase, or by detecting binding of nickel ion to a fusion polypeptide comprising a polyhistidine tag. Similarly, isolation of a fusion polypeptide comprising a tag can be performed, for example, by passing a fusion polypeptide comprising a myc epitope over a column having an anti-c-myc epitope antibody bound thereto, then eluting the bound fusion polypeptide, or by passing a fusion polypeptide comprising a polyhistidine tag over a nickel ion or cobalt ion affinity column and eluting the bound fusion polypeptide. Methods for detecting or isolating such fusion polypeptides will be well known to those in the art, based on the selected detectable label or tag (see, for example, Hopp et al., *BioTechnology* 6:1204, 1988; U.S. Pat. No. 5,011,912; each of which is incorporated herein by reference).

A method of the invention also can be used to detectably label a nucleotide sequence with a chemical or small organic or inorganic moiety such that the nucleotide sequence is useful as a probe. For example, a ds nucleotide sequence, which has a topoisomerase recognition site, or cleavage product thereof, at a 3' terminus, can have bound thereto a detectable moiety such as a biotin, which can be detected using avidin or streptavidin, a fluorescent compound (e.g., Cy3, Cy5, Fam, fluorescein, or rhodamine), a radionuclide (e.g., sulfur-35, technicium-99, phosphorus-32, or tritium), a paramagnetic spin label (e.g., carbon-13), a chemiluminescent compound, or the like, such that, upon generating a covalently linked double stranded recombinant nucleic acid molecule according to a method of the invention, the generated nucleic acid molecule will be labeled. Methods of detectably labeling a nucleotide sequence with such moieties are well known in the art (see, for example, Hermanson, "Bioconjugate Techniques" (Academic Press 1996), which is incorporated herein by reference). Furthermore, a detectable label can be used to allow capture of a ds nucleic acid molecule that is generated by the present invention. Finally, a detectable label, for example biotin, can be used to block ligation of a topoisomerase-charged end of a first ds nucleotide sequence to a labeled end of a second ds nucleotide sequence, thus providing a method to direct ligation to the unlabelled end of the second ds nucleotide sequence. It should be recognized that such elements as disclosed herein or otherwise known in the art, including nucleotide sequences encoding cell compartmentalization domains, or detectable labels or tags, or comprising transcriptional or translation regulatory elements can be useful components of a kit as disclosed herein.

A method of the invention provides a means to conveniently generate ds recombinant nucleic acid molecules that encode chimeric polypeptides useful, for example, for performing a two hybrid assay. In such a method, the first ds nucleotide sequence encodes a polypeptide, or a relevant domain thereof, that is suspected of having or being examined for the ability to interact specifically with one or more other polypeptides. The first ds nucleotide sequence is modified as disclosed herein to contain a topoisomerase recognition site at one or both ends and, if desired, a 5' overhanging sequence. The second ds nucleotide sequence, to which the first ds nucleotide sequence is to be covalently-linked according to a method of the invention, can encode a transcription activation domain or a DNA binding domain (Example 2.C), and contains a topoisomerase recognition site, or cleavage product thereof, and a 5' overhanging sequence complementary to that at the end of the first ds nucleotide sequence to which it is to be linked. Upon contact with a topoisomerase, if the nucleotide sequences are not already topoisomerase-charged, a first hybrid useful for performing a two hybrid assay (see, for example, Fields and Song, *Nature* 340:245-246, 1989; U.S. Pat. No. 5,283,173; Fearon et al., *Proc. Natl. Acad. Sci., USA* 89:7958-7962, 1992; Chien et al., *Proc. Natl. Acad. Sci., USA* 88:9578-9582, 1991; Young, *Biol. Reprod.* 58:302-311 (1998), each of which is incorporated herein by reference), or modified form of a two hybrid assay such as the reverse two hybrid assay (Leanna and Hannink, *Nucl. Acids Res.* 24:3341-3347, 1996, which is incorporated herein by reference), the repressed transactivator system (U.S. Pat. No. 5,885,779, which is incorporated herein by reference), the protein recruitment system (U.S. Pat. No. 5,776,689, which is incorporated herein by reference), and the like, is generated. Similar methods are used to generate the second hybrid protein, which can comprise a plurality of polypeptides to be tested for the ability to interact with the polypeptide, or domain thereof, of the first hybrid protein.

Similarly, such a method of generating a chimeric protein can be performed according to a method of the current invention for generating a ds recombinant nucleic acid molecule covalently linked in one strand, using first and second ds nucleotide sequences comprising a site-specific topoisomerase recognition site (e.g., a type IA or a type II topoisomerase recognition site), or cleavage product thereof, at least at one 5' terminus of an end to be joined, wherein the ds nucleotide sequences can further comprise complementary 3' overhangs upon cleavage by the topoisomerase.

Similarly, such a method of generating a chimeric protein can be performed according to a method of the current invention for generating a ds recombinant nucleic acid molecule covalently linked in both strands using first and second ds nucleotide sequences comprising a topoisomerase recognition site, or cleavage product thereof, at least at the 5' terminus of the ends to be joined, wherein the ds nucleotide sequences can further comprise complementary 3' overhangs upon cleavage by the topoisomerase; or one of the first or second ds nucleotide sequences can comprise topoisomerase recognition sites, or cleavage products thereof, at the 5' terminus and the 3' terminus of at least one end, and the other ds nucleotide sequence can contain a 3' hydroxyl group and a 5' hydroxyl group at the end to be joined, and wherein, upon cleavage by the topoisomerases, the topoisomerase-charged ds nucleotide sequence can contain a 5' or 3' overhang that is complementary to, and facilitates hybridization to, a 5' or 3' overhang, respectively, at the end of the other ds nucleotide sequence to be joined.

As disclosed herein, a first ds nucleotide sequence can be one of a plurality of nucleotide sequences, for example, a cDNA library, a combinatorial library of nucleotide sequences, or a population of variegated nucleotide sequences. As such, a particularly useful embodiment of a method of the invention is in generating recombinant polynucleotides encoding chimeric polypeptides for performing a high throughput two hybrid assay for identifying protein-protein interactions that occur among populations of polypeptides (see U.S. Pat. Nos. 6,057,101 and 6,083,693, each of which is incorporated herein by reference). In such a method, two populations (pluralities) of nucleotide sequences encoding polypeptides are examined, each plurality having a complexity of from a few related but different nucleotide sequences to as high as tens of thousands of such sequences. By performing a method of the invention, for example, using a PCR primer pair to amplify each nucleotide sequence in the plurality, wherein at least one primer of the PCR primer pair comprises at least a topoisomerase recognition site or complement thereof, covalently linked recombinant polynucleotides encoding a population of chimeric bait polypeptides and a population of chimeric prey polypeptides readily can be generated by contacting the amplified pluralities of nucleotide sequences, each of which comprises a topoisomerase recognition site, with a topoisomerase and a nucleotide sequence, which contains a topoisomerase recognition site and encodes a transcription activation domain or a DNA binding domain.

In practicing a method of the invention, a first ds nucleotide sequence also can encode a ribonucleic acid (RNA) molecule, which can function, for example, as a riboprobe, an antisense nucleotide sequence, a ribozyme, a triplexing nucleotide sequence, interference RNA (RNAi), or a suppressor tRNA, or can be used in an in vitro translation reaction, and the second ds nucleotide sequence can encode a regulatory element useful for expressing an RNA from the first nucleotide sequence (see Example 2.A). For example, where it is desired to produce a large amount of RNA, a second ds nucleotide sequence component for performing a method of the invention can comprise an RNA polymerase promoter such as a T7, T3 or SP6 RNA polymerase promoter. Where the RNA molecule is to be expressed in a cell, for example, an antisense molecule to be expressed in a mammalian cell, the second (or other) ds nucleotide sequence can include a promoter that is active in a mammalian cell, particularly a tissue specific promoter, which is active only in a target cell. Furthermore, where the RNA molecule is to be translated, for example, in a coupled in vitro transcription/translation reaction, the first nucleotide sequence or second (or other) nucleotide sequence can contain appropriate translational regulatory elements (see Example 2.B).

The methods of the invention can be used, for example, to generate covalently linked recombinant nucleic acid molecules that encode suppressor tRNA molecules. The nucleotide sequence encoding the suppressor tRNA can be operatively linked to an expression control element, particularly a transcriptional promoter, which can be constitutively active or inducible, and can be operative in prokaryotic cells or eukaryotic cells. In addition, the same recombinant nucleic acid molecule or a different recombinant nucleic acid molecule can contain a first and second coding sequence, which are separated by a nucleotide sequence containing a STOP codon that can be suppressed by the suppressor tRNA. Expression of the suppressor tRNA can then suppress the STOP codon, thereby allowing the generation of fusion protein. For example, where the suppressor tRNA is expressible from an inducible promoter, the system, which can be introduced into a cell, provides a means to express a polypeptide encoded by the first coding sequence (in the absence of expression of the suppressor tRNA) or a fusion protein comprising the polypeptide encoded by the first coding sequence operatively linked to the polypeptide encoded by the second coding sequence (in the presence of expression of the suppressor tRNA), as desired, simply by including or excluding the inducing agent specific for the inducible promoter. The polypeptides of such a system can be any polypeptide as exemplified herein or otherwise known in the art.

Methods of the invention may also be used to produce constructs which allow for silencing of genes in vivo. One method of silencing genes involves the production of double stranded RNAi (see, for example, Mette et al., *EMBO J.* 19:5194-5201, 2000, which is incorporated herein by reference). The mechanism by which RNAi is believed to function, which is reviewed in Fjose et al., *Biotechnol. Ann. Rev.* 7:31-57, 2001, appears to be based on the ability of double stranded RNA to induce the degradation of specific RNA molecules. This mechanism is reported to involve the conversion of double-stranded RNA into short RNAs that direct ribonucleases to homologous RNA targets (e.g., mRNA targets). Methods of the invention can be used in a number of ways to produce molecules such as RNAi. Thus, expression products of nucleic acid molecules of the invention can be used to silence gene expression.

One example of a nucleic acid molecule designed to produce RNAi is a molecule in which a nucleic acid segment is linked to one or more promoters such that RNA corresponding to both strands are produced as two separate transcripts or as part of the same transcript. For example, two separate RNA polymerase promoters, which can be the same or different (e.g., a T7 promoter and/or an SP6 promoter) can be located 5' and 3' to a polynucleotide sequence encoding a polypeptide. Further, the RNA polymerase promoters can be operatively linked to the expressible polynucleotide such that transcription driven by each promoter results in the production of RNA corresponding to each strand of the expressible polynucleotide. Thus, transcription from one promoter results in the production of a sense RNA and transcription from the other promoter results in the production of an antisense RNA. Since the RNA strands are complementary, they can hybridize to each other under physiological conditions to produce an RNAi molecule.

Another example of a recombinant nucleic acid molecule that can be used to produce RNAi is one in which an open reading frame is flanked on each end by promoters that drive transcription of the open reading frame in opposing directions. As a third example, double stranded RNA can be produced from a recombinant nucleic acid molecule encoding an RNA molecule having a "snapback" region (e.g., a region that is six, seven, eight, nine ten, etc. nucleotides in length) at one terminus. Such an RNA transcript can form a hairpin turn at or near one terminus and, when incubated under appropriate conditions in the presence of an RNA dependent RNA polymerase, the double stranded region formed by the hairpin can prime second strand synthesis to form a double stranded RNA molecule such as an RNAi molecule.

Nucleotide sequence designed to produce RNAi from a recombinant nucleic acid molecules as described above can, but need not, correspond to the entire coding sequence of a gene (i.e., at least the portion containing all of the exons) or a full length open reading frame (ORF). For example, when the nucleotide sequence corresponds to a portion of an ORF and, therefore, encodes an RNA molecule that does not correspond to all of the ORF, the nucleotide sequence can include at least about 15 (e.g., about 20, about 30, about 40, about 50, about 60, etc.) nucleotides, for example, at least about 15 to about 30 (e.g., 15, 16, 17, 18, 19, 20, 21, 22, 23, 24, 25, 26, 27, 28, 29, or 30) nucleotides at the 5' end of the ORF, the 3' end of the ORF, or internal to the ORF. Thus, in particular embodiments, the invention provides methods for preparing recombinant nucleic acid molecules containing at least three covalently operatively linked nucleotide sequences. In some embodiments, at least two of the nucleotide sequences share at least one region of sequence identity (e.g., a region at least about 20, at least about 30, at least about 40, at least about 50, at least about 60, at least about 70, at least about 80, at least about 90, at least about 100 nucleotides, etc.) nucleotides in length, for example, a region of about 15 to 30 (e.g., 15, 16, 17, 18, 19, 20, 21, 22, 23, 24, 25, 26, 27, 28, 29, or 30) nucleotides in length. In other embodiments, one nucleotide sequence is flanked by a region that can confer transcription from the interior portion of the nucleotide sequence molecule in opposing directions, thus allowing the generation of sense and antisense RNA transcripts. As such, the invention provides covalently linked recombinant nucleic acid molecules prepared by methods of the invention, and further provides methods of using of such molecules to either inhibit gene expression or facilitate degradation of specific target RNA molecules.

The invention also provides methods for generating covalently linked recombinant nucleic acid molecules that can be used to express antisense RNA (e.g., antisense mRNA). Methods similar to those described above for the production of RNAi can be employed, although only the non-coding strand generally will be transcribed, thereby generating antisense RNA molecules.

Gene silencing methods involving the use of compounds such as RNAi and antisense RNA, for example, are particularly useful for identifying gene functions. More specifically, gene silencing methods can be used to reduce or inhibit the expression of one or more genes in a cell or organism. Phenotypic manifestations associated with the selective inhibition of gene functions can then be used to assign role to the "silenced" gene or genes. As an example, Chuang et al. (*Proc. Natl. Acad. Sci., USA* 97:4985-4990, 2000) demonstrated that in vivo production of RNAi can alter gene activity in *Arabidopsis thaliana*. Thus, the invention provides methods for regulating expression of nucleic acid molecules in vivo (e.g., in cells and tissues) and/or in vitro by expressing RNAi molecules, antisense RNA molecules, or a combination thereof. The invention further provides methods for preparing covalently linked recombinant nucleic acid molecules useful for producing RNA that corresponding to one or both strands of an expressible polynucleotide.

In related embodiments, promoters that drive transcription of a sense RNA or antisense RNA can be either constitutive (e.g., CMV promoter, SV40 promoter, etc.), inducible (e.g., a metallothionein promoter, etc.), or repressible. Thus, for example, two different inducible promoters can be used to drive transcription of sense RNA and antisense RNA. In such an instance, promoter activation can be used to induce production of sense RNA, antisense RNA, or both sense RNA and antisense RNA. Further, the amount of sense RNA and/or antisense RNA produced can be related by using, for example, graduated induction and/or derepression of the promoters.

The invention also relates to methods of generating a covalently linked recombinant nucleic acid molecule encoding a ribozyme, as well as to compositions containing such recombinant nucleic acid molecules and methods of using such molecules for gene silencing. In particular, the invention provides antisense RNA/ribozymes fusions, which comprise 1) antisense RNA corresponding to a target gene and 2) one or more ribozymes that cleave RNA (e.g., hammerhead ribozyme, hairpin ribozyme, delta ribozyme, Tetrahymena L-21 ribozyme, etc.). Further provided by the invention are vectors that express such fusions, methods for producing such vectors, and methods for using such vector to suppress gene expression. Expression of antisense molecules fused to ribozymes can be used, for example, to cleave specific RNA molecules in a cell because the antisense RNA portion of the transcript can be designed to hybridize to particular mRNA molecules. Further, the ribozyme portion of the transcript can be designed to cleave the RNA molecule to which it has hybridized. For example, the ribozyme can be one which cleaves double stranded RNA (e.g., a Tetrahymena L-2 I ribozyme).

The present invention further provides nucleotide sequences suitable for performing cloning reactions in which a first nucleotide, which shares one or more regions of homology with a second nucleotide sequence, is used to insert all or a portion of the second nucleotide sequence into the first nucleotide sequence. The invention further provides compositions and methods for performing such cloning reactions.

One example of such a process is RecE/T cloning (see Internatl. Publ. No. WO 01/04288, which is incorporated herein by reference). Typically, in RecE/T cloning, a linear first nucleotide sequence (e.g., a vector) is introduced into a cell that contains 1) regions at the termini that share homology with two separate nearby regions (e.g., regions that are about 20 to 30, or about 20 to 40, or about 20 to 50, or about 30 to 40, or about 40 to 50, or about 40 to 60, or about 40 to 80, or about 50 to 90, etc. nucleotides in length) of a second nucleotide sequence, which is present in the cell (e.g., a plasmid, a bacterial artificial chromosome, a natural chromosome, etc.), 2) a selection marker, and 3) an origin of replication. The linear first nucleotide sequence generally replicates only if it becomes circularized. Further, the first nucleotide sequence typically becomes circularized upon undergoing recombination with the second nucleotide sequence and acquiring a portion of the second nucleotide sequence, which is intervening between the regions of homology. In such embodiments, the regions of homology in the first nucleotide sequence will typically be in a reverse orientation as compared to the second nucleotide sequence. Generally, the cell in which recombination occurs is one that expresses a recombinase such as RecE/T or RedAlpha/Beta. Thus, the invention provides, in part, methods for performing RecE/T cloning, covalently linked ds recombinant nucleic acid molecules prepared by such methods, compositions comprising such recombinant nucleic acid molecules, and methods for using such nucleic acid molecules and compositions.

Modifications of the RecE/T process can be used to generate a number of different end products. For example, when the regions of homology are arranged in various ways, the first nucleotide sequence can be designed to 1) insert into the second nucleotide sequence, or 2) delete a portion of the second nucleotide sequence. Typically, when insertion of the second nucleotide sequence into the second nucleotide sequence is desired, the regions of homology of the first nucleotide sequence are in the same orientation with respect to the regions of homology in the second nucleotide sequence. Further, when deletion of nucleic acid from the second nucleotide sequence is desired, the regions of homology of the first nucleotide sequence generally are in an inverse orientation with respect to the regions of homology in the second nucleotide sequence. Also, when insertion of the first nucleotide sequence into the second nucleotide sequence is desired, typically the first nucleotide sequence lacks an origin of replication. Accordingly, the present invention provides methods for performing such processes, as well as nucleotide sequences and compositions for use in the above methods.

A method of the invention can be particularly useful for generating an expressible ds recombinant nucleic acid molecule that can be inserted in a site specific manner into a target DNA sequence. The target DNA sequence can be any DNA sequence, particularly a genomic DNA sequence, and preferably a gene for which some or all of the nucleotide sequence is known. The method can be performed utilizing a first ds nucleotide sequence, which has a first end and a second end and encodes a polypeptide, for example, a selectable marker, wherein the first ds nucleotide sequence comprises a topoisomerase recognition site or cleavage product thereof at the 3' terminus of each end and, optionally, a hydroxyl group at the 5' terminus of each end, and wherein, preferably, the 5' termini comprise 5' overhanging sequences, which are different from each other; and covalently linking the first ds nucleotide sequence to first and second PCR amplification products according to a method of the invention. The first and second amplification products are generated from sequences upstream and downstream of the site at which the construct is to be inserted, and each amplification product contains a topoisomerase recognition site and, preferably, a 5' overhanging sequence, which is generated following contact with the site specific topoisomerase. Preferably, the first and second amplification products have different 5' overhanging sequences such that each can be linked to a predetermined end of the first ds nucleotide sequence. Such a method similarly can be performed using a ds amplification product comprising a topoisomerase recognition site, or cleavage product thereof, at the 5' terminus of one or both ends, wherein, upon cleavage by the topoisomerase, the topoisomerase-charged molecule can comprise a 3' overhang at one or both ends containing the topoisomerase. In addition, the method can be performed using a ds amplification product comprising topoisomerase recognition sites, or cleavage products thereof, at the 5' terminus and the 3' terminus of one or both ends, wherein, upon cleavage by the topoisomerases, the topoisomerase-charged ds nucleotide sequence preferably contains a 5' or 3' overhang at one or both ends containing the topoisomerases.

The first and second amplification products are generated using two sets of PCR primer pairs. The two sets of PCR primer pairs are selected such that, in the presence of an appropriate polymerase such as Taq polymerase and a template comprising the sequences to be amplified, the primers amplify portions of a target DNA sequence that are upstream of and adjacent to, and downstream of and adjacent to, the site for insertion of the selectable marker. In addition, the sets of PCR primer pairs are designed such that the amplification products contain a topoisomerase recognition site and, following cleavage by the site specific topoisomerase, a 5' overhanging sequence at the end to be covalently linked to the selectable marker. As such, the first PCR primer pair includes 1) a first primer, which comprises, in an orientation from 5' to 3', a nucleotide sequence complementary to a 5' overhanging sequence of the end of the selectable marker to which the amplification product is to be covalently linked, a nucleotide sequence complementary to a topoisomerase recognition site, and a nucleotide sequence complementary to a 3' sequence of a target DNA sequence upstream of the insertion site; and 2) a second primer, which comprises a nucleotide sequence of the target genomic DNA upstream of the 3' sequence to which the first primer is complementary, i.e., downstream of the insertion site. The second PCR primer pair includes 1) a first primer, which comprises, from 5' to 3', a nucleotide sequence complementary to the 5' overhanging sequence of the end of the selectable marker to which it is to be covalently linked, a nucleotide sequence complementary to a topoisomerase recognition site, and a nucleotide sequence of a 5' sequence of a target DNA sequence, wherein the 5' sequence of the target genomic DNA is downstream of the 3' sequence of the target DNA sequence to which the first primer of the first PCR primer pair is complementary; and the second primer of the second primer pair comprises a nucleotide sequence complementary to a 3' sequence of the target DNA sequence that is downstream of the 5' sequence of the target genomic DNA contained in the first primer. The skilled artisan will recognize that the sequences of the primer that are complementary to the target genomic DNA are selected based on the sequence of the target DNA.

Upon contact of the ds nucleotide sequence comprising the selectable marker, the first and second amplification products, and a topoisomerase (if the molecules are not topoisomerase-charged), a ds recombinant nucleic acid molecule covalently linked in both strands is generated according to a method of the invention. The generated ds recombinant nucleic acid molecule can be further amplified, if desired, using PCR primers that are specific for an upstream and downstream sequence of the target genomic DNA, thus ensuring that only functional constructs are amplified. The generated ds recombinant nucleic acid molecule is useful for performing homologous recombination in a genome, for example, to knock-out the function of a gene in a cell, or to confer a novel phenotype on the cell containing the generated recombinant nucleic acid molecule. The method can further be used to produce a transgenic non-human organism having the generated ds recombinant nucleic acid molecule stably maintained in its genome.

A method of the invention also is useful for covalently linking, an adapter or linker sequence to one or both ends of a ds nucleotide sequence of interest, including to each of a plurality of ds nucleotide sequences. For example, where it is desired to put linkers on both ends of a first ds nucleotide sequence, the method can be performed by contacting a topoisomerase with a first ds nucleotide sequence, which has a topoisomerase recognition site, or cleavage product thereof, at one or both 3' or 5' termini and which can include hydroxyl groups at both 5' termini; and a second ds nucleotide sequence and at least a third double stranded nucleotide sequence, each of which can include a topoisomerase recognition site, or cleavage product thereof at the appropriate 3' or 5' terminus and which can also include, where desirable, a 5' hydroxyl group at the same terminus. An appropriate terminus is the terminus to which the linker is to be covalently linked in at least one strand to the first nucleotide sequence. In one embodiment, one or both linker sequences contain an overhanging sequence that is complementary to a sequence at the 5' terminus of the end of the first ds nucleotide sequence to which the linker is to be covalently linked, thereby facilitating the initial association of the nucleotide sequences in the proper (predetermined) orientation (see, for example, FIG. 2 and Example 1.B). In performing such a method, the linker sequences comprising the second and at least third nucleotide sequence can be the same or different.

Figure 7:
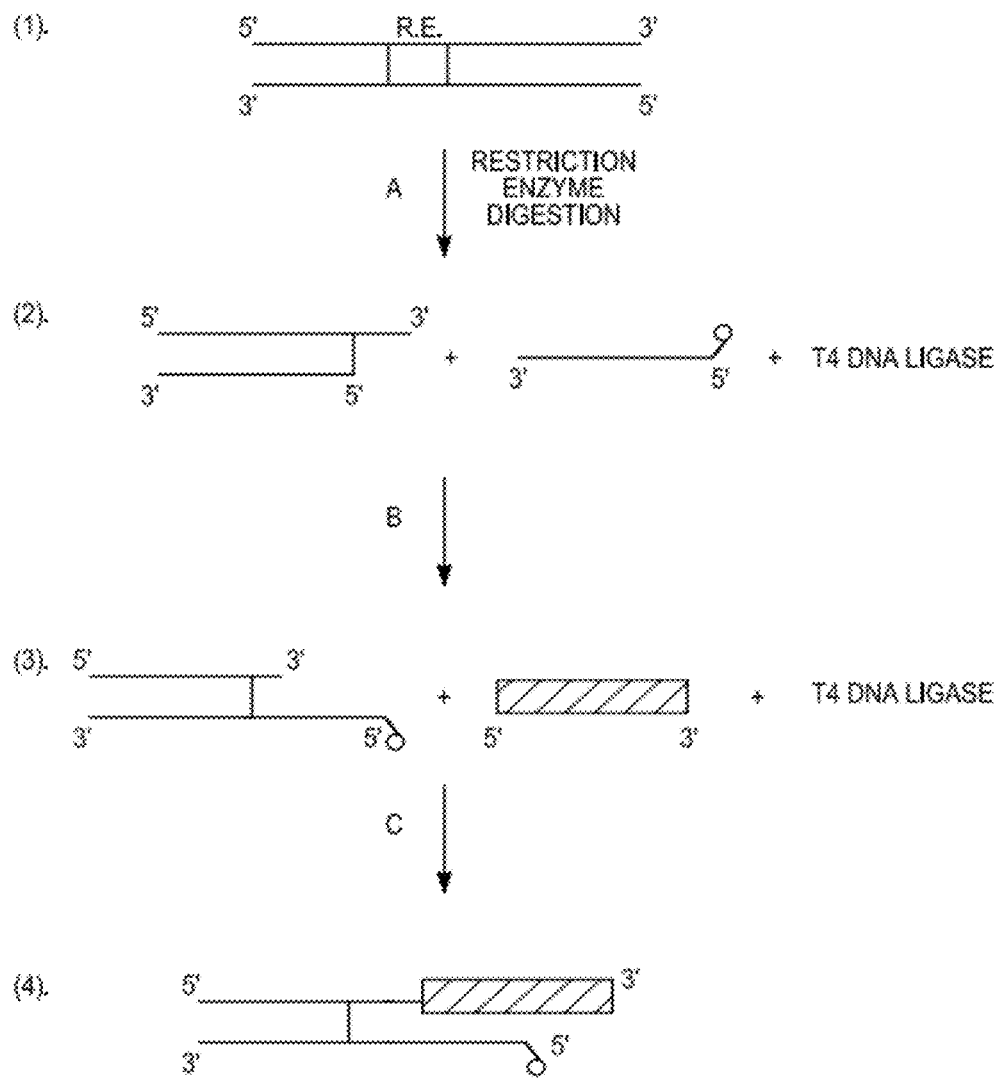
FIG. 7 shows one example of a process for preparing a double stranded nucleic acid molecule which contains a topoisomerase (e.g., a type IA topoisomerase) bound to the 5' terminus of one end of the molecule, wherein the same end of the molecule further comprise a 3' overhang (see (4) in this figure).

FIG. 7 shows one example of a process for preparing a ds nucleotide sequence containing a topoisomerase (e.g., a type IA topoisomerase) bound to the 5' terminus of one end of the sequence, and wherein the same end further comprise a 3' overhang (see (4) in FIG. 7). In step A, a nucleotide sequence to be modified with topoisomerase is digested with a restriction enzyme that generates a "sticky" end. The restricted nucleotide sequence is then contacted in step B with a linear, single stranded nucleotide sequence which contains a topoisomerase attached the 5' terminus and a ligase (e.g., a DNA ligase such as T4 DNA ligase). The linear, single stranded nucleotide sequence also contains a region at the 3' terminus which shares sufficient sequence complementarity to the "sticky" end generated by the restriction enzyme, such that the two molecules will hybridize. Thus, in step B, the two nucleotide sequences are ligated to each other. In step C, the product of the second step is contacted with a third nucleotide sequence which shares sequence complementarity to portions of the linear, single stranded nucleic acid molecule generated in step B, and a ligase. The product of step C, shown in (4), is a ds nucleotide sequence containing a topoisomerase attached to the 5' terminus of one end and a 3' overhang on the same end. It will be recognized that numerous variations of the exemplified method are within the scope of the invention. For example, similar processes can be performed to prepare nucleic acid molecules which comprise topoisomerase attached to the 3' terminus of one end or which have a 5' overhang or are blunt ended at the end to which a topoisomerase is attached. In another example, the nucleotide sequence labeled number 3 in FIG. 7 can be produced in the following manner: a ds nucleotide sequence can be digested with a restriction enzyme to generate a ds nucleotide sequence with a single-stranded 5' overhang that includes a type IA topoisomerase recognition site. The ds nucleotide sequence with the single stranded overhang can then be contacted with type IA topoisomerase to generate a type IA topoisomerase-charged ds nucleotide sequence.

Figure 8:
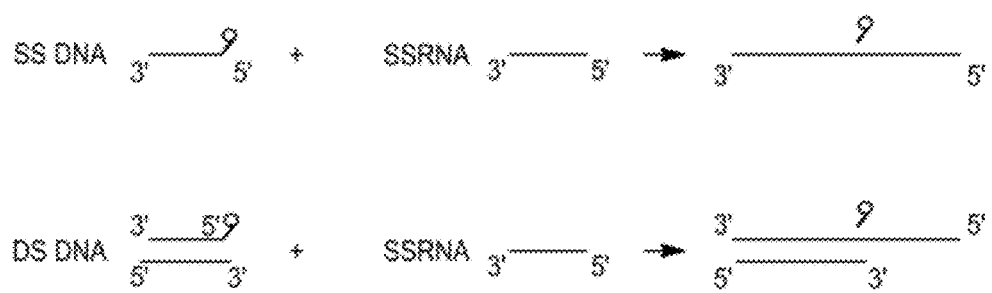
FIG. 8 shows two embodiments of the invention in which a single stranded or double stranded DNA nucleotide sequence is joined with a single stranded RNA nucleotide sequence.

FIG. 8 shows two embodiments of the invention in which single stranded or double stranded DNA is covalently linked to single stranded RNA. Where single stranded DNA is joined to single stranded RNA, the 3' end of the ribonucleotide sequence is covalently linked to the 5' end of the deoxyribonucleotide sequence. Where double stranded DNA is joined to single stranded RNA, the 3' terminus of the ribonucleotide sequence shares sufficient sequence complementarity to the 3' overhang of the deoxyribonucleotide sequence such that the two molecules hybridize. As above, the 3' end of the ribonucleotide sequence is also covalently linked to the 5' end of the deoxyribonucleotide sequence. As will be recognized, numerous variations of the above are within the scope of the invention. For example, the RNA molecule can be double stranded. In another example, all of the nucleotide sequences can be deoxyribonucleotide sequences.

The present invention provides a ds recombinant nucleic acid molecule having, or which can be made to have, a first end and a second end, each end including a 5' terminus and a 3' terminus, wherein the vector comprises a site-specific type IA topoisomerase recognition site at or near a 5' terminus of the first end, the second end, or both the first end and the second end. The ds recombinant nucleic acid molecule can further include a type IB topoisomerase recognition site at or near a 3' termini of an end that does not include a type IA topoisomerase recognition site. The ds recombinant nucleic acid molecule can be a vector.

The present invention further provides a topoisomerase-charged ds recombinant nucleic acid molecule having a first end and a second end, each end having a 5' terminus and a 3' terminus, wherein a site-specific type IA topoisomerase is bound at the 5' terminus of the first end, the second end, or both the first end and the second end. For example, the topoisomerase-charged ds recombinant nucleic acid molecule can include a type IA topoisomerase bound at the 5' termini of each of the first and second ends. The topoisomerase-charged nucleic acid ds recombinant nucleic acid molecule can include a type IB topoisomerase bound at a 3' termini of an end not bound by a type IA topoisomerase. The topoisomerase-charged ds recombinant nucleic acid molecule can be a vector.

The present invention also provides kits, which contain components useful for conveniently practicing the methods of the invention. Kits of the invention can contain any number of components, and generally contain at least two components. For example, a kit of the invention can contain 1) a first nucleotide sequence containing one or more topoisomerase recognition sites, and 2) instructions for covalently linking the first nucleotide sequence to a second (or other) nucleotide sequence using a method as disclosed herein. In particular embodiments, the instructions provide methods for covalently linking two or more nucleotide sequences in one or both strands. For example, the instructions can be for covalently linking two or more ds nucleotide sequences in both strands, and can include instructions for obtaining a second (or other) ds nucleotide sequence that contains a topoisomerase recognition site or that is topoisomerase-charged on one or more termini that are to covalently linked to the first ds nucleotide sequence, or can include instructions for making or obtaining a primer, which can be one of a primer pair, that includes, for example, a nucleotide sequence complementary to a type IB topoisomerase recognition site, such that a terminus of an amplification product generated using such a primer pair (including such a primer) can be covalently linked (in the presence of a type IB topoisomerase) to an end of a first ds nucleotide sequence that has a type IB topoisomerase recognition site at 3' terminus of the end to be linked or that is topoisomerase-charged at that terminus. In a related embodiment, the first nucleotide sequence is topoisomerase adapted (topoisomerase-charged) prior to inclusion in the kit.

In one embodiment, a kit of the invention contains a first ds nucleotide sequence, which encodes a polypeptide, particularly a selectable marker, and contains a topoisomerase recognition site at each end. Preferably, the first nucleotide sequence comprises a topoisomerase-activated nucleotide sequence. More preferably, the topoisomerase-charged first nucleotide sequence comprises a 5S overhanging sequence at each end, and most preferably the 5' overhanging sequences are different from each other. Optionally, each of the 5' termini comprises a 5' hydroxyl group.

In addition, the kit can contain at least a nucleotide sequence (or complement thereof) comprising a regulatory element, which can be an upstream or downstream regulatory element, or other element, and which contains a topoisomerase recognition site at one or both ends. Preferably, the kit contains a plurality of ds nucleotide sequences, each comprising a different regulatory element or other element, for example, a sequence encoding a tag or other detectable molecule or a cell compartmentalization domain. The different elements can be different types of a particular regulatory element, for example, constitutive promoters, inducible promoters and tissue specific promoters, or can be different types of elements including, for example, transcriptional and translational regulatory elements, epitope tags, and the like. Such ds nucleotide sequences can be topoisomerase-activated, and can contain 5' overhangs or 3' overhangs that facilitate operatively covalently linking the elements in a predetermined orientation, particularly such that a polypeptide such as a selectable marker is expressible in vitro or in one or more cell types.

The kit also can contain primers, including first and second primers, such that a primer pair comprising a first and second primer can be selected and used to amplify a desired ds recombinant nucleic acid molecule covalently linked in one or both strands, generated using components of the kit. For example, the primers can include first primers that are complementary to elements that generally are positioned at the 5' end of a generated ds recombinant nucleic acid molecule, for example, a portion of a ds nucleotide sequence comprising a promoter element, and second primers that are complementary to elements that generally are positioned at the 3' end of a generated ds recombinant nucleic acid molecule, for example, a portion of a ds nucleotide sequence comprising a transcription termination site or encoding an epitope tag. Depending on the elements selected from the kit for generating a ds recombinant nucleic acid molecule covalently linked in both strands, the appropriate first and second primers can be selected and used to amplify a full length functional construct.

In another embodiment, a kit of the invention contains a plurality of different elements, each of which can be topoisomerase-activated at one or both ends, and each of which can contain a 5' overhanging sequence or a 3' overhanging sequence or a combination thereof. The 5' or 3' overhanging sequences can be unique to a particular element, or can be common to plurality of related elements, for example, to a plurality of different promoter element. Preferably, the 5' overhanging sequences of elements are designed such that one or more elements can be operatively covalently linked to provide a useful function, for example, an element comprising a Kozak sequence and an element comprising a translation start site can have complementary 5' overhangs such that the elements can be operatively covalently linked according to a method of the invention.

The plurality of elements in the kit can comprise any elements, including transcription or translation regulatory elements; elements required for replication of a nucleotide sequence in a bacterial, insect, yeast, or mammalian host cell; elements comprising recognition sequences for site specific nucleic acid binding proteins such as restriction endonucleases or recombinases; elements encoding expressible products such as epitope tags or drug resistance genes; and the like. As such, a kit of the invention provides a convenient source of different elements that can be selected depending, for example, on the particular cells that a construct generated according to a method of the invention is to be introduced into or expressed in. The kit also can contain PCR primers, including first and second primers, which can be combined as described above to amplify a ds recombinant nucleic acid molecule covalently linked in one or both strands, generated using the elements of the kit. Optionally, the kit further contains a site specific topoisomerase in an amount useful for covalently linking in at least one strand, a first ds nucleotide sequence comprising a topoisomerase recognition site to a second (or other) ds nucleotide sequence, which can optionally be topoisomerase-activated ds nucleotide sequences or nucleotide sequences that comprise a topoisomerase recognition site.

In still another embodiment, a kit of the invention contains a first ds nucleotide sequence, which encodes a selectable marker, and contains a topoisomerase recognition site at each end; a first and second PCR primer pair, which can produce a first and second amplification products that can be covalently linked in one or both strands, to the first ds nucleotide sequence in a predetermined orientation according to a method of the invention. Such a generated construct can be introduced into a cell and can incorporate into the genome of the cell by homologous recombination in a site specific manner, where it can be stably maintained and can express a heterologous polypeptide in the cell or can knock-out a target gene function. A target gene to be knocked-out, for example, can be any gene for which at least part of the sequence is known or can be readily determined and the function of which it is desired to disrupt, for example, an oncogene, a gene involved in apoptosis, a gene encoding a serine/threonine or a tyrosine kinase, or any other gene.

The first PCR primer pair in a kit of the invention useful for generating a ds recombinant nucleic acid molecule covalently linked in both strands, includes a first primer that comprises, in an orientation from 5' to 3', a nucleotide sequence complementary to a 5' overhanging sequence of a ds nucleotide sequence to which it is to be covalently linked (for example, an end of the ds nucleotide sequence encoding the selectable marker), a nucleotide sequence complementary to a topoisomerase recognition site, and a nucleotide sequence complementary to a 3' sequence of the target DNA sequence. The first PCR primer pair also includes a second primer that comprises a nucleotide sequence of the target DNA sequence upstream of the 3' sequence to which the first primer is complementary.

The second PCR primer pair of a kit useful for generating a ds recombinant nucleic acid molecule covalently linked in both strands, includes a first primer that comprises, from 5' to 3', a nucleotide sequence complementary to a 5' overhanging sequence of a ds nucleotide sequence to which it is to be covalently linked, a nucleotide sequence complementary to a topoisomerase recognition site, and a nucleotide sequence of a 5' sequence of the target DNA sequence, wherein the 5' sequence of the target gene is downstream of the 3' sequence of the target DNA sequence to which the first primer of the first primer pair is complementary. The second PCR primer pair also includes a second primer that comprises a nucleotide sequence complementary to a 3' sequence of the target gene that is downstream of the 5' sequence of the target DNA sequence contained in the first primer.

In another embodiment, a kit of the invention useful for generating a ds recombinant nucleic acid molecule covalently linked in both strands contains a first ds nucleotide sequence, which encodes a transcription activation domain and comprises a topoisomerase recognition site, or cleavage product thereof, at a 3' terminus; and a second ds nucleotide sequence, which encodes a DNA binding domain and comprises a topoisomerase recognition site, or cleavage product thereof, at a 3' terminus. Upon cleavage by the site specific topoisomerase, the first or second ds nucleotide sequence can have a 5' overhang, or both sequences can have 5' overhangs, which are the same or are different from each other. Where the ds nucleotide sequences have a 5' overhang, the overhang generally is complementary to a ds nucleotide sequence to which first or second ds nucleotide sequence is to be covalently linked according to a method of the invention. The kit also can contain one or a pair of adapters, linkers or the like, which can comprise a topoisomerase recognition site, or cleavage product thereof, at one or both 3' termini, and, optionally, a hydroxyl group at the same terminus/termini. Such adapters, linkers, or the like are selected such that they contain a 5' overhang that is complementary to one or the other of the two ds nucleotide sequences described above and part of the kit.

Similarly, a kit of the invention can contain one or a pair of adapters, linkers or the like, which comprise a topoisomerase recognition site, or cleavage product thereof, at one or both 5' termini, and, optionally, a hydroxyl group at the same terminus (or termini). Such adapters, linkers, or the like are selected such that they contain a 3' overhang that is complementary to one or the other of the two ds nucleotide sequences described above and part of the kit. In addition, the kit can contain one or a pair of adapters, linkers or the like, which comprise a topoisomerase recognition site, or cleavage product thereof, at one or both 5' and/or 3' termini, and, optionally, a hydroxyl group at the same terminus/termini.

Adapters, linkers, or the like generally are selected such that they contain a 5' and/or a 3' overhang that is complementary to one or the other of the two ds nucleotide sequences as disclosed herein and part of the kit. Such adapters, linkers, or the like can be joined to the ends of ds nucleotide sequences that are to covalently linked to one or the other of the first or second ds nucleotide sequences provided with the kit, thus facilitating the construction of chimeric polynucleotides encoding the bait and prey polypeptides useful in a two hybrid assay. Such a kit also can contain a PCR primer or primer pair, which can be used to prepare an amplified plurality of nucleotide sequences comprising a topoisomerase recognition site, or cleavage product thereof (see Table 1 and Example 1).

A PCR primer pair in a kit of the invention, which can be used for generating a ds recombinant nucleic acid molecule covalently linked in one strand, can include a first primer that comprises, in an orientation from 5' to 3', a nucleotide sequence of a 5' overhanging sequence of a ds nucleotide sequence to which it is to be linked (for example, an end of the ds nucleotide sequence encoding the selectable marker), a topoisomerase recognition site (e.g., a type IA or type II topoisomerase recognition site), and a nucleotide sequence complementary to a 5' sequence of the target DNA sequence. The PCR primer pair also includes a second primer that comprises a nucleotide sequence of the target DNA sequence downstream of the 5' sequence to which the first primer is complementary.

In another embodiment, a kit of the invention contains a first ds nucleotide sequence, which encodes a transcription activation domain and comprises a site-specific topoisomerase recognition site (e.g., a type IA or a type II topoisomerase recognition site), or cleavage product thereof, at a 5' terminus; and a second ds nucleotide sequence, which encodes a DNA binding domain and comprises a site-specific topoisomerase recognition site (e.g., a type IA or a type II topoisomerase recognition site), or cleavage product thereof, at a 5' terminus. Upon cleavage by the site specific topoisomerase, the first or second ds nucleotide sequence can have a 3' overhang, or both sequences can have 3' overhangs, which are the same or are different from each other. Where the ds nucleotide sequences have a 3' overhang, the overhang generally is complementary to a ds nucleotide sequence to which first or second ds nucleotide sequence is to be linked according to a method of the invention. The kit also can contain one or a pair of adapters, linkers or the like, which comprise a site-specific topoisomerase recognition site (e.g., a type IA or a type II topoisomerase recognition site), or cleavage product thereof, at one or both 5' termini, and which can contain a 5' overhang that is complementary to one or the other of the two ds nucleotide sequences of the kit.

A kit of the invention also can contain a first isolated topoisomerase-charged ds nucleotide sequence and at least a second isolated topoisomerase-charged ds nucleotide sequence, wherein the sequences of the first and at least second ds nucleotide sequences are different from each other; or can contain at least two different ds nucleotide sequences, each of which comprises a topoisomerase recognition site at or near one or both ends, and a site specific topoisomerase, which can bind to and cleave the at least two different ds nucleotide sequences at the topoisomerase recognition site; or can contain a site specific topoisomerase and a covalently linked ds recombinant nucleic acid molecule, wherein the covalently linked ds recombinant nucleic acid molecule comprises at least one topoisomerase recognition site for the site specific topoisomerase in each complementary strand, wherein the topoisomerase recognition sites in each complementary strand are within about fifty nucleotides of each other, and wherein the site specific topoisomerase can bind to and cleave the topoisomerase recognition site in each complementary strand. In addition, a kit of the invention can contain a first ds nucleotide sequence, which contains a first end and a second end, and encodes a polypeptide, said first ds nucleotide sequence further comprising a topoisomerase bound at each end; and a plurality of ds nucleotide sequence populations, wherein each ds nucleotide sequence in a population contains a first end and a second end, and comprises a regulatory element, each ds nucleotide sequence further comprising a topoisomerase bound at the first end, the second end or both ends, wherein each population in the plurality is different from each other population, and wherein each ds nucleotide sequence in a population contains the same overhanging sequence, which is different from the overhanging sequence in the ds nucleotide sequences in each other population. Such a kit also can contain PCR primers specific for the ds nucleotide sequences in each population of nucleotide sequences. In one embodiment, the polypeptide encoded by the first ds nucleotide sequence is a selectable marker.

A ds recombinant nucleic acid molecule covalently linked in one or both strands, and generated according to a method of the invention, can be used for various purposes, including, for example, for expressing a polypeptide in a cell, for diagnosing or treating a pathologic condition, or the like. As such, the present invention provides a medicament, which can be useful for treating a pathologic condition by expressing a polypeptide in one or more cells or by expressing an antisense molecule, or the like. Such a ds recombinant nucleic acid molecule can be provided to a cell by contacting the cell ex vivo, then administering the cell to the subject, such a method also allowing for selection and/or expansion of the cells containing the ds recombinant nucleic acid molecule prior to such administration, or can be provided directly to the subject. For administration to a living subject, the ds recombinant nucleic acid molecule, which is covalently linked in one or both strands, generally is formulated in a composition suitable for administration to the subject. Thus, the invention provides compositions containing a ds recombinant nucleic acid molecule covalently linked in one or both strands, generated according to a method of the invention. As disclosed herein, such nucleic acid molecules are useful as medicaments for treating a subject suffering from a pathological condition.

A composition for administration generally is formulated using one or more pharmaceutically acceptable carriers as well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can be, for example, orally or parenterally such as intravenously, and by injection, intubation, or other such method known in the art. A composition of the invention also can contain a second reagent such as a diagnostic reagent, nutritional substance, toxin, or therapeutic agent, for example, a cancer chemotherapeutic agent.

The ds recombinant nucleic acid molecule covalently linked in one or both strands, can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77, 1981, each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212, each of which is incorporated herein by reference) are an example of such encapsulating materials particularly useful for preparing a pharmaceutical composition, and other "masked" liposomes similarly can be used, such liposomes extending the time that a nucleic acid molecule remains in the circulation. Cationic liposomes, for example, also can be modified with specific receptors or ligands (Morishita et al., *J. Clin. Invest.*, 91:2580-2585, 1993, which is incorporated herein by reference). The nucleic acid molecule also can be introduced into a cell by complexing it with an adenovirus-polylysine complex (see, for example, Michael et al., *J. Biol. Chem.* 268:6866-6869, 1993, which is incorporated herein by reference). Such compositions can be particularly useful for introducing a nucleic acid molecule into a cell in vivo or in vitro, including ex vivo, wherein the cell containing the nucleic acid molecule is administered back to the subject (see U.S. Pat. No. 5,399,346, which is incorporated herein by reference). A nucleic acid molecule generated according to a method of the invention also can be introduced into a cell using a biolistic method (see, for example, Sykes and Johnston, supra, 1999).

The following examples are intended to illustrate but not limit the invention.

EXAMPLE 1

Construction of Covalently Linked Double Stranded Recombinant Nucleic Acid Molecules Using Topoisomerase This experiment demonstrates that topoisomerase can be used to produce covalently linked double stranded (ds) recombinant nucleic acid molecules.

A. Methods

Except where indicated, experiments were performed using the following methods. PCR was performed in 50 Tl reactions, including 10 ng plasmid (template), 100 ng each primer, 2.5 Units Taq DNA polymerase (Sigma), 5 Tl 10×PCR buffer, and 4 Tl of dNTPs (200 TM each). An initial denaturation was performed by incubating the reaction at 94° C. for 4 min; followed by 30 cycles of PCR using 94° C. (45 sec) for denaturation, 55° C. (45 sec) for primer annealing and 72° C. (1 min per kb of target sequence) for extension. After cycling, the reactions were incubated at 72° C. (10 min), and then placed at 4° C.

Topoisomerase joining reactions were performed in 5 Tl, including 50-100 ng each amplified element (PCR-generated or synthetic), 0.5 Tl 500 mM Tris (pH 7.5), and 0.5 Tg topoisomerase. Reactions were incubated at room temperature for 5 min, then 1-2 Tl of the Topo-linked product was used for linear fragment generation.

Linear fragment generation by PCR was performed in 50 Tl reactions, including 1-2 Tl of the Topo-linked product (template), 100 ng each primer, 2.5 U Taq DNA polymerase (Sigma), 5 Tl 10×PCR buffer, and 4 Tl dNTPs (200 TM each). PCR was performed as described above.

The resultant linear fragment was purified using a SNAP Miniprep Kit (Invitrogen) as described by the manufacturer. Essentially, 100 Tl PCR product was mixed with 300 Tl Binding Buffer; 750 Tl isopropanol, and the mixture was applied to a SNAP Miniprep Column/Collection Tube and centrifuged at 7,000 rpm for 30 sec. The column was washed with 700 Tl Wash Buffer, centrifuged at 7,000 rpm for 30 sec; then washed with 900 Tl 1× Final Wash and centrifuged at 7,000 rpm for 30 sec. The column was then centrifuged at 7,000 rpm for an additional 30 sec to remove all remaining liquid. Water (30 to 50 Tl) was added and the column was centrifuged at 7,000 rpm for 30 sec to elute the purified DNA. DNA concentration was determined by spectrophotometry.

B. Generation of Topoisomerase Linked Linear Nucleic Acid Molecules

PCR primers were designed to examine the directional addition of elements to the coding sequence of green fluorescent protein (GFP; see FIG. 2). The CMV promoter (approximately 700 bp) and BGH polyadenylation signal sequence (approximately 380 bp) were amplified from a pCMV/myc/nuc plasmid template, and the GFP element (approximately 700 bp) was amplified from a pcDNA3.1/GFP plasmid template (Invitrogen) using the primers indicated in FIG. 2. The resultant amplification products were joined using topoisomerase as described above, and a portion of the ligation reaction was used as template for PCR with primers F6945 (SEQ ID NO: 11) and F6948 (SEQ ID NO: 15) to amplify the entire construct (CMV+GFP+BGH; approximately 1,700 bp). In addition, 5 Ti of the ligation mixture was treated with proteinase K for 30 min at 37° C. to remove any bound topoisomerase, and then subjected to electrophoresis on a 3-8% NuPAGE Tris-acetate gel to examine the ligated products.

Only a small amount of ligation product of the correct size (1.7 kb) was observed when the recombinant nucleic acid molecules were generated using elements having palindromic overhanging sequence (FIG. 2A or 2B), whereas significant quantities of the desired product were generated using elements having non-palindromic overhangs (FIG. 2C). These results demonstrate that the efficiency of generating a ds recombinant nucleic acid molecule covalently linked in both strands containing nucleotide sequences operatively linked in a predetermined orientation is related to the nature of the overhang sequence. In particular, the selection of overhanging sequences that lack palindromic regions result in the efficient generation of a desired ds recombinant nucleic acid molecule covalently linked in both strands, whereas the presence of palindromic sequences in the overhangs allows the formation of ligation products other than the intended product, thus decreasing the efficiency of generating a desired product.

EXAMPLE 2

Functional Characterization of Topoisomerase-Generated DS Recombinant Nucleic Acid Molecules This example demonstrates that a method of the invention provides a means to generate functional ds recombinant nucleic acid molecules covalently linked in both strands.
A. Expression of Sense and Antisense mRNA from a Topo-ligated Construct The ability to create a ds recombinant nucleic acid molecule containing functional upstream and downstream elements flanking a gene of interest was examined using two synthetic elements containing either a T7 or a T3 promoter sequence. The elements were made by annealing pairs of synthetic oligonucleotides. The T7 linker was generated by mixing equal molar amounts of T7top (F9304; SEQ ID NO: 20) and T7bottom (F9305; SEQ ID NO: 21) oligonucleotides (Table 1). The T3 linker was generated by mixing equal molar amounts of T3top (F9661; SEQ ID NO: 23) and T7bottom (F9662; SEQ ID NO: 24) oligonucleotides (Table 1). The mixtures were heated in boiling water for 5 min, then allowed to cool to room temperature. Both elements were designed to contain a topoisomerase recognition site at one end.

The GFP gene was amplified with GFP primers F8418 (SEQ ID NO: 17) and F8420 (SEQ ID NO: 18; Table 1; see, also, FIG. 2C). Unpurified GFP PCR product (2 Tl) was mixed with 50 ng of T7 linker and 50 ng of T3 linker, topoisomerase was added, and the topo-joining reaction was allowed to proceed at room temperature for 5 min. Two Tl of the joining reaction was used as template for a 50 Tl PCR reaction with primers for the T7 and T3 sequences.

After amplification, a 4 Tl aliquot of the PCR reaction was used as template for in vitro transcription. The reaction was performed using a Promega RiboProbe In Vitro Transcription Systems kit according to the manufacturer's instruction. The reaction was allowed to proceed for 60 min at 37° C. with T7 or T3 RNA polymerase (final volume, 20 Tl). Aliquots of the in vitro transcription reactions were digested with RNase or DNase, then undigested and digested samples were subjected to electrophoresis in a 2% TBE gel. A predominant band of the predicted size (either sense or antisense orientation) was observed in the undigested samples. No decrease in the product band was noted in samples treated with DNase. The product bands disappeared when samples were treated with RNase indicating the product was RNA. These results demonstrate that topoisomerase can be used according to a method of the invention to generate a ds recombinant nucleic acid molecule covalently linked in both strands in a predetermined orientation, and that an RNA transcript can be expressed from such a nucleic acid molecule.
B. Expression of a Translation Product from a Topo-ligated Construct The ability of topoisomerase ligated polynucleotide to support coupled in vitro transcription/translation was examined. A ds recombinant nucleic acid molecule was generated according to a method of the invention by linking an element containing a T7 promoter (plus a Kozak sequence) to lacZ PCR products of 1 kb, 2 kb, or 3 kb. Two Tl of the generated products were used as template for PCR amplification reactions (primers, SEQ ID NOS: 25-28; Table 1). Unpurified aliquots of the amplification reactions (3 Tl) were used as templates for coupled transcription/translation with a TNT T7 Quick for PCR DNA Kit according to the manufacturer's instructions (Promega).

Two Tl aliquots from each reaction were separated by electrophoresis on a Tris-glycine gel (Novex), then visualized by autoradiography, which revealed protein products that migrated at the expected sizes. These results demonstrate that a method of the invention can be used to produce a ds recombinant nucleic acid molecule covalently linked in both strands useful as a template for expressing a polypeptide by a coupled in vitro transcription/translation reaction.
C. Generation of Topo-ligated Constructs for Performing a Two Hybrid Assay Two hybrid assays provide a powerful method for detecting protein-protein interactions in vivo. These assays are based on the fact that many eukaryotic transcriptional activators consist of two physically and functionally separable domains, including a DNA binding domain, which binds to a specific DNA sequence, and a transcriptional activation domain, which interacts with the basal transcriptional machinery. The association of a transactivation domain with a DNA binding domain can promote the assembly of a functional RNA polymerase II complex, thereby allowing transcriptional activation, for example, of a detectable reporter gene (Field and Song, supra, 1989). Where a first protein, X, is fused to a DNA binding domain, for example, a GAL4 binding domain, and a second protein, Y, which can be the same or different from X, is fused into a transactivation domain, for example, a VP16 domain, an interaction of proteins X and Y can be identified by detecting transcription of a reporter gene having a GAL4 promoter.

The ability of a method of the invention to generate linear constructs for expressing fusion proteins for performing a mammalian two-hybrid assay was examined. PCR was used to generate GAL4 (F10779 and F12667 primers; SEQ ID NOS: 1 and 3, respectively), VP16 (F10779 and F12668 primers; SEQ ID NOS: 1 and 5, respectively), p53 (F12669 and F12505 primers; SEQ ID NOS: 8 and 4, respectively), T antigen (F12670 and F12505 primers; SEQ ID NOS: 9 and 4, respectively), and SV40A (F12016 and F561 primers; SEQ ID NOS: 6 and 7, respectively) elements containing topoisomerase sites at the appropriate ends. Topoisomerase was used to create the covalently linked, double stranded constructs GAL4+p53+SV40pA and VP16+T antigen+SV40pA, and the resultant ligation products were used as templates for PCR amplification.

Purified GAL4+p53+SV40pA and VP16+T antigen+SV40pA PCR constructs were co-transfected with a lacZ reporter gene (pGene/lacZ plasmid; Invitrogen) into CHO cells (6 well plate, $1\times10^5$ cells/well). In parallel experiments, the use of plasmid vectors containing the expression constructs was examined, as was the use of PCR reaction mixtures containing the unpurified constructs. Control reactions were performed using GAL4+pA and VP 16+pA without inserts (negative controls) or p53+VP16 (positive control). Cells were lysed 48 hr after transfection and reporter gene activity was measured using a β-galactosidase assay kit.

Figures 3A, 3B:
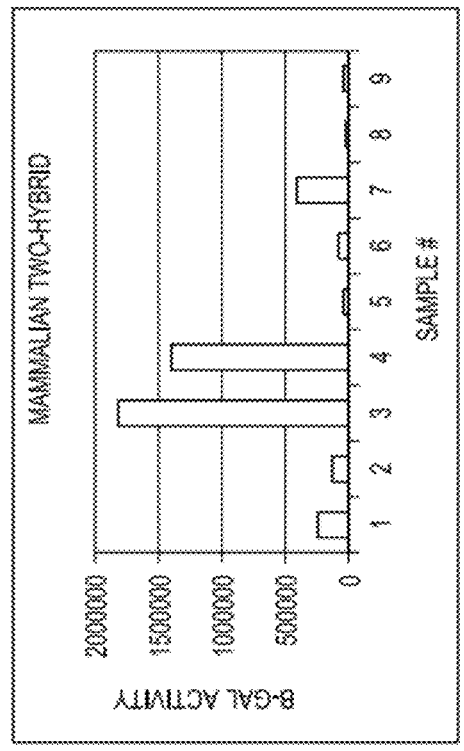
FIGS. 3A and 3B show constructs (FIG. 3A) and results (FIG. 3B) of experiments examining the ability to use ds recombinant nucleic acid molecule covalently linked in both strands that encode polypeptides for performing a two hybrid assay.

A high level of reporter gene activity was detected with the positive control (FIG. 3, sample 3) and in the sample co-transfected with the reporter gene and the linear GAL4+p53+SV40pA and VP 16+T antigen+SV40pA constructs (FIG. 3, sample 4). Low level activity (but greater than that of the negative controls; samples 5, 6, 8 and 9) was detected when the plasmid version of the constructs was used (FIG. 3, sample 1). Low level activity was also observed in the sample co-transfected with the unpurified, PCR-generated prey and bait constructs (sample 7). These results demonstrate that a method of the invention can be used to prepare constructs useful for performing a two hybrid assay.

EXAMPLE 3

Generation, Purification, and Transfection of Gene-Specific d-siRNA and Topo-Mediated Generation of Templates and Production of Double-Stranded RNA for Use in RNA Interference Analysis Exemplary product literature is provided below that describes the generation, purification, and transfection of gene-specific d-siRNA for use in RNA interference analysis, TOPO-mediated generation of templates and production of double-stranded RNA for use in RNA interference analysis. All catalog numbers provided below correspond to Invitrogen Corporation products, Carlsbad, Calif., unless otherwise noted. See also U.S. Ser. No. 10/902,704, entitled "Compositions and Methods for Preparing Short RNA Molecules and Other Nucleic Acids," filed Jul. 30, 2004, which is incorporated herein by reference.

D-siRNA Generation and Transfection Procedure

Produce dsRNA

Follow the guidelines to generate dsRNA. If you are using the BLOCK-iT™ Complete Dicer RNAi Kit, refer to the BLOCK-iT™ RNAi TOPO® Transcription Kit manual for instructions to generate dsRNA.

Perform the Dicing Reaction

1. Set up the following dicing reaction:

| | |
|---|---|
| 10X Dicer Buffer | 30 µl |
| RNase-Free Water | up to 210 µl |
| Purified dsRNA (60 µg) | 1-150 µl |
| BLOCK-iT ™ Dicer Enzyme (1 U/µl) | 60 µl |
| Total volume | 300 µl |

2. Mix reaction gently and incubate for 14-18 hours at 37° C.

3. Add 6 µl of 50× Dicer Stop Solution.

4. Check integrity of the d-siRNA, if desired. Proceed to purify d-siRNA.

Purify d-siRNA

1. To each 300 µl dicing reaction, add 300 µl of RNA Binding Buffer containing 1% (v/v) β-mercaptoethanol followed by 300 µl of isopropanol. Mix well by pipetting up and down 5 times.

2. Apply half the sample (~450 µl) to the RNA Spin Cartridge, and centrifuge at 14,000×g for 15 seconds at room temperature. Save the flow-through.

3. Transfer the RNA Spin Cartridge to an siRNA Collection Tube and repeat Step 2, using the other half of the dicing reaction sample (~450 µl). Save the flow-through.

4. Transfer the flow-through from Step 2 to the siRNA Collection Tube containing the flow-through from Step 3. Add 600 µl of isopropanol and mix well by pipetting up and down 5 times.

5. Apply one-third of the sample (~500 µl) to a new RNA Spin Cartridge. Centrifuge at 14,000×g for 15 seconds at room temperature. Discard the flow-through.

6. Repeat Step 5 twice, applying one-third of the remaining sample (~500 µl) to the RNA Spin Cartridge each time.

7. Add 500 µl of 1× RNA Wash Buffer to the RNA Spin Cartridge, and centrifuge at 14,000×g for 15 seconds at room temperature. Discard the flow-through.

8. Repeat Step 7.

9. Centrifuge the RNA Spin Cartridge at 14,000×g for 1 minute at room temperature.

10. Remove the RNA Spin Cartridge from the Wash Tube and place it in an RNA Recovery Tube.

11. Add 30 µl of RNase-Free Water to the RNA Spin Cartridge. Let stand at room temperature for 1 minute, then centrifuge the RNA Spin Cartridge at 14,000×g for 2 minutes at room temperature to elute the d-siRNA.

12. Add 30 µl of RNase-Free Water to the RNA Spin Cartridge and repeat Step 11, eluting the d-siRNA into the same RNA Recovery Tube.

13. Add 1.2 µl of 50× RNA Annealing Buffer to the eluted d-siRNA.

14. Quantitate the yield of d-siRNA by spectrophotometry. Aliquot and store the d-siRNA at −80° C.

Transfect d-siRNA

Follow the procedure below to transfect cells using Lipofectamine™ 2000. Refer to later table for the appropriate reagent amounts and volumes to add for different tissue culture formats.

1. One day before transfection, plate cells in growth medium without antibiotics such that they will be 30-50% confluent at the time of transfection.

2. For each transfection sample, prepare d-siRNA:Lipofectamine™ 2000 complexes as follows:

a. Dilute d-siRNA in the appropriate amount of Opti-MEM® 1 Reduced Serum Medium without serum. Mix gently.

b. Mix Lipofectamine™ 2000 gently before use, then dilute the appropriate amount in Opti-MEM® I. Mix gently and incubate for 5 minutes at room temperature.

c. After the 5 minute incubation, combine the diluted d-siRNA with the diluted Lipofectamine™ 2000. Mix gently and incubate for 20 minutes at room temperature.

3. Add the d-siRNA:Lipofectamine™ 2000 complexes to each well containing cells and medium. Mix gently by rocking the plate back and forth.

4. Incubate the cells at 37° C. in a CO2 incubator until they are ready to assay for gene knockdown.

Control Reaction

If you have purchased the BLOCK-iT™ Complete Dicer RNAi Kit, we recommend using the control template and control PCR primers included with the kit to produce dsRNA (see the BLOCK-iT™ RNAi TOPO® Transcription Kit manual for details). Once you have produced dsRNA, use this dsRNA as a control in your dicing, purification, and transfection experiments.

Kit Contents and Storage

Types of Kits

The BLOCK-iT™ Complete Dicer RNAi Kit is also supplied with the BLOCK-iT™ RNAi TOPO® Transcription Kit and the BLOCK-iT™ RNAi TOPO® Transcription Kit manual.

| Product | Catalog No. |
| --- | --- |
| BLOCK-iT™ Dicer RNAi Transfection Kit | K3600-01 |
| BLOCK-iT™ Complete Dicer RNAi Kit | K3650-01 |

Kit Components

The BLOCK-iT™ Dicer RNAi Kits include the following components. For a detailed description of the contents of each component, see later description. For a detailed description of the contents of the BLOCK-iT™ RNAi TOPO® Transcription Kit, see the BLOCK-iT™ RNAi TOPO® Transcription Kit manual.

| | Catalog no. | |
| --- | --- | --- |
| Component | K3600-01 | K3650-01 |
| BLOCK-iT™ Dicer Enzyme Kit | ✓ | ✓ |
| BLOCK-iT™ RNAi Purification Kit | ✓ | ✓ |
| Lipofectamine™ 2000 Reagent | ✓ | ✓ |
| BLOCK-iT™ RNAi TOPO® Transcription Kit |  | ✓ |

Shipping/Storage

The BLOCK-iT™ Dicer RNAi Kits are shipped as described below. Upon receipt, store each item as detailed below. For more detailed information about the reagents supplied with the BLOCK-iT™ RNAi TOPO® Transcription Kit, refer to the BLOCK-iT™ RNAi TOPO® Transcription Kit manual.

| Box | Component | Shipping | Storage |
| --- | --- | --- | --- |
| 1 | BLOCK-iT™ Dicer Enzyme Kit | Dry ice | −20° C. |
| 2 | BLOCK-iT™ RNAi Purification Kit | Room temperature | Room temperature |
| 3 | Lipofectamine™ 2000 Reagent | Wet ice | +4° C. (do not freeze) |
| 4-6 | BLOCK-iT™ RNAi TOPO® Transcription Kit | BLOCK-iT™ TOPO® Linker Kit and BLOCK-iT™ RNAi Transcription Kit: Dry ice BLOCK-iT™ RNAi Purification Kit: Room temperature | BLOCK-iT™ TOPO® Linker Kit and BLOCK-iT™ RNAi Transcription Kit: −20° C. BLOCK-iT™ RNAi Purification Kit: Room temperature |

BLOCK-iT™ Dicer Enzyme Kit

The following reagents are included with the BLOCK-iT™ Dicer Enzyme Kit (Box 1). Store the reagents at −20° C.

| Reagent | Composition | Amount |
| --- | --- | --- |
| BLOCK-iT™ Dicer Enzyme | 1 U/μl in a buffer | 300 μl |
| 10X Dicer Buffer | | 150 μl |
| 50X Dicer Stop Buffer | 0.5 mM EDTA, pH 8.0 | 30 μl |
| RNase-Free Water | — | 1.5 ml |

One unit of BLOCK-iT™ Dicer enzyme cleaves 1 μg of double-stranded RNA (dsRNA) in 16 hours at 37° C.

BLOCK-iT™ RNAi Purification Kit

The following reagents are included with the BLOCK-iT™ RNAi Purification Kit (Box 2). Store reagents at room temperature. Use caution when handling the RNA Binding Buffer.

Note: Catalog no. K3650-01 includes two boxes of BLOCK-iT™ RNAi Purification reagents. One box is supplied with the BLOCK-iT™ RNAi TOPO® Transcription Kit for purification of sense and antisense single-stranded RNA (ssRNA). The second box is supplied for purification of diced siRNA (d-siRNA).

| Reagent | Composition | Amount |
| --- | --- | --- |
| RNA Binding Buffer | | 1.8 ml |
| 5X RNA Wash Buffer | | 2.5 ml |
| RNase-Free Water | — | 800 μl |
| RNA Spin Cartridges | — | 10 |
| RNA Recovery Tubes | — | 10 |
| siRNA Collection Tubes* | — | 5 |
| 50X RNA Annealing Buffer | 500 mM Tris-HCl, pH 8.0 1 M NaCl 50 mM EDTA, pH 8.0 | 50 μl |

*siRNA Collection Tubes are used for purification of d-siRNA only, and are not required for the purification of the ssRNA.

The RNA Binding Buffer supplied in the BLOCK-iT™ RNAi Purification Kit contains guanidine isothiocyanate. This chemical is harmful if it comes in contact with the skin or is inhaled or swallowed. Always wear a laboratory coat, disposable gloves, and goggles when handling solutions containing this chemical.

Do not add bleach or acidic solutions directly to solutions containing guanidine isothiocyanate or sample preparation waste. Guanidine isothiocyanate forms reactive compounds and toxic gases when mixed with bleach or acids.

Lipofectamine™ 2000 Reagent

Each BLOCK-iT™ Dicer RNAi Kit includes Lipofectamine™ 2000 Reagent (Box 3) for high efficiency transfection of d-siRNA into mammalian cells. Lipofectamine™ 2000 Reagent is supplied as follows:

Size: 0.75 ml

Concentration: 1 mg/ml

Storage: +4° C.; do not freeze

BLOCK-iT™ RNAi TOPO® Transcription Kit

The BLOCK-iT™ Complete Dicer RNAi Kit (Catalog no. K3650-01) includes the BLOCK-iT™ RNAi TOPO® Transcription Kit to facilitate production of double-stranded RNA (dsRNA) from your gene of interest. Refer to the BLOCKiT™ RNAi TOPO® Transcription Kit manual for a detailed description of the reagents provided with the kit and instructions to produce dsRNA.

Accessory Products

The products listed in this section may be used with the BLOCK-iT™ Dicer RNAi Kits.

Accessory Products

Some of the reagents supplied in the BLOCK-iT™ Dicer RNAi Kits as well as other products suitable for use with the kit are available separately from Invitrogen.

| Item | Amount | Catalog no. |
|---|---|---|
| BLOCK-iT ™ RNAi TOPO ® Transcription Kit | 5 genes | K3500-01 |
| Lipofectamine ™ 2000 Reagent | 0.75 ml | 11668-027 |
| | 1.5 ml | 11668-019 |
| Opti-MEM ® I Reduced Serum Medium | 100 ml | 31985-062 |
| | 500 ml | 31985-070 |
| Phosphate-Buffered Saline (PBS), pH 7.4 | 500 ml | 10010-023 |
| 4% E-Gel ® Starter Pak | 9 gels and Base | G5000-04 |
| 20% Novex ® TBE Gel | 1 box | EC63152BOX |
| 10 bp DNA Ladder | 50 μg | 10821-015 |
| β-Gal Assay Kit | 100 reactions | K1455-01 |

Overview

The BLOCK-iT™ Dicer RNAi Transfection Kit and the BLOCK-iT™ Complete Dicer RNAi Kit facilitate generation of purified diced siRNA duplexes (d-siRNA) that are suitable for use in RNAi analysis of a target gene in mammalian cells. Both kits contain the BLOCK-iT™ Dicer Enzyme for dicing dsRNA, reagents to purify the d-siRNA, and an optimized transfection reagent for highly efficient delivery of d-siRNA to mammalian cells.

The BLOCK-iT™ Complete Dicer RNAi Kit also includes the BLOCK-iT™ RNAi TOPO® Transcription Kit to facilitate high-yield generation of purified dsRNA. For more information, refer to the BLOCK-iT™ RNAi TOPO® Transcription Kit manual. This manual is supplied with the BLOCK-iT™ Complete Dicer RNAi Kit.

Advantages of the BLOCK-iT™ Dicer RNAi Transfection Kit

Using the BLOCK-iT™ Dicer RNAi Transfection Kit and the BLOCK-iT™

Complete Dicer RNAi Kit to generate d-siRNA for RNAi analysis in mammalian provides the following advantages:

Provides a cost-effective means to enzymatically generate a pool of d-siRNA that cover a larger portion of the target gene (e.g. 500 bp to 1 kb) without the need for expensive chemical synthesis of siRNA.

Provides the BLOCK-iT™ Dicer Enzyme and an optimized protocol to facilitate generation of the highest yields of d-siRNA from a dsRNA substrate.

Includes BLOCK-iT™ RNAi Purification reagents for efficient purification of d-siRNA. Purified d-siRNA can be quantitated, enabling highly reproducible RNAi analysis.

Includes the Lipofectamine™ 2000 Reagent for the highest efficiency transfection in a wide variety of mammalian cell lines.

Purpose of this Manual

This manual provides the following information:
1. A description of the components in the BLOCK-iT™ Dicer RNAi Transfection Kit and an overview of the pathway by which d-siRNA facilitates gene knockdown in mammalian cells.
2. Guidelines to produce dsRNA corresponding to the target gene. For detailed instructions to produce dsRNA, refer to the BLOCK-iT™ RNAi TOPO® Transcription Kit manual.
3. Guidelines and instructions to use the BLOCK-iT™ Dicer Enzyme to cleave dsRNA to generate a complex pool of d-siRNA.
4. Instructions to purify d-siRNA.
5. Guidelines and instructions to transfect purified d-siRNA into mammalian cells using Lipofectamine™ 2000 Reagent for RNAi studies.

The BLOCK-iT™ Dicer RNAi Transfection Kit and the BLOCK-iT™ Complete Dicer RNAi Kit are designed to help generate d-siRNA for use in RNAi analysis in mammalian cell lines. Although the kits have been designed to help generate d-siRNA representing a particular target sequence in the simplest, most direct fashion, use of the resulting d-siRNA for RNAi analysis assumes that users are familiar with the principles of gene silencing and transfection in mammalian systems. We highly recommend that users possess a working knowledge of the RNAi pathway and lipid-mediated transfection.

For more information about the RNAi pathway in mammalian cells, refer to published reviews (Elbashir, S. M., et al., Methods 26:199-213 (2002); McManus, M. T. and Sharp, P. A., Nature Rev. Genet. 3:737-747 (2002)).

BLOCK-iT™ Dicer RNAi Kit

Components of the BLOCK-iT™ Dicer RNAi Kit

The BLOCK-iT™ Dicer RNAi Transfection Kit and the BLOCK-iT™ Complete Dicer RNAi Kit facilitate generation and delivery of purified d-siRNA duplexes into mammalian cells for RNAi analysis. The kits contain three major components:

1. The BLOCK-iT™ Dicer Enzyme and optimized reagents for production of high yields of d-siRNA from a dsRNA substrate. For more information about how the BLOCK-iT™ Dicer Enzyme works, below.
2. The BLOCK-iT™ RNAi Purification reagents for silica-based column purification of d-siRNA, and an RNA Annealing Buffer to stabilize d-siRNA duplexes for long-term storage.
3. Lipofectamine™ 2000 Reagent for high-efficiency transfection of d-siRNA into a wide range of mammalian cell types and cell lines for RNAi analysis.

If you are using the BLOCK-iT™ Complete Dicer RNAi Kit, note that the kit also includes a control expression plasmid containing the lacZ gene and PCR primers that may be used to generate control lacZ dsRNA. The control lacZ dsRNA may be used in a dicing and purification reaction to generate purified lacZ d-siRNA. Co-transfecting the purified lacZ d-siRNA and the control expression plasmid into mammalian cells provide a means to assess the RNAi response in your cell line by assaying for knockdown of β-galactosidase. In addition, the lacZ d-siRNA can be used as a negative control for non-specific off-target effects in your RNAi studies.

If you are using the BLOCK-iT™ Complete Dicer RNAi Kit, note that the kit includes 2 boxes of BLOCK-iT™ RNAi Purification reagents. One box is intended for purification of dsRNA, while the second box is intended for purification of d-siRNA. The protocols to purify dsRNA and d-siRNA differ significantly from one another. When purifying d-siRNA, be sure to use the purification procedure provided in this manual. To purify dsRNA, use the purification procedure provided in the BLOCK-iT™ RNAi TOPO® Transcription Kit manual.

Generating d-siRNA Using the Kit

Using the reagents supplied in the kit, you will perform the following steps to generate pure d-siRNA that is ready for transfection into the mammalian cell line of interest.

1. Use dsRNA representing your target sequence (generated with the BLOCK-iT™ RNAi TOPO®G Transcription Kit) in a reaction with the BLOCK-iT™ Dicer enzyme to generate d-siRNA.
2. Purify the d-siRNA using the purification reagents supplied in the kit. Quantitate the yield of purified d-siRNA obtained.
3. Transfect d-siRNA into the mammalian cell line of interest using Lipofectamine™ 2000 Reagent.

The RNAi Pathway and How Dicer Works

The RNAi Pathway

RNAi describes the phenomenon by which dsRNA induces potent and specific inhibition of eukaryotic gene expression via the degradation of complementary messenger RNA (mRNA), and is functionally similar to the processes of post-transcriptional gene silencing (PTGS) or cosuppression in plants (Cogoni, C., et al., *Antonie Van Leeuwenhoek* 65:205-209 (1994); Napoli, C., et al., *Plant Cell* 2:279-289 (1990); Smith, C. J., et al., *Mol. Gen. Genet.* 224:477-481 (1990); van der Krol, A. R., et al., *Plant Cell* 2:291-299 (1990)) and quelling in fungi (Cogoni, C. and Macino, G., *Nature* 399: 166-169 (1999); Cogoni, C. and Macino, G., *Proc. Natl. Acad. Sci. USA* 94:10233-10238 (1997); Romano, N. and Macino, G., *Mol. Microbiol.* 6:3343-3353 (1992)). In plants, the PTGS response is thought to occur as a natural defense against viral infection or transposon insertion (Anandalakshmi, R., et al., *Proc. Natl. Acad. Sci. USA* 95:13079-13084 (1998); Jones, A. L., et al., *EMBO J.* 17:6385-6393 (1998); Li, W. X. and Ding, S. W., *Curr. Opin. Biotechnol.* 12:150-154 (2001); Voinnet, O., et al., *Proc. Natl. Acad. Sci. USA* 96:14147-14152 (1999)).

In eukaryotic organisms, dsRNA produced in vivo or introduced by pathogens is processed into 21-23 nucleotide double-stranded short interfering RNA duplexes (siRNA) by an enzyme called Dicer (Bernstein, E., et al., *Nature* 409:363-366 (2001); Ketting, R. F., et al., *Genes Dev.* 15:2654-2659 (2001)). The siRNA then incorporate into the RNA-induced silencing complex (RISC), a second enzyme complex that serves to target cellular transcripts complementary to the siRNA for specific cleavage and degradation (Hammond, S. M., et al., *Nature* 404:293-296 (2000); Nykanen, A., et al., *Cell* 107:309-321 (2001)).

For more information about the RNAi pathway and the mechanism of gene silencing, refer to recent reviews (Bosher, J. M. and Labouesse, M., *Nature Cell Biol.* 2:E31-E36 (2000); Hannon, G. J., *Nature* 418:244-251 (2002); Plasterk, R. H. A. and Ketting, R. F., *Genet. Dev.* 10:562-567 (2000); Zamore, P. D., *Biol.* 8:746-750 (2001)).

Performing RNAi Analysis in Mammalian Cells

A number of kits including the BLOCK-iT™ RNAi TOPO® Transcription Kit now exist to facilitate in vitro production of dsRNA that is targeted to a particular gene of interest. The dsRNA may be introduced directly into some invertebrate organisms or cell lines, where it functions to trigger the endogenous RNAi pathway resulting in inhibition of the target gene. Long dsRNA duplexes cannot be used directly for RNAi analysis in most somatic mammalian cell lines because introduction of long dsRNA into these cell lines induces a non-specific, interferon-mediated response, resulting in shutdown of translation and initiation of cellular apoptosis (Kaufman, R. J., *Proc. Natl. Acad. Sci. USA* 96:11693-11695 (1999)). To avoid triggering the interferon-mediated host cell response, dsRNA duplexes of less than 30 nucleotides must be introduced into cells (Stark, G. R., et al., *Annu. Rev. Biochem.* 67:227-264 (1998)). For optimal results in gene knockdown studies, the size of the dsRNA duplexes (i.e. siRNA) introduced into mammalian cells is further limited to 21-23 nucleotides.

Using the Kit for RNAi Analysis

Figure 10:
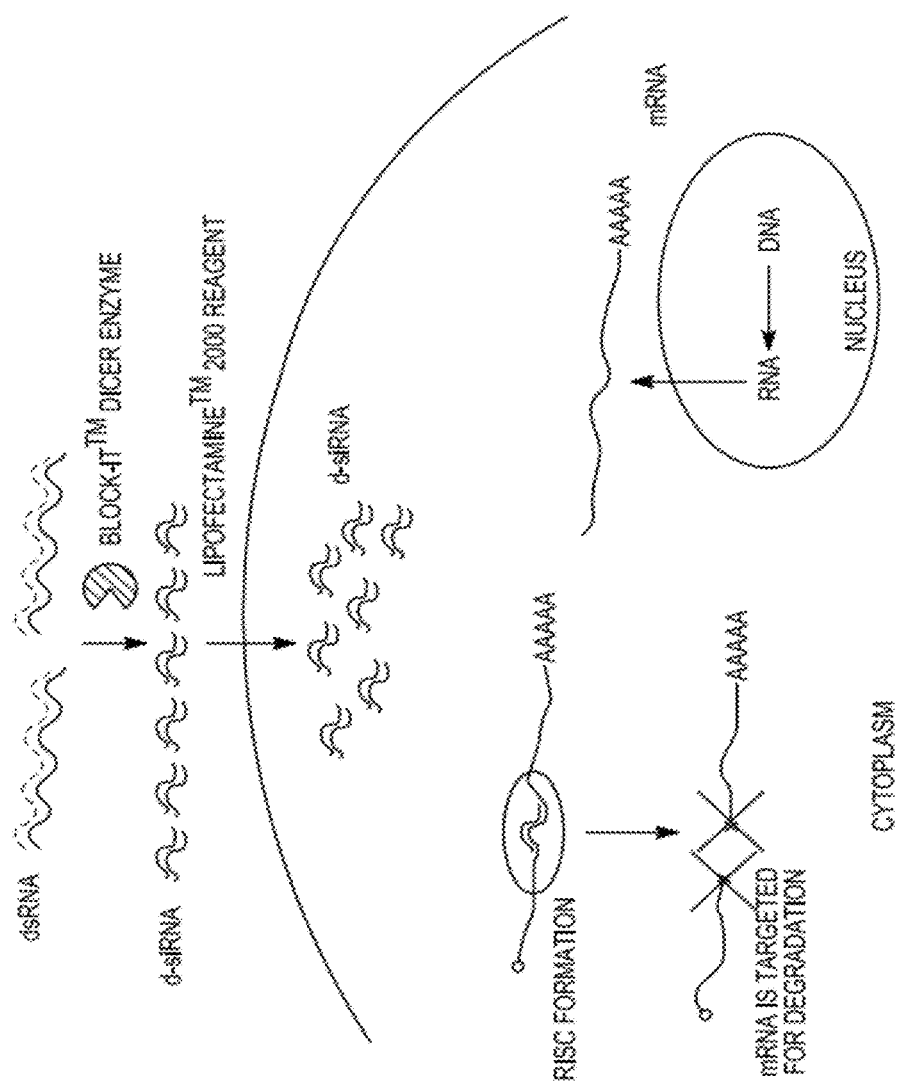
FIG. 10 shows a diagram of the iRNA process and pathway.

The BLOCK-iT™ Dicer RNAi Transfection Kit and the BLOCK-iT™ Complete Dicer RNAi Kit facilitate in vitro production of a complex pool of 21-23 nucleotide siRNA duplexes that is targeted to a particular gene of interest. The kits use a recombinant human Dicer enzyme (see below for more information) to cleave a long dsRNA substrate (produced with the BLOCK-iT™ RNAi TOPO® Transcription Kit) into a pool of 21-23 nucleotide d-siRNA that may be transfected into mammalian cells. Introduction of d-siRNA into the cells then triggers the endogenous RNAi pathway, resulting in inhibition of the target gene. For a diagram of the process, see FIG. 10.

BLOCK-iT™ Dicer Enzyme

BLOCK-iT™ Dicer is a recombinant human enzyme (Myers, J. W., et al., *Nat. Biotechnol.* 21:324-328 (2003); Provost, P., et al., *EMBO J.* 21:5864-5874 (2002)) that cleaves long dsRNA processively into 21-23 nucleotide d-siRNA duplexes with 2 nucleotide 3' overhangs. The Dicer enzyme is a member of the RNase III family of double-stranded RNA-specific endonucleases, and consists of an ATP-dependent RNA helicase domain, a Piwi/Argonaute/Zwille (PAZ) domain, two RNase III domains, and a dsRNA-binding domain (Bernstein, E., et al., *Nature* 409:363-366 (2001); Zamore, P. D., *Biol.* 8:746-750 (2001)). In addition to its role in the generation of siRNA, Dicer is also involved in the processing of short temporal RNA (stRNA) (Hutvagner, G., et al., *Science* 293:811-813 (2001); Ketting, R. F., et al., *Genes Dev.* 15:2654-2659 (2001)) and microRNA (miRNA) (Carrington, J. C. and Ambros, V., *Science* 301:336-338 (2003)) from stable hairpin or stem-loop precursors.

Experimental Outline

The table below outlines the desired steps when using the BLOCK-iT™ Dicer RNAi Kits to generate, purify, and transfect your d-siRNA of interest.

| Step | Action |
| --- | --- |
| 1 | Produce dsRNA from your target gene. |
| 2 | Use the dsRNA in a reaction with the BLOCK-iT ™ Dicer enzyme to generate d-siRNA. |
| 3 | Purify d-siRNA using the BLOCK-iT ™ RNAi Purification Reagents. |
| 4 | Transfect purified d-siRNA into your mammalian cell line of interest using Lipofectamine ™ 2000 Reagent. |
| 5 | Assay for inhibition of target gene expression using your method of choice. |

Methods

Generating Double-Stranded RNA (dsRNA)

Introduction

Before you can use the BLOCK-iT™ Dicer Enzyme to produce short interfering RNA (siRNA), you should generate double-stranded RNA (dsRNA) substrate representing your target sequence of interest. Guidelines and recommendations to generate dsRNA are provided below.

For optimal, high-yield production of dsRNA, we recommend using the BLOCK-iT™ RNAi TOPO® Transcription Kit available from Invitrogen (Catalog no. K3500-01). The BLOCK-iT™ RNAi TOPO® Transcription Kit supplies the reagents necessary to generate T7 promoter-based DNA templates from any Taq-amplified PCR product, then use these templates in in vitro transcription reactions to generate sense and antisense RNA transcripts. The kit also includes reagents to enable purification and annealing of the RNA transcripts to produce high yields of dsRNA that are ready-to-use in the dicing reaction.

For detailed protocols and guidelines to generate dsRNA from your target gene sequence, refer to the BLOCK-iT™ RNAi TOPO® Transcription Kit manual. This manual is supplied with the BLOCK-iT™ Complete Dicer RNAi Kit.

Choosing the Target Sequence

When performing RNAi analysis, your choice of target sequence can significantly affect the degree of gene knockdown observed. In addition, the size of the target sequence and the resulting dsRNA can affect the yields of d-siRNA produced. Consider the following factors when choosing your target sequence.

Select a target sequence that covers a reasonable portion of the gene of interest and that does not contain regions of strong homology with other genes.

Limit the size of the target sequence. Although smaller or larger target sequences are possible, we recommend limiting the initial target sequence to a size range of 500 bp to 1 kb for the following reasons.
  a) This balances the risk of including regions of strong homology between the target gene and other genes that could result in non-specific off-target effects during RNAi analysis with the benefits of using a more complex pool of siRNA.
  b) When producing sense and antisense transcripts of the target template, the highest transcription efficiencies are obtained with transcripts in the 500 bp to 1 kb size range. Target templates outside this size range transcribe less efficiently, resulting in lower yields of dsRNA.
  c) Double-stranded RNA that is under 1 kb in size is efficiently diced. Larger dsRNA substrates can be used but yields may decline as the size increases.

The BLOCK-iT™ Dicer RNAi Kits have been used successfully to knock down gene activity with dsRNA substrates ranging from 150 bp to 1.3 kb in size.

Factors to Consider when Generating dsRNA

If you are using your own method or another kit to produce dsRNA, consider the following factors when generating your dsRNA. These factors will influence the yields of d-siRNA produced from the dicing reaction.

Amount of dsRNA desired for dicing: We use 60 µg of dsRNA in a typical 300 µl dicing reaction to recover 12-18 µg of d-siRNA after purification. This amount of d-siRNA is generally sufficient to transfect approximately 150 wells of cells plated in a 24-well format. You should have an idea of the scale and scope of your RNAi experiment to determine how much dsRNA you will need to dice.

If you wish to dice less than 60 µg of dsRNA, you will need to scale down the dicing reaction proportionally.

Concentration of dsRNA: The amount of dsRNA in a dicing reaction should not exceed half the reaction volume; therefore, the concentration of your dsRNA should be ≧400 ng/µl if you wish to dice 60 µg of dsRNA.

Buffering of dsRNA: We recommend storing your dsRNA sample in a buffered solution containing 1 mM EDTA and no more than 100 mM salt (i.e. TE Buffer at pH 7-8 or 1× RNA Annealing Buffer). This helps to stabilize the dsRNA and provides the optimal environment for efficient cleavage by the Dicer Enzyme.

If you have used the BLOCK-iT™ RNAi TOPO® Transcription Kit to produce dsRNA, your dsRNA sample will be in 1× RNA Annealing Buffer (10 mM Tris-HCl, 20 mM NaCl, 1 mM EDTA, pH 8.0).

The quality of your dsRNA: To obtain the highest yields of d-siRNA, we recommend using purified dsRNA in the dicing reaction.

Once you have generated your purified dsRNA, we recommend saving an aliquot of the dsRNA for future gel analysis. We generally use agarose or polyacrylamide gel electrophoresis to assess the success of the dicing reaction by comparing an aliquot of the dicing reaction to an aliquot of the dsRNA substrate.

Performing the Dicing Reaction

Once you have produced your target dsRNA, you will perform an in vitro dicing reaction using the reagents supplied in the BLOCK-iT™ Dicer Enzyme Kit (Box 1) to generate d-siRNA duplexes of 21-23 nucleotides in size.

BLOCK-iT™ Dicer Enzyme Activity

One unit of BLOCK-iT™ Dicer Enzyme cleaves 1 µg of dsRNA in 16 hours at 37° C. Note that the Dicer enzyme does not cleave dsRNA to d-siRNA with 100% efficiency, i.e. dicing 1 µg of dsRNA does not generate 1 µg of d-siRNA. Under these optimal reaction conditions, the Dicer enzyme cleaves dsRNA to d-siRNA with an efficiency of approximately 25-35%. For example, dicing 60 µg of dsRNA in a 300 µl dicing reaction typically yields 12-18 µg of d-siRNA following purification.

For best results, we recommend following the dicing procedure exactly as described as the reaction conditions have been optimized to provide the highest mass yield of d-siRNA under the most efficient dicing conditions.

It is possible to use more than 60 µg of dsRNA in a 300 µl dicing reaction; however, the BLOCK-iT™ Dicer Enzyme becomes less efficient under these conditions. Although you may generate a higher mass yield of d-siRNA, the % yield of d-siRNA will decrease.

Do not increase the amount of BLOCK-iT™ Dicer Enzyme used in the dicing reaction (to greater than 60 units in a 300 µl reaction) or increase the length of the dicing reaction (to greater than 18 hours). Under either of these conditions, the BLOCK-iT™ Dicer Enzyme can bind to d-siRNA and cleave the 21-23 nt duplexes into smaller products, resulting in lower yields of d-siRNA.

Amount of dsRNA to Use

For a typical 300 µl dicing reaction, you will need 60 µg of target dsRNA. If you want to dice less than 60 µg of dsRNA, scale down the entire reaction proportionally.

The total volume of dsRNA added should not exceed half the volume of the reaction. Thus, for best results, make sure that the starting concentration of your dsRNA is ≧400 ng/µl.

Positive Control

If you are using the BLOCK-iT™ Complete Dicer RNAi Kit, and have performed all of the recommended control reactions using the control reagents supplied in the BLOCK-iT™ RNAi TOPO® Transcription portion of the kit, you should have purified dsRNA representing a 1 kb portion of the lacZ gene. We recommend setting up a separate dicing and purification reaction using the control lacZ dsRNA. You can then co-transfect the resulting purified lacZ d-siRNA and the pcDNA™ 1.2/V5-GW/lacZ control plasmid supplied with the kit into your mammalian cell line as a positive control for the RNAi response in that cell line. Alternatively, you may use the lacZ d-siRNA as a negative control for non-specific, off-target effects in your cell line.

When performing the dicing reaction and subsequent purification of d-siRNA, take precautions to avoid RNase contamination.

Use RNase-free sterile pipette tips and supplies for all manipulations.

Use DEPC-treated solutions as necessary.

Wear gloves when handling reagents and solutions, and when performing reactions.

Materials Needed

Have the following reagents on hand before beginning:
1. Purified dsRNA (>400 ng/μl in 1× RNA Annealing Buffer or TE Buffer, pH 7-8)
2. BLOCK-iT™ Dicer Enzyme (1 U/μl; supplied with the kit, Box 1; keep at −20° C. until immediately before use)
3. 10× Dicer Buffer (supplied with the kit, Box 1)
4. RNase-Free Water (supplied with the kit, Box 1)
5. 50× Dicer Stop Buffer (supplied with the kit, Box 1)

Dicing Procedure

Follow the procedure below to perform the dicing reaction. Make sure that the volume of dsRNA added does not exceed half the volume of the reaction (i.e. ≦150 μl).

1. Set up a 300 μl dicing reaction on ice using the following reagents in the order shown.

| Reagent | Sample |
| --- | --- |
| 10X Dicer Buffer | 30 μl |
| RNase-Free Water | up to 210 μl |
| Purified dsRNA (60 μg) | 1-150 μl |
| BLOCK-iT ™ Dicer Enzyme (1 U/μl) | 60 μl |
| Total volume | 300 μl |

2. Mix reaction gently and incubate for 14-18 hours at 37° C. Do not incubate the reaction for longer than 18 hours as this may result in a lower yield of d-siRNA due to cleavage of d-siRNA by the Dicer enzyme.

3. Add 6 μl of 50× Dicer Stop Solution to the reaction.

4. Check the integrity of your d-siRNA, if desired.

5. Proceed to purify the d-siRNA (see Purifying Diced siRNA (d-siRNA)) or store the dicing reaction overnight at −20° C.

Checking the Integrity of d-siRNA

You may verify the integrity of your d-siRNA using polyacrylamide or agarose gel electrophoresis, if desired. We suggest running an aliquot of your dicing reaction (0.5-1 μl of a 300 μl reaction; equivalent to 100-200 ng of dsRNA) on the appropriate gel and comparing it to an aliquot of your starting dsRNA. Be sure to include an appropriate molecular weight standard. We generally use the following gels and molecular weight standard:

Agarose gel: 4% E-Gel® (Invitrogen, Catalog no. G5000-04)

Polyacrylamide gel: 20% Novex® TBE Gel (Invitrogen, Catalog no. EC63152BOX)

Molecular weight standard: 10 bp DNA Ladder (Invitrogen, Catalog no. 10821-015)

When analyzing an aliquot of the dicing reaction by gel electrophoresis, we generally see the following:

A predominant band of approximately 21-23 nt representing the d-siRNA.

4% E-Gel®: A high molecular weight smear representing uncleaved dsRNA and partially cleaved products. Generally, this band does not resolve well on an agarose gel and runs close to the well.

Novex® 20% TBE Gel: A high molecular weight band and a smear representing uncleaved dsRNA and partially cleaved products. The dsRNA band generally resolves better on a polyacrylamide gel.

If the band representing d-siRNA is weak or if you do not see a band, see Troubleshooting for tips to troubleshoot your dicing reaction.

Example of Expected Results

In this experiment, purified dsRNA representing a 1 kb region of the lacZ gene was generated following the recommended protocols and using the reagents supplied in the BLOCK-iT™ RNAi TOPO® Transcription Kit. The lacZ dsRNA was diced using the procedure outlined below. Aliquots of the dicing reaction (equivalent to 200 ng of dsRNA) and the initial dsRNA substrate were analyzed on a 4% E-Gel®.

Figure 11:
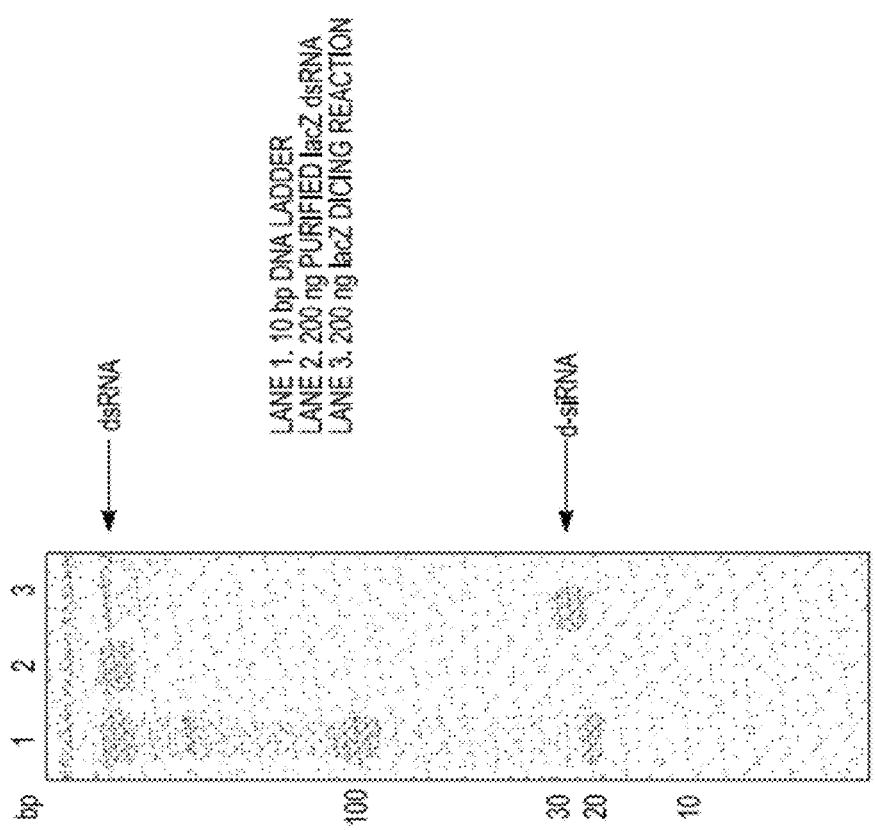
FIG. 11 shows an example of expected results of a lacZ dicing reaction.

Results are shown in FIG. 11: A prominent band representing d-siRNA of the expected size is clearly visible in the dicing reaction sample (lane 3). This band is not visible in the initial dsRNA substrate sample (lane 2). Lane 1. 10 bp DNA Ladder. Lane 2. 200 ng purified lacZ dsRNA. Lane 3. 200 ng lacZ dicing reaction.

Purifying Diced siRNA (d-siRNA)

Introduction

This section provides guidelines and instructions to purify the d-siRNA produced in the dicing reaction. Use the BLOCK-iT™ RNAi Purification reagents (Box 2) supplied with the kit.

Before proceeding to transfection, note that you should purify the d-siRNA produced in the dicing reaction to remove contaminating long dsRNA duplexes. Transfection of unpurified d-siRNA can trigger the interferon-mediated response and cause host cell shutdown and cellular apoptosis. When purifying d-siRNA, follow the purification procedure provided below exactly as instructed. This procedure is optimized to allow removal of contaminating long dsRNA and recovery of high yields of d-siRNA.

Experimental Outline

To purify d-siRNA, you will:

1. Add RNA Binding Buffer and isopropanol to the dicing reaction to denature the proteins and to enable the contaminating dsRNA to bind to the column.
2. Add half the volume of the sample to an RNA spin cartridge. The dsRNA binds to the silica-based membrane in the cartridge, and the d-siRNA and denatured proteins flow through the cartridge. Save the flow-through.
3. Transfer the RNA spin cartridge to an siRNA Collection Tube and add the remaining sample to the RNA spin cartridge. Repeat Step 2. Save the flow-through.
4. Pool the flow-throughs from Step 2 and Step 3 in the siRNA Collection Tube and add isopropanol to the sample to enable the d-siRNA to bind to the column.
5. Add the sample to a second RNA spin cartridge. The d-siRNA bind to the membrane in the cartridge.
6. Wash the membrane-bound d-siRNA to eliminate residual RNA Binding Buffer, isopropanol, and any remaining impurities.
7. Elute the d-siRNA from the RNA spin cartridge with water.
8. Add 50× RNA Annealing Buffer to the eluted d-siRNA to stabilize the d-siRNA for storage.

Figure 12:
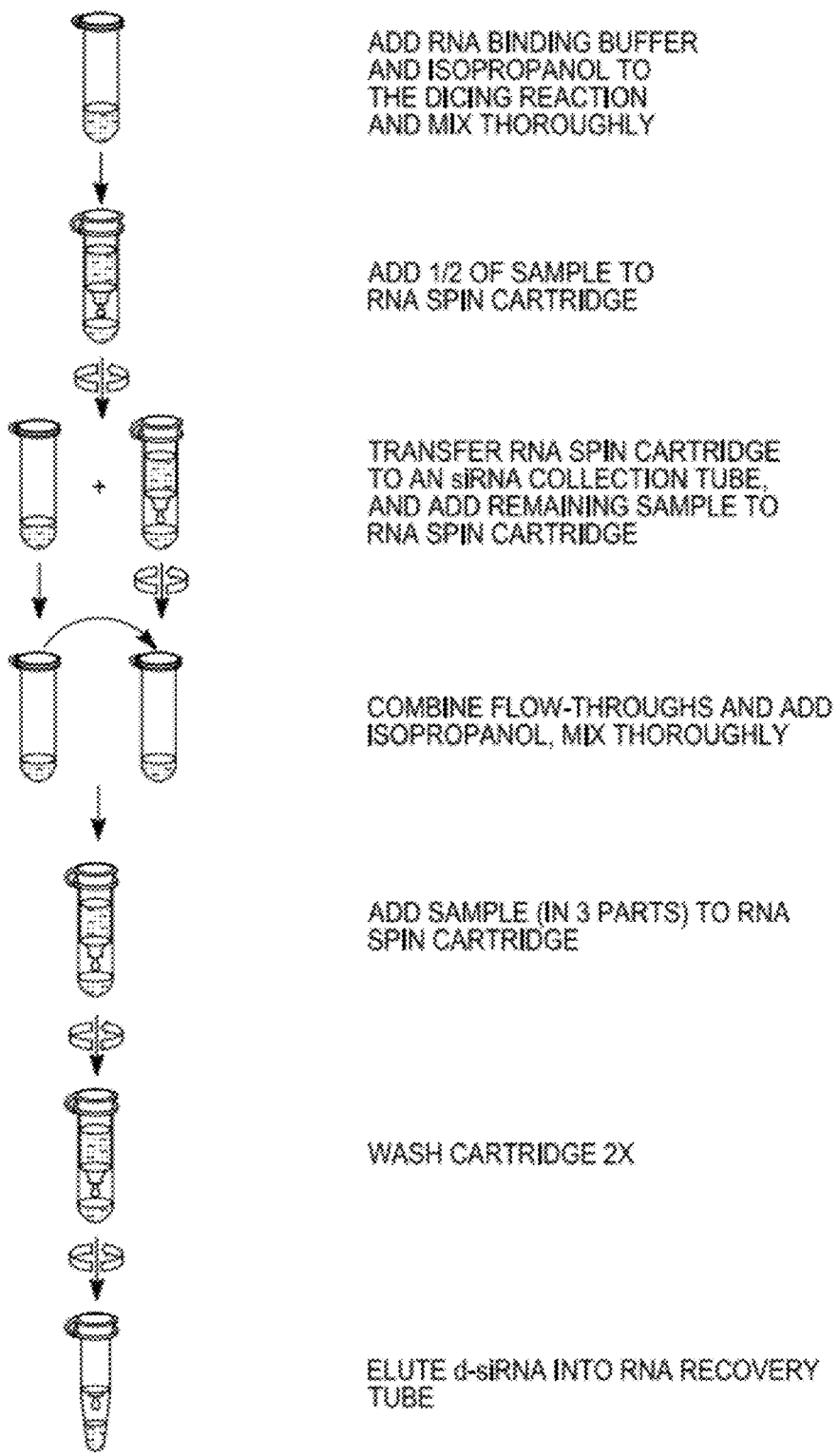
FIG. 12 shows a flow diagram illustrating the d-siRNA purification process.

For an illustration of the d-siRNA purification process, see FIG. 12.

Advance Preparation

Before using the BLOCK-iT™ RNA Purification reagents for the first time, add 10 ml of 100% ethanol to the entire amount of 5× RNA Wash Buffer to obtain a 1× RNA Wash Buffer (total volume=12.5 ml). Place a check in the box on the 5× RNA Wash Buffer label to indicate that the ethanol was added. Store the 1× RNA Wash Buffer at room temperature.

The RNA Binding Buffer contains guanidine isothiocyanate. This chemical is harmful if it comes in contact with the skin or is inhaled or swallowed. Always wear a laboratory coat, disposable gloves, and goggles when handling solutions containing this chemical.

Do not add bleach or acidic solutions directly to solutions containing guanidine isothiocyanate or sample preparation waste. Guanidine isothiocyanate forms reactive compounds and toxic gases when mixed with bleach or acids.

Materials Needed

Have the following materials on hand before beginning:
1. Dicing reaction (from Step 5)
2. RNA Binding Buffer (supplied with the kit, Box 2)
3. β-mercaptoethanol
4. Isopropanol
5. RNA Spin Cartridges (supplied with the kit, Box 2; two for each sample)
6. siRNA Collection Tube (supplied with the kit, Box 2)
7. 1× RNA Wash Buffer (see Advance Preparation, above)
8. RNase-Free Water (supplied with the kit, Box 2)
9. RNA Recovery Tube (supplied with the kit, Box 2)
10. 50× RNA Annealing Buffer (supplied with the kit, Box 2)
11. RNase-free supplies d-siRNA Purification Procedure Use this procedure to purify d-siRNA produced from dicing 60 µg of dsRNA in a 300 µl reaction volume (see Step 5). If you have digested <60 µg of dsRNA and have scaled down the volume of your dicing reaction, scale down the volume of your purification reagents proportionally. For example, if you have digested 30 µg of dsRNA in a 150 µl dicing reaction, scale down the volume of purification reagents used by half.

Before beginning, remove the amount of RNA Binding Buffer needed and add β-mercaptoethanol to a final concentration of 1% (v/v). Use fresh and discard any unused solution.

1. To each dicing reaction (~300 µl volume), add 300 µl of RNA Binding Buffer containing 1% (v/v) β-mercaptoethanol followed by 300 µl of isopropanol to obtain a final volume of 900 µl. Mix well by pipetting up and down 5 times.
2. Apply half of the sample (~450 µl) to the RNA Spin Cartridge. Centrifuge at 14,000×g for 15 seconds at room temperature.
3. Transfer the RNA spin cartridge to an siRNA Collection Tube. Save the flow-through containing d-siRNA from Step 2.
4. Apply the remaining half of the sample (~450 µl) to the RNA Spin Cartridge. Centrifuge at 14,000×g for 2 minutes at room temperature.
5. Remove the RNA Spin Cartridge from the siRNA Collection Tube and discard. Save the flow-through containing d-siRNA.
6. Transfer the flow-through from Step 2 (~450 µl) to the siRNA Collection Tube containing the flow-through from Step 4 (~450 µl) to obtain a final volume of 900 µl. Add 600 µl of isopropanol to the sample to obtain a final volume of 1.5 ml. Mix well by pipetting up and down.
7. Apply one-third of the sample (~500 µl) to a new RNA Spin Cartridge. Centrifuge at 14,000×g for 15 seconds at room temperature. Discard the flow-through.
8. Repeat Step 7 twice, applying one-third of the remaining sample (~500 µl) to the RNA Spin Cartridge each time.
9. Add 500 µl of 1× RNA Wash Buffer to the RNA Spin Cartridge containing bound d-siRNA. Centrifuge at 14,000×g for 15 seconds at room temperature. Discard the flow-through.
10. Repeat the wash step (Step 9).
11. Centrifuge the RNA Spin Cartridge at 14,000×g for 1 minute at room temperature to remove residual 1× RNA Wash Buffer from the cartridge and to dry the membrane.
12. Remove the RNA Spin Cartridge from the Wash Tube, and place it in an RNA Recovery Tube.
13. Add 30 µl of RNase-Free Water to the RNA Spin Cartridge. Let stand at room temperature for 1 minute, then centrifuge the RNA Spin Cartridge at 14,000×g for 2 minutes at room temperature to elute the d-siRNA. Proceed to Step 14.
14. Add 30 µl of RNase-Free Water to the RNA Spin Cartridge and repeat Step 13, eluting the d-siRNA into the same RNA Recovery Tube. The total volume of eluted d-siRNA is 60 µl.
15. Add 1.2 µl of the 50× RNA Annealing Buffer to the eluted d-siRNA to obtain a final concentration of 1× RNA Annealing Buffer. Adding RNA Annealing Buffer to the sample increases the stability of the d-siRNA.
16. Proceed to quantitate the concentration of your purified d-siRNA (see Determining the Purity and Concentration of d-siRNA, below).
17. Store the purified d-siRNA at −80° C. Depending on the amount of d-siRNA produced and your downstream application, you may want to aliquot the d-siRNA before storage at −80° C.

When using the d-siRNA, avoid repeated freezing and thawing as d-siRNA can degrade with each freeze/thaw cycle.

Determining the Purity and Concentration of d-siRNA

Use the procedure below to determine the purity and concentration of your purified d-siRNA.

1. Dilute an aliquot of the purified d-siRNA 20-fold into 1× RNA Annealing Buffer in a total volume appropriate for your quartz cuvettes and spectrophotometer.
2. Measure OD at A260 and A280 in a spectrophotometer. Blank the sample against 1× RNA Annealing Buffer.
3. Calculate the concentration of the d-siRNA by using the following equation: d-siRNA concentration (µg/ml) =A260× Dilution factor (20)×40 µg/ml.
4. Calculate the yield of the d-siRNA by using the following equation: d-siRNA yield (µg)=d-siRNA concentration (1 µg/ml)×vol. of d-siRNA (ml)
5. Evaluate the purity of the purified d-siRNA by determining the A260/A280 ratio. For optimal purity, the A260/A280 ratio should range from 1.9-2.2.

Verifying the Quality of Your d-siRNA

You may verify the quality of your purified d-siRNA using polyacrylamide or agarose gel electrophoresis, if desired. We suggest running a small aliquot of your purified d-siRNA (0.5-1 µl) on the appropriate gel and comparing it to an aliquot of your dicing reaction (equivalent to 100-200 ng of dsRNA). Be sure to include an appropriate molecular weight standard. For recommended gels and a molecular weight standard, we generally use the same gels and molecular weight standard that we use to analyze the quality of the dicing reaction.

If the band representing purified d-siRNA is weak or if you do not see a band, see Troubleshooting for tips to purify your d-siRNA.

Example of Expected Results

In this experiment, the lacZ d-siRNA generated in the dicing reaction depicted above were purified using the procedure described above. Aliquots of the purified lacZ d-siRNA (80 ng) and the lacZ dicing reaction (equivalent to 200 ng of dsRNA) were analyzed on a 4% E-Gel®.

Figure 13:
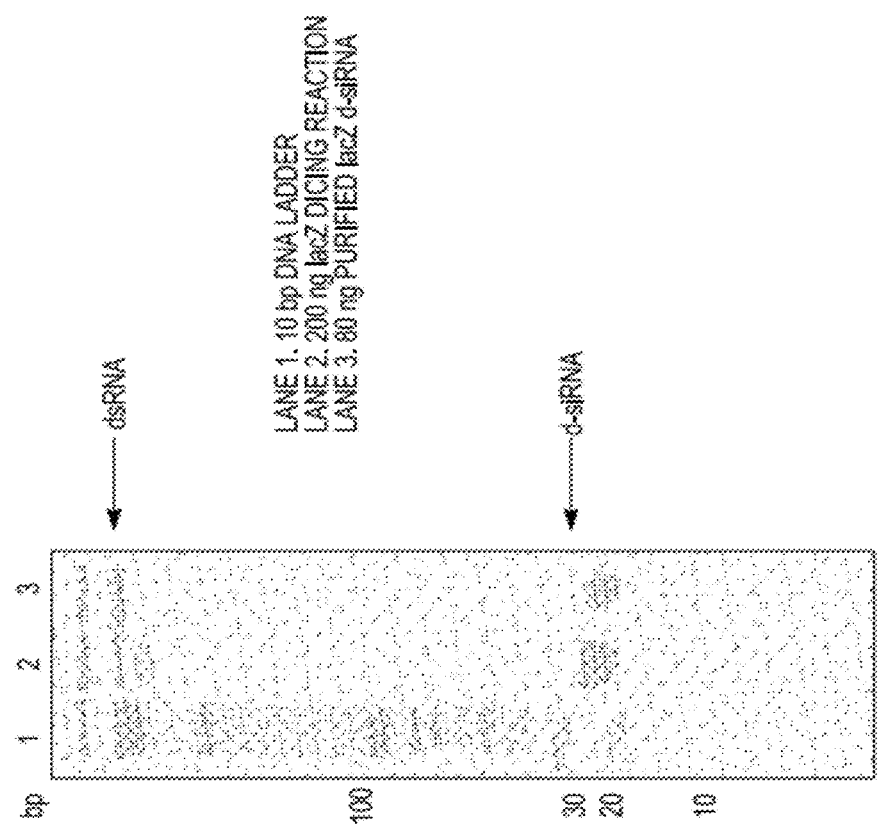
FIG. 13 shows an example of expected results following purification of lacZ d-siRNA.

Results are demonstrated in FIG. 13.: A prominent band representing purified d-siRNA of the expected size is clearly visible in lane 3. No contaminating dsRNA or other high molecular weight products remain in the purified d-siRNA sample. Lane 1. 10 bp DNA Ladder, Lane 2. 200 ng lacZ dicing reaction, Lane 3. 80 ng purified lacZ d-siRNA.

The typical yield of d-siRNA obtained from dicing 60 μg of dsRNA (500 bp to 1 kb in size) in a 300 μl dicing reaction ranges from 12-18 μg, with a concentration of 200-300 ng/μl. Note that yields may vary depending on the size and quality of the dsRNA.

Transfecting Cells

Introduction

Once you have purified your d-siRNA, you may perform RNAi analysis by transfecting the d-siRNA into the mammalian cell line of interest, and assaying for inhibition of expression from your target gene. This section provides general guidelines and protocols to transfect your purified d-siRNA into mammalian cells using the Lipofectamine™ 2000 Reagent (Box 3) supplied with the kit. Suggested transfection conditions are provided as a starting point. You will need to optimize transfection conditions to obtain the best results for your target gene and mammalian cell line.

You must transfect mammalian cells with purified d-siRNA. Note that transfecting cells with unpurified d-siRNA containing contaminating long dsRNA (i.e. with material directly taken from the dicing reaction) can trigger the interferon-mediated cellular response, resulting in host cell shutdown and cellular apoptosis.

Factors Affecting Gene Knockdown Levels

A number of factors can influence the degree to which expression of your gene of interest is reduced (i.e. gene knockdown) in an RNAi experiment including:
1. Transfection efficiency
2. Transcription rate of the target gene of interest
3. Stability of the target protein
4. Growth characteristics of your mammalian cell line Take these factors into account when designing your transfection and RNAi experiments.

Lipofectamine™ 2000 Reagent

The Lipofectamine™ 2000 Reagent supplied with the kit is a cationic lipid-based formulation suitable for the transfection of nucleic acids including d-siRNA and siRNA into eukaryotic cells (Ciccarone, V., et al., *Focus* 21:54-55 (1999); Gitlin, L., et al., *Nature* 418:430-434 (2002); Yu, J. Y., et al., *Proc. Nat. Acad. Sci. USA* 99:6047-6052 (2002)). Using Lipofectamine™ 2000 to transfect d-siRNA into eukaryotic cells offers the following advantages:
1. Provides the highest transfection efficiency in many cell types
2. Is the most widely used transfection reagent for delivery of d-siRNA or siRNA into eukaryotic cells (Gitlin, L., et al., *Nature* 418:430-434 (2002); Yu, J. Y., et al., *Proc. Nat. Acad. Sci. USA* 99:6047-6052 (2002))
3. d-siRNA-Lipofectamine™ 2000 complexes can be added directly to cells in culture medium in the presence of serum.
4. Removal of complexes, medium change, or medium addition following transfection are not required, although complexes can be removed after 4-6 hours without loss of activity.

Lipofectamine™ 2000 is also available separately from Invitrogen.

Important Guidelines

Follow these guidelines when transfecting siRNA into mammalian cells using Lipofectamine™ 2000:
1. Cell density: For optimal results, we recommend plating cells such that they will be 30-50% confluent at the time of transfection. Gene knockdown levels are generally assayed 24-72 hours following transfection. Transfecting cells at a lower density allows a longer interval between transfection and assay time, and minimizes the loss of cell viability due to cell overgrowth. Depending on the nature of the target gene, higher or lower cell densities may be suitable with optimization of conditions.
2. For optimal results, use Opti-MEM® I Reduced Serum Medium (Invitrogen, Catalog no. 31985-062) to dilute Lipofectamine™ 2000 and d-siRNA prior to complex formation.
3. Do not include antibiotics in media used during transfection as this will reduce transfection efficiency and cause cell death.

Materials to Have on Hand

Have the following materials on hand before beginning:
1. Mammalian cell line of interest (make sure that cells are healthy and greater than 90% viable before transfection)
2. Purified d-siRNA of interest (>40 ng/μl)
3. If you have diced 60 μg of dsRNA, the typical yield of d-siRNA obtained after purification is 12-18 μg at a concentration of 200-300 ng/μl)
4. Positive control, if desired (see below)
5. Lipofectamine™ 2000 Reagent (supplied with the kit; store at +4° C. until use)
6. Opti-MEM® I Reduced Serum Medium (Invitrogen, Catalog no. 31985-062; pre-warmed)
7. Sterile tissue culture plates and other tissue culture supplies Positive Control If you are using the BLOCK-iT™ Complete Dicer RNAi Kit, and have diced the control lacZ dsRNA, two options exist to use the resulting purified lacZ d-siRNA for RNAi analysis:
1. Use the lacZ d-siRNA as a negative control for non-specific off-target effects.
2. Use the lacZ d-siRNA as a positive control to assess the RNAi response in your cell line by co-transfecting the lacZ d-siRNA and the pcDNA™ 1.2/V5-GW/lacZ reporter plasmid supplied with the kit into your mammalian cells using Lipofectamine™ 2000. Assay for knockdown of β-galactosidase expression 24 hours post-transfection using Western blot analysis or activity assay.

Transfection conditions (i.e. cell density and reagent amounts) vary slightly when d-siRNA and plasmid DNA are co-transfected into mammalian cells. For details, see Co-transfecting d-siRNA and Plasmid DNA.

Transfection Procedure

Use this procedure to transfect mammalian cells using Lipofectamine™ 2000. Refer to the table in Recommended Reagent Amounts and Volumes, below for the appropriate reagent amounts and volumes to add for different tissue culture formats. Use the recommended Lipofectamine™ 2000 amounts as a starting point for your experiments, and optimize conditions for your cell line and d-siRNA.

1. One day before transfection, plate cells in the appropriate amount of growth medium without antibiotics such that they will be 30-50% confluent at the time of transfection.
2. For each transfection sample, prepare d-siRNA:Lipofectamine™ 2000 complexes as follows:
   (a) Dilute d-siRNA in the appropriate amount of Opti-MEM® I Reduced Serum Medium without serum. Mix gently.
   (b) Mix Lipofectamine™ 2000 gently before use, then dilute the appropriate amount in Opti-MEM® I Reduced Serum Medium. Mix gently and incubate for 5 minutes at room temperature. Combine the diluted Lipofectamine™ 2000 with the diluted d-siRNA within 30 minutes. Longer incubation times may decrease activity.
   (c) After the 5 minute incubation, combine the diluted d-siRNA with the diluted Lipofectamine™ 2000. Mix gently and incubate for 20 minutes at room temperature to allow the d-siRNA:Lipofectamine™ 2000 complexes to form. The solution may appear cloudy, but this will not inhibit transfection.
3. Add the d-siRNA:Lipofectamine™ 2000 complexes to each well containing cells and medium. Mix gently by rocking the plate back and forth.
4. Incubate the cells at 37° C. in a $CO_2$ incubator for 24-96 hours as appropriate until they are ready to assay for gene knockdown. It is not necessary to remove the complexes or change the medium; however, growth medium may be replaced after 4-6 hours without loss of transfection activity.

Recommended Reagent Amounts and Volumes

The table below lists the recommended reagent amounts and volumes to use to transfect cells in various tissue culture formats. Use the recommended amounts of d-siRNA (see column 4) and Lipofectamine™ 2000 (see column 6) as a starting point for your experiments, and optimize conditions for your cell line and target gene. With automated, high-throughput systems, larger complexing volumes are recommended for transfections in 96-well plates.

Optimizing Transfection

To obtain the highest transfection efficiency and low non-specific effects, optimize transfection conditions by varying the cell density (from 30-50% confluence) and the amounts of d-siRNA (see column 5) and Lipofectamine™ 2000 (see column 7) as suggested in the table above. For cell lines that are particularly sensitive to transfection-mediated cytotoxicity (e.g. HeLa, HT1080), use the lower amounts of Lipofectamine™ 2000 suggested in the table above.

What You should See

When performing RNAi experiments using d-siRNA, we generally observe inhibition of the gene of interest within 24 to 96 hours after transfection. The degree of gene knockdown depends on the time of assay, stability of the protein of interest, and on the other factors. Note that 100% gene knockdown is generally not observed, but >95% is possible with optimized conditions.

Co-Transfecting d-siRNA and Plasmid DNA

If you are using the lacZ d-siRNA as a positive control to assess the RNAi response in your cell line, you will co-transfect the lacZ d-siRNA and the pcDNA™ 1.2/V5-GW/lacZ reporter plasmid into the mammalian cell line and assay for inhibition of β-galactosidase expression after 24 hours. When co-transfecting d-siRNA and plasmid DNA, follow the procedure on the previous page with the following exceptions:

Plate cells such that they will be 90% confluent at the time of transfection.

Refer to the table below for the recommended amount of d-siRNA (see column 3) and plasmid DNA (see column 4) to transfect in a particular tissue culture format.

We generally transfect twice the mass of plasmid DNA as d-siRNA.

Use the recommended Lipofectamine™ 2000 amounts in the table below (see column 6) as a starting point, and optimize conditions for your cell line if desired. To optimize conditions, vary the amount of Lipofectamine™ 2000 as suggested in the table below (see column 7).

| Culture Vessel | Relative Surface Area (vs. 24-well) | Volume of Plating Medium | d-siRNA (μg) and Dilution Volume (μl) | d-siRNA Amounts (μl) for Optimization | Lipofectamine™ 2000 (μl) and Dilution Volume (μl) | Lipofectamine™ 2000 Amounts (μl) for Optimization |
|---|---|---|---|---|---|---|
| 96-well | 0.2 | 100 μl | 20 ng in 25 μl | 5-50 ng | 0.6 μl in 25 μl | 0.2-1.0 μl |
| 24-well | 1 | 500 μl | 50 ng in 50 μl | 20-200 ng | 1 μl in 50 μl | 0.5-1.5 μl |
| 6-well | 5 | 2 ml | 250 ng in 250 μl | 100 ng-1 μg | 5 μl in 250 μl | 2.5-6 μl |

| Culture Vessel | Volume of Plating Medium | d-siRNA (μg) | Plasmid DNA (μg) | Nucleic Acid Dilution Volume | Lipofect-amine™ 2000 (μl) and Dilution Volume (μl) | Lipofect-amine™ 2000 Amounts (μl) for Optimization |
|---|---|---|---|---|---|---|
| 96-well | 100 μl | 20 ng | 40 ng | 25 μl | 0.6 μl in 25 μl | 0.2-1.0 μl |
| 24-well | 500 μl | 50 ng | 100 ng | 50 μl | 2 μl in 50 μl | 0.5-2.0 μl |
| 6-well | 2 ml | 250 ng | 500 ng | 250 μl | 10 μl in 250 μl | 2.5-10 μl |

Assaying for β-Galactosidase Expression

If you perform RNAi analysis using the control lacZ d-siRNA, you may assay for β-galactosidase expression and knockdown by Western blot analysis or activity assay using cell-free lysates (Miller, J. H., Experiments in Molecular Genetics (Cold Spring Harbor, N.Y.: Cold Spring Harbor Laboratory (1972)). Invitrogen offers the β-gal Antiserum (Catalog no. R901-25) and the β-Gal Assay Kit (Catalog no. K1455-01) for fast and easy detection of β-galactosidase expression.

The β-galactosidase protein expressed from the pcDNA™ 1.2/V5-GW/lacZ control plasmid is fused to a V5 epitope and is approximately 119 kDa in size. If you are performing Western blot analysis, you may also use the Anti V5 Antibodies available from Invitrogen (e.g. Anti-V5-HRP Antibody; Catalog no. R961-25 or Anti-V5-AP Antibody, Catalog no. R962-25) for detection.

Examples of Expected Results

Introduction

This section provides some examples of results obtained from RNAi experiments performed with d-siRNA generated using the BLOCK-iT™ Complete Dicer RNAi Kit. The first example depicts knockdown of expression of a reporter gene, and the second example depicts knockdown of expression of the endogenous lamin A/C gene.

Example of Expected Results: Knockdown of a Reporter Gene

In this experiment, d-siRNA targeting two reporter genes (i.e. luciferase and lacZ) and an endogenous gene (i.e. lamin A/C) was generated following the recommended protocols and using the reagents supplied in the BLOCK-iT™Complete Dicer RNAi Kit.

GripTite™ 293 MSR cells (Invitrogen, Catalog no. R795-07) were grown to 90% confluence. Individual wells in a 24-well plate were transfected using Lipofectamine™ 2000 Reagent with 100 ng each of lacZ and luciferase-containing reporter plasmids. In some wells, the reporter plasmids were co-transfected with 50 ng of purified lacZ, luciferase, or lamin A/C d-siRNA. Cell lysates were prepared 24 hours after transfection and assayed for luciferase and β-galactosidase activity. Activities were normalized to those of the reporter plasmids alone.

Figure 14:
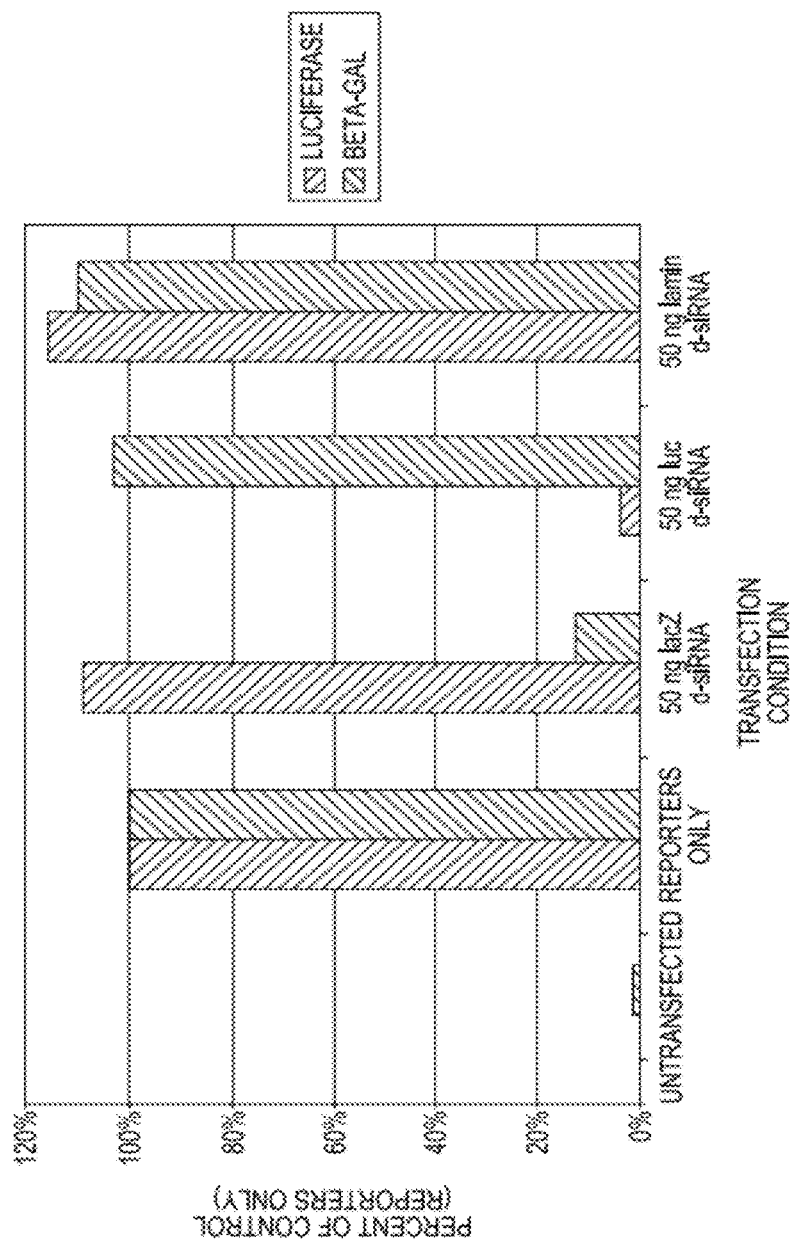
FIG. 14 shows ds-iRNA inhibition of luciferase and β-galactosidase as percent of control versus transfection condition.

Results are shown in FIG. 14: Potent and specific inhibition is evident from luciferase and lacZ-derived d-siRNA. Note that in this experiment, lamin A/C d-siRNA serves as a negative control and does not inhibit luciferase or β-galactosidase expression.

Introduction of d-siRNA into mammalian cells can, in some cases lead to a slight induction of gene expression, as is observed with β-galactosidase and luciferase expression upon transfection of lamin d-siRNA.

Example of Expected Results: Knockdown of an Endogenous Gene

In this experiment, dsRNA representing a 1 kb region of the lamin A/C gene and the luciferase gene were produced following the recommended protocols and using reagents supplied in the BLOCK-iT™ RNAi TOPO® Transcription Kit. The target sequences chosen for the lamin A/C and luciferase genes were as described by (Elbashir, S. M., et al., Nature 411:494-498 (2001)). The resulting dsRNA were used as substrates to generate lamin A/C and luciferase d-siRNA following the recommended protocols and using the reagents supplied in the BLOCK-iT™Complete Dicer RNAi Kit.

50 ng each of lamin A/C and luciferase d-siRNA as well as 4 pmoles each (about 50 ng) of synthetic lamin A/C and luciferase siRNA (21 nucleotide duplexes) were transfected into A549 (human lung carcinoma) cells plated in a 24-well plate using Lipofectamine™ 2000. Cell lysates were prepared 48 hours post-transfection and analyzed by Western blot using an Anti-Lamin A/C Antibody (1:1000 dilution, BD Biosciences, Catalog no. 612162) and an Anti-β-Actin Antibody (1:5000 dilution, Abcam, Catalog no. ab6276).

Figure 15:
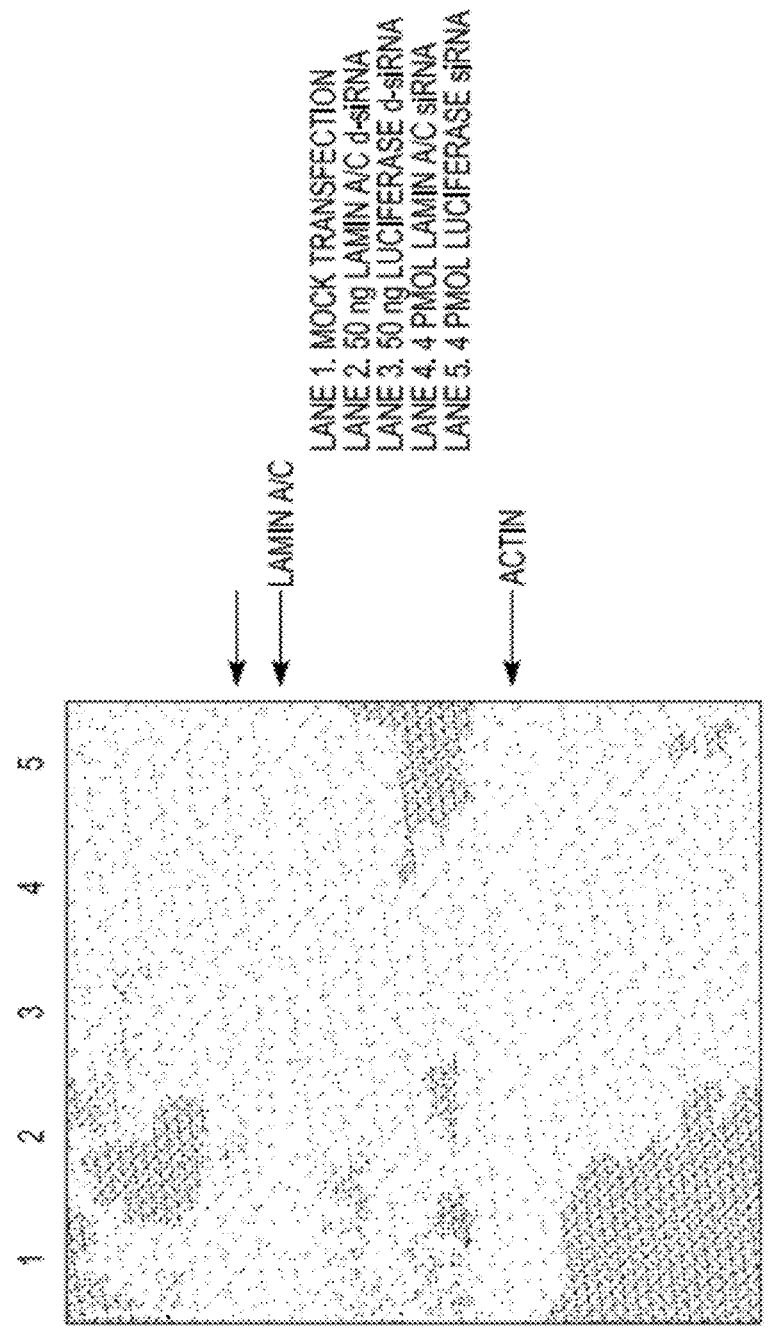
FIG. 15 shows inhibition of expression of lamin A/C expression using d-siRNA.

Results are shown in FIG. 15: Only the lamin A/C-specific d-siRNA (lane 2) and siRNA (lane 4) were able to inhibit expression of the lamin A/C gene, while no lamin A/C gene knockdown was observed with the luciferase d-siRNA (lane 3) or siRNA (lane 5). In addition, the degree of lamin A/C gene blocking achieved using the lamin A/C d-siRNA was similar to that achieved with the well-characterized, chemically-synthesized siRNA. Lane 1. Mock transfection, Lane 2. 50 ng lamin A/C d-siRNA, Lane 3. 50 ng luciferase d-siRNA, Lane 4. 4 μmol lamin A/C siRNA, Lane 5. 4 μmol luciferase siRNA.

Troubleshooting

Use the information in this section to troubleshoot your dicing, purification, and transfection experiments.

Dicing Reaction

The table below lists some potential problems and possible solutions that may help you troubleshoot the dicing reaction.

| Problem | Reason | Solution |
|---|---|---|
| Weak band representing d-siRNA observed on a polyacrylamide or agarose gel (i.e. low yield of d-siRNA) | Poor quality dsRNA | Generate dsRNA using the BLOCK-iT ™ RNAi TOPO ® Transcription Kit (refer to the BLOCK-iT ™ RNAi TOPO ® Transcription Kit manual for instructions). Verify the concentration of your dsRNA. |
| | Didn't use enough dsRNA in the dicing reaction | Use 60 μg of dsRNA in a 300 μl dicing reaction. If you are dicing less dsRNA, scale down the entire dicing reaction proportionally. Make sure that the amount of dsRNA added does not exceed half the reaction volume (i.e. concentration of initial dsRNA substrate >400 ng/μl). |

103 -continued

| Problem | Reason | Solution |
|---|---|---|
| | dsRNA was degraded | Make sure that the dsRNA sample is in a buffer containing 1 mM EDTA (i.e. TE Buffer, pH 7-8 or 1X RNA Annealing Buffer). Avoid repeated freeze/thaw cycles. Aliquot the dsRNA and store at −80° C. |
| | Incubated the dicing reaction for longer than 18 hours | Do not incubate the dicing reaction longer than 18 hours. |
| | Incubated the dicing reaction for less than 14 hours | Incubate the dicing reaction at 37° C. for 14-18 hours. |
| Smear with molecular weight < 21 nt observed on a poly-acrylamide gel | Used too much BLOCK-iT ™ Dicer Enzyme in the dicing reaction | Follow the recommended procedure to set up the dicing reaction. Do not use more than 60 units of BLOCK-iT ™ Dicer Enzyme in a 300 μl reaction. |
| | Incubated the dicing reaction for longer than 18 hours | Do not incubate the dicing reaction for longer than 18 hours. |
| | Sample contaminated with RNase | Use RNase-free supplies and solutions. Wear gloves when handling reagents and setting up the dicing reaction. |
| No d-siRNA produced | dsRNA was degraded | Make sure that the dsRNA sample is in a buffer containing 1 mM EDTA (i.e. TE Buffer, pH 7-8 or 1X RNA Annealing Buffer). Avoid repeated freeze/thaw cycles. Aliquot the dsRNA and store at −80° C. |
| | Sample was contaminated with RNase | Use RNase-free supplies and solutions. Wear gloves when handling reagents and setting |
| | ssRNA used as substrate | If you have used to the BLOCK-iT ™ RNAi TOPO ® Transcription Kit to generate sense and antisense ssRNA, you should anneal the ssRNA to generate dsRNA prior to dicing. |

Purifying d-siRNA

The table below lists some potential problems and possible solutions that may help you troubleshoot the purification procedure.

| Problem | Reason | Solution |
|---|---|---|
| Low yield of purified d-siRNA obtained | Eluted d-siRNA from the RNA Spin Cartridge using TE Buffer | Elute d-siRNA from the RNA Spin Cartridge using water. |
| | Concentration of d-siRNA incorrectly determined | |
| | Sample diluted into water for spectrophotometry | Dilute sample in 1X RNA Annealing Buffer for spectrophotometry. |
| | Sample blanked against water | Blank sample against 1X RNA Annealing Buffer. |

104 -continued

| Problem | Reason | Solution |
|---|---|---|
| No d-siRNA obtained | Forgot to add ethanol to the 5X RNA Wash Buffer | Add 10 ml of ethanol to the 5X RNA Wash Buffer (2.5 ml) to obtain a 1X RNA Wash Buffer. |
| | Forgot to add isopropanol to the combined flow-throughs from the first RNA Spin Cartridge | You should add isopropanol to the combined flow-throughs from the first RNA Spin Cartridge to enable the d-siRNA to bind to the second RNA Spin Cartridge. |
| | Forgot to keep flow-throughs from the first RNA Spin Cartridge | Keep the flow-throughs from the first RNA Spin Cartridge (Steps 3 and 5). The flow-throughs contain the d-siRNA. |
| dsRNA present in purified d-siRNA sample | Forgot to add isopropanol to the dicing reaction | You should add RNA Binding Buffer containing 1% (v/v) β-mercaptoethanol and isopropanol to the dicing reaction to denature the proteins and enable the dsRNA to bind the first RNA Spin Cartridge. |
| | Added the mixture containing the flow-through and isopropanol from the first RNA Spin Cartridge (Step 6) back onto the first RNA Spin Cartridge | You should add the mixture containing the flow-through and isopropanol from the first RNA Spin Cartridge (Step 6) to a second RNA Spin Cartridge as the first RNA Spin Cartridge contains bound dsRNA. |
| A260/A280 ratio not in the 1.9-2.2 range | Sample was not washed with 1X RNA Wash Buffer | Wash the RNA Spin Cartridge containing bound d-siRNA twice with 1X RNA Wash Buffer (see Steps 9 and 10). |
| | RNA Spin Cartridge containing bound d-siRNA not centrifuged to remove residual 1X RNA Wash Buffer | Centrifuge RNA Spin Cartridge at 14,000 × g for 1 minute at room temperature to remove residual 1X RNA Wash Buffer and to dry the membrane (see Step 11). |

Transfection and RNAi Analysis

The table below lists some potential problems and possible solutions that may help you troubleshoot your transfection and knockdown experiment.

| Problem | Reason | Solution |
|---|---|---|
| Low levels of gene knockdown observed | Low transfection efficiency | |
| | Antibiotics added to the media during transfection | Do not add antibiotics to the media during transfection. |
| | Cells were confluent at the time of transfection | Plate cells such that they will be 30-50% confluent at the time of transfection. |
| | Not enough d-siRNA transfected | Increase the amount of d-siRNA transfected. |
| | Not enough Lipofectamine ™ 2000 used | Optimize the transfection conditions for your cell line by varying the amount of Lipofectamine ™ 2000 used. |
| | Didn't wait long enough after transfection before assaying for gene knockdown | Repeat the transfection and wait for a longer period of time after transfection before assaying for gene knockdown. Perform a time course of expression to determine the point at which the highest degree of gene knockdown occurs. |

-continued

| Problem | Reason | Solution |
|---|---|---|
| | d-siRNA was degraded | Make sure that the d-siRNA is stored in 1X RNA Annealing Buffer. Aliquot purified d-siRNA and avoid repeated freeze/thaw cycles. |
| Cytotoxic effects observed after transfection | Too much Lipofectamine ™ 2000 Reagent used | Optimize the transfection conditions for your cell line by varying the amount of Lipofectamine ™ 2000 Reagent used. |
| | Cells transfected with unpurified d-siRNA | Purify d-siRNA using the RNAi Purification reagents supplied with the kit. Transfecting unpurified d-siRNA is not recommended as the contaminating dsRNA will cause host cell shutdown and apoptosis. |
| No gene knockdown observed | d-siRNA was degraded d-siRNA was stored in water | Make sure that the d-siRNA is stored in 1X RNA Annealing Buffer. |
| | d-siRNA was repeatedly frozen and thawed | Aliquot purified d-siRNA and avoid repeated freeze/thaw cycles. |
| | Target region contains no active siRNA | Select a larger target region or a different region. |
| Non-specific off-target gene knockdown observed | Target sequence contains strong homology to other genes | Select a new target sequence. Limit the size range of the target sequence to 1 kb. |

Product Qualification

Introduction The components of the BLOCK-iT™ Dicer RNAi Kits are qualified as described below.

Functional Qualification

The BLOCK-iT™ Dicer enzyme and RNAi Purification reagents are functionally qualified as follows:

1. The BLOCK-iT™ Dicer enzyme is diluted to 1 U/μl and tested (in triplicate) in a dicing reaction following the procedure above using lacZ dsRNA produced using the BLOCK-iT™ RNAi TOPO® Transcription Kit. Each dicing reaction is assessed by analyzing an aliquot of the reaction on a 20% Novex® TBE gel (Catalog no. EC63152BOX). The 10 bp DNA Ladder (Catalog no. 10821-015) is included as a molecular weight standard. Polyacrylamide gel analysis should demonstrate a minimal amount of dsRNA remaining in the reaction and minimal to no degradation of siRNA apparent.

2. The dicing reactions are purified using the RNAi purification reagents supplied in the kit and following the procedure above. Purified d-siRNA is quantitated using spectrophotometry. The amount of d-siRNA recovered should be at least 25%. Lipofectamine™ 2000 Reagent Lipofectamine™ 2000 is tested for the absence of microbial contamination using blood agar plates, Sabaraud dextrose agar plates, and fluid thioglycolate medium, and functionally by transfection of CHO-K1 cells with a luciferase reporter-containing plasmid.

BLOCK-iT™ RNAi TOPO® Transcription Kit

Introduction

This quick reference sheet is provided for experienced users of the dsRNA generation procedure. If you are performing the TOPO® Linking, secondary amplification, transcription, purification, or annealing steps for the first time, follow the detailed protocols provided in the manual. We recommend using the pcDNA™1.2/V5-GW/lacZ plasmid and the control PCR primers (lacZ Forward 2 and lacZ Reverse 2 primers) included with the kit to generate dsRNA.

| Step | Action | | |
|---|---|---|---|
| Produce the PCR product | 1. Amplify your sequence of interest using Platinum ® Taq DNA polymerase and your own protocol. End the PCR reaction with a final 7 minute extension step. 2. Use agarose gel electrophoresis to check the integrity and yield of your PCR product. | | |
| Perform the TOPO ® Linking reaction | 1. Set up the following TOPO ® Linking reaction. | | |
| | Your PCR product (≧20 ng/μl) | | 1 μl |
| | Salt Solution | | 1 μl |
| | Sterile water | | 3 μl |
| | BLOCK-iT ™ T7-TOPO ® Linker | | 1 μl |
| | Total volume | | 6 μl |
| | 2. Mix reaction gently and incubate for 15 minutes at 37° C. 3. Place the reaction on ice and proceed directly to perform secondary amplification, below. | | |
| Perform secondary amplification reactions to generate sense and antisense DNA templates | 1. Set up 2 PCR reactions - in each reaction, amplify 1 μl of the TOPO ® Linking reaction using Platinum ® Taq DNA polymerase and your own protocol. End the PCR reaction with a final 7 minute extension step. For PCR primers, use the following: Sense template: use the BLOCK-iT ™ T7 Primer and your gene-specific reverse primer Antisense template: use the BLOCK-iT ™ T7 Primer and your gene-specific forward primer 2. Use agarose gel electrophoresis to check the integrity and yield of your PCR products. 3. Proceed to perform the RNA transcription reactions, next page. | | |
| Perform the RNA transcription reaction to generate sense and antisense ssRNA | 1. Set up two separate transcription reactions using either the sense or antisense linear DNA template. | | |
| | RNase-free water | | up to 21 μl |
| | 75 mM NTPs | | 8 μl |
| | DNA template (250 ng-1 μg) | | 1-10 μl |
| | 10X Transcription buffer | | 4 μl |
| | BLOCK-iT ™ T7 Enzyme Mix | | 6 μl |
| | Total volume | | 40 μl |
| | 2. Incubate the reaction at 37° C. for 2 hours. 3. Add 2 μl of DNase I to each reaction. Incubate at 37° C. for 15 minutes. | | |
| Purify the sense and antisense transcripts | 1. To each RNA transcription reaction, add 160 μl of RNA Binding Buffer containing 1% (v/v) β-mercaptoethanol followed by 100 μl of 100% ethanol. Mix well by pipetting up and down 5 times. 2. Apply the sample to the RNA Spin Cartridge, and centrifuge at 14,000 × g for 15 seconds at room temperature. Discard the flow-through. 3. Add 500 μl of 1X RNA Wash Buffer to the RNA Spin Cartridge, and centrifuge at 14,000 × g for 15 seconds at room temperature. Discard the flow-through. 4. Repeat Step 3. 5. Centrifuge the RNA Spin Cartridge at 14,000 × g for 1 minute at room temperature. 6. Remove the RNA Spin Cartridge from the Wash Tube, and place it in an RNA Recovery Tube. Add 40 μl of RNase-free water to the RNA Spin Cartridge. Let stand at room temperature for 1 minute, then centrifuge the RNA Spin Cartridge at 14,000 × g for 2 minutes at room temperature to elute the ssRNA. 7. Add 40 μl of RNase-Free Water to the RNA Spin Cartridge and repeat Step 7, eluting the ssRNA into the same RNA Recovery Tube. Add 1.4 μl of 50X RNA Annealing Buffer to the eluted ssRNA. 8. Quantitate the yield of ssRNA by spectrophotometry. | | |
| Anneal the sense and antisense transcripts to produce | 1. In a microcentrifuge tube, mix equal amounts of purified sense and antisense ssRNA. 2. Heat 250 ml of water to boiling in a 500 ml glass beaker, remove from the heat, and set the beaker on the laboratory bench. | | |

| Step | Action |
|---|---|
| dsRNA | 3. Place the tube containing the ssRNA mixture (in a tube float) in the glass beaker and allow the water to cool to room temperature for 1-1.5 hours.<br>4. Aliquot and store the dsRNA at −80° C. |

Kit Contents and Storage

Types of Kits

This manual is supplied with the products listed below.

The BLOCK-iT™ Complete Dicer RNAi Kit is also supplied with the BLOCK-iT™ Dicer RNAi Transfection Kit and the BLOCK-iT™ Dicer RNAi Kits manual.

| Product | Catalog no. |
|---|---|
| BLOCK-iT ™ RNAi TOPO ® Transcription Kit | K3500-01 |
| BLOCK-iT ™ Complete Dicer RNAi Kit | K3650-01 |

Kit Components

The BLOCK-iT™ RNAi Kits include the following components. For a detailed description of the contents of the BLOCK-iT™ RNAi TOPO® Transcription Kit.

The BLOCK-iT™ Complete Dicer RNAi Kit also includes the BLOCK-iT™ Dicer RNAi Transfection Kit. For a detailed description of the reagents supplied in the BLOCK-iT™ Dicer RNAi Transfection Kit, refer to the BLOCK-iT™ Dicer RNAi Kits manual.

| | Catalog no. | |
|---|---|---|
| Component | K3500-01 | K3650-01 |
| BLOCK-iT ™ RNAi TOPO ® Transcription Kit | ✓ | ✓ |
| BLOCK-iT ™ Dicer RNAi Transfection Kit | | ✓ |

Shipping/Storage

The BLOCK-iT™ RNAi TOPO® Transcription Kit is shipped as described below. Upon receipt, store each item as detailed below.

| Box | Component | Shipping | Storage |
|---|---|---|---|
| 1 | BLOCK-iT ™ TOPO ® Linker Kit | Dry ice | −20° C. |
| 2 | BLOCK-iT ™ RNAi Transcription Kit | Dry ice | −20° C. |
| 3 | BLOCK-iT ™ RNAi Purification Kit | Room temperature | Room temperature |

BLOCK-iT™ TOPO® Linker Kit Reagents

The following reagents are supplied with the BLOCK-iT™ TOPO® Linker Kit (Box 1). Note that the user must supply Taq polymerase. Store the reagents at −20° C.

| Reagent | Composition | Amount |
|---|---|---|
| BLOCK-iT ™ T7-TOPO ® Linker | 0.1-1 ng/μl double-stranded DNA in:<br>50 mM Tris-HCl, pH 7.3<br>100 mM NaCl<br>0.2 mM EDTA<br>0.9 mM DTT<br>45 μg/ml BSA<br>0.05% (v/v) Triton X-100<br>40% (v/v) glycerol | 5 μl |
| 10X PCR Buffer | 100 mM Tris-HCl, pH 8.3 (at 42° C.)<br>500 mM KCl<br>25 mM MgCl$_2$<br>0.01% gelatin | 75 μl |
| 40 mM dNTPs | 10 mM dATP<br>10 mM dTTP<br>10 mM dGTP<br>10 mM dCTP<br>neutralized at pH 8.0 in water | 15 μl |
| Salt Solution | 1.2 M NaCl<br>0.06 M MgCl$_2$ | 10 μl |
| Sterile Water | — | 750 μl |
| BLOCK-iT ™ T7 Primer | 75 ng/μl in TE Buffer, pH 8.0 | 10 μl |
| LacZ Forward 2 Primer | 65 ng/μl in TE Buffer, pH 8.0 | 10 μl |
| LacZ Reverse 2 Primer | 65 ng/μl in TE Buffer, pH 8.0 | 10 μl |
| pcDNA ™ 1.2/V5-GW/lacZ control plasmid | Lyophilized in TE Buffer, pH 8.0 | 10 μg |

Primer Sequences

The table below provides the sequence and the amount supplied of the primers included in the kit.

| Primer | Sequence | Amount |
|---|---|---|
| BLOCK-iT ™ T7 | 5'-GATGACTCGTAATACGACTCACTA-3'<br>(SEQ ID NO. 48) | 103 pmoles |
| LacZ Forward 2 | 5'-ACCAGAAGCGGTGCCGGAAA-3'<br>(SEQ ID NO. 49) | 105 pmoles |
| LacZ Reverse 2 | 5'-CCACAGCGGATGGTTCGGAT-3'<br>(SEQ ID NO. 50) | 106 pmoles |

BLOCK-iT™ RNAi Transcription Kit Reagents

The following reagents are included with the BLOCK-iT™ RNAi Transcription Kit. Store reagents at −20° C.

| Reagent | Composition | Amount |
|---|---|---|
| BLOCK-iT ™ T7 Enzyme Mix | | 60 μl |
| 10X Transcription Buffer | | 40 μl |
| 75 mM NTPs | 18.75 mM ATP<br>18.75 mM UTP<br>18.75 mM CTP<br>18.75 mM GTP<br>neutralized at pH 8.0 in water | 80 μl |
| RNase-Free Water | — | 800 μl |
| DNase I | 1 U/μl in<br>20 mM sodium acetate, pH 6.5<br>5 mM CaCl$_2$<br>0.1 mM PMSF<br>50% (v/v) glycerol | 20 μl |

BLOCK-iT™ RNAi Purification Kit

The following reagents are included with the BLOCK-iT™ RNAi Purification Kit. Store reagents at room temperature. Use caution when handling the RNA Binding Buffer.

Catalog no. K3650-01 includes two boxes of BLOCK-iT™ RNAi Purification reagents. One box is supplied with the BLOCK-iT™ RNAi TOPO® Transcription Kit for purification of the single-stranded RNA (ssRNA). The second box is supplied with the BLOCK-iT™ Dicer RNAi Transfection Kit for purification of diced siRNA (d-siRNA).

| Reagent | Composition | Amount |
|---|---|---|
| RNA Binding Buffer | — | 1.8 ml |
| 5X RNA Wash Buffer | — | 2.5 ml |
| RNase-Free Water | — | 800 µl |
| RNA Spin Cartridges | — | 10 |
| RNA Recovery Tubes | — | 10 |
| siRNA Collection Tubes* | — | 5 |
| 50X RNA Annealing Buffer | 500 mM Tris-HCl, pH 8.0<br>1 M NaCl<br>50 mM EDTA, pH 8.0 | 50 µl | siRNA Collection Tubes are not required for the purification of the ssRNA, and are used for purification of d-siRNA only.

The RNA Binding Buffer supplied in the BLOCK-iT™ RNAi Purification Kit contains guanidine isothiocyanate. This chemical is harmful if it comes in contact with the skin or is inhaled or swallowed. Always wear a laboratory coat, disposable gloves, and goggles when handling solutions containing this chemical.

Do not add bleach or acidic solutions directly to solutions containing guanidine isothiocyanate or sample preparation waste. Guanidine isothiocyanate forms reactive compounds and toxic gases when mixed with bleach or acids.

Accessory Products

The table below provides ordering information for products available from Invitrogen that are suitable for use with the BLOCK-iT™ RNAi TOPOS Transcription Kit.

| Item | Amount | Catalog no. |
|---|---|---|
| BLOCK-iT ™ Dicer RNAi Transfection Kit | 5 genes × 150 transfections each* | K3600-01 |
| Taq DNA Polymerase, Native | 100 units<br>500 units | 18038-018<br>18038-042 |
| Taq DNA Polymerase, Recombinant | 100 units<br>500 units | 10342-053<br>10342-020 |
| Platinum ® Taq DNA Polymerase | 100 reactions<br>250 reactions<br>500 reactions | 10966-018<br>10966-026<br>10966-034 |
| 6% Novex ® TBE Gel | 1 box | EC6265BOX |
| 0.16-1.77 kb RNA Ladder | 75 µg | 15623-010 |

*Based on transfection in 24-well plates.

Introduction

The BLOCK-iT™ RNAi TOPO® Transcription Kit facilitates rapid generation of T7 promoter-based DNA templates. Using the DNA templates and reagents supplied with the kit, RNA transcripts are produced, purified, and annealed to generate double-stranded RNA (dsRNA). The resulting dsRNA may be used directly for RNA interference (RNAi) analysis in invertebrate systems and other systems lacking the interferon response or as a substrate to produce short interfering RNA (siRNA) for RNAi analysis in mammalian cells.

Advantages of the BLOCK-iT™ RNAi TOPO® Transcription Kit

Use of the BLOCK-iT™ RNAi TOPO® Transcription Kit to facilitate production of dsRNA provides the following advantages:

1. The BLOCK-iT™ T7-TOPO® Linker provides a method to quickly and easily add a T7 promoter to any existing Taq-amplified PCR product without the need for new primers or subcloning.
2. Use of the TOPO® Linking Technology and secondary amplification enables simultaneous production of linear DNA templates that may be used directly for in vitro transcription to generate sense and antisense transcripts. Creation of a T7 expression plasmid, bacterial transformation, and plasmid purification are not required.
3. Separate transcription reactions using sense and antisense templates allow precise quantitation of ssRNA concentration prior to annealing.
4. Provides optimized purification reagents to obtain highly pure sense and antisense transcripts that can be annealed to generate an optimal yield of dsRNA.

Double-stranded RNA can be used directly for RNAi analysis in invertebrate systems or as a substrate for the Dicer enzyme to generate siRNA.

This manual provides instructions and guidelines to:
1. Amplify your sequence of interest and use TOPO® Linking to join the primary PCR product to the BLOCK-iT™ T7-TOPO® Linker.
2. Use the appropriate primers to amplify the TOPO® Linked PCR product to generate linear sense and antisense DNA templates.
3. Use the linear sense and antisense DNA templates in transcription reactions to generate sense and antisense single-stranded RNA (ssRNA) transcripts of the sequence of interest.
4. Purify the sense and antisense ssRNA transcripts and anneal them to generate dsRNA. The resulting dsRNA may then be used in the application of choice (e.g. RNAi analysis in invertebrate organisms or as a substrate for "dicing" to produce d-siRNA for RNAi analysis in mammalian cells).

For details and instructions to generate d-siRNA using Dicer, refer to the BLOCK-iT™ Dicer RNAi Kits manual. This manual is supplied with the BLOCK-iT™ Dicer RNAi Transfection and Complete Dicer RNAi Kits.

The BLOCK-iT™ RNAi TOPO® Transcription Kit is designed to help you generate dsRNA for direct use in RNAi analysis in invertebrate systems or as a substrate in a dicing reaction to produce d-siRNA for RNAi analysis in mammalian cells. Although the kit has been designed to help you generate dsRNA representing a particular target sequence in the simplest, most direct fashion, use of the resulting dsRNA for RNAi analysis assumes that users are familiar with the mechanism of gene silencing and the techniques that exist to introduce dsRNA into the organism or cell type of choice. We highly recommend that users possess a working knowledge of the RNAi pathway and the methodologies required to perform RNAi analysis in the organism or cell type of choice.

For more information about these topics, refer to published reviews (Bosher and Labouesse, 2000; Hannon, 2002; Plasterk and Ketting, 2000; Zamore, 2001). A variety of BLOCK-iT™ RNAi products are available from Invitrogen to facilitate your RNAi analysis.

Description of the System

The BLOCK-iT™ RNAi TOPO® Transcription Kit facilitates generation of T7 promoter-based DNA templates for in vitro transcription and production of dsRNA, and consists of three major components:

1. The BLOCK-iT™ T7-TOPO® Linker for quick and easy creation of T7 promoter-based DNA templates for in vitro transcription. Using TOPO® Linking Technology, the BLOCK-iT™ T7-TOPO® Linker may be linked to any Taq-amplified PCR product. The linked PCR product is then amplified to generate a linear DNA template.
2. BLOCK-iT™ RNAi Transcription reagents for generation of sense and antisense ssRNA transcripts from your T7-based, linear DNA template. The reagents include an optimized T7 Enzyme Mix for highly efficient production of ssRNA.

3. The BLOCK-iT™ RNAi Purification reagents for silica-based column purification of sense and antisense ssRNA transcripts, and an RNA Annealing Buffer to stabilize dsRNA duplexes for long-term storage.

The BLOCK-iT™ RNAi TOPO® Transcription Kit also includes a control expression plasmid containing the lacZ gene and PCR primers that may be used as controls to generate dsRNA. Once generated, the lacZ dsRNA may be used for the following types of RNAi analysis:

Invertebrate Systems

As a negative control for non-specific gene knockdown in any invertebrate system. The lacZ dsRNA is not suitable for use as a positive control to knock down β-galactosidase expression from the control pcDNA™ 1.2/V5-GW/lacZ plasmid in any invertebrate system. This is because expression of the lacZ gene from the control plasmid is controlled by the human cytomegalovirus (CMV) promoter, and this promoter is not active in most invertebrate systems.

Mammalian Systems

As a negative control for non-specific gene knockdown or as a positive control for knockdown of β-galactosidase expression from the pcDNA™ 1.2V-GW/lacZ reporter plasmid. Note that to perform RNAi analysis in mammalian cells, the lacZ dsRNA should first be "diced" to generate d-siRNA. For details, refer to the BLOCK-iT™ Dicer RNAi Kits manual.

Generating dsRNA Using the BLOCK-iT™ RNAi TOPO® Transcription Kit

Figure 16:
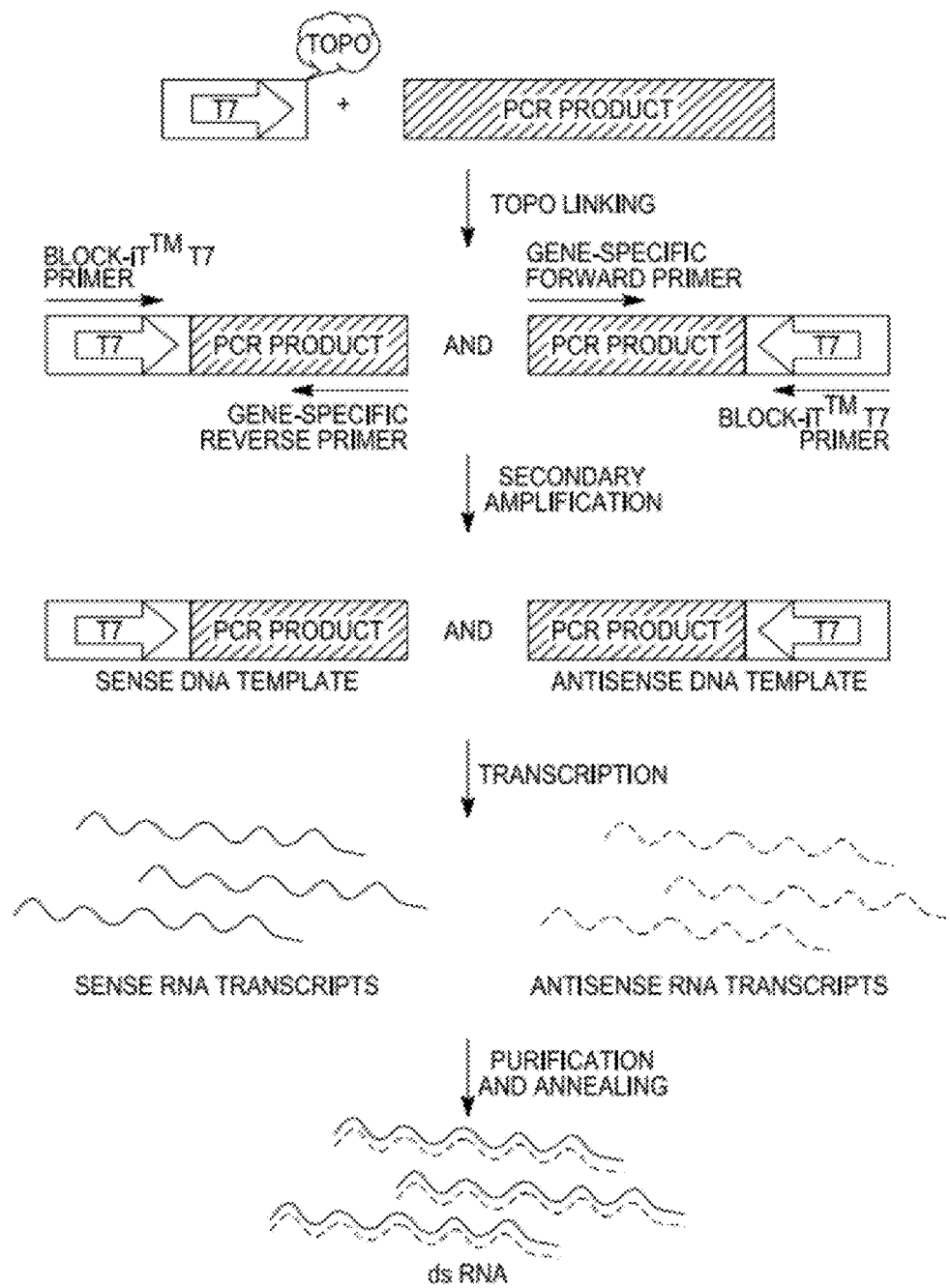
FIG. 16 illustrates the major steps necessary to generate dsRNA using the BLOCK-iT™ RNAi TOPO® Transcription System.

You will perform the following steps to generate dsRNA using the BLOCK-iT™ RNAi TOPO® Transcription Kit. For a diagram, see FIG. 16 illustrating the major steps necessary to generate dsRNA using the BLOCK-iT™ RNAi TOPO® Transcription System.

1. Amplify your sequence of interest using Taq polymerase.
2. Perform a TOPO® Linking reaction to link your PCR product to the BLOCK-iT™ T7-TOPO® Linker containing the T7 promoter.
3. Using a combination of the BLOCK-iT™ T7 Primer (supplied with the kit) and your gene-specific forward or reverse primer, amplify the TOPO® Linked PCR product with Taq polymerase to produce linear sense and antisense DNA templates.
4. Use the sense and antisense DNA templates and the reagents supplied in the kit in an in vitro transcription reaction to produce sense and antisense RNA transcripts, respectively.
5. Purify the sense and antisense RNA transcripts using the RNAi Purification reagents supplied in the kit.
6. Quantitate the yield of purified sense and antisense ssRNA transcripts, and anneal equal amounts of each single-stranded transcript to form dsRNA.

How TOPO® Linking Works

How Topoisomerase 1 Works

Topoisomerase 1 from Vaccinia virus binds to duplex DNA at specific sites and cleaves the phosphodiester backbone after 5'-CCCTT in one strand (Shuman, 1991). The energy from the broken phosphodiester backbone is conserved by formation of a covalent bond between the 3' phosphate of the cleaved strand and a tyrosyl residue (Tyr-274) of topoisomerase I. The phospho-tyrosyl bond between the DNA and enzyme can subsequently be attacked by the 5' hydroxyl of the original cleaved strand, reversing the reaction and releasing topoisomerase (Shuman, 1994). TOPO® Linking exploits this reaction to efficiently join PCR products to the BLOCK-iT™ T7-TOPO® Linker.

TOPO® Linking

The BLOCK-iT™ T7-TOPO® Linker is supplied linearized with:

A single 3' thymidine (T) overhang for TA Cloning®
Topoisomerase 1 covalently bound to the linker (this is referred to as "activated linker")

Taq polymerase has a nontemplate-dependent terminal transferase activity that adds a single deoxyadenosine (A) to the 3' ends of PCR products. The linear BLOCK-iT™ T7-TOPO® linker supplied in this kit has a single, overhanging 3 deoxythymidine (T) residue. This allows PCR products to ligate efficiently with the linker.

Figure 17:
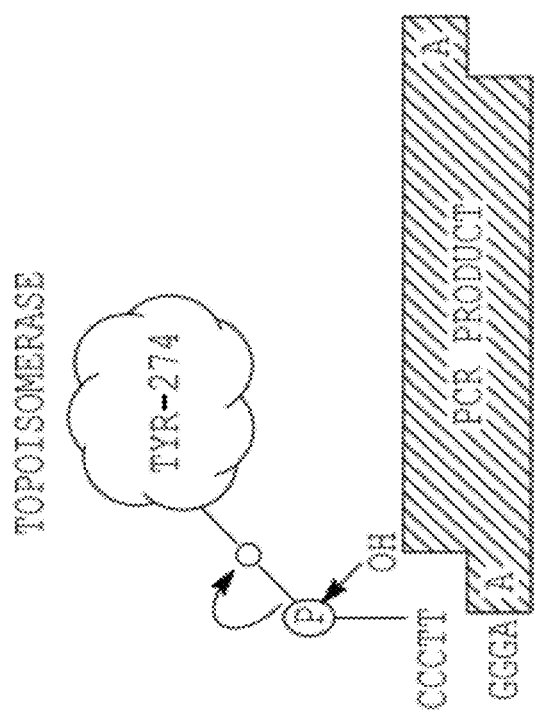
FIG. 17 shows TOPO® linking to a PCR product.

TOPO® Linking as shown in FIG. 17 exploits the ligation activity of topoisomerase I by providing an "activated" linearized TA linker (Shuman, 1994). Ligation of the linker with a PCR product containing 3' A-overhangs is very efficient and occurs spontaneously with maximum efficiency at 37° C. within 15 minutes.

The RNAi Pathway

RNAi describes the phenomenon by which dsRNA induces potent and specific inhibition of eukaryotic gene expression via the degradation of complementary messenger RNA (mRNA), and is functionally similar to the processes of post-transcriptional gene silencing (PTGS) or cosuppression in plants (Cogoni et al., 1994; Napoli et al., 1990; Smith et al., 1990; van der Krol et al., 1990) and quelling in fungi (Cogoni and Macino, 1999; Cogoni and Macino, 1997; Romano and Macino, 1992). In plants, the PTGS response is thought to occur as a natural defense against viral infection or transposon insertion (Anandalakshmi et al., 1998; Jones et al., 1998; Li and Ding, 2001; Voinnet et al., 1999).

In eukaryotic organisms, dsRNA produced in vivo or introduced by pathogens is processed into 21-23 nucleotide double-stranded short interfering RNA duplexes (siRNA) by an enzyme called Dicer, a member of the RNase III family of double-stranded RNA-specific endonucleases (Bernstein et al., 2001; Ketting et al., 2001). The siRNA then incorporate into the RNA-induced silencing complex (RISC), a second enzyme complex that serves to target cellular transcripts complementary to the siRNA for specific cleavage and degradation (Hammond et al., 2000; Nykanen et al., 2001).

For more information about the RNAi pathway and the mechanism of gene silencing, refer to reviews (Bosher and Labouesse, 2000; Hannon, 2002; Plasterk and Ketting, 2000; Zamore, 2001).

Using the Kit for RNAi Analysis

Figure 18:
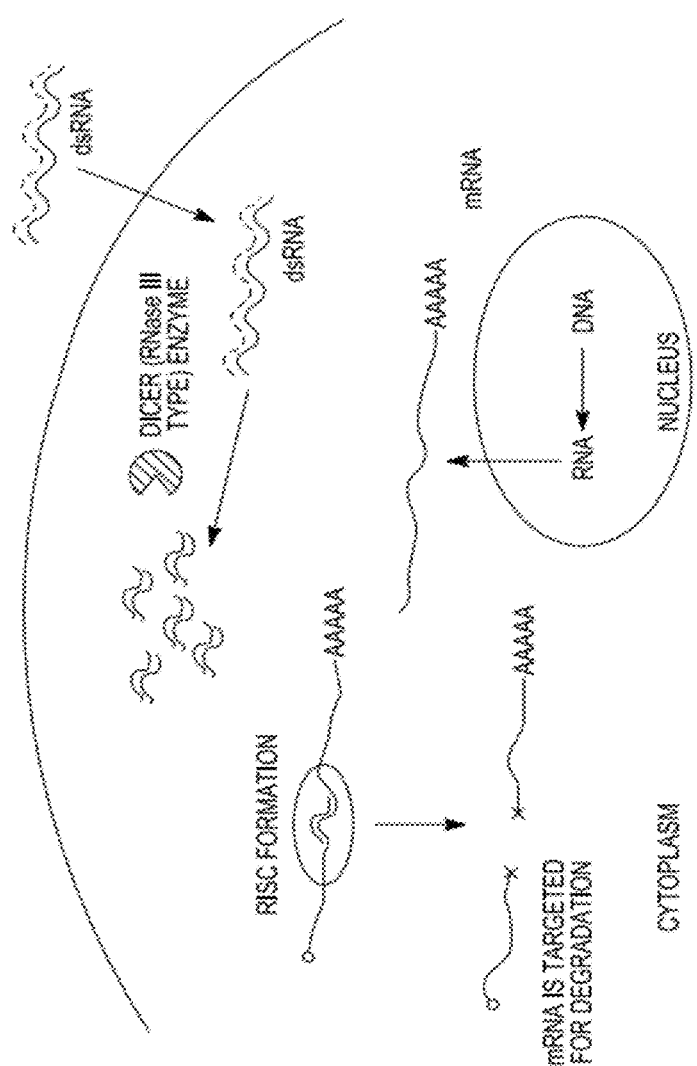
FIG. 18 shows the RNAi process and pathway.

The BLOCK-iT™ RNAi TOPO® Transcription Kit facilitates in vitro production of dsRNA that is targeted to a particular gene of interest. The long dsRNA is introduced into the appropriate organism or cells, where the endogenous Dicer enzyme processes the dsRNA into siRNA. The resulting siRNA can then inhibit expression of the target gene. For a diagram of the process, see FIG. 18.

Use of dsRNA for RNAi Analysis

Long dsRNA duplexes can be used directly for RNAi analysis in organisms and systems lacking the interferon response, including insects (Kennerdell and Carthew, 1998; Misquitta and Paterson, 1999), insect cell lines (Caplen et al., 2000), *C. elegans* (Fire et al., 1998), trypanosomes (Ngo et al., 1998), some mammalian embryonic cell lines (Billy et al., 2001; Yang et al., 2001), and mouse oocytes and preimplantation embryos (Svoboda et al., 2000; Wianny and Zernicka-Goetz, 2000).

Long dsRNA duplexes cannot be used directly for RNAi analysis in most somatic mammalian cell lines. This is because introduction of dsRNA into these cell lines induces a non-specific, interferon-mediated response resulting in shutdown of translation and initiation of cellular apoptosis (Kaufman, 1999). To perform RNAi analysis in mammalian cell lines, long dsRNA should first be cleaved into 21-23 nucleotide siRNA duplexes. This cleavage process may be performed in vitro using recombinant Dicer enzyme such as is provided in the BLOCK-iT™ Dicer RNAi Transfection Kit or the BLOCK-iT™ Complete Dicer RNAi Kit. For more information, refer to the BLOCK-iT™ Dicer RNAi Kits manual.

Experimental Outline

The table below describes the major desired steps to generate a dsRNA using the BLOCK-iT™ RNAi TOPO® Transcription Kit.

| Step | Action |
| --- | --- |
| 1 | Produce your PCR product using Taq polymerase or Platinum ® Taq DNA polymerase. |
| 2 | Verify the integrity and concentration of your PCR product. |
| 3 | Perform the TOPO ® Linking reaction to link your PCR product to the BLOCK-iT ™ T7-TOPO ® Linker. |
| 4 | Amplify the TOPO ® Linked PCR product using the appropriate primers to produce sense and antisense linear DNA templates. |
| 5 | Use each linear DNA template in an RNA transcription reaction to produce sense and antisense RNA transcripts. |
| 6 | Purify sense and antisense RNA transcripts. |
| 7 | Quantitate the yield of each purified ssRNA obtained, and anneal equal amounts of sense and antisense ssRNA to generate dsRNA. |

Methods

Designing PCR Primers

To use the BLOCK-iT™ RNAi TOPO® Transcription Kit, you will first need to design PCR primers to amplify your sequence of interest. Guidelines to choose the target sequence and to design PCR primers are provided below.

Choosing the Target Sequence

When performing RNAi analysis, your choice of target sequence can significantly affect the degree of gene knockdown observed. In addition, the size of the target sequence and the resulting dsRNA can affect the transcription efficiency and thus the yield of dsRNA produced. Consider the following factors when choosing your target sequence.

1. Select a target sequence that covers a reasonable portion of the gene of interest and that does not contain regions of strong homology with other genes.
2. Limit the size of the target sequence. Although smaller or larger target sequences are possible, we recommend limiting the initial target sequence to a size range of 500 bp to 1 kb for the following reasons.

(a) This balances the risk of including regions of strong homology between the target gene and other genes that could result in non-specific off-target effects during RNAi analysis with the benefits of using a more complex pool of siRNA.

(b) When producing sense and antisense transcripts of the target template, the highest transcription efficiencies are obtained with transcripts in the 500 bp to 1 kb size range. Target templates outside this size range transcribe less efficiently, resulting in lower yields of dsRNA.

(c) If you plan to "dice" the dsRNA to produce d-siRNA for use in mammalian RNAi analysis, note that dsRNA that are under 1 kb in size are efficiently diced. Larger dsRNA can be used but yields may decline as the size increases.

The BLOCK-iT™ Complete Dicer RNAi Kit has been used successfully to knock down gene activity with dsRNA substrates ranging from 150 bp to 1.3 kb in size.

Factors to Consider When Designing PCR Primers

Once you have selected an appropriate target sequence, you will need to design gene-specific primers to amplify your target sequence of interest. Consider the following factors when designing gene-specific primers.

1. Make sure that your primers do not contain sequence that is homologous to other genes.
2. Once you have linked your primary PCR product to the BLOCK-iT™ T7-TOPO® Linker, you will amplify the resulting linked product using the BLOCK-iT™ T7 Primer and either your gene-specific forward primer or gene-specific reverse primer. When designing your gene-specific PCR primers, make sure that the Tm of each primer is compatible with the Tm of the BLOCK-iT™ T7 primer (i.e. Tm=62° C.).

Figure 19:
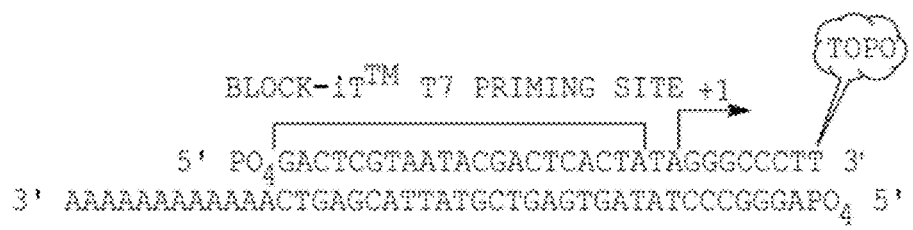
FIG. 19 is a diagram of the BLOCK-iT T7-TOPO linker.

FIG. 19 can be used to design appropriate PCR primers to join your sequence of interest with the BLOCK-iT™ T7-TOPO® Linker. The BLOCK-iT™ T7-TOPO® Linker is supplied as a double-stranded DNA fragment adapted with topoisomerase I.

Features of the BLOCK-iT™ T7-TOPO® Linker:

The sequence of the T7 promoter is indicated in bold.

The transcription start site is indicated by +1.

To obtain consistent and efficient results in the TOPO® Linking reaction, we recommend using HPLC-purified oligonucleotides to produce your PCR products. Using a mixture of full-length and non full-length primers to produce your PCR products can reduce the efficiency of TOPO® Linking and result in poor yield of the linear DNA templates after secondary amplification.

Do not add 5' phosphates to your primers for PCR. This will prevent TOPO® Linking.

Amplifying Your Sequence of Interest

Once you have decided on a PCR strategy and have synthesized the primers, you are ready to produce your PCR product.

Choosing a Thermostable DNA Polymerase

To amplify your sequence of interest, use a thermostable DNA polymerase that generates PCR products with 3' A-overhangs. We recommend using Platinum® Taq polymerase available from Invitrogen. Taq polymerase is also suitable.

You may use Taq polymerase and proofreading polymerase mixtures to generate PCR products, however, a certain proportion of your PCR products will be blunt-ended. You can add 3' A-overhangs to your PCR products using the method below.

Control Plasmid

Figure 21:
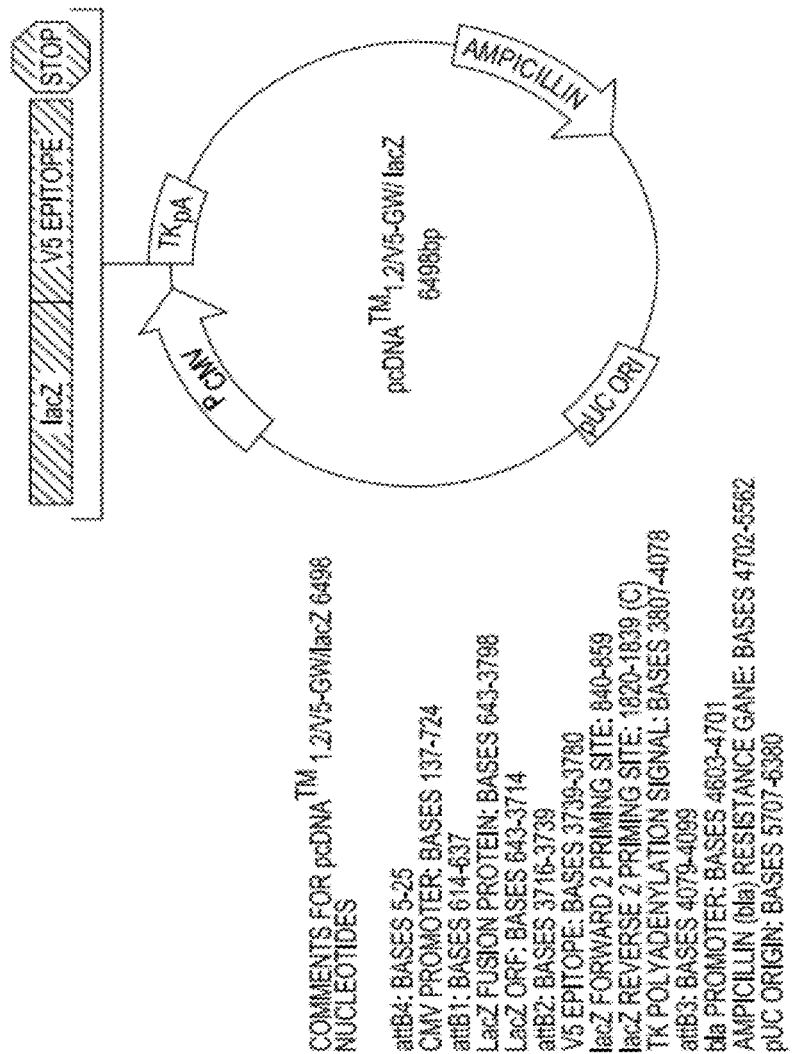
FIG. 21 is a vector map of pcDNA™ 0.2/V5-GW/lacZ.

We recommend amplifying the control template included with the kit in parallel with your sample. Use the LacZ Forward 2 and the LacZ Reverse 2 primers included with the kit to amplify the pcDNA™ 1.2/V5-GW/lacZ plasmid. The resulting control PCR product (representing a 1 kb fragment of the lacZ gene) may then be used as a positive control for subsequent procedures including TOPO® Linking, transcription, and production of dsRNA. For a map of pcDNA™ 1.2/V5-GW/lacZ, refer to FIG. 21.

To use the pcDNA™ 1.2/V5-GW/lacZ plasmid as a template for amplification, resuspend the plasmid in 10 µl of sterile water to obtain a final concentration of 1 µg/µl. Dilute as appropriate and use 1-10 ng of plasmid DNA in the PCR reaction.

Materials Needed

You should have the following materials on hand before beginning:
1. Thermocycler
2. Thermostable DNA polymerase (e.g. Platinum® Taq DNA Polymerase)
3. DNA template
4. Gene-specific forward and reverse PCR primers (10 μM each)
5. 10×PCR Buffer (supplied with the kit, Box 1)
6. 40 mM dNTPs (supplied with the kit, Box 1)
7. Sterile water (supplied with the kit, Box 1)

Setting Up the PCR Reaction

Use the procedure below to amplify your sequence of interest using Platinum® Taq DNA polymerase. Use less DNA if you are using plasmid DNA as a template (1-10 ng) and more DNA if you are using genomic DNA as a template (10-100 ng).

If you are using a different thermostable DNA polymerase, reaction conditions may vary.

1. Set up the following 50 μl PCR reaction.

| | |
|---|---|
| DNA Template | 1-100 ng |
| 10X PCR Buffer | 5 μl |
| 40 mM dNTPs | 1 μl |
| PCR Primers (10 μM each) | 1 μl each |
| Sterile water | add to a final volume of 49.5 μl |
| Platinum ® Taq polymerase (5 U/μl) | 0.5 μl |
| Total volume | 50 μl |

2. Use the cycling parameters suitable for your primers and template. Be sure to include a 7 minute extension at 72° C. after the last cycle to ensure that all PCR products are full-length and 3' adenylated.
3. After cycling, place the tube on ice. Proceed to Checking the PCR Product, below.

Checking the PCR Product

Analyze 1-5 μl of the PCR reaction using agarose gel electrophoresis to verify the quality and quantity of your PCR product. Check for the following:
1. A single discrete band of the expected size corresponding to your sequence of interest. If you do not obtain a single, discrete band from your PCR, follow the manufacturer's recommendations or use the PCR Optimizer™ Kit (Catalog no. K1220-01) from Invitrogen to optimize your PCR conditions using your DNA polymerase. Other tips may be found below or in published reference sources (Innis et al., 1990). Alternatively, you may gel-purify your fragment before proceeding to TOPO™ Linking.
2. Estimate the concentration of your PCR product. For optimal TOPO® Linking, the concentration of your PCR should be ≧20 ng/μl. If your PCR product is too dilute, see Concentrating Dilute PCR Products, below.

Once you have verified that your PCR product is of the appropriate quality and concentration, proceed to Performing the TOPO® Linking Reaction.

For optimal results, use fresh PCR product in the TOPO® Linking reaction.

You may store the PCR product at −20° C. for up to 1 week.

Concentrating Dilute PCR Products

If you obtain a single band from PCR, but your PCR product is too dilute, you may purify and concentrate the PCR product before proceeding to the TOPO® Linking reaction. A procedure to purify and concentrate PCR products is provided below. Performing the TOPO® Linking Reaction Introduction Once you have produced your PCR product, you will use TOPO® Linking to join the PCR product to the BLOCK-iT™ T7-TOPO® Linker. Before performing the TOPO® Linking reaction, you should have everything you need set up and ready to use to ensure that you obtain the best results. If you have produced the control PCR product and this is the first time you have performed TOPO® Linking, we recommend performing the control TOPO® Linking reaction below in parallel with your samples.

Materials Needed

Have the following reagents on hand before beginning:
1. Your primary PCR product (≧20 ng/μl)
2. BLOCK-iT™ T7-TOPO® Linker (supplied with the kit, Box 1; keep at −20° C. until use)
3. Salt Solution (supplied with the kit; Box 1)
4. Sterile Water (supplied with the kit; Box 1)
5. 37° C. water bath TOPO® Linking Procedure Follow the procedure below to perform the TOPO® Linking reaction.

1. Set up a 6 μl TOPO® Linking reaction using the following reagents in the order given.

| | |
|---|---|
| Your PCR product (≧20 ng/μl) | 1 μl |
| Salt Solution | 1 μl |
| Sterile water | 3 μl |
| BLOCK-iT ™ T7-TOPO ® Linker | 1 μl |
| Total volume | 6 μl |

2. Mix reaction gently and incubate for 15 minutes at 37° C. Do not incubate the reaction for longer than 15 minutes as this may negatively affect TOPO® Linking.
3. Place the reaction on ice and proceed directly to Performing Secondary Amplification.

You may store the TOPO® Linking reaction at −20° C. overnight, if desired.

Performing Secondary Amplification Reactions

Introduction

Once you have performed the TOPO® Linking reaction, you will use this reaction mixture in two PCR reactions with the appropriate PCR primers to produce sense and antisense linear DNA templates. Guidelines to perform secondary amplification are provided in this section.

Thermostable DNA Polymerase

You may use any thermostable DNA polymerase to produce sense and antisense linear DNA templates. We generally use the same thermostable DNA polymerase to perform secondary amplification as we use to generate the primary PCR product (i.e. Platinum® Taq DNA Polymerase).

PCR Primers

To produce sense and antisense linear DNA templates, you will perform two amplification reactions using the TOPO® Linking reaction and the appropriate primers (see table below). For gene-specific PCR primers, use the primers that you used to produce your primary PCR product. The BLOCK-iT™ T7 Primer is supplied with the kit.

| Sense Template | Antisense Template |
| --- | --- |
| BLOCK-iT™ T7 Primer | BLOCK-iT™ T7 Primer |
| Gene-specific reverse primer | Gene-specific forward primer |

General Guidelines

When amplifying the TOPO® Linked PCR product, we recommend the following:
1. Perform the PCR reaction in a total volume of 50 µl.
2. Use 1 µl of the TOPO® Linking reaction as the DNA template.
3. If you use the same thermostable DNA polymerase to perform secondary amplification as was used to generate the primary PCR product, you may generally use similar cycling conditions. However, because you are using different PCR primers, you may need to adjust the cycling conditions.

Materials Needed

You should have the following materials on hand before beginning:
1. Thermocycler
2. Thermostable DNA polymerase (e.g. Platinum® Taq DNA Polymerase)
3. TOPO® Linking reaction (from Step 3)
4. Gene-specific forward and reverse primers (10 µM each)
5. BLOCK-iT™ T7 Primer (supplied with the kit, Box 1)
6. 10×PCR Buffer (supplied with the kit, Box 1)
7. 40 mM dNTPs (supplied with the kit, Box 1)
8. Sterile water (supplied with the kit, Box 1)

Setting Up the Secondary PCR Reactions

Use the procedure below to amplify the TOPO® Linked PCR product using Platinum® Taq DNA polymerase. If you are using a different thermostable DNA polymerase, reaction conditions may vary.
1. Set up the following 50 µl PCR reactions:

| Reagent | Sense Template | Antisense Template |
| --- | --- | --- |
| 10X PCR Buffer | 5 µl | 5 µl |
| 40 mM dNTPs | 1 µl | 1 µl |
| BLOCK-iT™ T7 Primer (75 ng/µl) | 1 µl | 1 µl |
| Gene-specific forward primer (10 µM) | — | 1 µl |
| Gene-specific reverse primer (10 µM) | 1 µl | — |
| Sterile water | 40.5 µl | 40.5 µl |
| TOPO® Linking reaction | 1 µl | 1 µl |
| Platinum® Taq Polymerase (5 U/µl) | 0.5 µl | 0.5 µl |
| Total volume | 50 µl | 50 µl |

2. Use the cycling parameters suitable for your primers and template. Be sure to include a 7 minute extension at 72° C. after the last cycle to ensure that all PCR products are full-length.
3. After cycling, place the tube on ice. Proceed to Checking the PCR Products, below.

Checking the PCR Products

Analyze 1-5 µl of each PCR reaction using agarose gel electrophoresis to verify the quality and quantity of your PCR product. Check for the following:
1. A single discrete band of the expected size corresponding to your linked linear DNA template.
2. You may see some minor background bands. These are generally due to smaller PCR products that were in the primary PCR reaction and should not affect the efficiency of the transcription reaction.
3. Estimate the concentration of each PCR product. For optimal transcription efficiency, the concentration of each PCR product should be $\geq$25 ng/µl. If your PCR product(s) is too dilute, you may increase the number of cycles of the amplification reaction or use the procedure provided below to purify and concentrate your PCR product.

Once you have verified that your PCR products are of the appropriate quality and concentration, proceed to Performing the RNA Transcription Reaction.

Storing the PCR Products

For optimal results, use fresh PCR products in the RNA transcription reaction. You may store the PCR products at −20° C. for up to 1 month, if desired.

Performing the RNA Transcription Reactions

Once you have produced the sense and antisense DNA templates of your target sequence, you will perform two transcription reactions using the reagents supplied in the RNA Transcription Kit (Box 2) to generate sense and antisense transcripts.

Amount of DNA Template to Use

For each RNA transcription reaction, you will need 250 ng to 1 µg of your DNA template. For best results, make sure that the concentration of your sense and antisense DNA templates is $\geq$25 ng/µl.

Positive Control

If you have performed the control reactions described, we recommend using the resulting sense and antisense lacZ templates as controls in the RNA transcription, purification, and annealing procedures. Once you have produced control lacZ dsRNA, you may:

Use this dsrNA as a negative control for non-specific, off-target effects in your RNAi studies.

Include the lacZ dsRNA in a dicing reaction (refer to the BLOCK-iT™ Dicer RNAi Kits manual for instructions), then use the resulting lacZ d-siRNA as a positive control for RNAi in mammalian cells. Co-transfect the lacZ d-siRNA and the pcDNA™ 1.2/V5-GW/lacZ plasmid into mammalian cells and assay for knockdown of β-galactosidase expression.

When performing the RNA transcription reaction and all subsequent procedures, take precautions to avoid RNase contamination.

Use RNase-free, sterile pipette tips and supplies for all manipulations.

Use DEPC-treated solutions as necessary.

Wear gloves when handling reagents and solutions and when setting up the transcription reaction.

Materials Needed

You should have the following materials on hand before beginning:
1. Sense and antisense DNA templates (from the Secondary Amplification reactions, Step 3; $\geq$25 ng/µl each)
2. RNase-Free Water (supplied with the kit, Box 2)
3. 75 mM NTPs (supplied with the kit, Box 2)
4. 10× Transcription Buffer (supplied with the kit, Box 2; keep on ice until use)
5. BLOCK-iT™ T7 Enzyme Mix (supplied with the kit, Box 2; keep at −20° C. until use)
6. DNase I (supplied with the kit, Box 2)
7. RNase-free supplies (e.g. microcentrifuge tubes and pipette tips)
8. 37° C. waterbath Guidelines to Set Up the Transcription Reactions Follow the guidelines below when setting up the transcription reactions.

a) Set up the transcription reaction at room temperature. Do not set up the reaction on ice as components in the transcription buffer may precipitate the DNA template.

b) Keep the 10× Transcription Buffer on ice; do not thaw until immediately before use.

c) Upon thawing the 10× Transcription Buffer, you may notice some precipitate in the bottom of the tube. Warn the buffer to 37° C. and vortex briefly to allow the precipitate to go back into solution.

d) When setting up the transcription reaction, add the components to the microcentrifuge tube exactly in the order stated. Add the 10× Transcription Buffer to the mixture directly before adding the BLOCK-iT™ T7 Enzyme Mix, and mix immediately to avoid precipitation of the template. After use, return the 10× Transcription Buffer and the BLOCK-iT™ T7 Enzyme Mix to −20° C.

RNA Transcription Procedure

Use the procedure below to synthesize transcripts from your DNA template. Remember that for each gene, you will generate sense and antisense transcripts using the sense and antisense DNA templates, respectively. Be sure to use RNase-free supplies and wear gloves to prevent RNase contamination.

If you wish to include a negative control, set up the transcription reaction as described below, except omit the DNA template.

1. For each sample, add the following components exactly in the order stated to a 0.5 ml sterile, microcentrifuge tube at room temperature and mix. The amount of RNase-free water added will depend on the concentration of your DNA template.

| Reagents | Amount |
| --- | --- |
| RNase-Free Water | up to 21 µl |
| 75 mM NTPs | 8 µl |
| DNA template (250 ng-1 µg) | 1-10 µl |
| 10X Transcription Buffer | 4 µl |
| BLOCK-iT ™ T7 Enzyme Mix | 6 µl |
| Total volume | 40 µl |

2. Incubate the reaction at 37° C. for 2 hours.

The length of the RNA transcription reaction can be extended up to 6 hours. Most of the transcripts are produced within the first 2 hours, but yields can be increased with longer incubation.

3. Add 2 µl of DNase I to each reaction. Incubate for 15 minutes at 37° C.

4. Proceed to Purifying RNA Transcripts.

You may store the RNA transcription reactions at −20° C. overnight before purification, if desired.

Purifying RNA Transcripts

This section provides guidelines and instructions to purify the single-stranded RNA transcripts (ssRNA) produced in the RNA transcription reaction. Use the BLOCK-iT™ RNA Purification reagents (Box 3) supplied with the kit. Remember that for each gene, you will perform 2 purification reactions to purify sense and antisense RNA transcripts.

Experimental Outline

To purify RNA transcripts, you will:

1. Add RNA Binding Buffer and ethanol to the transcription reaction to denature the proteins and to enable the ssRNA to bind to the column.
2. Add the sample to an RNA spin cartridge. The ssRNA binds to the silica-based membrane in the cartridge, and the digested DNA, free NTPs, and denatured proteins flow through the cartridge.
3. Wash the membrane-bound ssRNA to eliminate residual RNA Binding Buffer and any remaining impurities.
4. Elute the ssRNA from the RNA spin cartridge with water.

Advance Preparation

Before using the BLOCK-iT™ RNA Purification reagents for the first time, add 10 ml of 100% ethanol to the entire amount of 5× RNA Wash Buffer to generate a 1× RNA Wash Buffer (total volume=12.5 ml). Place a check in the box on the 5× RNA Wash Buffer label to indicate that the ethanol was added. Store the 1× RNA Wash Buffer at room temperature.

The RNA Binding Buffer contains guanidine isothiocyanate. This chemical is harmful if it comes in contact with the skin or is inhaled or swallowed. Always wear a laboratory coat, disposable gloves, and goggles when handling solutions containing this chemical.

Do not add bleach or acidic solutions directly to solutions containing guanidine isothiocyanate or sample preparation waste. Guanidine isothiocyanate forms reactive compounds and toxic gases when mixed with bleach or acids.

Materials Needed

Have the following materials on hand before beginning:

1. RNA transcription reactions (from Step 4; for each gene, you should have a sense transcription reaction and an antisense transcription reaction)
2. RNA Binding Buffer (supplied with the kit, Box 3)
3. β-mercaptoethanol
4. 100% ethanol
5. RNA spin cartridges (supplied with the kit, Box 3; one for each sample)
6. 1× RNA Wash Buffer (see Advance Preparation, above)
7. RNase-Free Water (supplied with the kit, Box 3)
8. RNA Recovery Tubes (supplied with the kit, Box 3; one for each sample)
9. 50× RNA Annealing Buffer (supplied with the kit, Box 3)

ssRNA Purification Procedure

Use this procedure to purify ssRNA produced in the transcription reaction, Step 4.

Immediately before beginning, remove the amount of RNA Binding Buffer needed and add β-mercaptoethanol to a final concentration of 1% (v/v). Use fresh and discard any unused solution.

1. To each RNA transcription reaction (~40 µl volume), add 160 µl of RNA Binding Buffer containing 1% (v/v) β-mercaptoethanol followed by 100 µl of 100% ethanol to obtain a final volume of 300 µl. Mix well by pipetting up and down 5 times.
2. Apply the sample (~300 µl) to the RNA Spin Cartridge. Centrifuge at 14,000×g for 15 seconds at room temperature. Discard the flow-through.
3. Add 500 µl of 1× RNA Wash Buffer to the RNA Spin Cartridge containing bound ssRNA. Centrifuge at 14,000×g for 15 seconds at room temperature. Discard the flow-through.
4. Repeat the wash step (Step 3, above).
5. Centrifuge the RNA Spin Cartridge at 14,000×g for 1 minute at room temperature to remove residual 1× RNA Wash Buffer from the cartridge and to dry the membrane.

6. Remove the RNA Spin Cartridge from the Wash Tube, and place it in an RNA Recovery Tube.
7. Add 40 μl of RNase-Free Water to the RNA Spin Cartridge. Let stand at room temperature for 1 minute, then centrifuge the RNA Spin Cartridge at 14,000×g for 2 minutes at room temperature to elute the ssRNA.
8. Add 40 μl of RNase-Free Water to the RNA Spin Cartridge and repeat Step 7, eluting the ssRNA into the same RNA Recovery Tube. The total volume of eluted ssRNA is 80 μl.
9. Depending on your downstream application, perform the following:
(a) If you plan to use the purified ssRNA to generate dsRNA for use in RNAi studies, add 1.4 μl of 50× RNA Annealing Buffer to the eluate to obtain a final concentration of 1× RNA Annealing Buffer. Proceed to Determining the RNA Concentration, or to Step 10.
(b) If you plan to use the purified ssRNA for applications such as Northern analysis, proceed to Step 10.
10. Store the purified ssRNA at −80° C.

Determining the ssRNA Purity and Concentration

Follow the guidelines below to determine the purity and concentration of your purified ssRNA.
1. Dilute an aliquot of the purified ssRNA 100-fold into 1× RNA Annealing Buffer in a total volume appropriate for your quartz cuvette and spectrophotometer.
2. Measure OD at A260 and A280 in a spectrophotometer. Blank the sample against 1× RNA Annealing Buffer.
3. Calculate the concentration of the ssRNA by using the following equation: ssRNA concentration (μg/ml)=A260× Dilution factor (100)×40 μg/ml.
4. Calculate the yield of the ssRNA by using the following equation: ssRNA yield (μg)=ssRNA concentration (μg/ml)×volume of ssRNA (ml)
5. Evaluate the purity of the purified ssRNA by determining the A260/A280 ratio. For optimal purity, the A260/A280 ratio should range from 1.9-2.2.

How Much ssRNA to Expect

The typical yield of purified ssRNA obtained from a 1 kb DNA template ranges from 50-80 μg in a 40 μl transcription reaction. However, yields may vary depending on the size of the DNA template and its sequence. Generally, ssRNA yields are lower for DNA templates smaller than 500 bp or larger than 1 kb.

After purification, we recommend saving an aliquot of your sense and antisense ssRNA samples for gel analysis. We generally verify the integrity of the dsRNA sample (after annealing) and compare it to the sense and antisense ssRNA samples using agarose or polyacrylamide gel electrophoresis.

If you wish to verify the integrity of your sense and antisense ssRNA samples before annealing, we suggest running a small aliquot of each sample on a 6% Novex® TBE-Urea Gel (Invitrogen, Catalog no. EC68652BOX), and including the 0.16-1.77 kb RNA Ladder (Invitrogen, Catalog no. 15623-010) as a molecular weight standard.

Generating dsRNA

To generate dsRNA, you will anneal equal amounts of the purified sense and antisense transcripts of your gene of interest (from ssRNA Purification Procedure, Step 8). Guidelines and instructions are provided below.

Amount of ssRNA to Anneal

You may anneal any amount of sense and antisense transcripts to generate dsRNA; however, use equal amounts of each transcript for optimal results. We generally anneal 50-80 μg of ssRNA to generate 100-160 μg of dsRNA, respectively (e.g. annealing 50 μg of sense transcripts and 50 μg of antisense transcripts results in 100 μg of dsRNA). You may assume that the annealing step is nearly 100% efficient. You will need to know the concentration of each ssRNA before beginning.

Materials Needed

Have the following materials on hand before beginning.
1. Purified sense transcripts of your gene of interest
2. Purified antisense transcripts of your gene of interest
3. 50× RNA Annealing Buffer (supplied with the kit, Box 3)
4. 0.5 ml sterile, RNase-free microcentrifuge tube
5. 500 ml glass beaker Annealing Procedure Use the procedure below to anneal sense and antisense transcripts to generate dsRNA. Remember to use RNase-free supplies and wear gloves to prevent RNase contamination.
1. In a sterile, RNase-free microcentrifuge tube, mix equal amounts of purified sense and antisense transcripts. Place the tube on ice.
2. Heat approximately 250 ml of water to boiling in a 500 ml glass beaker.
3. Remove the beaker of water from the hot plate or microwave and set on your laboratory bench.
4. Place the tube containing the mixture of sense and antisense transcripts in a tube float or a rack in the glass beaker.
5. Allow the water to cool to room temperature for 1-1.5 hours. The ssRNAs will anneal during this time.
6. Remove a small aliquot of dsRNA and analyze by agarose or polyacrylamide gel electrophoresis to check the quality of your dsRNA.
7. Store the dsRNA at −80° C. Depending on the amount of dsRNA produced and your downstream application, you may want to aliquot the dsRNA before storage at −80° C. When using the dsRNA, avoid repeated freezing and thawing as dsRNA can degrade with each freeze/thaw cycle.

Alternative Annealing Procedure

If you want to generate dsRNA more quickly, use the alternative annealing procedure below. Note however, that this method is less efficient and will result in lower yields of dsRNA than the slow-annealing method described above.
1. In a sterile, RNase-free microcentrifuge tube, mix equal amounts of purified sense and antisense transcripts.
2. Place the tube in a 75° C. heat block for 5 minutes.
3. Remove the tube from the heat block and place in a rack at room temperature for 5 minutes. The ssRNAs will anneal during this time.
4. Remove a small aliquot of dsRNA and analyze by agarose or polyacrylamide gel electrophoresis to check the quality of your dsRNA (see below).
5. Store the dsRNA at −80° C. Depending on the amount of dsRNA produced and your downstream application, you may want to aliquot the dsRNA before storage at −80° C. When using the dsRNA, avoid repeated freezing and thawing as dsRNA can degrade with each freeze/thaw cycle.

Checking the Integrity of dsRNA

You may verify the integrity of your dsRNA using agarose or polyacrylamide gel electrophoresis, if desired. We suggest running a small aliquot of your annealing reaction (equivalent to 100-200 ng of dsRNA) on the appropriate gel and comparing it to an aliquot (100-200 ng) of your starting sense and antisense ssRNA. Be sure to include an appropriate molecular weight standard. We generally use the following gels and molecular weight standard:

Agarose gel: 1.2% agarose-TAE gel

Polyacrylamide gel: 6% Novex® TBE Gel (Invitrogen, Catalog no. EC6265BOX)

Molecular weight standard: 0.16-1.77 kb RNA Ladder (Invitrogen, Catalog no. 15623-010)

What You Should See

Figure 20:
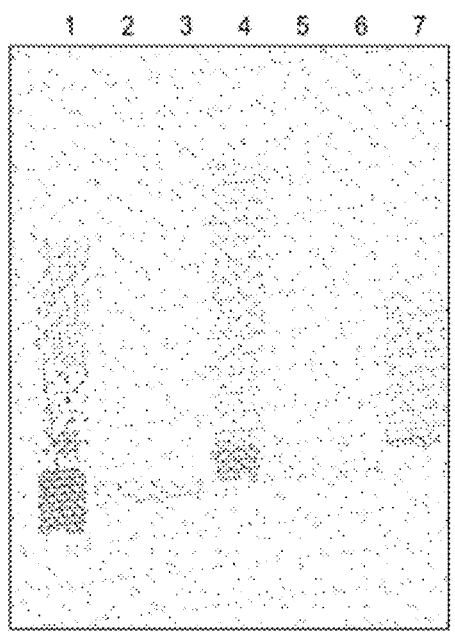
FIG. 20 shows an analysis of an annealing reaction of GFP and luciferase dsRNA samples.

When analyzing the annealing reaction (see above) using gel electrophoresis, we generally observe a predominant band corresponding to the dsRNA (see FIG. 20). If you have used one of the recommended annealing procedures (see above), no ssRNA molecules should be detected.

A high molecular weight smear is often visible in the annealed samples. This is generally due to branched annealing that occurs when multiple overlapping ssRNA anneal to each other. These products can be diced in vitro or in vivo to generate siRNA.

Example of Expected Results

In this experiment, dsRNA representing a 730 bp region of the green fluorescent protein (GFP) gene and a 1 kb region of the luciferase gene were generated using the reagents supplied in the kit and following the recommended protocols in the manual. One microgram of each dsRNA was analyzed on a 1.2% agarose-TAE gel and compared to 0.5 µg of each corresponding purified sense and antisense ssRNA (non-denatured).

Results are shown in FIG. 20: The annealed GFP (lane 4) and luciferase (lane 7) dsRNA samples both show a predominant band that differs in size from each component sense and antisense ssRNA. No ssRNA is visible in the annealed sample. A high molecular weight smear due to branched annealing products is also visible in the annealed samples (lanes 4 and 7).

In some cases, multiple bands due to secondary structure are observed in the ssRNA samples (e.g., lanes 5 and 6). This is a result of analysis on non-denaturing agarose gels.

What to Do Next

Once you have obtained dsRNA, you have the following options:

1. Use the dsRNA directly to perform RNAi studies in invertebrate systems. Depending on the invertebrate system chosen (e.g. *C. elegans, Drosophila*, trypanosomes), multiple methods may exist to introduce the dsRNA into the organism or cell line of choice including injection, soaking in media containing dsRNA, or transfection. Choose the method best suited for your invertebrate system.

2. Use the dsRNA in an in vitro reaction with the Dicer enzyme to generate d-siRNA. The resulting d-siRNA may then be transfected into mammalian cells for RNAi studies. For optimized reagents and protocols to generate highly pure d-siRNA from a dsRNA substrate using recombinant human Dicer enzyme, and to efficiently transfect the d-siRNA into a mammalian cell line of interest using Lipofectamine™ 2000 Reagent, we recommend using the BLOCK-iT™ Dicer RNAi Transfection Kit (Catalog no. K3600-01) or the BLOCK-iT™ Complete Dicer RNAi Kit (Catalog no. K3650-01) available from Invitrogen. For detailed instructions to perform the dicing and transfection reactions, refer to the BLOCK-iT™ Dicer RNAi Kits manual.

Troubleshooting

Review the information in this section to troubleshoot the amplification, TOPO® Linking, transcription, and purification procedures.

Amplifying the Gene of Interest

The table below lists some potential problems and possible solutions that may help you troubleshoot your amplification reactions.

| Problem | Reason | Solution |
| --- | --- | --- |
| No PCR product | Poor quality of DNA template | Prepare new template DNA and verify the integrity of the DNA before amplification. |
| | Poor quality PCR reagents or inactive thermostable DNA polymerase | Amplify the control vector using the primers supplied with the kit and the protocol above. If no PCR product is produced, use fresh PCR reagents and thermostable DNA polymerase. |
| | Suboptimal PCR conditions | Check the $T_m$ of the PCR primers and adjust your cycling conditions. Optimize PCR conditions. Refer to the manufacturer's recommendations for your polymerase. |
| Low yield of PCR product | Suboptimal PCR conditions | Optimize PCR conditions. Refer to the manufacturer's recommendations for your polymerase. |
| | Used old DNA polymerase | Use fresh thermostable DNA polymerase. |
| | Not enough PCR cycles performed | Increase the number of PCR cycles. |
| Multiple non-specific bands or smearing observed on agarose gel | Suboptimal cycling conditions | Optimize PCR conditions. Refer to the manufacturer's recommendations for your polymerase. |
| | DNA template contaminated with other DNA | Prepare new template DNA and verify the integrity of the DNA before amplification. |
| | Poor quality PCR primers | Use HPLC-purified primers to produce your PCR product. |

TOPO® Linking and Secondary Amplification

The table below lists some potential problems and possible solutions that you may use to help you troubleshoot the TOPO® Linking reaction and the secondary amplification reactions.

| Problem | Reason | Solution |
| --- | --- | --- |
| No linear DNA template(s) of the expected size obtained | Inefficient TOPO® Linking Incubated the TOPO® Linking reaction at 37° C. for too long | Do not incubate the TOPO® Linking reaction at 37° C. for longer than 15 minutes. |
| | Used a proofreading polymerase to generate the primary PCR product | Use Taq polymerase (e.g. Platinum® Taq) to generate the primary PCR product. Alternatively, add 3' A-overhangs to the PCR product (see procedure above). |
| | Poor quality PCR reagents or inactive thermostable DNA polymerase | Use fresh PCR reagents and thermostable DNA polymerase for the secondary amplification reactions. |
| | Primers used to produce the primary PCR product contained 5' phosphates | Do not add 5' phosphates to the primers used to produce the primary PCR product. |
| | TOPO® Linking reaction stored incorrectly | For optimal results, perform secondary amplification reactions directly after TOPO® Linking. If desired, store the TOPO® Linking reaction at −20° C. overnight. |
| Low yield of linear DNA template obtained | Inefficient TOPO® Linking Primary PCR product was too dilute | Purify and concentrate the PCR product using the procedure above. |
| | Primary PCR product was not fresh | For optimal results, use fresh PCR product in the TOPO® Linking reaction. |
| | Taq polymerase and proofreading polymerase mixture used to generate primary PCR product | Use Taq polymerase to generate the primary PCR product or use the procedure above to add 3' A-over-hangs to the PCR product prior to TOPO® Linking. |
| | Annealing temperature was too high | Check the $T_m$s of your PCR primers. Reduce the annealing temperature. |
| | $T_m$ of the gene-specific primer(s) not compatible with the $T_m$ of the BLOCK-iT™ T7 Primer | Re-design the gene-specific primer(s), making sure that the $T_m$ of each primer is compatible with the $T_m$ of the BLOCK-iT™ T7 Primer. |
| | Not enough PCR cycles performed | Increase the number of PCR cycles. |

Transcribing and Purifying ssRNA

The table below lists some potential problems and possible solutions that may help you troubleshoot the transcription and purification steps.

| Problem | Reason | Solution |
| --- | --- | --- |
| Low ssRNA yield | No ethanol or RNA Binding Buffer added to the sample | Add RNA Binding Buffer containing 1% (v/v) β-mercaptoethanol followed by 100% ethanol to the sample (see ssRNA Purification Procedure, Step 1, above). |

-continued

| Problem | Reason | Solution |
|---|---|---|
| | Linear DNA template too dilute | Purify and concentrate the linear DNA template using the procedure on above. Extend the incubation time of the transcription reaction up to 6 hours at 37° C. |
| | Transcription reaction not incubated long enough | Extend the incubation time of the transcription reaction up to 6 hours at 37° C. |
| | Eluted ssRNA from the RNA Spin Cartridge using buffer, not water | Elute ssRNA from the RNA Spin Cartridge using RNase-free water. |
| | Concentration of ssRNA incorrectly determined Sample diluted into water for spectrophotometry Sample blanked against water | Dilute sample in 1X RNA Annealing Buffer for spectrophotometry. Blank sample against 1X RNA Annealing Buffer. |
| No ssRNA obtained | Sample contaminated with RNase | Use RNase-free reagents and supplies. Wear gloves when handling RNA-containing samples. |
| | Gene-specific primers used to amplify TOPO ® Linked products, not the BLOCK-iT ™ T7 Primer | Use the BLOCK-iT ™ T7 Primer and the gene-specific forward or reverse primer in the secondary amplification reaction to generate sense and antisense DNA templates, respectively. |
| | Forgot to add ethanol to the 5X RNA Wash Buffer | Add 10 ml of ethanol to the 5X RNA Wash Buffer (2.5 ml) to obtain a 1X RNA Wash Buffer. |
| Volume of eluted ssRNA is >80 µl | RNA Spin Cartridge containing bound ssRNA not centrifuged to remove residual 1X RNA Wash Buffer | Centrifuge RNA Spin Cartridge at 14,000 × g for 1 minute at room temperature to remove residual 1X RNA Wash Buffer and to dry the membrane (see Step 5, above). Contamination of eluted ssRNA with 1X RNA Wash Buffer or other impurities can result in inaccurate quantitation of ssRNA, potential toxic effects on invertebrate cells, or reduced dicing efficiency. |
| A260/A280 ratio not in the 1.9-2.2 range | Sample was not washed with 1X RNA Wash Buffer | Wash the RNA Spin Cartridge containing bound ssRNA twice with 1X RNA Wash Buffer (see Steps 3 and 4, above). |
| | RNA Spin Cartridge containing bound ssRNA not centrifuged to remove residual 1X RNA Wash Buffer | Centrifuge RNA Spin Cartridge at 14,000 × g for 1 minute at room temperature to remove residual 1X RNA Wash Buffer and to dry the membrane (see Step 5, above). |

RNAi Analysis

The table below lists some potential problems and possible solutions that may help you troubleshoot your RNAi analysis using dsRNA.

| Problem | Reason | Solution |
|---|---|---|
| Low levels of gene knockdown observed | dsRNA was degraded dsRNA was not stored in 1X RNA Annealing Buffer | Be sure to store the dsRNA in 1X RNA Annealing Buffer. |
| | dsRNA was frozen and thawed multiple times | Aliquot dsRNA and avoid repeated freeze/thaw cycles. |
| No gene knockdown observed | Target sequence contains no active siRNA | Select a larger target region or a different target sequence. |
| | dsRNA contaminated with RNase | Use RNase-free reagents and supplies. Wear gloves when handling RNA-containing samples. |

-continued

| Problem | Reason | Solution |
|---|---|---|
| Non-specific gene knockdown effects observed | Target sequence contains strong homology to other genes | Select a new target sequence. Limit the size range of the target sequence to 1 kb. |

Performing the Control Reactions

We recommend performing the following control reactions the first time you use the kit to help you evaluate your results. Performing the control reactions involves the following steps:
1. Producing a control PCR product using the pcDNA™ 1.2/V5-GW/lacZ control plasmid and the LacZ Forward 2 and LacZ Reverse 2 primers supplied with the kit.
2. Performing a TOPO® Linking reaction with the control PCR product and the BLOCK-iT™ T7-TOPO® Linker.
3. Performing two secondary amplification reactions with the TOPO® Linked PCR product to produce sense and anti-sense control DNA templates.
4. Using the control DNA templates in transcription reactions to generate sense and antisense RNA transcripts.
5. Purifying the sense and antisense RNA transcripts, and annealing the ssRNAs to produce control dsRNA.

Producing the Control PCR Product

Use this procedure to amplify the pcDNA™ 1.2/V5-GW/lacZ control plasmid using Platinum® Taq polymerase. If you are using another thermostable DNA polymerase, follow the manufacturer's instructions to set up the PCR reaction.
1. To produce the 1 kb control PCR product, set up the following 50 µl PCR:

| | |
|---|---|
| pcDNA™ 1.2/V5-GW/lacZ (10 ng/µl) | 1 µl |
| 10X PCR Buffer | 5 µl |
| 40 mM dNTPs | 1 µl |
| LacZ forward 2 primer (65 ng/µl) | 1 µl |
| LacZ reverse 2 primer (65 ng/µl) | 1 µl |
| Sterile Water | 40.5 µl |
| Platinum® Taq Polymerase (5 U/µl) | 0.5 µl |
| Total Volume | 50 µl |

2. Amplify using the following cycling parameters:

| Step | Time | Temperature | Cycles |
|---|---|---|---|
| Initial Denaturation | 2 minutes | 94° C. | 1X |
| Denaturation | 15 seconds | 94° C. | 30X |
| Annealing | 30 seconds | 55° C. | |
| Extension | 1 minute | 72° C. | |
| Final Extension | 7 minutes | 72° C. | 1X |

3. Remove 1-5 µl from the reaction and analyze by agarose gel electrophoresis. A discrete 1 kb band should be visible.

Control TOPO® Linking Reaction

Using the control PCR product produced in Step 3, above and the BLOCK-iT™ T7-TOPO® Linker, set up the TOPO® Linking reaction as described below.
1. Set up the following control TOPO® Linking reaction:

| | |
|---|---|
| Control PCR product | 1 µl |
| Salt Solution | 1 µl |

-continued

| | |
|---|---|
| Sterile water | 3 µl |
| BLOCK-iT™ T7-TOPO® Linker | 1 µl |
| Total volume | 6 µl |

2. Incubate at 37° C. for 15 minutes and place on ice.
3. Proceed directly to the Secondary Control PCR Reactions, below.

Secondary Control PCR Reactions

Use this procedure to amplify the TOPO® Linked control PCR product using Platinum® Taq polymerase to generate sense and antisense control DNA templates. If you are using another thermostable DNA polymerase, follow the manufacturer's instructions to set up the PCR reaction.
1. Set up the following 50 µl PCR reactions:

| Reagent | Sense Template | Antisense Template |
|---|---|---|
| Control TOPO® Linking Reaction | 1 µl | 1 µl |
| 10X PCR Buffer | 5 µl | 5 µl |
| 40 mM dNTPs | 1 µl | 1 µl |
| BLOCK-iT™ T7 Primer (75 ng/µl) | 1 µl | 1 µl |
| LacZ Forward 2 Primer (65 ng/µl) | — | 1 µl |
| LacZ Reverse 2 Primer (65 ng/µl) | 1 µl | — |
| Sterile Water | 40.5 µl | 40.5 µl |
| Platinum® Taq Polymerase (5 U/µl) | 0.5 µl | 0.5 µl |
| Total volume | 50 µl | 50 µl |

2. Amplify using the following cycling parameters:

| Step | Time | Temperature | Cycles |
|---|---|---|---|
| Initial Denaturation | 2 minutes | 94° C. | 1X |
| Denaturation | 15 seconds | 94° C. | 30X |
| Annealing | 30 seconds | 55° C. | |
| Extension | 1 minute | 72° C. | |
| Final Extension | 7 minutes | 72° C. | 1X |

3. Remove 1-5 µl from the reaction and analyze by agarose gel electrophoresis. A discrete band of approximately 1 kb should be visible.

Generating Control dsRNA

Once you have generated the sense and antisense control DNA templates, you may use these templates in transcription reactions to produce sense and antisense control transcripts. After purification, these transcripts may then be annealed to produce control dsRNA. Follow the protocols above to produce and purify sense and antisense transcripts, and to anneal the purified transcripts to produce dsRNA.

What To Do With the Control dsRNA

The lacZ dsRNA may be used as a control for RNAi analysis in the following ways:

Invertebrate Systems:

Use as a negative control for non-specific activity in any invertebrate system.

Mammalian Systems:

For some embryonic stem cell (ES) cell lines in which the CMV promoter is active (e.g. AB2.2), you may use the lacZ dsRNA as a positive control for gene knockdown (Yang et al., 2001). Simply introduce the pcDNA™ 1.2/V5-GW/lacZ reporter plasmid and the lacZ dsRNA into cells and assay for inhibition of β-galactosidase expression.

Alternatively, you may use the lacZ dsRNA in an Invitrogen BLOCK-iT™ Dicer RNAi Transfection Kit as a substrate to produce diced short interfering RNA (d-siRNA). The lacZ d-siRNA may then be used as a negative control for non-specific activity in the mammalian cell line of interest or as a positive control for knockdown of β-galactosidase expression from the pcDNA™ 1.2/V5-GW/lacZ reporter plasmid. For detailed instructions to produce d-siRNA, refer to the BLOCK-iT™ Dicer RNAi Kits manual.

Gel Purifying PCR Products

Smearing, multiple banding, primer-dimer artifacts, or large PCR products (>1 kb) may necessitate gel purification. If you intend to purify your PCR product, be extremely careful to remove all sources of nuclease contamination. There are many protocols to isolate DNA fragments or remove oligonucleotides. Refer to Current Protocols in Molecular Biology, Unit 2.6 (Ausubel et al., 1994) for the most common protocols. Two simple protocols are provided below.

Using the S.N.A.P.™ Gel Purification Kit

The S.N.A.P.™ Gel Purification Kit (Catalog no. K1999-25) allows you to rapidly purify PCR products from regular agarose gels.

1. Electrophorese amplification reaction on a 1 to 5% regular TAE agarose gel. Do not use TBE to prepare agarose gels. Borate will interfere with the sodium iodide step, below.
2. Cut out the gel slice containing the PCR product and melt it at 65° C. in 2 volumes of 6 M sodium iodide solution. Add 1.5 volumes of Binding Buffer.
3. Load solution (no more than 1 ml at a time) from Step 3 onto a S.N.A.P.™ column. Centrifuge 1 minute at 3000×g in a microcentrifuge and discard the supernatant.
4. If you have solution remaining from Step 3, repeat Step 4.
5. Add 900 µl of the Final Wash Buffer.
6. Centrifuge-1 minute at full speed in a microcentrifuge and discard the flow-through.
7. Repeat Step 7.
8. Elute the purified PCR product in 30 µl of sterile water. Use 1 µl for the TOPO® Linking reaction and proceed as described above.

Quick S.N.A.P.™ Method

An even easier method is to simply cut out the gel slice containing your PCR product, place it on top of the S.N.A.P.™ column bed, and centrifuge at full speed for 10 seconds. Use 1-2 µl of the flow-through in the TOPO® Linking reaction. Be sure to make the gel slice as small as possible for best results.

Adding 3' A-Overhangs Post-Amplification

Direct TOPO® Linking of DNA amplified by proofreading polymerases with the BLOCK-iT™ T7-TOPO® Linker is difficult because of very low TOPO® Linking efficiencies. These low efficiencies are caused by the 3' to 5' exonuclease activity associated with proofreading polymerases which removes the 3' A-overhangs necessary for TA Cloning®. A simple method is provided below to clone these blunt-ended fragments.

Before Starting

You will need the following items:
1. Taq polymerase
2. A heat block equilibrated to 72° C.
3. Phenol-chloroform (optional)
4. 3 M sodium acetate (optional)
5. 100% ethanol (optional)
6. 80% ethanol (optional)
7. TE buffer (optional)

Procedure

This is just one method for adding 3' adenines. Other protocols may be suitable.

1. After amplification with Vent® or Pfu polymerase, place vials on ice and add 0.7-1 unit of Taq polymerase per tube. Mix well. It is not necessary to change the buffer.
2. Incubate at 72° C. for 8-10 minutes (do not cycle).
3. Place the vials on ice. Proceed to TOPO® Linking (see above).

If you plan to store your sample(s) overnight before proceeding with TOPO® Linking, you may want to extract your sample(s) with phenol-chloroform to remove the polymerases. After phenol-chloroform extraction, precipitate the DNA with ethanol and resuspend the DNA in TE buffer to the starting volume of the amplification reaction.

Purifying and Concentrating PCR Products

If your gene of interest has not amplified efficiently and the yield of your PCR product is low, you may use the S.N.A.P.™ MiniPrep Kit available from Invitrogen (Catalog no. K1900-25) to rapidly purify and concentrate the PCR product. Other resin-based purification kits are suitable.

Materials Needed

You should have the following reagents on hand before beginning:
1. Isopropanol
2. Binding Buffer (supplied with the S.N.A.P.™ MiniPrep Kit)
3. Wash Buffer (supplied with the S.N.A.P.™ MiniPrep Kit)
4. Final Wash Buffer (supplied with the S.N.A.P.™ MiniPrep Kit)
5. Sterile water
6. S.N.A.P.™ MiniPrep columns (supplied with the S.N.A.P.™ MiniPrep Kit)

Purification Protocol

Follow the protocol below to purify your PCR product using the S.N.A.P.™ MiniPrep Kit. The protocol provides instructions to purify PCR products from a 50 µl reaction volume. To purify PCR products from larger reaction volumes (e.g. several PCR reactions pooled together), scale up the volumes of each buffer accordingly. Details about the components of the S.N.A.P.™ MiniPrep Kit can be found in the S.N.A.P.™ MiniPrep Kit manual.

1. Add 150 µl of Binding Buffer to the 50 µl PCR reaction. Mix well by pipetting up and down.
2. Add 350 µl of isopropanol. Mix well by vortexing.
3. Immediately load solution from Step 2 onto a S.N.A.P.™ MiniPrep column. Centrifuge for 30 seconds at 1000×g in a microcentrifuge and discard the flow-through.
4. Add 250 µl of the Wash Buffer and centrifuge for 30 seconds at 1000×g in a microcentrifuge. Discard the flow-through.
5. Add 450 µl of the Final Wash Buffer and centrifuge for 30 seconds at 1000×g in a microcentrifuge. Discard the flow-through.

6. Centrifuge for an additional 30 seconds at full-speed in a microcentrifuge to dry the column.
7. Transfer the column to a new collection tube. Add 30 μl of sterile water to the column. Incubate at room temperature for 1 minute.
8. Centrifuge for 30 seconds at full-speed in a microcentrifuge to elute the DNA. Collect the flow-through. Use 1 μl in the TOPO® Linking reaction (see above).

pcDNA™ 1.2/V5-GW/lacZ (6498 bp) (see FIG. 21) is a control vector expressing a C-terminally-tagged β-galactosidase fusion protein under the control of the human cytomegalovirus (CMV) promoter (Andersson et al., 1989; Boshart et al., 1985; Nelson et al., 1987), and was generated using the MultiSite Gateway® Three-Fragment Vector Construction Kit available from Invitrogen (Catalog no. 12537-023). Briefly, a MultiSite Gateway® LR recombination reaction was performed with pDEST™ R4-R3 and entry clones containing the CMV promoter, lacZ gene, and V5 epitope and TK polyadenylation signal to generate the pcDNA™ 1.2/V5-GW/lacZ vector. β-galactosidase is expressed as a C-terminal V5 fusion protein with a molecular weight of approximately 119 kDa. The complete sequence of pcDNA™ 1.2/V5-GW/lacZ is available from Invitrogen.

Product Qualification

This section describes the criteria used to qualify the components of the BLOCK-iT™ RNAi TOPO® Transcription Kit.

Functional Qualification

The components of the BLOCK-iT™ RNAi TOPO® Transcription Kit are functionally qualified as follows:
1. Using the pcDNA™ 1.2/V5-GW/lacZ plasmid and the LacZ Forward 2 and LacZ Reverse 2 primers supplied with the kit, a control PCR product is generated and TOPO® Linked to the BLOCK-iT™ T7-TOPO® Linker following the protocols above.
2. Using the BLOCK-iT™ T7 Primer and the LacZ Forward 2 or LacZ Reverse 2 primer, two aliquots of the TOPO® Linking reaction are amplified following the procedure above to generate sense and antisense DNA templates. An aliquot of each secondary PCR reaction is analyzed on an agarose gel and compared to an aliquot of the primary PCR product. The sense and antisense DNA template should demonstrate a gel shift (1043 bp) when compared to the primary PCR product (1000 bp).
3. The sense and antisense DNA templates are transcribed using the reagents supplied in the kit and following the procedure above. The sense and antisense transcripts are analyzed on a 6% Novex® TBE-Urea Gel (Invitrogen, Catalog no. EC68652BOX). The 0.16-1.77 kb RNA Ladder (Invitrogen, Catalog no. 15623-010) is included as a molecular weight standard. RNA should be visible in the lanes containing sense and antisense transcripts, while no RNA should be observed from a transcription reaction using a template generated from a PCR product that was not linked to the BLOCK-iT™ T7 Linker.
4. The sense and antisense transcripts are purified using the reagents supplied in the kit and following the procedure above. Following purification, the purified sense and antisense ssRNA are quantitated using spectrophotometry. Each transcription reaction should yield at least 60 μg of ssRNA, and the A260/A280 ratio should be between 1.9 and 2.2.
5. Equal amounts of sense and antisense RNA are annealed following the procedure above. The dsRNA is analyzed on a 6% Novex® TBE Gel (Invitrogen, Catalog no. EC6265BOX) with the 0.16-1.77 kb RNA Ladder included as a molecular weight standard. A gel shift representing dsRNA should be observed in the annealed sample when compared to sense or antisense ssRNA.

pcDNA™ 1.2/V5-GW/lacZ Plasmid

The pcDNA™ 1.2/V5-GW/lacZ plasmid is qualified by restriction analysis. Restriction digest should demonstrate the correct banding pattern when electrophoresed on an agarose gel.

PCR Primers

The BLOCK-iT™ T7, LacZ Forward 2, and LacZ Reverse 2 primers are functionally qualified by performing the control PCR reactions described on pages above.

REFERENCES

Anandalakshmi, R., Pruss, G. J., Ge, X., Marathe, R., Mallory, A. C., Smith, T. H., and Vance, V. B. (1998). A Viral Suppressor of Gene Silencing in Plants. *Proc. Natl. Acad. Sci. USA* 95, 13079-13084.

Andersson, S., Davis, D. L., Dahlbäck, H., Jömvall, H., and Russell, D. W. (1989). Cloning, Structure, and Expression of the Mitochondrial Cytochrome P-450 Sterol 26-Hydroxylase, a Bile Acid Biosynthetic Enzyme. *J. Biol. Chem.* 264, 8222-8229.

Ausubel, F. M., Brent, R., Kingston, R. E., Moore, D. D., Seidman, J. G., Smith, J. A., and Struhl, K. (1994). Current Protocols in Molecular Biology (New York: Greene Publishing Associates and Wiley-Interscience).

Bernstein, E., Caudy, A. A., Hammond, S. M., and Hannon, G. J. (2001). Role for a Bidentate Ribonuclease in the Initiation Step of RNA Interference. *Nature* 409, 363-366.

Billy, E., Brondani, V., Zhang, H., Muller, U., and Filipowicz, W. (2001). Specific Interference with Gene Expression Induced by Long, Double-Stranded RNA in Mouse Embryonal Teratocarcinoma Cell Lines. *Proc. Natl. Acad. Sci. USA* 98, 14428-14433.

Boshart, M., Weber, F., Jahn, G., Dorsch-Häsler, K., Fleckenstein, B., and Schaffner, W. (1985). A Very Strong Enhancer is Located Upstream of an Immediate Early Gene of Human Cytomegalovirus. *Cell* 41, 521-530.

Bosher, J. M., and Labouesse, M. (2000). RNA Interference: Genetic Wand and Genetic Watchdog. *Nature Cell Biol.* 2, E31-E36.

Caplen, N. J., Fleenor, J., Fire, A., and Morgan, R. A. (2000). dsRNA-Mediated Gene Silencing in Cultured *Drosophila* Cells: A Tissue Culture Model for the Analysis of RNA Interference. *Gene* 252, 95-105.

Cogoni, C., and Macino, G. (1999). Gene Silencing in *Neurospora crassa* Requires a Protein Homologous to RNA-Dependent RNA Polymerase. *Nature* 399, 166-169.

Cogoni, C., and Macino, G. (1997). Isolation of Quelling-Defective (qde) Mutants Impaired in Posttranscriptional Transgene-Induced Gene Silencing in *Neurospora crassa*. *Proc. Natl. Acad. Sci. USA* 94, 10233-10238.

Cogoni, C., Romano, N., and Macino, G. (1994). Suppression of Gene Expression by Homologous Transgenes. *Antonie Van Leeuwenhoek* 65, 205-209.

Fire, A., Xu, S., Montgomery, M. K., Kostas, S. A., Driver, S. E., and Mello, C. C. (1998). Potent and Specific Genetic Interference by Double-Stranded RNA in *Caenorliabditis elegans*. *Nature* 391, 806-811.

Hammond, S. M., Bernstein, E., Beach, D., and Hannon, G. J. (2000). An RNA-Directed Nuclease Mediates Genetic Interference in *Caenorhabditis elegans*. *Nature* 404, 293-296.

Hannon, G. J. (2002). RNA Interference. *Nature* 418, 244-251.

Innis, M. A., Gelfand, D. H., Sninsky, J. J., and White, T. S. (1990) PCR Protocols: A Guide to Methods and Applications. Academic Press, San Diego, Calif.

Jones, A. L., Thomas, C. L., and Maule, A. J. (1998). De novo Methylation and Co-Suppression Induced by a Cytoplasmically Replicating Plant RNA Virus. *EMBO J.* 17, 6385-6393.

Kaufman, R. J. (1999). Double-Stranded RNA-Activated Protein Kinase Mediates Virus-Induced Apoptosis: A New Role for an Old Actor. *Proc. Natl. Acad. Sci. USA* 96, 11693-11695.

Kennerdell, J. R., and Carthew, R. W. (1998). Use of dsRNA-Mediated Genetic Interference to Demonstrate that frizzled and frizzled 2 Act in the Wingless Pathway. *Cell* 95, 1017-1026.

Ketting, R. F., Fischer, S. E., Bernstein, E., Sijen, T., Hannon, G. J., and Plasterk, R. H. (2001). Dicer Functions in RNA Interference and in Synthesis of Small RNA Involved in Developmental Timing in *C. elegans. Genes Dev.* 15, 2654-2659.

Li, W. X., and Ding, S. W. (2001). Viral Suppressors of RNA Silencing. *Curr. Opin. Biotechnol.* 12, 150-154.

Misquitta, L., and Paterson, B. M. (1999). Targeted Disruption of Gene Function in *Drosophila* by RNA Interference (RNAi): A Role for Nautilis in Embryonic Muscle Formation. *Proc. Natl. Acad. Sci. USA* 96, 1451-1456.

Napoli, C., Lemieux, C., and Jorgensen, R. (1990). Introduction of a Chalcone Synthase Gene into Petunia Results in Reversible Co-Suppression of Homologous Genes in trans. *Plant Cell* 2, 279-289.

Nelson, J. A., Reynolds-Kohler, C., and Smith, B. A. (1987). Negative and Positive Regulation by a Short Segment in the 5'-Flanking Region of the Human Cytomegalovirus Major Immediate-Early Gene. *Molec. Cell. Biol.* 7, 4125-4129.

Ngo, H., Tschudi, C., Gull, K., and Ullu, E. (1998). Double-Stranded RNA Induces mRNA Degradation in *Trypanosoma brucei. Proc. Natl. Acad. Sci. USA* 95, 14687-14692.

Nykanen, A., Haley, B., and Zamore, P. D. (2001). ATP Requirements and Small Interfering RNA Structure in the RNA Interference Pathway. *Cell* 107, 309-321.

Plasterk, R. H. A., and Ketting, R. F. (2000). The Silence of the Genes. *Curr. Opin. Genet. Dev.* 10, 562-567.

Romano, N., and Macino, G. (1992). Quelling: Transient Inactivation of Gene Expression in *Neurospora crassa* by Transformation with Homologous Sequences. *Mol. Microbiol.* 6, 3343-3353.

Shuman, S. (1994). Novel Approach to Molecular Cloning and Polynucleotide Synthesis Using Vaccinia DNA Topoisomerase. *J. Biol. Chem.* 269, 32678-32684.

Shuman, S. (1991). Recombination Mediated by Vaccinia Virus DNA Topoisomerase I in *Escherichia coli* is Sequence Specific. *Proc. Natl. Acad. Sci. USA* 88, 10104-10108.

Smith, C. J., Watson, C. F., Bird, C. R., Ray, J., Schuch, W., and Grierson, D. (1990). Expression of a Truncated Tomato Polygalacturonase Gene Inhibits Expression of the Endogenous Gene in Transgenic Plants. *Mol. Gen. Genet.* 224, 477-481.

Svoboda, P., Stein, P., Hayasbi, H., and Schult, R. M. (2000). Selective Reduction of Dormant Maternal mRNAs in Mouse Oocytes by RNA Interference. *Development* 127, 4147-4156.

van der Krol, A. R., Mur, L. A., Beld, M., Mol, J. N., and Stuitje, A. R. (1990). Flavonoid Genes in Petunia: Addition of a Limited Number of Gene Copies May Lead to a Suppression of Gene Expression. *Plant Cell* 2, 291-299.

Voinnet, O., Pinto, Y. M., and Baulcombe, D.C. (1999). Suppression of Gene Silencing: A General Strategy Used by Diverse DNA and RNA Viruses of Plants. *Proc. Natl. Acad. Sci. USA* 96, 14147-14152.

Wianny, F., and Zernicka-Goetz, M. (2000). Specific Interference with Gene Function by Double-Stranded RNA in Early Mouse Development. *Nature Cell Biol.* 2, 70-75.

Yang, S., Tutton, S., Pierce, E., and Yoon, K. (2001). Specific Double-Stranded RNA Interference in Undifferentiated Mouse Embryonic Stem Cells. *Mol. Cell. Biol.* 21, 7807-7816.

Zamore, P. D. (2001). RNA Interference: Listening to the Sound of Silence. *Nat. Struct. Biol.* 8, 746-750.

EXAMPLE 4

Small Nucleic Acids Purification System

All catalog numbers provided below correspond to Invitrogen Corporation products, Carlsbad, Calif., unless otherwise noted.

Small nucleic acid molecules, especially siRNA, is getting great attention with function in gene specific knockout or silencing of gene expression. Recently, many researchers demonstrated that gene specific siRNA can be generated in vitro via a combination of transcription and a ribonuclease enzyme. The digestion of long transcripts is accomplished with a ribonuclease called RNase III or Dicer and the digested sample is required to be purified from the non-processed template, intermediate and buffer component of enzyme reaction. If residual long dsRNA template and other intermediates remained in the sample and were transfected along with siRNA into cells, it might lead to non-specific response. Thus removal of this residual template and intermediate is required for accurate functional analysis of the gene specific siRNA. Pre-existing total RNA purification systems are not suitable and not designed to purify less than 30 bp nucleic acids and only a size exclusion spin column has been utilized to select small size nucleic acid from mixtures.

We have developed a buffer formulation to purify dsRNA that is smaller than 30 bp using our pre-existing glass fiber filter. Both single-column and double-column method were developed to purify siRNAs generated using Dicer and RNase III. The purified siRNA can be used to assay cellular functional via gene specific knock out without non-specific interference by >30 bp dsRNA (complete buffer exchange; eluted in DEPC treated $H_2O$). This purification procedure can be utilized for other applications such as linker, aptamer, protein binding domain extraction, etc.

Introduction

Total RNA is composed of three main transcript categories. These are ribosomal RNAs (28S, 18S, and 5S in the case of mammalian cells), mRNA, and low molecular weight RNA species such as tRNA, snRNA, and others. The recent discovery and rudimentary elucidation of the mechanism of action of RNA interference and the identification of a new regulatory RNA termed short interfering RNA (siRNA) as well as micro RNA are receiving increasing attention by the scientific community. This increased interest is based on siRNA's ability to mediate down-regulation of gene expression by sequence specific, and hence gene specific, degradation of targeted mRNA. The popularity of the siRNA approach is justified as it has distinct advantages over anti-sense methods and knockout approaches. It appears that the siRNA approach is capable of down-regulating gene expression with higher efficiency and efficacy than the antisense approach and offers greater flexibility and ease of use compared to knockout approaches.

RNA interference is a cellular defense mechanism where a long double-stranded RNA molecule is processed by an endogenous (endo)ribonuclease resulting in the production of small interfering RNAs (siRNAs), which are generally 21 to 23 nucleotides in length. The siRNA molecules bind to a protein complex, RNA Induced Silencing Complex (RISC), which contains a helicase activity that unwinds siRNA molecules, allowing the anti-sense strand of siRNA to bind to complementary mRNA, thus triggering targeted mRNA degradation by endonucleases or blocking mRNA translation into protein (for a review see Denli and Hannon, 2003, Carrington and Ambros, 2003). In addition, siRNA does not trigger an immune response, because it is a natural cellular mechanism (Sledz et. al., 2003)

Initial attempts of gene specific knockdown using long dsRNA transcripts failed in mammalian cells because of activation of protein kinase PKR and 2',5'-oligoadenylate synthetase that trigger non-specific shutdown of protein synthesis and non-specific degradation of mRNA. Elbashir and co-workers demonstrated that transfection of chemically synthesized 21-23 nt dsRNA fragments could specifically suppress gene expression without triggering non-specific gene silencing effects in mammalian cells. However, different suppression levels are often observed with synthetic short siRNAs as they target a single specific site. Under these conditions site accessibility becomes an issue as mRNA containing high levels of secondary or tertiary structure may prevent siRNA/target/RISC complex formation and affect efficacy of the siRNA used. Thus, multiple double-stranded siRNA molecules, usually 4-5, need to be screened that target different sequences in a targeted mRNA to identify one siRNA construct with adequate potency for gene suppression in a given mRNA. Short interfering RNA constructs can also be generated by transcription in vitro from short DNA templates or by transcription in vivo from a transfected DNA construct. However, none of the latter methods are easily scaled up for multiple gene screens due to high cost of oligonucleotides and/or difficulties of target region selection. A new method was recently developed to generate gene specific functional siRNA pools using a combination of RNA transcription followed by digestion with Dicer enzyme. This method generates multiple functional siRNAs from long dsRNA target sequences which correspond to the gene transcript of interest. With this new method, low cost and highly efficient screening of gene knockdown effects is possible and high throughput screening of multiple genes can be achieved. However, the latter methodology requires purification of functional siRNA after digestion of long dsRNA substrate with Dicer. Undigested, long dsRNA substrates as well as intermediate digestion products longer than approximately 30 bp elicit non-specific responses such as non-specific shutdown of translation and initiation of apoptosis (Kaufman, 1999). Others have used size exclusion columns for purification of functional siRNA. However, this purification is not efficient and does not provide high quality siRNA for transfection.

Our Small Nucleic Acids Purification System provides an efficient means of purification for functional, diced siRNA and other small dsRNA molecules. The purification is based on glass fiber purification technology. The small nucleic acids purification system eliminates dsRNA that exceeds 30 bp in length and selectively and specifically purifies dsRNA shorter than 30 base pairs. In the case of siRNA, the purified dsRNA is of high quality, highly functional for transcript specific gene suppression, and exhibits no cell toxicity. Currently, Invitrogen Block-iT™ Dicer RNAi Kits provide complete Dicer RNAi transfection kit, include RNAi purification kit, Dicer Enzyme kit, Lipofectamine™ 2000 Reagent and/or TOPO® transcription Kit, as bundle product. Small Nucleic Acids Purification kit is a stand-alone product of the siRNA purification module from Block-iT™ that accommodates not only siRNA purification generated by Dicer and RNase III but also other small nucleic acids applications. The Small Nucleic Acids Purification Kit, as related to the purification of enzymatically-generated siRNA (Dicer & RNaseIII), will generally meet the following criteria: (1) Purified siRNA expected not to contain dsRNA molecules greater than 30 bp in length, (2) Suppression levels observed with purified siRNA will be the same or higher than those observed with synthesized siRNA, (3) Recovery of purified material expected to exceed 80%.

Spin Column Purification Kit Components
1. 50 individual spin columns assembled in collection tubes in one bag
2. 50 individual recovery tubes in one bag
3. Binding Buffer (47-6001): 11 mL
4. 5× Wash Buffer (47-6003): 15 mL, EtOH (95-100%) added by end user
5. Elution Buffer (47-6002): 3 mL, 1.5 mL EtOH (95-100%) and 1.5 mL RNase-free water to be added by end user
6. DEPC water (47-0005): 10 mL
7. Manual
8. QRC The components provided in the kit are sufficient for 50 purifications using the single-column protocol, in which a final ethanol precipitation step in the presence of glycogen as a co-precipitant is desired. The components provided in the kit are sufficient for 25 purifications when using the two-column protocol, in which the second column is used for selective binding of the short target nucleic acids followed by elution in DEPC-treated water to obtain the final, purified product (see Purification Protocol Flowchart)

Optional Materials:
Crude small nucleic acids preparation for purification
Materials for generating long dsRNA template
Materials for digestion of long dsRNA template to generate crude siRNA product
Chemically synthesized siRNA
EtOH (95 or 100%)
UltraPure™ Glycogen (20 µg/µl) (Invitrogen cat #10814-010)
Purification Protocol Flowchart The Small Nucleic Acids Purification System is designed to purify Micro-RNA molecules such as micro RNA, tiny RNA, small nuclear RNA, guide RNAs, telomerase RNA, small non-mRNA, catalytic RNA, and small regulatory RNAs (such as aptamer). Also, RNAi molecules RNase III-generated diced siRNA (15-16 bp), Dicer-generated siRNA (21-23 bp), other short hairpin RNA, and small temporary regulatory RNA can be purified with the Small Nucleic Acids Purification System.

| Single-Column Protocol** | Two-Column Protocol* |
|---|---|
| Add 150 µl of Binding Buffer to 50 µl of sample reaction volume* and mix it well (Total volume: 200 µl) Add 600 µl of EtOH (95-100%) (Final EtOH concentration 71-75%, total volume: 800 µl) | Add 50 µl of Binding Buffer to 50 µl of sample reaction volume* and mix it well. (Total volume 100 µl) Add 59 µl of EtOH (95-100%) (Final EtOH concentration 31-33%, sample volume: 150 µl) |
| Mix sample well and load onto spin column Centrifuge at 20,000 × g for 1 min | |
| Expected recovery volume: ca. 750 µl | Expected recovery volume: ca. 130 µl Remove spin column from collection tube Add 185 µl of EtOH (95-100%) to pass-through and mix it well. (Final EtOH conc. ca. 70-74%) Load sample onto $2^{nd}$ column Centrifuge at 20,000 × g for 1 min |
| Wash spin column with 500 µl of 1X Wash Buffer Repeat the washing step (optional) Centrifuge at 20,000 × g for 1 min to dry the filter | |
| Add 100 µl of Elution Buffer to dried spin column and incubate at ambient temperature for 1 min | Add 100 µl of DEPC-treated water to dried spin column & incubate at ambient temperature for 1 min |
| Centrifuge at 20,000 × g for 1 min Expected elution volume: ca. 95 µl The eluate contains the purified, short dsRNA | |
| EtOH precipitation of short nucleic acids: | |
| a. Add 200 µl of ice cold 100% EtOH and 1 µl glycogen solution (20 µg/µl). b. Incubate at −20° C. for 15 min and centrifuge for 15 min at 20,000 × g c. Discard supenatant carefully and wash pellet with 0.5 ml of 70% EtOH d. Centrifuge for 10 min at 20,000 × g e. Discard supernatant and air dry pellet Resuspend pellet of purified, short dsRNA in 50 µl (or desirable amount) of DEPC-treated water | |

*Higher sample reaction volumes may require proportionally increased Binding Buffer and EtOH volumes. (Two-Column protocol provide here is scaled down procedure from siRNA purification kit module of Block-iT(Dicer RNAi Kit). Either EtOH or isopropanol can be used to mixing step with Binding Buffer.
**Single column purification will limit its reaction volume to 50 µl reaction. (up to 10 µg of dsRNA reaction).

Please see detail description of Purification of Small Nucleic Acids-General Consideration in Results and Discussion section.

Materials and Methods

Generation of dsRNA and siRNA

Crude siRNA needed for purifications was generated in a two-step process. First, in-vitro T7 RNA polymerase transcription reaction was used to generate the individual strands that form dsRNA, which then, in a second reaction, served as a template for either Dicer or RNase III digestion yielding crude siRNA preparations that were used for purification with the new kit. The genes of LacZ (Accession number: AY150267) and Luciferase (Accession number: AAL30778.1) were selected as the target genes for siRNA inhibition. LacZ dsRNA template was generated as follows: (1) PCR was performed with lacZ gene-specific primer I (5'-ACC AGA AGC GGT GCC GGA AA-3' (SEQ ID NO: 49)) and primer 2 (5'-CCA CAG GGG ATG GTT CGG AT-3' (SEQ ID NO: 50)), (2) PCR was performed to incorporate T7 sequences at both ends of the amplicon generated in step 1 with Primer 3 (5'-GAC TCG TAA TAC GAC TCA CTA TAG GGA CCA GAA GCG GTG CCG GAA A-3' (SEQ ID NO: 52)) and primer 4 (5'-GAC TCG TAA TAC GAC TCA CTA TAG GGC CAC AGC GGA TGG TTC GGA T-3' (SEQ ID NO: 53)). The resulting amplicon was purified with Qiagen's PCR clean up kit (QIAquick PCR Purification Kit, cat #28104) and used as template for the T7 RNA polymerase reverse transcription reaction to generate dsRNA. Long dsRNA was treated in a final step before Dicer or RNaseIII digestion with DNase I and RNaseA to remove template DNA and unhybridized single-stranded RNA. Luciferase specific dsRNA was generated analogously using the following primer sets: primer 5 (5'-TGA ACA TTT CGC AGC CTA CC-3' (SEQ ID NO: 51)) and primer 6 (5'-GCC ACC TGA TAT CCT TT-3' (SEQ ID NO: 54)) for the first round of PCR, primer 7 (5'-GAC TCG TAA TAC GAC TCA CTA TAG GGT GAA CAT TTC GCA GCC TAC C-3' (SEQ ID NO: 55)) and primer 8 (5'-GAC TCG TAA TAC GAC TCA CTA TAG GGG CCA CCT GAT ATC CTT T-3' (SEQ ID NO: 56)) for the second round of PCR. Plasmids containing the LacZ and luciferase gene used as templates (pcDNA 1.2/V5/GW-lacZ and pcDNA5-FRT-luc). These two plasmids were also used for transfection to serve as reporter plasmid for functional testing. The two plasmids used are components of the BLOCK-iT™ Dicer RNAi Kit (Invitrogen, cat. # K3600-01). Double-stranded RNA, which was to serve as template for siRNA generation, was purified using the glass fiber filter columns developed for siRNA purification as well as with Ambion's purification columns and protocol. Purified dsRNA template was digested with either Dicer (Invitrogen) or RNase III (Ambion) to generate functional siRNA. The latter was purified using the single-column as well as the two-column protocol outlined above.

Mammalian Cell Culture and Transfection

For functional testing GripTite™ 293 MSR cells (Invitrogen, cat. # R79507) and F1pIn 293 cells were used. Grip- Tite™ 293 MSR cells were cultured in DMEM containing 4 mM L-glutamine, 10% FBS, and 600 µg/ml geneticin (Invitrogen, cat.# 11811-023). In co-transfection experiments 100 ng of each reporter plasmid (see above) was co-transfected with either unpurified siRNA, purified siRNA, or synthetic siRNA specific for lacZ or for Green Fluorescent Protein (GFP) into 90% confluent GripTite™ 293 cells plated at 2×105 cells/well. FlpIn 293 cells (FlpIn 293 luc) expressing luciferase from a single integrated copy were used to test luciferase specific siRNA. LacZ activity was also monitored as a control to assess any general, non-specific changes in mRNA expression. FlpIn 293 cells were cultured in DMEM containing 4 mM L-glutamine, 10% FBS, and 100 µg/ml hygromycin B (Invitrogen, cat. #10687-010). Cells were seeded in 24-well plates and grown to 30=50% confluence before transfection with siRNA.

β-Galactosidase and Luciferase Assays

Activity and specificity of siRNA transfected was assessed by monitoring the activity of the reporter gene products luciferase and β-galactosidase. One to two days after transfection the medium was removed from each well of the 24-well plates and replaced with 500 µl cold luciferase lysis buffer from Promega (25 mM Tris-HCl pH 8.0, 0.1 mM EDTA pH 8.0, 10% v/v glycerol, 0.1% v/v Triton X-100). Plates were then frozen at −80° C. for at least 1 hour. Samples were thawed for 30 min at RT and 50 µl (for luciferase assay) or 10 µl (for β-galactosidase assay) were transferred to a black 96-well plate. For β-galactosidase, 90 µl of Reaction Dilution Buffer containing 1% (v/v) Galacton-Plus® (Applied Biosystems, cat #T1006) was added to each sample and incubated for 30 min at room temperature. Luminescence was measured on a MicroLumat Plus luminometer using Winglow v.1.24 software (EG&G Berthold). For luciferase, either 50 µl of Luciferase Assay Reagent (Promega, cat #E1483) or 100 µl Accelerator II (Tropix) were injected per well and readings were taken for 5 seconds after a 2-second delay.

Other Materials Used i. Silencer siRNA Cocktail Kit (Cat. no. 1625, Ambion Inc.)
ii. RNA purification Column 1 and 2 (Cat. no., T510004, T510005, Gene Therapy Systems, Inc.)
iii. Yeast tRNA (Cat. no. 15401-011, Invitrogen Inc.)
iv. E-Gel 4% (Cat. no. G5018-04, Invitrogen Inc.)
v. 10 bp DNA ladder (Cat. no. 10821-015, Invitrogen Inc.)

Results and Discussion

Purification of Small Nucleic Acids—General Considerations

Commercially available kits for the isolation and purification of double-stranded nucleic acids, RNA as well as DNA, generally do not address the need for purification of short double-stranded nucleic acids. A notable exception is the use of size exclusion filtration technology. However, this technology suffers from several drawbacks (limited automation capabilities, broad cut-off size ranges, low recoveries, etc.) that have limited its use. Short double-stranded nucleic acids shall be defined here as nucleic acids that are shorter than about 100 bp in length. Ribonucleic acids falling into this category include, but are not limited to, RNA species that are described in the literature as tiny RNA, small RNA (sRNA), non-coding RNA (ncRNA), micro-RNA (miRNA), small non mRNA (snmRNA), functional RNA (fRNA), transfer RNA (tRNA), catalytic RNA such as ribozymes, small nucleolar RNA (snRNA), short hairpin RNA (shRNA), small temporally regulated RNA (strRNA), aptamers, and RNAi molecules including without limitation small interfering RNA (siRNA). With recent developments in the field of RNAi/siRNA technology, a particular need for the purification of siRNA from crude enzymatic preparations of siRNA has become apparent. Small interfering RNAs (siRNA) are small dsRNA molecules in the size range of approximately 12 to 25 bp, which can be generated either enzymatically or chemically (Elbashir et. al., 2001). Short deoxyribonucleic acids potentially requiring purification may comprise, but are not limited to, dsDNA molecules such as adapters, linkers, short restriction fragments and PCR products. The purification system described here is based on nucleic acids binding to a glass fiber filter under controlled conditions permitting size-dependant, efficient, high-recovery, high-purity purification of short nucleic acids.

Two general approaches for the purification of small nucleic acids, are outlined in the purification protocol flowchart above pertaining to the purification of enzymatically-generated siRNA. Using a single-column protocol, all double-stranded nucleic acids exceeding a length of approximately 10 base pairs are bound to the glass fiber matrix during an initial step in the presence of a chaotropic salt, which is contained in the Binding Buffer, and EtOH in excess of 70% (v/v). The binding step is followed by a wash step, which removes non-nucleic acids components from the target nucleic acids bound to the glass fiber matrix. In a third step small nucleic acids are selectively eluted in Elution Buffer containing a controlled amount of EtOH that is specific for the release of the targeted nucleic acids size range. Nucleic acids exceeding the targeted size range will remain bound to the glass fiber filter. In the case of siRNA, either generated by Dicer or RNaseIII digestion of larger dsRNA template molecules, the optimal concentration of EtOH was determined to be 25% (v/v). Use of the single-column protocol for small nucleic acids purification typically employs a final EtOH precipitation step in order to remove chaotropic salts, which are present in the Elution Buffer, followed by resuspension of purified nucleic acids in a buffer of choice.

In the two-column protocol double-stranded nucleic acids fragments exceeding a length of approximately 30 base pairs are bound to the glass fiber matrix during the initial binding step, while fragments shorter than approximately 30 base pairs are washed through the glass fiber matrix and are recovered in the flow through. This size fractionation is achieved by applying the mixture of nucleic acids fragment of various sizes in a Binding Buffer containing a chaotropic salt and a controlled concentration of EtOH. In the case of siRNA the optimal concentration of EtOH was determined to be approximately 33% (v/v). The size cut-off for flow through of short nucleic acids can be fine tuned by adjusting the relative amount of EtOH contained in the binding solution. Increased EtOH concentrations result in retention of shorter nucleic acid fragments on the glass fiber filter, while decreased EtOH concentrations in the binding solution result in the elution of larger nucleic acids fragments. In a second step the EtOH concentration of the flow through from the first column containing the small nucleic acids of interest is increased to >70% (v/v) and applied to a second glass fiber filter column. Under these conditions small, double-stranded nucleic acids are bound to the matrix of the second filter column. This second binding step is followed by a wash step, which removes any remaining non-nucleic acid components from the targeted small nucleic acids bound to the glass fiber matrix. In a final step the targeted small nucleic acids are eluted off the glass fiber matrix at low ionic strength with water.

The single-column and the two-column protocol provide two alternatives for the purification of small nucleic acids molecules. The single-column protocol is more economical as it uses only one filtration step. However, this protocol typically employs a final EtOH precipitation step, which is more time consuming than a filtration step and holds the risk of incomplete nucleic acid precipitation. On the other hand, EtOH precipitation is generally considered to yield a cleaner nucleic acid preparation. The two-column protocol, while more costly per sample purification, is generally faster than the single-column protocol by virtue of avoiding the EtOH precipitation step.

Single-Column Protocol: EtOH Fractionation of Crude siRNA

Experimental Setup

Crude lacZ siRNA, which was generated from 1 μg of dsRNA template in a 50-μl reaction volume according to the procedure outlined above, was mixed with 50 μl of Binding Buffer and 100 μl of EtOH at various concentrations. Final EtOH concentrations ranged from 5-50%. Samples were applied to spin columns, centrifuged, and the flow-through was collected and analyzed on a 4% E-Gel after EtOH precipitation of nucleic acids in the presence of glycogen.

Results and Discussion

Figure 22:
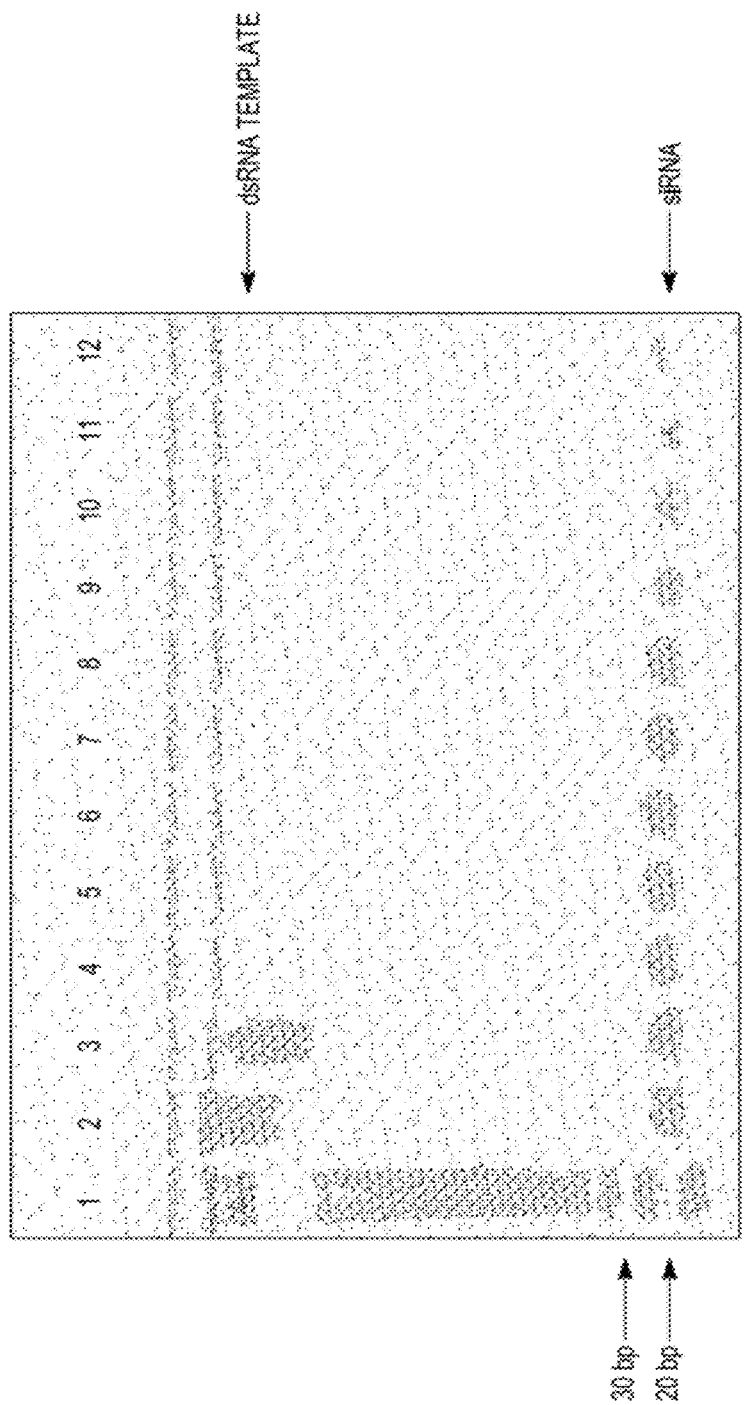
FIG. 22 shows fractionation of double-stranded RNA using different ethanol concentrations.

See FIG. 22. Lane I in FIG. 22 shows a 10-bp DNA ladder for size reference. The 20- and 30-bp fragments are marked. The crude lacZ/Dicer reaction is shown in lane 2. Undigested, 1-kb dsRNA template migrates close to the well. The undigested material generally accounts for a significant portion of the initial starting material after the dicing reaction, i.e. the Dicer reaction does not completely digest dsRNA substrate even after prolonged reaction times. Since the presence of undigested and partially digested dsRNA substrate is incompatible with cell viability, purification is essential. In the case shown, undigested template accounts for more than 50% of the starting material. The dsRNA Dicer reaction product, which has a length of 21-23 bp, migrates between the 20- and 30-bp fragments of the DNA ladder shown in lane 1. Reaction intermediates, partially digested dsRNA template which are apparent as a background smear in the lane, migrate between the undigested template and the siRNA reaction product. At an EtOH concentration of 5% in the Binding Buffer most of the 1-kb dsRNA template as well as shorter dsRNA molecules do not bind to the filter matrix and are consequently recovered in the flow-through (FIG. 22, lane 3). Increasing ethanol concentration in the Binding Buffer leads to the binding of progressively shorter dsRNA fragments to the filter matrix resulting in the selective binding of unwanted longer dsRNA fragments and selective flow-through of targeted siRNA molecules (FIG. 22, lanes 4-12). At an EtOH concentration exceeding 20% it appears that only targeted 21-23 bp siRNA selectively elute while longer dsRNA fragments are retained on the filter. At EtOH concentrations of 20-30% (lanes 6-8) recovery appears to be efficient, while at higher ethanol concentrations (35-50%, lanes 9-12) recovery decreases due to binding of even short dsRNA molecules at these elevated EtOH concentrations. At EtOH concentrations exceeding 50% siRNA showed increasing affinity for the glass fiber matrix of the filter. Efficient binding of siRNA can be achieved with EtOH concentrations of 70% or more even for the shorter siRNA products derived from RNase III digestion (see below).

FIG. 22 shows fractionation of double-stranded RNA using different ethanol concentrations. Flow-through samples were analyzed on a 4% E-Gel after EtOH precipitation in the presence of glycogen and resuspension in RNase-free water.

Lane 1: 10 bp DNA Ladder (Invitrogen Cat # 18021-015)
Lane 2: Crude lacZ/Dicer siRNA reaction with 1-kb dsRNA template
Lane 3: Flow-through of 5% EtOH-containing Binding Buffer
Lane 4: Flow-through of 10% EtOH-containing Binding Buffer
Lane 5: Flow-through of 15% EtOH-containing Binding Buffer
Lane 6: Flow-through of 20% EtOH-containing Binding Buffer
Lane 7: Flow-through of 25% EtOH-containing Binding Buffer
Lane 8: Flow-through of 30% EtOH-containing Binding Buffer
Lane 9: Flow-through of 35% EtOH-containing Binding Buffer
Lane 10: Flow-through of 40% EtOH-containing Binding Buffer
Lane 11: Flow-through of 45% EtOH-containing Binding Buffer
Lane 12: Flow-through of 50% EtOH-containing Binding Buffer Conclusion Removal of undigested and partially digested dsRNA substrate and high-purity recovery of Dicer-generated siRNA can be achieved by controlling EtOH concentration in the final binding solution. Optimal results are achieved with final EtOH concentrations ranging from 20-30% in the binding solution.

Functional Testing of Purified siRNA (Single-Column and Two-Column Protocol Comparison)

Experimental Setup

As outlined above in the Purification Protocol Flowchart, two alternative purification approaches are feasible depending mainly on individual preferences regarding ethanol precipitation and procedure time. In the following experiments, which are illustrated in FIGS. 19A-19C, lacZ siRNA was purified according to the single-column and two-column protocols described earlier. The siRNA obtained was tested for specificity and functionality in transfection experiments using GripTite™ 293 MSR cells, which contained either luciferase or β-galactosidase gene constructs in reporter plasmids, as described in detail above. In the case of the single-column purification protocol, elution was performed with Elution Buffer containing ethanol at final concentrations of between 5 and 30%. Transfection experiments were performed in duplicate.

Results and Discussion

Figure 23A:
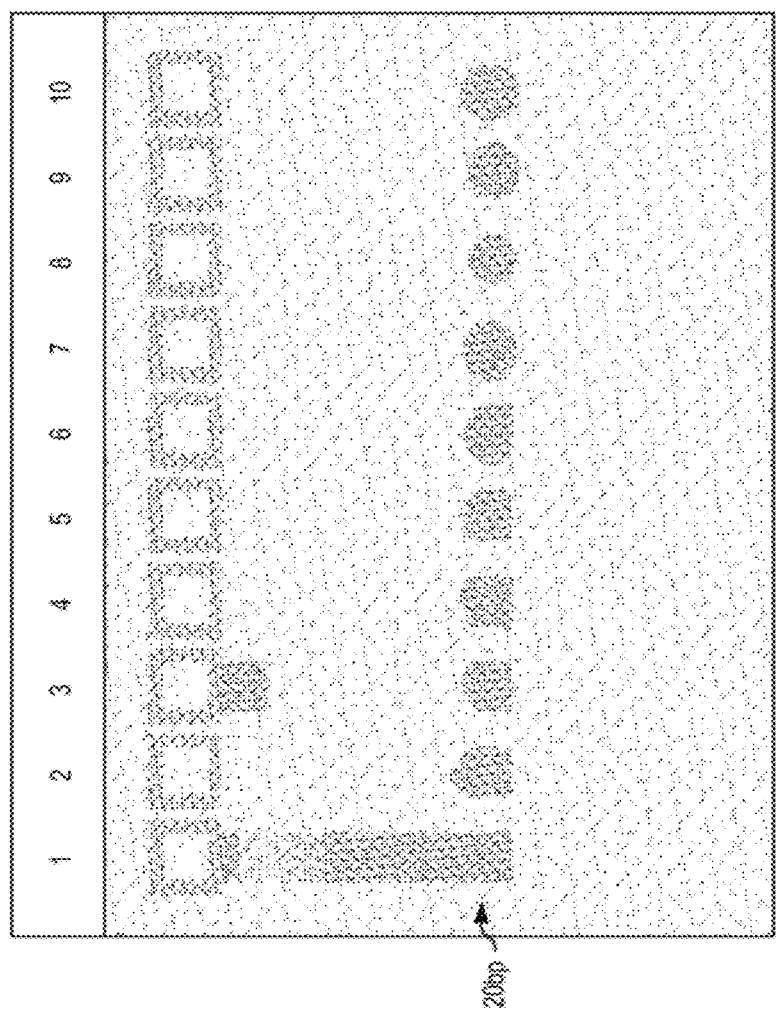
FIGS. 23A-23C show: 23A) gel analysis results of crude lacZ siRNA, siRNA purified using the two-column protocol, various fractions of the single-column purification protocol, as well as chemically synthesized siRNA analyzed on a 4% E-Gel, which were used for functional testing; 23B) measurements of luciferase activities after transfection of cells with lacZ siRNA; 23C) measurements of β-galactosidase activities after transfection of cells with lacZ siRNA

FIG. 23A shows gel analysis results of crude lacZ siRNA, siRNA purified using the two-column protocol, various fractions of the single-column purification protocol, as well as chemically synthesized siRNA analyzed on a 4% E-Gel, which were used for functional testing. Green Fluorescent Protein (GFP) siRNA, by virtue of being chemically synthesized, does not contain any long dsRNA impurities. The siRNA that was purified with the two-column protocol and siRNA fractions eluted with 20, 25, and 30% EtOH using the single-column protocol appear to be devoid of intermediate Dicer reaction products and full-length dsRNA template. Therefore, these siRNA preparations are expected to be potent and specific in the suppression of their target genes and are not expected to exhibit any of the adverse effects associated with the presence of long dsRNA. Unpurified lacZ siRNA contains significant amounts of undigested and partially digested long dsRNA molecules and is hence expected to result in cell death upon transfection. Likewise, siRNA purified with the single-column protocol and eluted with Elution Buffer containing 5, 15, and 20% EtOH is expected to result in cell death, albeit at decreasing degrees as ethanol concentration increases.

FIG. 23A:

Lane 1: 10 bp DNA Ladder (Invitrogen Cat #18021-015)—The 10-bp fragment only shows as a faint band.

Lane 2: Chemically synthesized, unpurified Green Fluorescent Protein (GFP) siRNA Lane 3: Crude lacZ siRNA reaction mixture Lane 4: LacZ siRNA purified using the two-column protocol (see flowchart above)

Figure 23B:
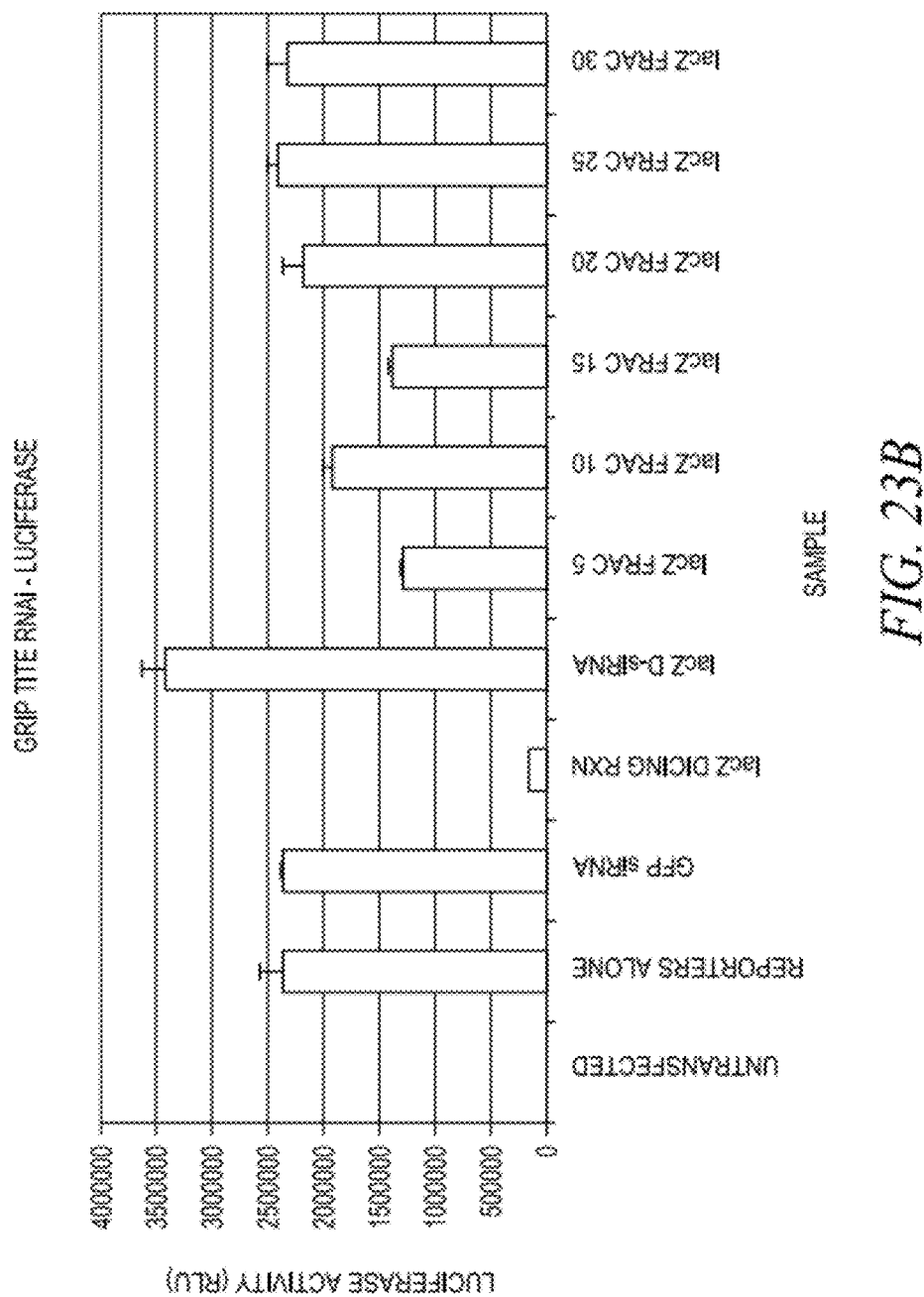

Lane 5: LacZ siRNA eluted with 5% EtOH-containing Elution Buffer according to the single-column protocol Lane 6: LacZ siRNA eluted with 10% EtOH-containing Elution Buffer according to the single-column protocol Lane 7: LacZ siRNA eluted with 15% EtOH-containing Elution Buffer according to the single-column protocol Lane 8: LacZ siRNA eluted with 20% EtOH-containing Elution Buffer according to the single-column protocol Lane 9: LacZ siRNA eluted with 25% EtOH-containing Elution Buffer according to the single-column protocol Lane 10: LacZ siRNA eluted with 30% EtOH-containing Elution Buffer according to the single-column protocol The effects of lacZ siRNA on luciferase activity are shown in FIG. 23B. This is a negative control experiment. Since lacZ siRNA does not have sequence homology to the luciferase gene, its activity should remain unperturbed by the presence of lacZ siRNA. Any changes in luciferase activity will thus be attributed to nonspecific effects such as the effect that the presence of long dsRNA may have on the transfected cells or the effects of transfection itself. Cells that do not carry the reporter plasmid for luciferase (untransfected) do not exhibit luciferase activity. Cells transfected with the reporter plasmid for luciferase (reporters alone) exhibit baseline luciferase activity serving as a point of reference for the action of siRNA in the following experiments. Transfection of cells carrying luciferase reporter plasmid with chemically synthesized, unrelated GFP siRNA (GFP siRNA) did not alter luciferase activity, as expected. Unpurified, crude lacZ Dicer reaction containing undigested and partially digested long dsRNA resulted in cell death and a concomitant lack of luciferase activity (lacZ dicing reaction). Transfection of target cells with lacZ siRNA purified using the two-column purification protocol (lacZ d-siRNA) did not suppress luciferase activity as expected. However, nonspecific induction of luciferase activity by about 40% was apparent. LacZ siRNA obtained by elution with Elution Buffer containing 5, 10, or 15% ethanol using the single-column protocol (lacZ fract 5, lacZ fract 10, lacZ fract 15) resulted in suppression of luciferase activity. This observation, however, is attributed to residual long dsRNA template and partial digestion products thereof in these fractions eliciting cell death as observed for unpurified Dicer reactions. The observed suppression of luciferase activity in these cases is not the result of specific siRNA action. LacZ siRNA obtained by elution with Elution Buffer containing 20, 25, and 30% EtOH did not alter luciferase activity. Hence, these fractions of purified siRNA do not elicit nonspecific effects such as induction or suppression of luciferase activity upon transfection.

Figure 23C:
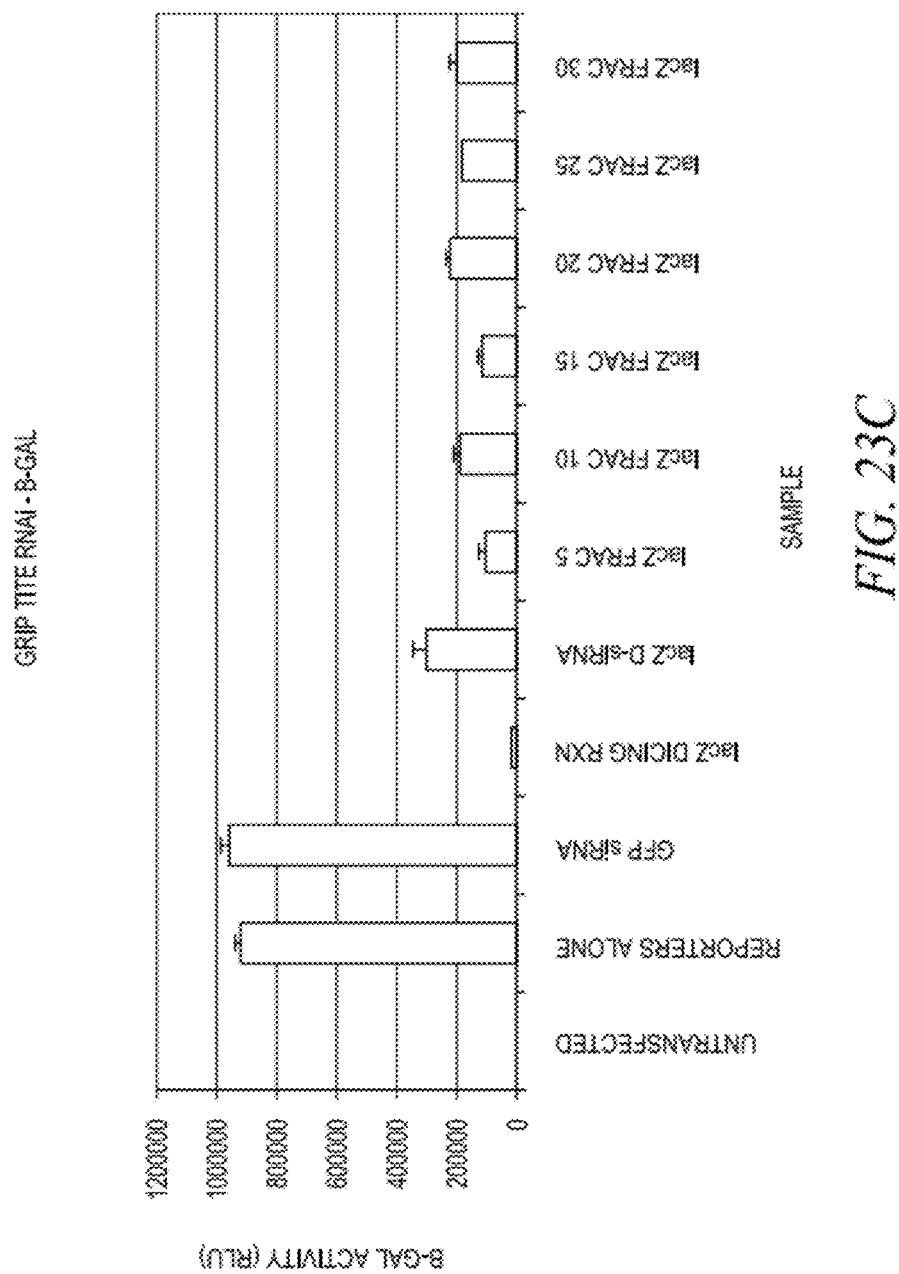

The effects of lacZ siRNA on its target transcripts, as evidenced and measurable through the activity of β-galactosidase, are shown in FIG. 23C. Cells that do not carry the reporter plasmid for β-galactosidase (untransfected) do not exhibit β-galactosidase activity. Cells transfected with the reporter plasmid for β-galactosidase (reporters alone) exhibit baseline β-galactosidase activity serving as a point of reference for the action of siRNA in the following experiments. Transfection of cells carrying β-galactosidase reporter plasmid with chemically synthesized, unrelated GFP siRNA (GFP siRNA) did not alter β-galactosidase activity. Unpurified, crude lacZ Dicer reaction containing undigested and partially digested long dsRNA resulted in cell death and a concomitant lack of β-galactosidase activity (lacZ dicing reaction). Transfection of target cells with lacZ siRNA purified using the two-column purification protocol (lacZ d-siRNA) suppressed β-galactosidase activity by approximately 70%. LacZ siRNA obtained by elution with Elution Buffer containing 5, 10, or 15% ethanol using the single-column protocol (lacZ fract 5, lacZ fract 10, lacZ fract 15) resulted in suppression of β-galactosidase activity. This observation, however, may be attributed to residual long dsRNA template and partial digestion products thereof in these fractions, eliciting cell death as observed for unpurified Dicer reactions. In addition, β-galactosidase activity in surviving cells may further be suppressed by the presence of siRNA specific for the lacZ gene. Thus, while suppression appears to be efficient, it is mainly caused by cell death and not by the specific action of the siRNA used. LacZ siRNA obtained by elution with Elution Buffer containing 20, 25, and 30% EtOH did profoundly suppress the activity of the β-galactosidase enzyme by approximately 80%. In the latter case cells appeared healthy after transfection with purified siRNA. Hence, these fractions of purified siRNA are highly effective and specific in the suppression of their targeted mRNA.

Fractionated siRNA samples used were obtained using either the single-column or two-column protocol as a means of purification. The effects of lacZ siRNA are specific for the β-galactosidase gene due to sequence homologies and a reduction of β-galactosidase activity is expected as a result of the presence of lacZ siRNA.

FIGS. 23B and C:

Untransfected: Cells have not been transfected with reporter plasmids carrying the luciferase or β-galactosidase gene Reporters alone: Cells have been transfected with reporter plasmid only, but not with siRNA GFP siRNA: Transfection with chemically synthesized, crude siRNA specific for the green fluorescent protein gene LacZ dicing reaction: Transfection with crude, unpurified lacZ siRNA from Dicer reaction LacZ d-siRNA: Transfection with lacZ siRNA purified using the two-column protocol LacZ frac 5: Transfection with lacZ siRNA from 5% EtOH containing fraction (single-column protocol)

LacZ frac 10: Transfection with lacZ siRNA from 10% EtOH containing fraction (single-column protocol)

LacZ frac 15: Transfection with lacZ siRNA from 15% EtOH containing fraction (single-column protocol)

LacZ frac 20: Transfection with lacZ siRNA from 20% EtOH containing fraction (single-column protocol)

LacZ frac 25: Transfection with lacZ siRNA from 25% EtOH containing fraction (single-column protocol)

LacZ frac 30: Transfection with lacZ siRNA from 30% EtOH containing fraction (single-column protocol)

Purification of siRNA Generated by Dicer or RNase III

Experimental Setup

One-kb dsRNA transcript of either lacZ or luciferase was incubated with Dicer or RNaseIII to generate double-stranded siRNA products. Dicer reactions were carried out using a protocol as described in the BLOCK-iT™ Complete Dicer RNAi Kit (Invitrogen cat. # K3650-01). Digestion with RNaseIII (Ambion, cat. # 2290) was performed according to the manufacturer's suggestions. Crude RNase III and Dicer siRNA reactions were purified using the single-column and two-column purification protocol and subsequently tested for functionality.

Results and Discussion

Figure 24A:
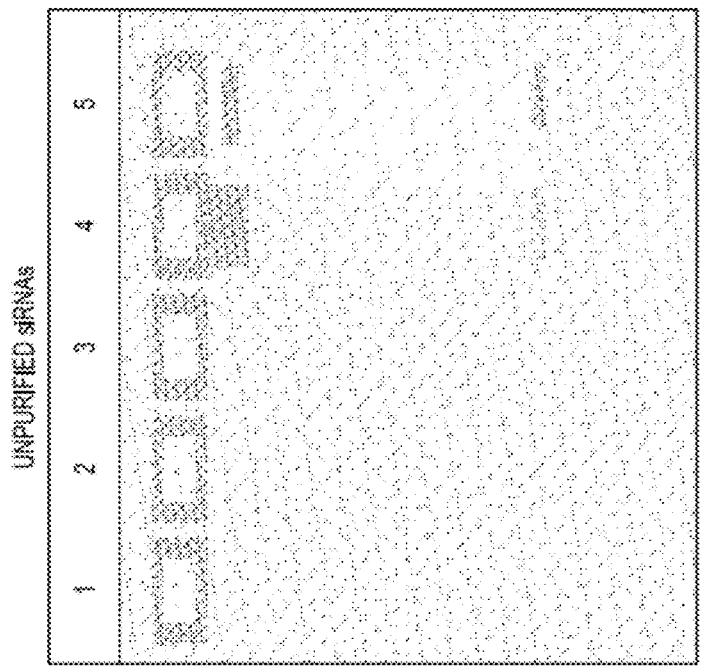
FIGS. 24A-24B show purification of siRNA generated with Dicer and RNaseIII.

The Dicer enzyme is a member of the RNaseIII family of ribonucleases and digests long dsRNA templates into 21-23 nucleotide, double-stranded siRNA that have been shown to function as key intermediates in triggering sequence specific RNA degradation during posttranscriptional gene silencing. Likewise, RNaseIII digests long dsRNA templates into short double-stranded siRNA molecules. However, the siRNA generated by RNaseIII is generally only approximately 12-15 base pairs long. Dicer enzyme is found in all eukaryotic cells and RNaseIII is mainly found in prokaryotes. Dicer enzyme is speculated to bind to the ends of long dsRNA and progressively cleave the template dsRNA. The mode of action of RNaseIII may involve random cleavage of template dsRNA into smaller, compared to the Dicer enzyme, 12-15 bp siRNA fragments. The RnaseIII enzyme is considerably more active than the corresponding Dicer enzyme, which leads to complete digestion of template dsRNA by RNaseIII enzyme, while Dicer enzyme, even after prolonged digestion, results in only incomplete digestion of template dsRNA. These findings are illustrated in FIG. 24A. Neither enzyme requires ATP for function. However, both enzymes require divalent metal cations and a specific, optimal pH range for optimal activity, which are provided by enzyme-specific reaction buffers. The purification procedures for siRNA used here result in the removal of proteins and buffer components. The purified siRNA is resuspended in RNase-free water in the final purification step independent of the purification protocol used. Short interfering RNA generated by the action of RNase III as well as by Dicer enzyme were successfully purified using Invitrogen spin columns applying either the single- or two-column purification protocol as shown in FIG. 24B.

Figure 24B:
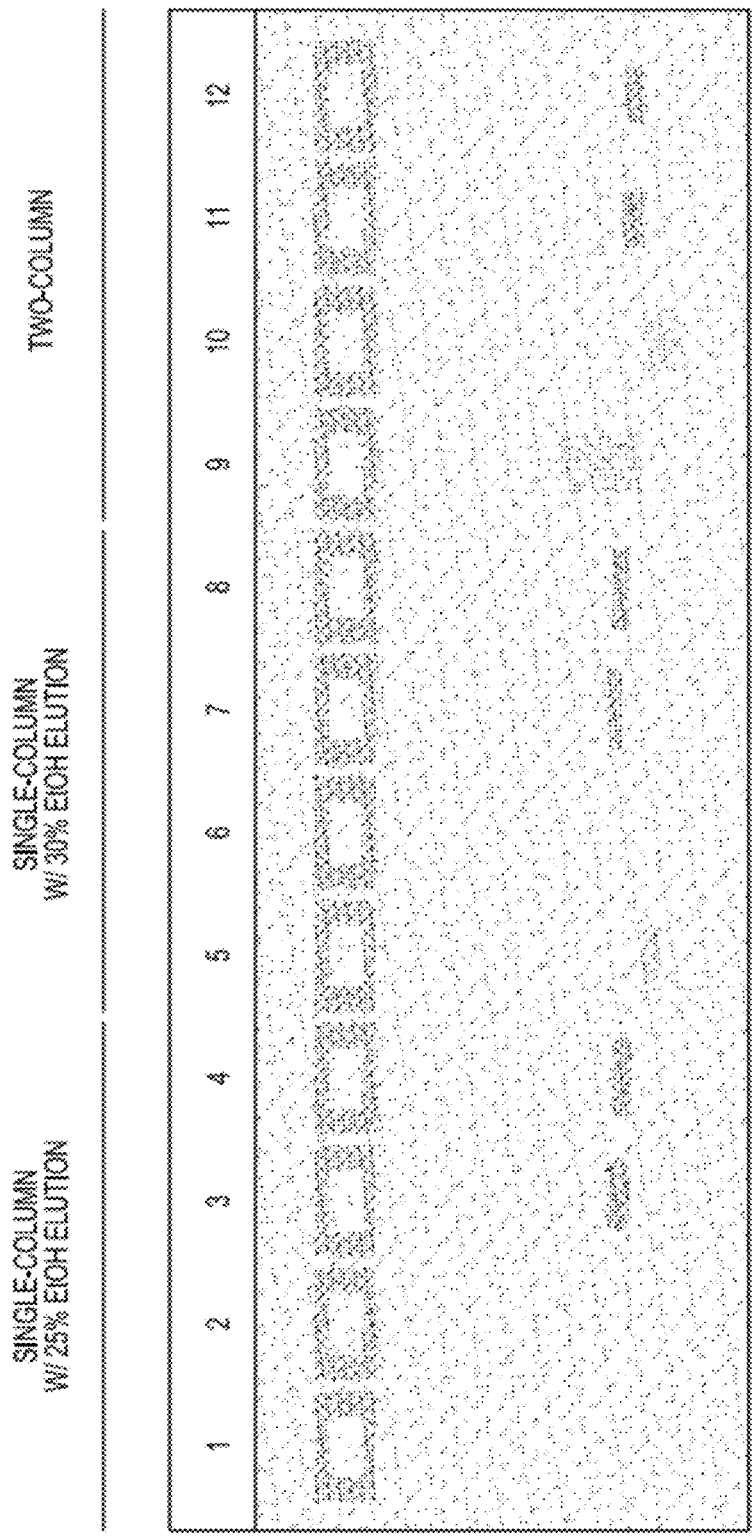

FIGS. 24A and 24B show purification of siRNA generated with Dicer and RNaseIII

FIG. 24A:
Lane 2: unpurified lacZ siRNA cleaved by RNaseIII,
Lane 3 unpurified luciferase siRNA cleaved by RNaseIII,
Lane 4: unpurified lacZ siRNA cleaved by Dicer,
Lane 5: unpurified luciferase siRNA cleaved by Dicer FIG. 24B:
Lane 1, 5, 9: lacZ siRNA cleaved by RNaseIII,
Lane 2, 6, 10: luciferase siRNA cleaved by RNaseIII,
Lane 3, 7, 11 lacZ siRNA cleaved by Dicer,
Lane 4, 8, 12 luciferase siRNA cleaved by Dicer Conclusion Short interfering RNA generated by digestion of long dsRNA templates with either Dicer or RNaseIII enzyme can be efficiently purified using the single-column or two-column purification protocol.

Functional Testing of SiRNA Preparations with FlpIn 293 luc Cells

Experimental Setup

Short interfering RNA was generated by digestion of long dsRNA templates (1 µg) with either RNase III or Dicer enzyme. Samples were purified using the single- and two-column purification protocol. Concentrations of purified siRNA were determined by A260 measurements and 20 ng of purified sample was used for each transfection into FlpIn 293 luc cells.

Results and Discussion

Figure 25:
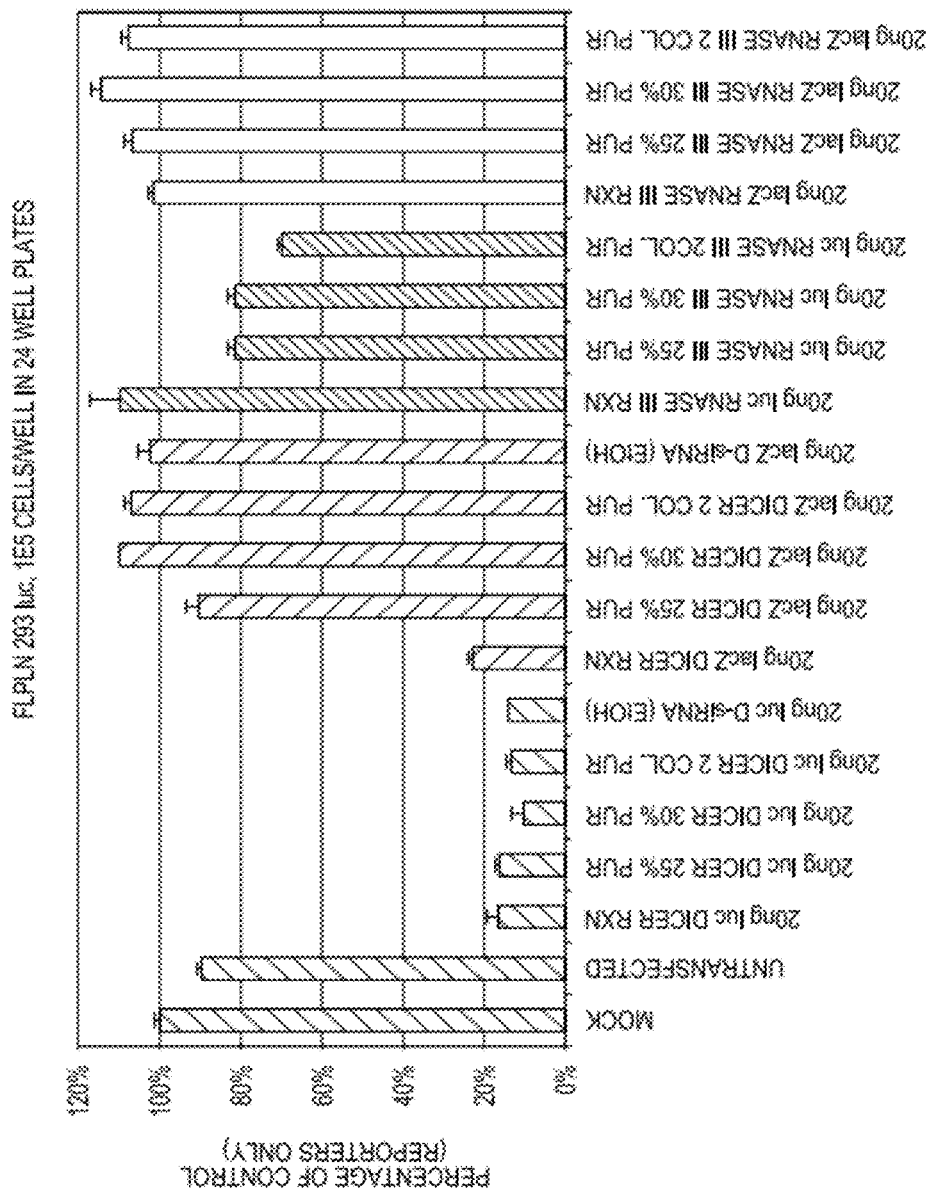
FIG. 25 shows functional testing of siRNA preparations with FipIn293-luc cells. Relative luciferase activity was measured for siRNA samples.

Transfection experiments were performed in 5 experimental groups with each experiment being conducted in duplicate. Experimental group I consisted of two control reactions of mock transfected (Mock), i.e. transfection with transfection agent but without siRNA, as well as FlpIn 293 luc cells expressing baseline levels of luciferase (Untransfected). The luciferase activity was measured in these latter two experiments and served as reference for luciferase activity that was determined in group 2-5 experiments. In experimental groups 2 and 3 the effect of luciferase activities by Dicer generated luciferase specific siRNA (luc siRNA) and β-galactosidase specific siRNA (lacZ siRNA) were assessed. Likewise, in groups 4 and 5 the effect of siRNA generated with RNaseIII enzyme on luciferase activity was assessed.

siRNA (20 ng luc Dicer reaction) resulted in cell death and nonspecific lack of luciferase activity (see FIG. 25). SiRNA that was purified using the single-column purification protocol, where siRNA was eluted with Elution Buffer containing 25 or 30% EtOH (20 ng luc Dicer 25% pur. & 20 ng luc Dicer 30% pur.), resulted in efficient suppression of luciferase activity by more than 80%. Equally efficient suppression was achieved with siRNA purified using the two-column purification protocol (20 ng luc Dicer 2 col. pur.) and with the latter siRNA that was subjected to an additional step of EtOH precipitation (20 ng luc d-siRNA (EtOH)). Thus, luciferase specific siRNA purified with either the single-column or two-column purification protocol is highly potent in suppressing the activity of luciferase.

As shown in experimental group 3 in FIG. 25, all purified and β-galactosidase-specific siRNA samples generated with the Dicer enzyme failed, as expected, to significantly change expression levels of the luciferase gene as determined by assessing luciferase activity. Variations in the activity of the luciferase enzyme caused by β-galactosidase-specific siRNA were generally less than 10%. As observed earlier, unpurified Dicer-generated siRNA (20 ng luc Dicer reaction) resulted in cell death and nonspecific lack of luciferase activity. Thus, β-galactosidase-specific siRNA purified with the single-column or two-column protocol does not cause any significant nonspecific induction or suppression of bystander proteins, in this case luciferase.

In experimental groups 4 and 5 the effect of luciferase specific siRNA (luc siRNA) as well as β-galactosidase enzyme specific siRNA (lacZ siRNA) generated with RNaseIII enzyme (Ambion) on luciferase activity was assessed. Unlike unpurified Dicer reactions, which contain significant amounts of undigested or partially digested long dsRNA template, unpurified RNaseIII reactions do not contain significant amounts of undigested or partially digested long dsRNA template as previously shown in FIG. 24A. Consequently, transfection with unpurified RNaseIII reaction products (20 ng luc RNaseIII reaction & 20 ng lacZ RNaseIII reaction) does not lead to cell death and concomitant nonspecific reduction of luciferase activity. RNase III digestion products are in the 13-15 bp size range, which is well below the size range reported for potent siRNA (~20-23 bp). Consequently, purified RNaseIII-generated luciferase specific siRNA (20 ng luc RNaseIII 25% pur., 20 ng luc RNaseIII 30% pur, and 20 ng luc RNaseIII 2 col. pur.) suppressed luciferase activity by only approximately 25% under the conditions used here. This lack of efficient suppression at the siRNA concentrations used may be attributable to a lack of functional siRNA present after digestion with RNaseIII since the siRNA size generated by RNaseIII is less than 20 base pairs (see FIGS. 24A and 24B). Czauderna et al. (Nucleic Acids Research 2003) reported that synthetic siRNAs shorter than 19 base pairs in size were not effective in suppressing gene expression. Concentrations of up to 200 ng/transfection of RNaseIII-generated siRNA were tested. However, even at these elevated amounts no significant suppression was observed. As shown in experimental group 5, neither unpurified nor purified lacZ siRNA that was generated by digestion of long dsRNA templates with RNaseIII had any effect on luciferase activity.

Functional Testing of siRNA Preparations with GripTite™ MSR Cells

Experimental Setup

Two reporter plasmids (see above) expressing luciferase and β-galactosidase, respectively, were co-transfected into GripTite™ 293 MSR cells with siRNA specific for luciferase mRNA (luc) or β-galactosidase mRNA (lacZ) generated by Dicer or RNaseIII using the experimental scheme described in the previous experiment. Luciferase and β-galactosidase activity was determined as described above to assess the effect of specific siRNA preparations on the expression of the two gene transcripts under investigation.

Results and Discussion

Figure 26A:
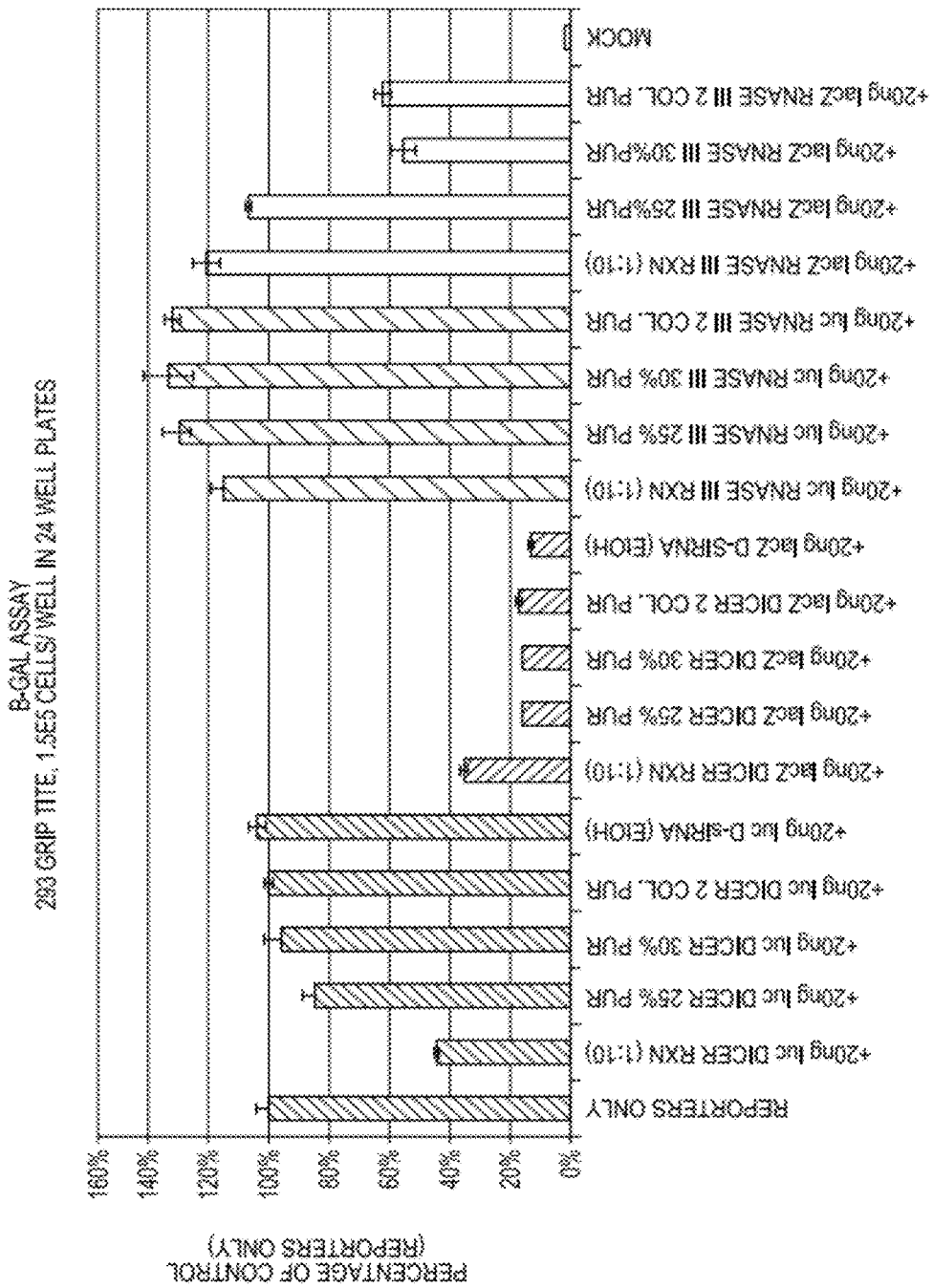
FIGS. 26A-26B show functional testing of siRNA preparations with GripTite™ 293 MSR cells. 26A) Beta-galactosidase assay: Effect of luc siRNA and lacZ siRNA generated with Dicer and RNaseIII enzyme on β-galactosidase activity. 26B) Luciferase assay: Effect of luc siRNA and lacZ siRNA generated with Dicer and RNaseIII enzyme on luciferase activity.

Results presented in FIG. 26A demonstrate the effect of different luc siRNA and lacZ siRNA preparations generated with Dicer and RNaseIII enzyme on β-galactosidase activity. The results obtained are in good agreement with the results shown in FIG. 25. In brief, GripTite 293 MSR cells transfected with the reporter plasmid alone (Reporters Only) exhibited reference levels of β-galactosidase activity. Cells not transfected with the reporter plasmid (Mock) did not yield any β-galactosidase activity. As seen previously, crude Dicer reactions (20 ng luc Dicer reaction & 20 ng lacZ Dicer reaction) caused cell death and nonspecific suppression of β-galactosidase activity, while this effect was not observed with crude RNaseIII reactions (20 ng luc RNaseIII reaction & 20 ng lacZ RNaseIII reaction). All preparations of purified, Dicer-generated lacZ siRNA efficiently suppressed expression of α-galactosidase activity by more than 80%. On the other hand, neither preparation of the negative control luc siRNA affected β-galactosidase activity to any significant degree. SiRNA generated by digestion with RNaseIII elicited similar responses to those observed above. Suppression of α-galactosidase activity by lacZ siRNA preparations was inefficient with maximum suppressions of 40%. However, from the results shown in FIG. 26A it is apparent that luciferase specific siRNA preparations generated with RNaseIII enzyme caused significant nonspecific induction of the β-galactosidase gene.

Figure 26B:
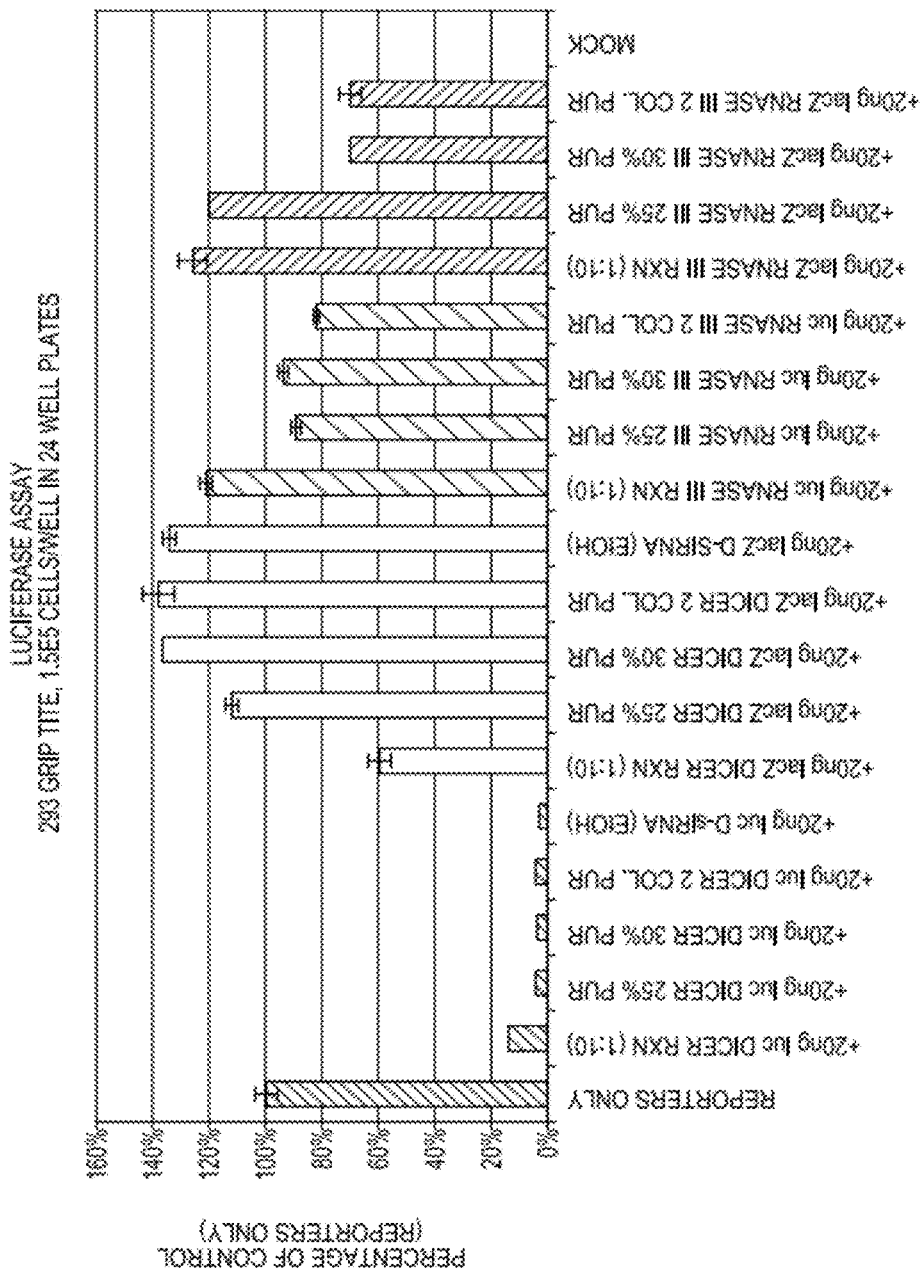

Results presented in FIG. 26B demonstrate the effect of different luc siRNA and lacZ siRNA preparations generated with Dicer and RNaseIII enzyme on luciferase activity. The results obtained are in good agreement with the results shown in FIG. 25. In brief, GripTite 293 MSR cells transfected with the reporter plasmid alone (Reporters Only) exhibited reference levels of luciferase activity. Cells not transfected with the reporter plasmid (Mock) did not yield any luciferase activity. Crude Dicer reactions (20 ng luc Dicer reaction & 20 ng lacZ Dicer reaction) caused cell death and nonspecific suppression of luciferase activity, while this effect was not observed with crude RNaseIII reactions (20 ng luc RNaseIII reaction & 20 ng lacZ RNaseIII reaction). All preparations of purified, Dicer-generated luc siRNA efficiently suppressed expression of luciferase activity by more than 90%. On the other hand, neither preparation of the negative control lacZ siRNA suppressed luciferase activity. However, in the series of experiments shown here, luciferase activity was stimulated by up to 40% by α-galactosidase specific lacZ siRNA. SiRNA generated by digestion with RNaseIII elicited similar responses to those observed above. The suppression of luciferase activity by luc siRNA preparations was inefficient with maximum suppressions of approximately 20%. The effects of lacZ siRNA preparations generated with RNaseIII on luciferase activity were inconsistent with both induction (20 ng lacZ RNaseIII 25% pur.) and suppression (20 ng lacZ RNaseIII 30% pur. & 20 ng lacZ RNaseIII 2 col. pur.) being observed.

Conclusion

SiRNA generated by digestion of long dsRNA templates with Dicer enzyme and purified using either the single-column or two-column purification protocol efficiently suppressed gene specific expression with minimal nonspecific induction of bystander proteins. Short interfering RNA generated by digestion of long dsRNA templates with RNaseIII enzyme, while efficiently purified with either the single-column or two-column purification protocol, did not perform well under the experimental conditions used here.

Column Capacity and Recovery Determination

Experimental Setup.

These experiments were intended to determine the recovery of RNA, tRNA and a 1-kb dsRNA fragment, after binding to the glass fiber matrix of the spin column as a function of elution volume. The experiments were also designed to provide information about the general loading capacity of the spin column for short double-stranded nucleic acids and long dsRNA fragments, the latter are used as templates for RNase digestion assays. In order to assess the column capacity for siRNA, yeast tRNA was used, because it was available in the quantities needed. Yeast tRNA constitutes a sensible alternative for column testing to siRNA as its linear, single-stranded size is approximately 75 nucleotides that are involved in extensive secondary structure formation, i.e. tRNA is present predominantly in dsRNA form. The tRNA used here migrates like a 40-bp double-stranded nucleic acid fragment on agarose gels. The efficiency of recovery and approximate loading capacity was also determined for a 1-kb dsRNA fragment. These long dsRNA fragments serve as templates for Dicer and RNaseIII digestion and require purification after clean up of the transcription reaction with DNaseI and RNaseA and prior to Dicer/RNaseIII digestion for generating siRNA. Purifications were carried out using the single-column purification protocol with 10-1000 µg of yeast tRNA or 4-240 µg of the 1-kb dsRNA fragment. Bound dsRNA was eluted from the spin columns with either a single elution of 100 µl DEPC-treated water or two successive elutions of 50 µl DEPC-treated water. Amounts of eluted RNA were quantified by A260 measurements and compared to the initial amount of RNA loaded.

Results and Discussion

Figure 27A:
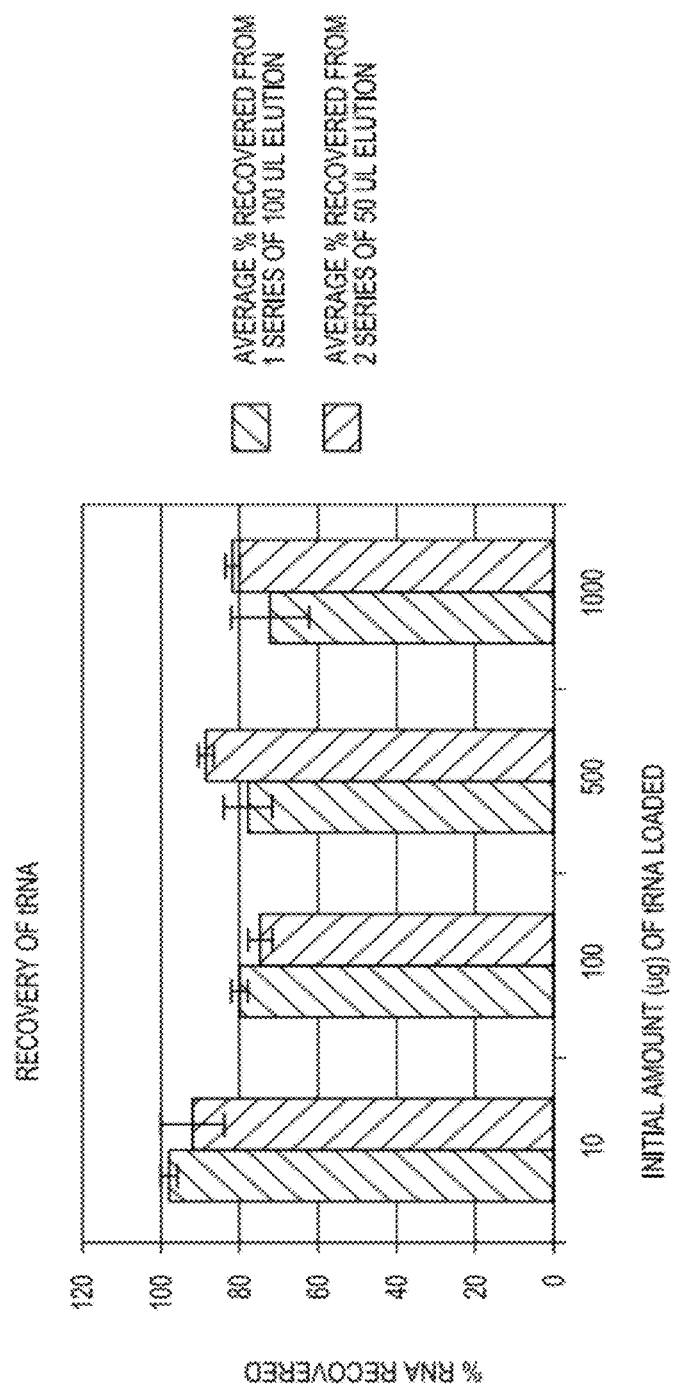
FIGS. 27A-27B show determination of column capacity and recovery efficiency. 27A) Recovery of tRNA after binding to the column matrix with a single 100-µl or two 50-µl elutions. 27B) Recovery of a 1-kb dsRNA fragment after binding to the column matrix with a single 100-µl or two 50-µl elutions.

Ten µg of tRNA were eluted with either a single 100-µl elution or two 50-µl elutions with an efficiency exceeding 90% (FIG. 27A). Amounts of tRNA of up to 1 mg can be eluted with efficiencies of approximately 80%, independent of whether a single 100-µl elution or two 50-µl elutions were used. Recovery can be further increased to about 95% with a second 100-µl elution or a third 50-µl elution. It shall be noted that for yeast tRNA amounts in excess of about 100 µg the addition of Binding Buffer and EtOH to the sample results in precipitation of presumably tRNA. The results shown in FIG. 27A demonstrate that tRNA, and by correlation siRNA, can be recovered almost quantitatively from the spin column matrix by elution with DEPC-treated water. Also, the results show that the column capacity exceeds 1 mg for tRNA/siRNA.

Figure 27B:
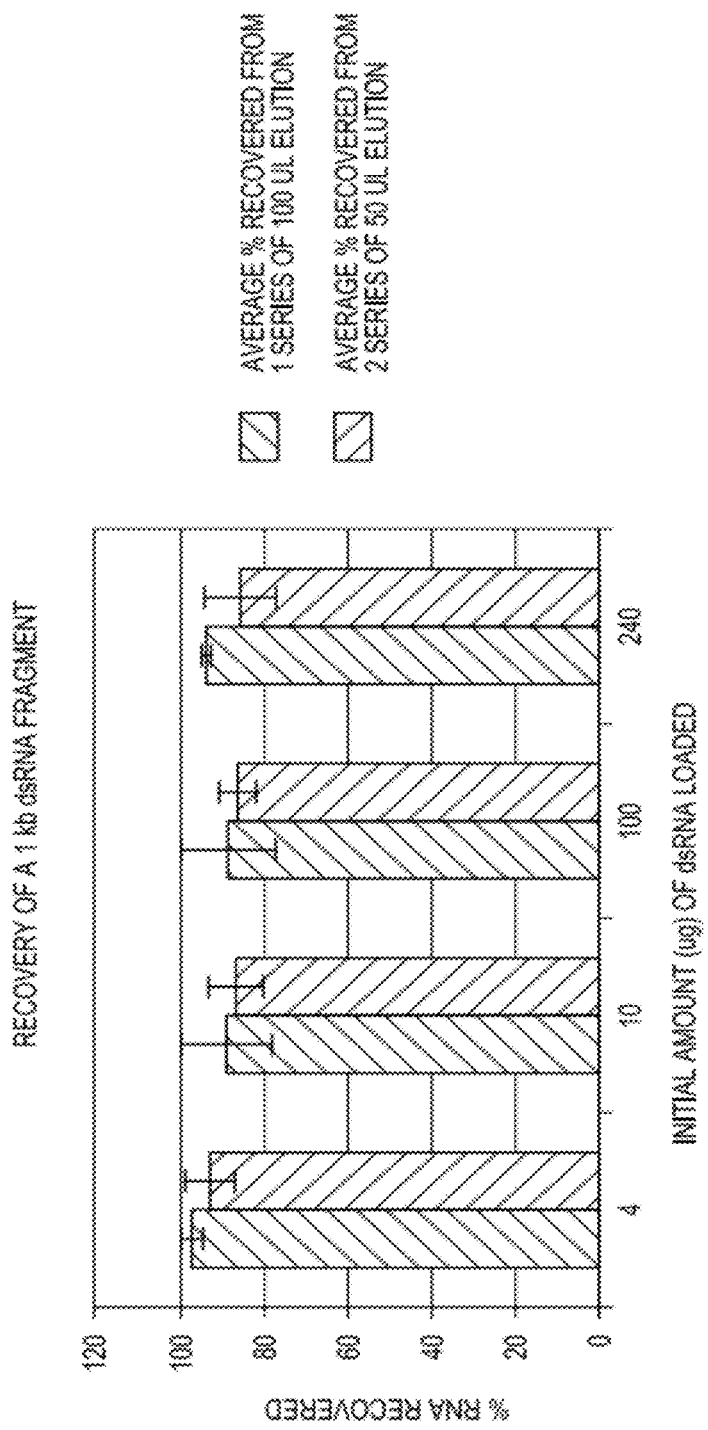

FIG. 27B shows the recovery results obtained with a 1-kb dsRNA fragment loaded at amounts ranging from 4-240 µg. Independent of whether a single 100-µl elution or two 50-µl elutions were used recovery efficiency was about 90%. It shall be noted that the long dsRNA fragment was more susceptible to form a precipitate after the addition of Binding Buffer and EtOH than tRNA. Loading of dsRNA amounts exceeding about 500 µg resulted in progressively decreasing recoveries with either a single 100-µl elution or two 50-µl elutions, which could be improved with additional elutions.

Conclusion

Short dsRNA, e.g., siRNA or tRNA, as well as long dsRNA fragments can be efficiently eluted after binding to the spin column with DEPC-treated water. No major differences in recovery were observed for either a single elution with 100 µl or two successive 50-µl elutions.

Clean-up of Long dsRNA Substrate and tRNA

Experimental Setup

Three different sizes of long dsRNA (100, 500 and 1 kb) of the lacZ gene were generated by T7 polymerase reactions as described above. The 100-bp and 500-bp lacZ dsRNA fragments were generated using primer 1 (see above) and primer 9 (5'-GCA TCG TAA CCG TGC ATC 3' (SEQ ID NO: 57) and primer 10 (5' GCG AGT GCC AAC ATG G 3' (SEQ ID NO: 58), respectively, for the first round PCR. Primer 3 (see above) in combination with primer 11 (5'-GAC TCG TAA TAC GAC TCA CTA TAG GTA CTG CAT CG T AAC CGT GCA TC-3' (SEQ ID NO: 59)) and primer 12 (5'-GAC TCG TAA TAC GAC TCA CTA TAG GTA CTG CGA GTG GCA ACA TGG-3' (SEQ ID NO: 60)), respectively, were used for the second round of PCR. The 1-kb dsRNA fragment was generated as described above. All dsRNA fragments generated were cleaned up by DNase I and RNase A digestion to remove DNA and single-stranded RNA from the reactions before purification using a modified single-column protocol (see below).

Results and Discussion

Figure 28A:
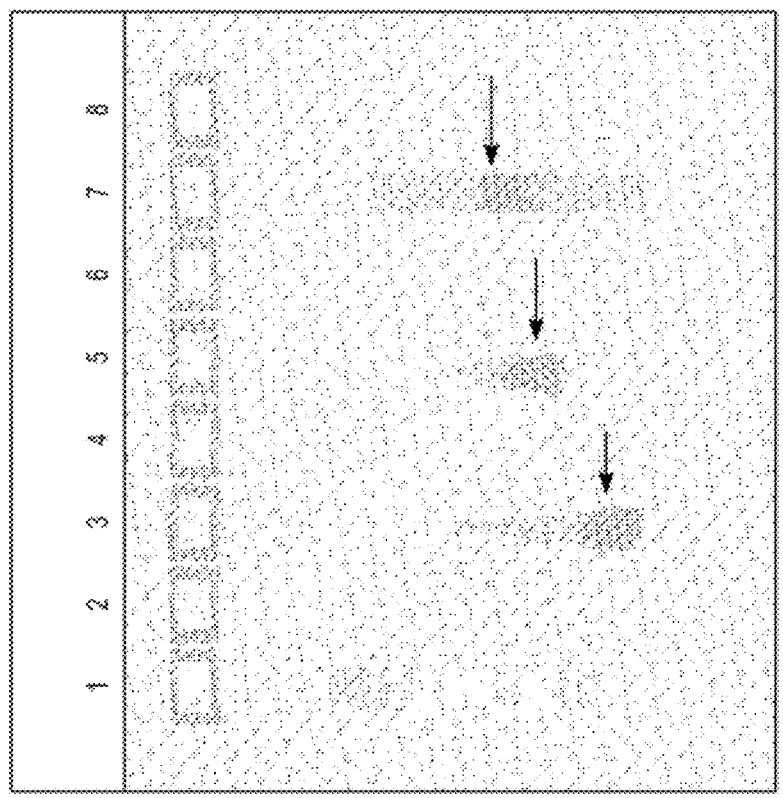
FIGS. 28A-28B show clean-up of long dsRNA and tRNA. 28A) Clean-up of 100-, 500-, and 1000-bp fragments of dsRNA. 28B) Clean-up of yeast tRNA.
Figure 28B:
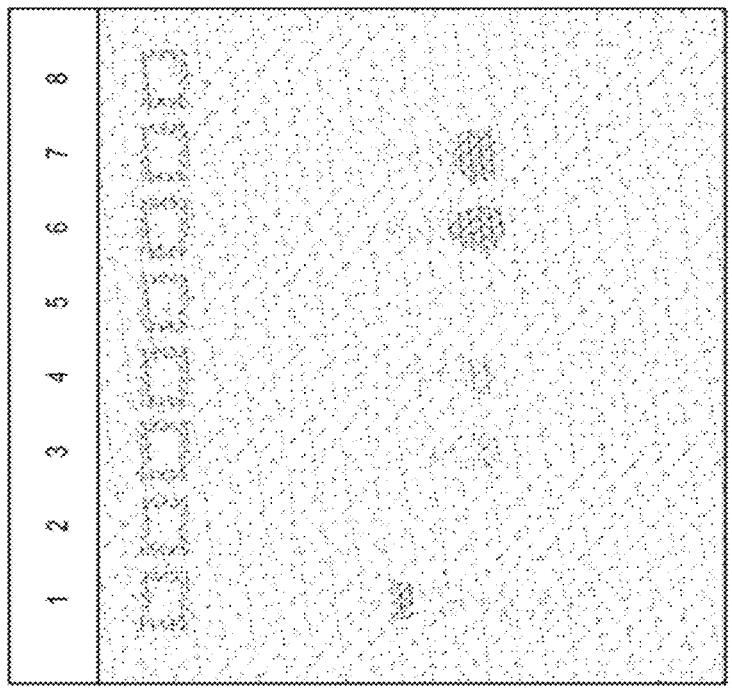

Long dsRNA intended for Dicer or RNaseIII digestion has to be cleaned up with DNase I and RNase A to remove DNA and unhybridized single-stranded RNA. Subsequently, the latter enzymes, their digestion products, and buffer components need to be removed prior to digestion of the long dsRNA templates with Dicer or RNaseIII. A modified version of the single-column protocol was used to purify long dsRNA suitable for Dicer and RNaseIII digestion. Binding capacity and recovery of dsRNA from the glass fiber filters was determined previously. Purification results of long dsRNA and tRNA are shown in FIGS. 28A and 28B.

Purification of dsRNA (50 ul sample)
1. Add 150 µl of Binding Buffer and mix well
2. Add 600 µl of 100% EtOH (Final EtOH concentration of 75%)
3. Mix well and load onto column
4. Centrifuge at 14000 rpm for 1 min
5. Wash with 500 µl of diluted Wash Buffer
6. Repeat the washing step
7. Centrifuge at 14000 rpm for 1 min to dry column
8. Add 100 µl of DEPC-treated water
9. Wait for 1 min
10. Centrifuge at 14000 rpm for 1 min to recover dsRNA FIG. 28A:
Lane 1:1 kb Plus DNA Ladder (Invitrogen)
Lane 3: 100-bp lacZ dsRNA fragment
Lane 5: 500-bp lacZ dsRNA fragment
Lane 7: 1-kb lacZ dsRNA fragment FIG. 28B:
Lane 1: 10 bp DNA Ladder (Invitrogen)
Lane 3: Unpurified yeast tRNA (0.3 µg)
Lane 4: Cleaned-up yeast tRNA (0.3 µg))
Lane 6: Unpurified (1.5 µg)
Lane 7: Cleaned-up yeast tRNA (1.5 µg))

REFERENCES

Kaufman, R. J., *Proc Natl. Acad. Sci. USA* 96:11693-11695 (1999).

Denli, A. M. and Hannon, G. J., *Trends Biochem. Sci.* 28:196-201 (2003).

Carrington, J. C. and Ambros, V., *Science.* 301:336-338 (2003).

Sledz, C. A, et al., *Nat Cell Biol.* 5:834-839 (2003).

Illangasekare, M. and Yarus, M., *RNA.* 5:1482-1489 (1999).

Elbashir, S. M., et al., *Nature* 411:494-498 (2001).

Czauderna, F., et al., *Nucleic Acids Res.* 31:2705-2716 (2003).

Elbashir, S. M., et al., *EMBO J.* 20:6877-6888 (2001).

Although the invention has been described with reference to the above examples, it will be understood that modifications and variations are encompassed within the spirit and scope of the invention. Accordingly, the invention is limited only by the following claims.

What is claimed is:

1. A reaction mixture comprising:
   (a) a first double-stranded DNA molecule which comprises a promoter,
   (b) a second double-stranded DNA molecule, and
   (c) a recombinant nucleic acid molecule formed from the first double-stranded DNA molecule and the second double-stranded DNA molecule,
   wherein at least one end of at least one strand of the first double-stranded DNA molecule is topoisomerase-charged,
   wherein at least one end of at least one strand of the second double-stranded DNA molecule is topoisomerase-charged, and
   wherein the topoisomerase-charged ends of the first double-stranded DNA molecule and the second double-stranded DNA molecule are capable of hybridizing to each other such that in the recombinant nucleic acid molecule formed from the first double-stranded DNA molecule and the second double-stranded DNA molecule each strand of the first double-stranded DNA molecule is covalently linked to each strand of the second double-stranded DNA molecule and the recombinant nucleic acid molecule-does not contain a nick in either strand at the position where the first and second nucleic acid molecules are joined.

2. The reaction mixture of claim 1, wherein the first double-stranded DNA molecule comprises a T7 promoter.

3. The reaction mixture of claim 1, wherein the topoisomerase is a type IB topoisomerase or a catalytic domain of a type IB topoisomerase.

4. The reaction mixture of claim 1, wherein the topoisomerases are of different types.

5. The reaction mixture of claim 1, wherein the second double-stranded DNA molecule is the product of a polymerase chain reaction.

6. The reaction mixture of claim 1, wherein the first double-stranded DNA molecule is a vector.

7. The reaction mixture of claim 1, wherein the second double-stranded DNA molecule is a cDNA.

8. The reaction mixture of claim 1, wherein the second double-stranded DNA molecule is genomic DNA.

9. The reaction mixture of claim 1, further comprising one or more components selected from the group consisting of buffers, salts and polyamines.

10. The reaction mixture of claim 1, wherein the second double-stranded DNA molecule is synthetic DNA.

* * * * *

SEQUENCE LISTING

```
<160> NUMBER OF SEQ ID NOS: 62

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tatgtatcat acacatacga tttaggt                                           27

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
accgcctctc cccgcgcgtt                                              20

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttccgaagg gggcgataca gtcaactgtc tttg                              34

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttggccaagg gtatctagaa gcttctgcag acgcgt                            36

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gttccgaagg gccaccgtac tcgtcaattc caag                              34

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggccaaaagg gaacttgttt attgcagctt ataatg                            36

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctctgacttg agcgtcgatt tt                                           22

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
cggaacaagg ggaattccct gtcaccgaga cc                                32

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggaacaagg ggaattcccg gggatctgga attc                              34

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgaaagggt cgaggtcgac ctgcagctg                                    29

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aattcacatt gattattgag tagtta                                       26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcgaaagggt aatggccagc aaaggagaag                                   30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggccaagggt ttgtagagct catccat                                      27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14
ggccaagggt ctgaatgggg ccgcatagt                                      29

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagccataga gcccgggcca                                                20

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttccgaagg gtcgaggtcg acctgcagct g                                   31

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggaacaagg gatggccagc aaaggagaag                                     30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taggccaagg gtttgtagag ctcatccatg c                                   31

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcctaaagg gtgaatgggg ccgcatagt                                      29

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 20
gaaggagtaa tacgactcac tatagggagc caccatgggc ccttcggaac             50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gttccgaagg gcccatggtg gctccctata gtgagtcgta ttactccttc             50

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaggagtaa tacgactcac t                                            21

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcctaaagg gtccctttag tgagggttaa ttgcgcgc                          38

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgcgcaatt aaccctcact aaagggaccc tttaggcc                          38

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cggaacaagg gatgatagat cccgtcgttt taca                              34

<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 26
taggccaagg ggaccatttt caatccgcac ct                              32

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taggccaagg ggaggcactt caccgcttgc ca                              32

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taggccaagg gtttgacacc agaccaactg gta                             33

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 tcgaaaggg                                                         9

<210> SEQ ID NO 30
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30 tcgaaaggg                                                         9

<210> SEQ ID NO 31
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 ggccaaggg                                                         9

<210> SEQ ID NO 32
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 32 ggccaaggg                                                                 9

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttccgaagg g                                                             11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cggaacaagg g                                                             11

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 ggccaaggg                                                                 9

<210> SEQ ID NO 36
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 ggccaaggg                                                                 9

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gttccgaagg g                                                             11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 38
cggaacaagg g                                                            11

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
taggccaagg g                                                            11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggcctaaagg g                                                            11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
atccggttcc c                                                            11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gccttgttcc c                                                            11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ggccataagg g                                                            11

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 44
cccttggcca taaggg                                              16

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccctttaggc caaggg                                              16

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cccttcggaa caaggg                                              16

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cccttgttcc gaaggg                                              16

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gatgactcgt aatacgactc acta                                     24

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
accagaagcg gtgccggaaa                                          20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 50
ccacagcgga tggttcggat                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tgaacatttc gcagcctacc                                              20

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gactcgtaat acgactcact atagggacca gaagcggtgc cggaaa                 46

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gactcgtaat acgactcact atagggccac agcggatggt tcggat                 46

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gccacctgat atccttt                                                 17

<210> SEQ ID NO 55
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gactcgtaat acgactcact atagggtgaa catttcgcag cctacc                 46

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 56
gactcgtaat acgactcact atagggggcca cctgatatcc ttt                    43

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcatcgtaac cgtgcatc                                                 18

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcgagtgcca acatgg                                                   16

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gactcgtaat acgactcact ataggtactg catcgtaacc gtgcatc                 47

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gactcgtaat acgactcact ataggtactg cgagtggcaa catgg                   45

<210> SEQ ID NO 61
<211> LENGTH: 31
<212> TYPE: DNA
<213> ORGANISM: T7 virus

<400> SEQUENCE: 61
gactcgtaat acgactcact atagggccct t                                  31

<210> SEQ ID NO 62
<211> LENGTH: 42
<212> TYPE: DNA
<213> ORGANISM: T7 virus

<400> SEQUENCE: 62
agggccctat agtgagtcgt attacgagtc aaaaaaaaaa aa                      42
```